US007276206B2

(12) United States Patent
Augustine et al.

(10) Patent No.: US 7,276,206 B2
(45) Date of Patent: Oct. 2, 2007

(54) ELECTRICAL FIELD STIMULATION OF EUKARYOTIC CELLS

(75) Inventors: Paul R. Augustine, Carteret, NJ (US); Randal M. Bugianesi, Bridgewater, NJ (US); Gary S. Kath, Scotch Plains, NJ (US); Owen B. McManus, Skillman, NJ (US); Paul B. Bennett, Doylestown, PA (US); Tina A. Garyantes, Warren, NJ (US); John P. Imredy, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 416 days.

(21) Appl. No.: 10/483,467

(22) PCT Filed: Jul. 12, 2002

(86) PCT No.: PCT/US02/22161

§ 371 (c)(1),
(2), (4) Date: Jan. 12, 2004

(87) PCT Pub. No.: WO03/006103

PCT Pub. Date: Jan. 23, 2003

(65) Prior Publication Data

US 2005/0164161 A1 Jul. 28, 2005

Related U.S. Application Data

(60) Provisional application No. 60/304,955, filed on Jul. 12, 2001.

(51) Int. Cl.
*G01N 21/64* (2006.01)
*G01N 35/00* (2006.01)
*G01R 27/00* (2006.01)

(52) U.S. Cl. ............... 422/55; 324/600; 422/50; 422/67; 436/43

(58) Field of Classification Search ............ None
See application file for complete search history.

(56) References Cited

U.S. PATENT DOCUMENTS

| | | | |
|---|---|---|---|
| 4,828,386 A * | 5/1989 | Matkovich et al. | 356/246 |
| 5,422,266 A | 6/1995 | Cormier et al. | |
| 5,541,309 A | 7/1996 | Prasher | |
| 5,563,067 A * | 10/1996 | Sugihara et al. | 435/287.1 |
| 5,661,035 A | 8/1997 | Tsien et al. | |
| 5,714,666 A | 2/1998 | Pritchett et al. | |
| 5,741,657 A | 4/1998 | Tsien et al. | |
| 5,744,579 A | 4/1998 | Cormier et al. | |
| 6,057,114 A | 5/2000 | Akong et al. | |
| 6,377,057 B1 | 4/2002 | Borkholder | |
| 2002/0045159 A1 * | 4/2002 | Maher et al. | 435/4 |

FOREIGN PATENT DOCUMENTS

| | | |
|---|---|---|
| DE | 100 08 373 C2 | 11/2002 |
| EP | 0973 040 B1 | 3/2003 |
| WO | WO93/13423 | 7/1993 |
| WO | WO99/19729 | 4/1999 |
| WO | WO99/39829 | 8/1999 |
| WO | WO99/66329 | * 12/1999 |

OTHER PUBLICATIONS

Bennett et al., 1999, Cardiovascular Drugs and Therapy, 7:585-592.
Johnson et al., 1999, J. Gen. Physiol. 113:565-580.
Bennett & Shin, "Biophysics of Cardiac Sodium Channels", Cardiac Electrophysiology: From Cell to Bedside, 3rd edition, D. Zipes and J. Jalife, eds., 2000, W.B.Saunders Co., p. 67-86.
Bennett & Johnson, "Molecular Physiology of Cardiac Ion Channels", Ch. 2, An Introduction to Electrophysiology, 1st edition, A. Zasa & M. Rosen, eds., 2000, Harwood Academic Press, p. 29-57.
Wang et al., 1998, Science 282:1890-1893.
Catterall, 1993, Trends Neuroscience, 16:500-506.
Rogart et al., 1989, Proc. Natl. Acad. Sci. USA 86:8170-8174.
Trimmer et al., 1989, Neuron 3:33-49.
Hamill et al., 1981, Pflugers Arch. 391:85-100.
Gonzalez et al., 1997, Chemistry & Biology 4:269-277.
Hodgkin & Huxley, 1952, J. Physiol (London) 153:449-472.
Strichartz et al., 1987, Ann. Rev. Neurosci., 10:237-267.
Straub et al., 2001, Nature Biotechnol. 19:121-124.
Velicelebi et a., 1999, Meth. Enzymol., 294:20-47.
Inouye et al., 1985, Proc. Natl. Acad. Sci. USA, 82:3154-3158.
Prasher et al., 1985, Biochem. Biophys. Res. Comm. 126:1259-1268.
Button & Brownstein, 1993, Cell Calcium 14:663-671.
Shimomura et al., 1989, Biochem J. 261:913-920.
Shimomura et al., 1993, Cell Calcium 14:373-378.
Creton et al., 1999 Microscopy Research & Technique 46:390-397.
Brini et al., 1995, J. Biol. Chem. 270:9896-9903.
Knight & Knight, 1995, Methods in Cell Biology 49:201-216.
Rutter et al., 1998, Chemistry & Biology 5:R285-R290.
Zlokarnik et al., 1998, Science 279:84-88.
Gonzalez & Tsien, 1995, Biophys. J., 69:1272-1280.
Connolly et al., Biosensors & Bioelectronics, 1990, 5:223-234.

* cited by examiner

*Primary Examiner*—Robert A. Wax
(74) *Attorney, Agent, or Firm*—Joan E. Switzer; William Krovatin

(57) ABSTRACT

Methods of identifying activators and inhibitors of voltage-gated ion channels are provided in which the methods employ electrical field stimulation of the cells in order to manipulate the open/close state transition of the voltage-gated ion channels. This allows for more convenient, more precise experimental manipulation of these transitions, and, coupled with efficient methods of detecting the result of ion flux through the channels, provides methods that are especially suitable for high throughput screening.

7 Claims, 57 Drawing Sheets

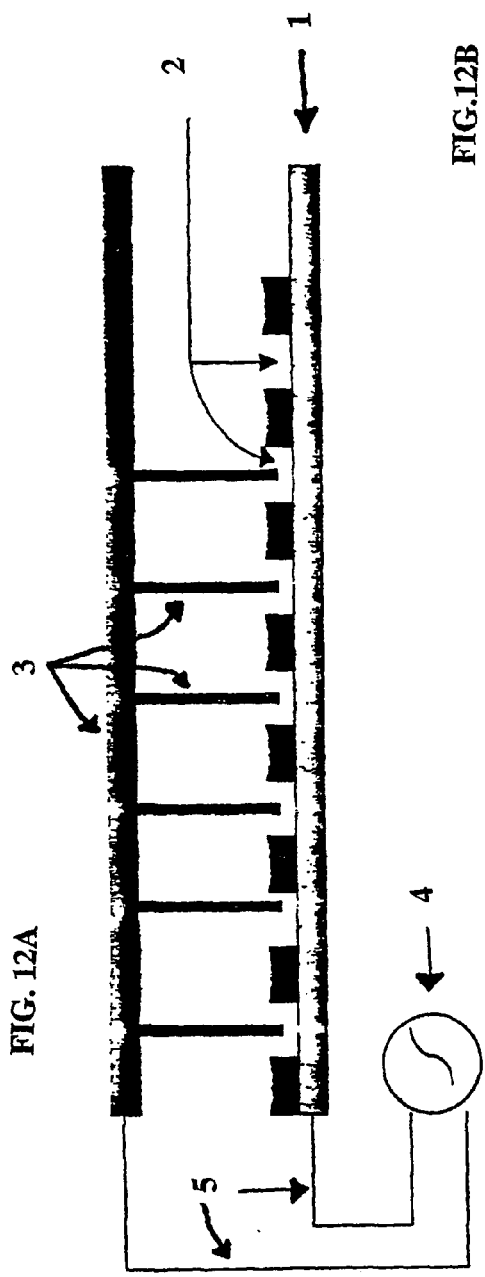
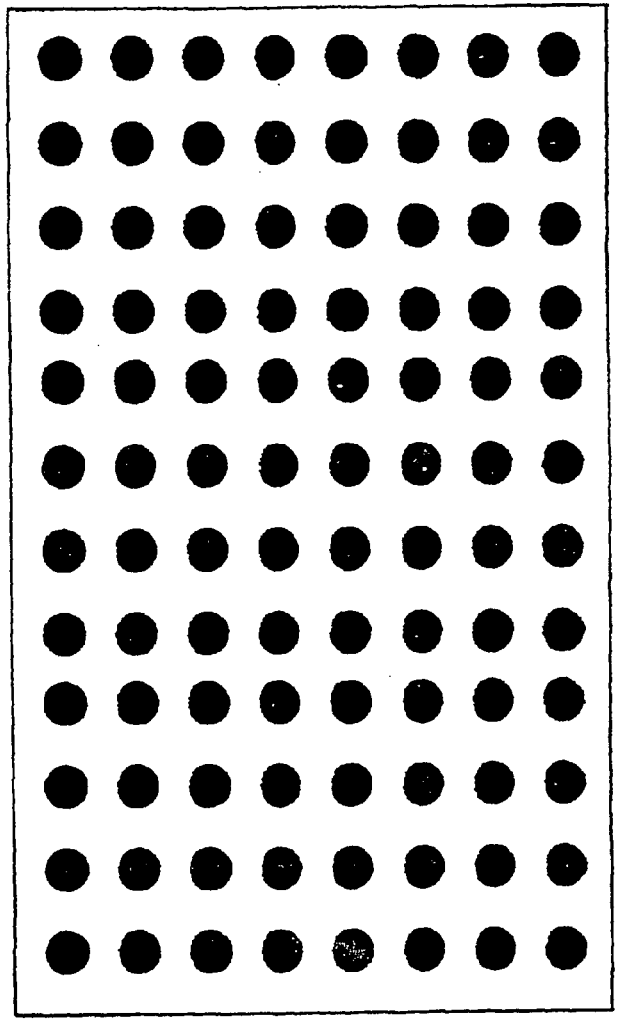
FIG. 12A
FIG. 12B

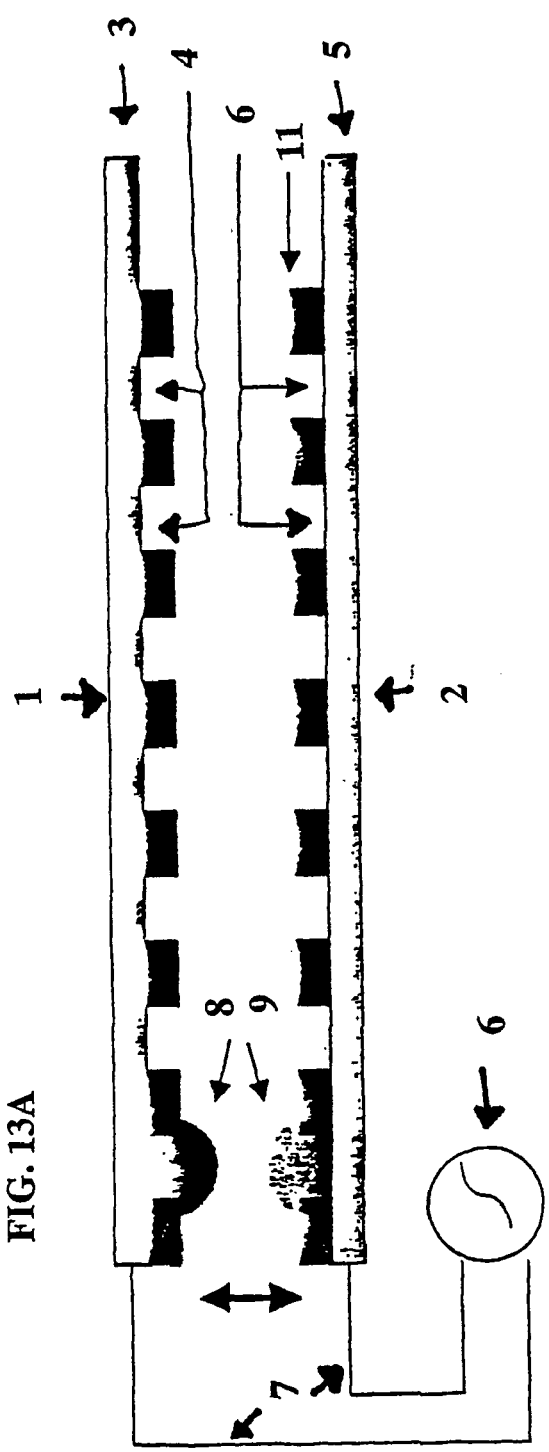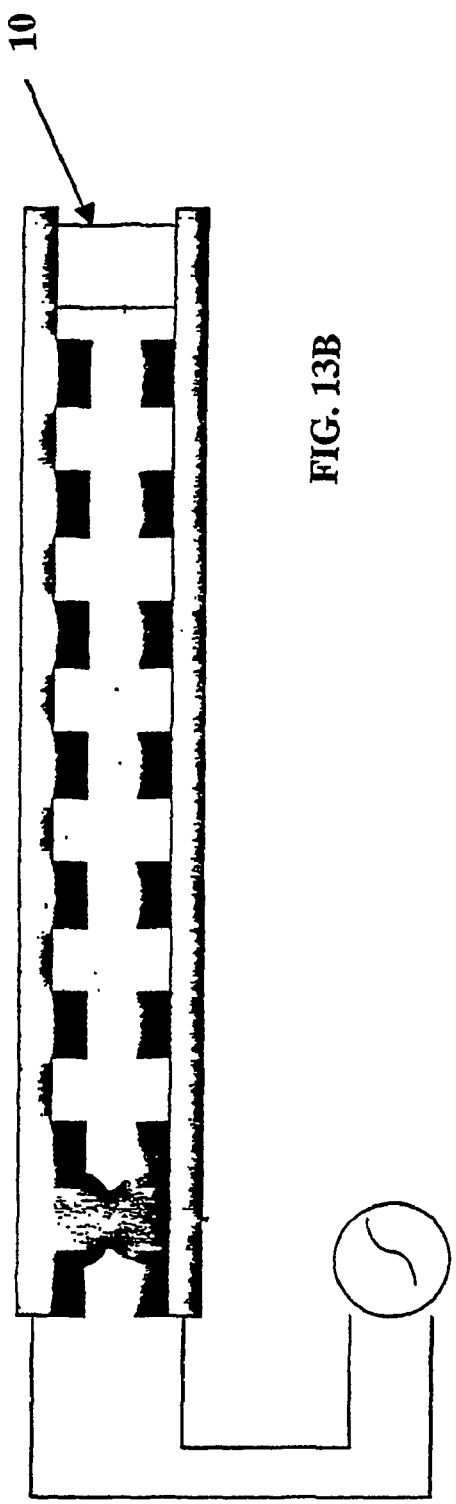
FIG. 13A
FIG. 13B

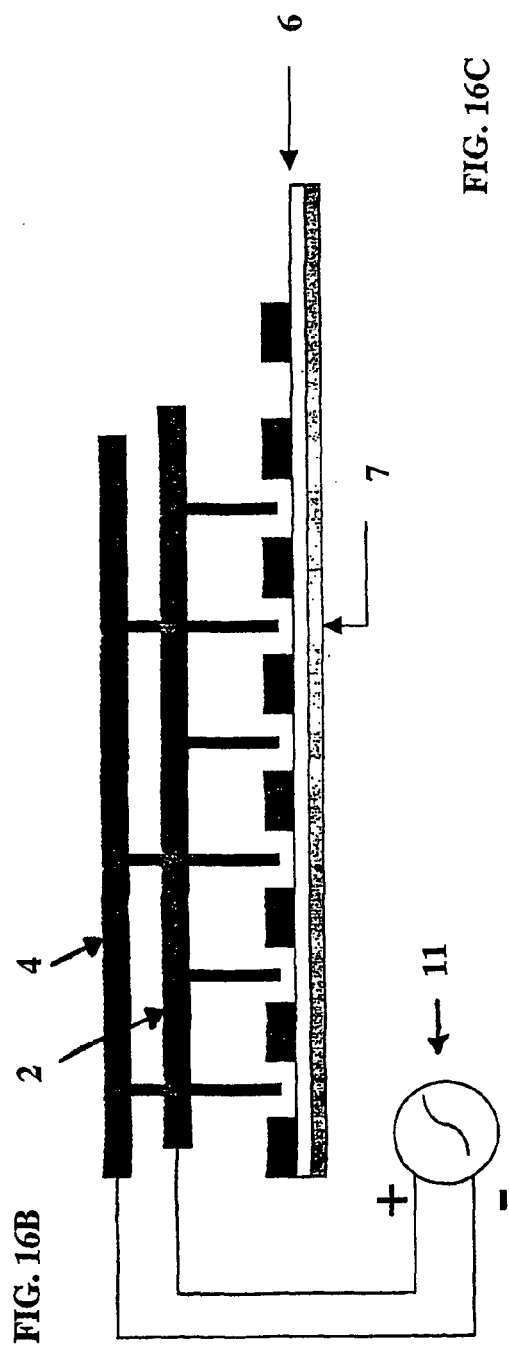
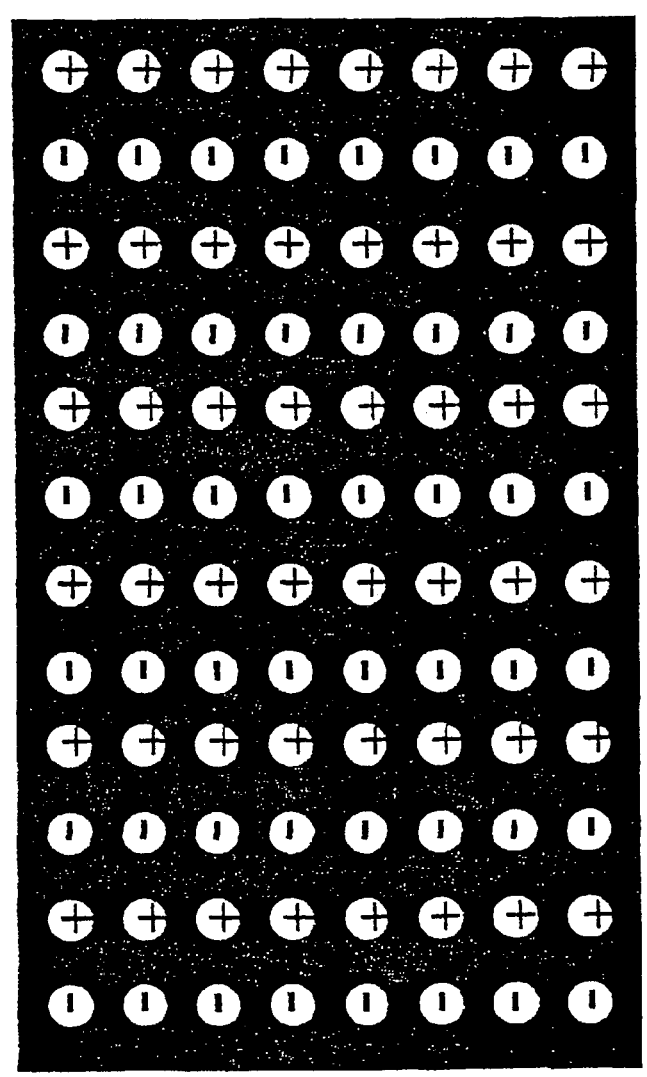
FIG. 16B
FIG. 16C

FIGURE 18A

```
   1 atggaattcc ccattggatc cctcgaaact aacaacttcc gtcgctttac tccggagtca
  61 ctggtggaga tagagaagca aattgctgcc aagcagggaa caaagaaagc cagagagaag
 121 catagggagc agaaggacca agaagagaag cctcggcccc agctggactt gaaagcctgc
 181 aaccagctgc ccaagttcta tggtgagctc ccagcagaac tgatcgggga gcccctggag
 241 gatctagatc cgttctacag cacacaccgg acatttatgg tgctgaacaa agggaggacc
 301 atttcccggt ttagtgccac tcgggccctg tggctattca gtcctttcaa cctgatcaga
 361 agaacggcca tcaaagtgtc tgtccactcg tggttcagtt tatttattac ggtcactatt
 421 ttggttaatt gtgtgtgcat gacccgaact gaccttccag agaaaattga atatgtcttc
 481 actgtcattt acacctttga agccttgata aagatactgg caagaggatt ttgtctaaat
 541 gagttcacgt acctgagaga tccttggaac tggctggatt ttagcgtcat taccctggca
 601 tatgttggca cagcaataga tctccgtggg atctcaggcc tgcggacatt cagagttctt
 661 agagcattaa aaacagtttc tgtgatccca ggcctgaagg tcattgtggg ggccctgatt
 721 cactcagtga agaaactggc tgatgtgacc atcctcacca tcttctgcct aagtgttttt
 781 gccttggtgg ggctgcaact cttcaagggc aacctcaaaa ataaatgtgt caagaatgac
 841 atggctgtca atgagacaac caactactca tctcacagaa aaccagatat ctacataaat
 901 aagcgaggca cttctgaccc cttactgtgt ggcaatggat ctgactcagg ccactgccct
 961 gatggttata tctgccttaa aacttctgac aacccggatt ttaactacac cagctttgat
1021 tcctttgctt gggctttcct ctcactgttc cgcctcatga cacaggattc tgggaacgc
1081 ctctaccagc agaccctgag gacttctggg aaaatctata tgatcttttt tgtgctcgta
1141 atcttcctgg gatctttcta cctggtcaac ttgatcttgg ctgtagtcac catggcgtat
1201 gaggagcaga accaggcaac cactgatgaa attgaagcaa aggagaagaa gttccaggag
1261 gccctcgaga tgctccggaa ggagcaggag gtgctagcag cactagggat tgcacacaacc
1321 tctctccact cccacaatgg atcaccttta acctccaaaa atgccagtga gagaaggcat
1381 agaataaagc caagagtgtc agagggctcc acagaagaca caaatcacc ccgctctgat
1441 ccttacaacc agcgcaggat gtcttttcta ggcctcgcct ctggaaaacg ccgggctagt
1501 catggcagtg tgttccattt ccggtcccct ggccgagata tctcactccc tgagggagtc
1561 acagatgatg gagtctttcc tggagaccac gaaagccatc ggggctctct gctgctgggt
1621 gggggtgctg ccagcaagg ccccctccct agaagccctc ttcctcaacc cagcaaccct
1681 gactccaggc atggagaaga tgaacaccaa ccgccgccca ctagtgagct tgcccctgga
1741 gctgtcgatg tctcggcatt cgatgcagga caaaagaaga ctttcttgtc agcagaatac
1801 ttagatgaac ctttccgggc ccaaagggca atgagtgttg tcagtatcat aacctccgtc
1861 cttgaggaac tcgaggagtc tgaacagaag tgcccacccct gcttgaccag cttgtctcag
1921 aagtatctga tctgggattg ctgccccatg tgggtgaagc tcaagacaat tctctttggg
1981 cttgtgacgg atcccttttgc agagctcacc atcaccttgt gcatcgtggt gaacaccatc
2041 ttcatggcca tggagcacca tggcatgagc cctaccttcg aagccatgct ccagataggc
2101 aacatcgtct ttaccatatt ttttactgct gaaatggtct tcaaaatcat tgccttcgac
2161 ccatactatt atttccagaa gaagtggaat atctttgact gcatcatcgt cactgtgagt
2221 ctgctagagc tgggcgtggc caagaaggga agcctgtctg tgctgcggag cttccgcttg
2281 ctgcgcgtat tcaagctggc caaatcctgg cccaccttaa acacactcat caagatcatc
2341 ggaaactcag tgggggcact ggggaacctc accatcatcc tggccatcat tgtctttgtc
2401 tttgctctgg ttggcaagca gctccagggg gaaaactacc gtaacaaccg aaaaaatatc
2461 tccgcgcccc atgaagactg gccccgctgg cacatgcacg acttcttcca ctcttttcctc
2521 attgtcttcc gtatcctctg tggagagtgg attgagaaca tgtgggcctg catggaagtt
2581 ggccaaaaat ccatatgcct catcctttc ttgacggtga tggtgctagg gaacctggtg
2641 gtgcttaacc tgttcatcgc cctgctattg aactcttca gtctgacaa cctcacagcc
2701 ccggaggacg atggggaggt gaacaacctg caggtggccc tggcacggat ccaggtcttt
2761 ggccatcgta ccaaacaggc tctttgcagc tctttcagca ggtcctgccc attccccag
2821 cccaaggcag agcctgagct ggtggtgaaa ctcccactct ccagctccaa ggctgagaac
2881 cacattgctg ccaacactgc caggggggagc tctggagggc tccaagctcc cagaggcccc
```

FIG. 18B

```
2941 agggatgagc acagtgactt catcgctaat ccgactgtgt gggtctctgt gcccattgct
3001 gagggtgaat ctgatcttga tgacttggag gatgatggtg gggaagatgc tcagagcttc
3061 cagcaggaag tgatccccaa aggacagcag gagcagctgc agcaagtcga gaggtgtggg
3121 gaccacctga cacccaggag cccaggcact ggaacatctt ctgaggacct ggctccatcc
3181 ctgggtgaga cgtggaaaga tgagtctgtt cctcaggccc ctgctgaggg agtggacgac
3241 acaagctcct ctgagggcag cacggtggac tgcctagatc ctgaggaaat cctgaggaag
3301 atccctgagc tggcagatga cctggaagaa ccagatgact gcttcacaga aggatgcatt
3361 cgccactgtc cctgctgcaa actggatacc accaagagtc catgggatgt gggctggcag
3421 gtgcgcaaga cttgctaccg tatcgtggag cacagctggt ttgagagctt catcatcttc
3481 atgatcctgc tcagcagtgg atctctggcc tttgaagact attacctgga ccagaagccc
3541 acggtgaaag ctttgctgga gtacactgac agggtcttca cctttatctt tgtgttcgag
3601 atgctgctta agtgggtggc ctatggcttc aaaaagtact tcaccaatgc ctggtgctgg
3661 ctggacttcc tcattgtgaa tatctcactg ataagtctca cagcgaagat tctggaatat
3721 tctgaagtgg ctcccatcaa agcccttcga acccttcgcg ctctgcggcc actgcgggct
3781 ctttctcgat ttgaaggcat gcgggtggtg gtggatgccc tggtgggcgc catcccatcc
3841 atcatgaatg tcctcctcgt ctgcctcatc ttctggctca tcttcagcat catgggtgtg
3901 aacctcttcg cagggaagtt ttggaggtgc atcaactata ccgatggaga gttttcccct
3961 gtacctttgt cgattgtgaa taacaagtct gactgcaaga ttcaaaactc cactggcagc
4021 ttcttctggg tcaatgtgaa agtcaacttt gataatgttg caatgggtta ccttgcactt
4081 ctgcaggtgg caacctttaa aggctggatg gacattatgt atgcagctgt tgattcccgg
4141 gaggtcaaca tgcaacccaa gtgggaggac aacgtgtaca tgtatttgta ctttgtcatc
4201 ttcatcattt ttggaggctt cttcacactg aatctctttg ttggggtcat aattgacaac
4261 ttcaatcaac agaaaaaaaa gttaggggc caggacatct tcatgacaga ggagcagaag
4321 aaatactaca atgccatgaa gaagttgggc tccaagaagc cccagaagcc catcccacgg
4381 cccctgaaca agttccaggg tttttgtcttt gacatcgtga ccagacaagc ttttgacatc
4441 accatcatgg tcctcatctg cctcaacatg atcaccatga tggtggagac tgatgaccaa
4501 agtgaagaaa agacgaaaat tctgggcaaa atcaaccagt tctttgtggc cgtcttcaca
4561 ggcgaatgtg tcatgaagat gttcgctttg aggcagtact acttcacaaa tggctggaat
4621 gtgtttgact tcattgtggt ggttctctcc attgcgagcc tgattttttc tgcaattctt
4681 aagtcacttc aaagttactt ctccccaacg ctcttcagag tcatccgcct ggcccgaatt
4741 ggccgcatcc tcagactgat ccgagcggcc aagggggatcc gcacactgct ctttgccctc
4801 atgatgtccc tgcctgccct cttcaacatc gggctgttgc tattccttgt catgttcatc
4861 tactccatct tcggtatgtc cagctttccc catgtgaggt gggaggctgg catcgacgac
4921 atgttcaact tccagacctt cgccaacagc atgctgtgcc tcttccagat taccacgtcg
4981 gccggctggg atggcctcct cagcccatc ctcaacacag gcccccccta ctgtgacccc
5041 aatctgccca cagcaatgg caccagaggg gactgtggga gcccagccgt aggcatcatc
5101 ttcttcacca cctacatcat catctccttc ctcatcgtgg tcaacatgta cattgcagtg
5161 attctggaga acttcaatgt ggccacggag gagagcactg agcctctgag tgaggacgac
5221 tttgacatgt tctatgagac ctgggagaag tttgacccag aggccactca gtttattacc
5281 tttttctgtc tctcggactt tgcagacact ctctctggtc cctgagaat cccaaaaccc
5341 aatcgaaata tactgatcca gatggacctg cctttggtcc ctggagataa gatccactgc
5401 ttggacatcc ttttgctttt caccaagaat gtcctaggag aatccgggga gttggattct
5461 ctgaaggcaa atatggagga gaagtttatg gcaactaatc tttcaaaatc atcctatgaa
5521 ccaatagcaa ccactctccg atggaagcaa gaagacattt cagccactgt cattcaaaag
5581 gcctatcgga gctatgtgct gcaccgctcc atggcactct ctaacacccc atgtgtgccc
5641 agagctgagg aggaggctgc atcactccca gatgaaggtt ttgttgcatt cacagcaaat
5701 gagaatttcg tactcccaga caaatctgaa actgcttctg ccacatcatt cccaccgtcc
```

FIG. 18C

MEFPIGSLETNNFRRFTPESLVEIEKQIAAKQGTKKAREKHREQ
KDQEEKPRPQLDLKACNQLPKFYGELPAELIGEPLEDLDPFYSTHRTFMVLNKGRTIS
RFSATRALWLFSPFNLIRRTAIKVSVHSWFSLFITVTILVNCVCMTRTDLPEKIEYVF
TVTYTFEALIKILARGFCLNEFTYLRDPWNWLDFSVITLAYVGTAIDLRGISGLRTFR
VLRALKTVSVIPGLKVTVGALIHSVKKLADVTILTIFCLSVFALVGLQLFKGNLKNKC
VKNDMAVNETTNYSSHRKPDIYINKRGTSDPLLCGNGSDSGHCPDGYICLKTSDNPDF
NYTSFDSFAWAFLSLFRLMTQDSWERLYQQTLRTSGKIYMIFFVLVIFLGSFYLVNLI
LAVVTMAYEEQNQATTDEIEAKEKKFQEALEMLRKEQEVLAALGIDTTSLHSHNGSPL
TSKNASERRHRIKPRVSEGSTEDNKSPRSDPYNQRRMSFLGLASGKRRASHGSVFHFR
SPGRDISLPEGVTDDGVFPGDHESHRGSLLLGGGAGQQGPLPRSPLPQPSNPDSRHGE
DEHQPPPTSELAPGAVDVSAFDAGQKKTFLSAEYLDEPFRAQRAMSVVSITSVLEEL
EESEQKCPPCLTSLSQKYLIWDCCPMWVKLKTILFGLVTDPFAELTITLCIVVNTIFM
AMEHHGMSPTFEAMLQIGNIVFTIFFTAEMVFKIIAFDPYYYFQKKWNIFDCIIVTVS
LLELGVAKKGSLSVLRSFRLLRVFKLAKSWPTLNTLIKIIGNSVGALGNLTILAIIV
FVFALVGKQLLGENYRNNRKNISAPHEDWPRWHMHDFFHSFLIVFRILCGEWIENMWA
CMEVGQKSICLILFLTVMVLGNLVVLNLFIALLLNSFSADNLTAPEDDGEVNNLQVAL
ARIQVFGHRTKQALCSFFSRSCPFPQPKAEPELVVKLPLSSSKAENHIAANTARGSSG
GLQAPRGPRDEHSDFIANPTVWVSVPIAEGESDLDDLEDDGGEDAQSFQQEVIPKGQQ
EQLQQVERCGDHLTPRSPGTGTSSEDLAPSLGETWKDESVPQAPAEGVDDTSSSEGST
VDCLDPEEILRKIPELADDLEEPDDCFTEGCIRHCPCCKLDTTKSPWDVGWQVRKTCY
RIVEHSWFESFIIFMILLSSGSLAFEDYYLDQKPTVKALLEYTDRVFTFIFVFEMLLK
WVAYGFKKYFTNAWCWLDFLIVNISLISLTAKILEYSEVAPIKALRTLRALRPLRALS
RFEGMRVVVDALVGAIPSIMNVLLVCLIFWLIFSIMGVNLFAGKFWRCINYTDGEFSL
VPLSIVNNKSDCKIQNSTGSFFWVNVKVNFDNVAMGYLALLQVATFKGWMDIMYAAVD
SREVNMQPKWEDNVYMYLYFVIFIIFGGFFTLNLFVGVIIDNFNQQKKKLGGQDIFMT
EEQKKYYNAMKKLGSKKPQKPIPRPLNKFQGFVFDIVTRQAFDITIMVLICLNMITMM
VETDDQSEEKTKILGKINQFFVAVFTGECVMKMFALRQYYFTNGWNVFDFIVVVLSIA
SLIFSAILKSLQSYFSPTLFRVIRLARIGRILRLIRAAKGIRTLLFALMMSLPALFNI
GLLLFLVMFIYSIFGMSSFPHVRWEAGIDDMFNFQTFANSMLCLFQITTSAGWDGLLS
PILNTGPPYCDPNLPNSNGTRGDCGSPAVGIIFFTTYIIISFLIVVNMYIAVILENFN
VATEESTEPLSEDDFDMFYETWEKFDPEATQFITFSALSDFADTLSGPLRIPKPNRNI
LIQMDLPLVPGDKIHCLDILFAFTKNVLGESGELDSLKANMEEKFMATNLSKSSYEPI
ATTLRWKQEDISATVIQKAYRSYVLHRSMALSNTPCVPRAEEEAASLPDEGFVAFTAN
ENCVLPDKSETASATSFPPSYESVTRGLSDRVNMRTSSSIQNEDEATSMELIAPGP

FIGURE 19A

```
   1 cgaggccgcc gccgtcgcct ccgccgggcg agccggagcc ggagtcgagc cgcggccggg
  61 agccgggcgg gctggggacg cgggccgggg gcggaggcgc tgggggccgg ggccggggcc
 121 ggggggcggag gcgctggggg ccggggccgg ggccgggcgc cgagcgggt ccgcggtgac
 181 cgcgccgccc gggcgatgcc cgcggggacg ccgccggcca gcagagcgag gtgctgccgg
 241 ccgccaccat gaccgagggc gcacgggccg ccgacgaggt ccgggtgccc ctgggcgcgc
 301 cgccccctgg ccctgcggcg ttggtggggg cgtccccgga gagccccggg gcgccgggac
 361 gcgaggcgga gcggggggtcc gagctcggcg tgtcaccctc cgagagcccg gcggccgagc
 421 gcggcgcgga gctgggtgcc gacgaggagc agcgcgtccc gtacccggcc ttggcggcca
 481 cggtcttctt ctgcctcggt cagaccacgc ggccgcgcag ctggtgcctc cggctggtct
 541 gcaacccatg gttcgagcac gtgagcatgc tggtaatcat gctcaactgc gtgaccctgg
 601 gcatgttccg gccctgtgag gacgttgagt gcggctccga gcgctgcaac atcctggagg
 661 cctttgacgc cttcattttc gccttttttg cggtggagat ggtcatcaag atggtggcct
 721 tggggctgtt cgggcagaag tgttacctgg gtgacacgtg gaacaggctg gatttcttca
 781 tcgtcgtggc gggcatgatg gagtactcgt tggacggaca caacgtgagc ctctcggcta
 841 tcaggaccgt gcgggtgctg cggcccctcc gcgccatcaa ccgcgtgcct agcatgcgga
 901 tcctggtcac tctgctgctg gatacgctgc ccatgctcgg gaacgtcctt ctgctgtgct
 961 tcttcgtctt cttcattttc ggcatcgttg gcgtccagct ctgggctggc ctcctgcgga
1021 accgctgctt cctggacagt gcctttgtca ggaacaacaa cctgaccttc ctgcggccgt
1081 actaccagac ggaggagggc gaggagaacc cgttcatctg ctcctcacgc cgagacaacg
1141 gcatgcagaa gtgctcgcac atccccggcc gccgcgagct gcgcatgccc tgcaccctgg
1201 gctgggaggc ctacacgcag ccgcaggccg aggggggtggg cgctgcacgc aacgcctgca
1261 tcaactggaa ccagtactac aacgtgtgcc gctcgggtga ctccaacccc cacaacggtg
1321 ccatcaactt cgacaacatc ggctacgcct ggattgccat cttccaggtg atcacgctgg
1381 aaggctgggt ggacatcatg tactacgtca tggacgccca ctcattctac aacttcatct
1441 atttcatcct gctcatcatc gtgggctcct tcttcatgat caacctgtgc ctggtggtga
1501 ttgccacgca gttctcggag acgaagcagc gggagagtca gctgatgcgg gagcagcggg
1561 cacgccacct gtccaacgac agcacgctgg ccagcttctc cgagcctggc agctgctacg
1621 aagagctgct gaagtacgtg ggccacatat tccgcaaggt caagcggcgc agcttgcgcc
1681 tctacgcccg ctggcagagc cgctggcgca agaaggtgga ccccagtgct gtgcaaggcc
1741 agggtcccgg gcaccgccag cgccgggcag gcaggcacac agcctcggtg caccacctgg
1801 tctaccacca ccatcaccac caccaccacc actaccattt cagccatggc agccccgca
1861 ggcccggcc cgagccaggc gcctgcgaca ccaggctggt ccgagctggc gcgccccct
1921 cgccaccttc cccaggccgc ggaccccccg acgcagagtc tgtgcacagc atctaccatg
1981 ccgactgcca catagagggg ccgcaggaga gggcccgggt ggcacatgcc gcagccactg
2041 ccgctgccag cctcaggctg gccacagggc tgggcaccat gaactacccc acgatcctgc
2101 cctcaggggt gggcagcggc aaaggcagca ccagccccgg acccaagggg aagtgggccg
2161 gtggaccgcc aggcaccggg gggcacggcc cgttgagctt gaacagccct gatccctacg
2221 agaagatccc gcatgtggtc ggggagcatg gactgggcca ggcccctggc catctgtcgg
2281 gcctcagtgt gccctgcccc ctgccagcc ccccagcggg cacactgacc tgtgagctga
2341 agagctgccc gtactgcacc cgtgccctgg aggacccgga gggtgagctc agcggctcgg
2401 aaagtggaga ctcagatggc cgtggcgtct atgaattcac gcaggacgtc cggcacggtg
2461 accgctggga ccccacgcga ccacccgtg cgacggacac accaggccca ggcccaggca
2521 gcccccagcg gcgggcacag cagagggcag ccccgggcga gccaggctgg atgggccgcc
2581 tctgggttac cttcagcggc aagctgcgcc gcatcgtgga cagcaagtac ttcagccgtg
2641 gcatcatgat ggccatcctt gtcaacacgc tgagcatggg cgtggagtac catgagcagc
2701 ccgaggagct gactaatgct ctggagatca gcaacatcgt gttcaccagc atgtttgccc
2761 tggagatgct gctgaagctg ctggcctgcg gccctctggg ctacatccgg aacccgtaca
2821 acatcttcga cggcatcatc gtggtcatca gcgtctggga gatcgtgggg caggcggacg
```

FIG. 19B

```
2881 gtggcttgtc tgtgctgcgc accttccggc tgctgcgtgt gctgaagctg gtgcgctttc
2941 tgccagccct gcggcgccag ctcgtggtgc tggtgaagac catggacaac gtggctacct
3001 tctgcacgct gctcatgctc ttcattttca tcttcagcat cctgggcatg caccttttcg
3061 gctgcaagtt cagcctgaag acagacaccg gagacaccgt gcctgacagg aagaacttcg
3121 actccctgct gtgggccatc gtcaccgtgt tccagatcct gacccaggag gactggaacg
3181 tggtcctgta caacggcatg gcctccacct cctcctgggc cgccctctac ttcgtggccc
3241 tcatgacctt cggcaactat gtgctcttca acctgctggt ggccatcctc gtggagggct
3301 tccaggcgga gggcgatgcc aacagatccg acacggacga ggacaagacg tcggtccact
3361 tcgaggagga cttccacaag ctcagagaac tccagaccac agagctgaag atgtgttccc
3421 tggccgtgac ccccaacggg cacctggagg gacgaggcag cctgtcccct cccctcatca
3481 tgtgcacagc tgccacgccc atgcctaccc ccaagagctc accattcctg gatgcagccc
3541 ccagcctccc agactctcgg cgtggcagca gcagctccgg ggacccgcca ctgggagacc
3601 agaagcctcc ggccagcctc cgaagttctc cctgtgcccc ctggggcccc agtggcgcct
3661 ggagcagccg gcgctccagc tggagcagcc tgggccgtgc ccccagcctc aagcgccgcg
3721 gccagtgtgg ggaacgtgag tccctgctgt ctggcgaggg caagggcagc accgacgacg
3781 aagctgagga cggcagggcc gcgcccgggc cccgtgccac cccactgcgg cgggccgagt
3841 ccctggaccc acggccgctg cggccggccg cctccccgcc taccaagtgc cgcgatcgcg
3901 acgggcaggt ggtggccctg cccagcgact tcttcctgcg catcgacagc caccgtgagg
3961 atgcagccga gcttgacgac gactcggagg acagctgctg cctccgcctg cataaagtgc
4021 tggagcccta caagccccag tggtgccgga gccgcgaggc ctgggccctc tacctcttct
4081 ccccacagaa ccggttccgc gtctcctgcc agaaggtcat cacacacaag atgtttgatc
4141 acgtggtcct cgtcttcatc ttcctcaact gcgtcaccat cgccctggag aggcctgaca
4201 ttgaccccgg cagcaccgag cgggtcttcc tcagcgtctc caattacatc ttcacggcca
4261 tcttcgtggc ggagatgatg gtgaaggtgg tggccctggg gctgctgtcc ggcgagcacg
4321 cctacctgca gagcagctgg aacctgctgg atgggctgct ggtgctggtg tccctggtgg
4381 acattgtcgt ggccatggcc tcggctggtg gcgccaagat cctgggtgtt ctgcgcgtgc
4441 tgcgtctgct gcggacccctg cggcctctaa gggtcatcag ccgggccccg ggcctcaagc
4501 tggtggtgga gacgctgata tcgtcgctca ggcccattgg gaacatcgtc ctcatctgct
4561 gcgccttctt catcattttt ggcatcttgg gtgtgcagct cttcaaaggg aagttctact
4621 actgcgaggg ccccgacacc aggaacatct ccaccaaggc acagtgccgg gccgcccact
4681 accgctgggt gcgacgcaag tacaacttcg acaacctggg ccaggccctg atgtcgctgt
4741 tcgtgctgtc atccaaggat ggatgggtga acatcatgta cgacgggctg gatgccgtgg
4801 tgtcgacca gcagcctgtg cagaaccaca accctggat gctgctgtac ttcatctcct
4861 tcctgctcat cgtcagcttc ttcgtgctca acatgttcgt gggcgtcgtg gtcgagaact
4921 tccacaagtg ccggcagcac caggaggcgg aggaggcgcg gcggcgagag gagaagcggc
4981 tgcggcgcct agagaggagg cgcaggagca ctttccccag cccagaggcc cagcgccggc
5041 cctactatgc cgactactcg cccacgcgcc gctccattca ctcgctgtgc accagccact
5101 atctcgacct cttcatcacc ttcatcatct gtgtcaacgt catcaccatg tccatggagc
5161 actataacca acccaagtcg ctggacgagg ccctcaagta ctgcaactac gtcttcacca
5221 tcgtgtttgt cttcgaggct gcactgaagc tggtagcatt tgggttccgt cggttcttca
5281 aggacaggtg gaaccagctg gacctggcca tcgtgctgct gtcactcatg ggcatcacgc
5341 tggaggagat agagatgagc gccgcgctgc ccatcaaccc caccatcatc cgcatcatgc
5401 gcgtgcttcg cattgcccgt gtgctgaagc tgctgaagat ggctacgggc atgcgcgccc
5461 tgctggacac tgtggtgcaa gctctccccc aggtggggaa cctgggcctt cttttcatgc
5521 tcctgttttt tatctatgct gcgctgggag tggagctgtt cgggaggctg gagtgcagtg
5581 aagacaaccc ctgcgagggc ctgagcaggc acgccacctt cagcaacttc ggcatggcct
5641 tcctcacgct gttccgcgtg tccacgggag acaactggaa cgggatcatg aaggacacgc
```

FIG. 19C

```
5761 tctacttcgt gaccttcgtg ctggtggccc agttcgtgct ggtgaacgtg gtggtggccg
5821 tgctcatgaa gcacctggag gagagcaaca aggaggcacg ggaggatgcg gagctggacg
5881 ccgagatcga gctggagatg gcgcagggcc ccgggagtgc acgccgggtg gacgcggaca
5941 ggcctcccct gccccaggag agtccgggcg ccagggatgc cccaaacctg gttgcacgca
6001 aggtgtccgt gtccaggatg ctctcgctgc ccaacgacag ctacatgttc aggcccgtgg
6061 tgcctgcctc ggcgccccac ccccgcccgc tgcaggaggt ggagatggag acctatgggg
6121 ccggcacccc cttgggctcc gttgcctctg tgcactctcc gcccgcagag tcctgtgcct
6181 ccctccagat cccactggct gtgtcgtccc cagccaggag cggcgagccc ctccacgccc
6241 tgtcccctcg gggcacagcc cgctccccca gtctcagccg gctgctctgc agacaggagg
6301 ctgtgcacac cgattccttg gaagggaaga ttgacagccc tagggacacc ctggatcctg
6361 cagagcctgg tgagaaaacc ccggtgaggc cggtgaccca gggggctcc ctgcagtccc
6421 caccacgctc cccacggccc gccagcgtcc gcactcgtaa gcataccttc ggacagcact
6481 gcgtctccag ccggccggcg gccccaggcg gagaggaggc cgaggcctcg gacccagccg
6541 acgaggaggt cagccacatc accagctccg cctgcccctg gcagcccaca gccgagcccc
6601 atggccccga agcctctccg gtggccggcg gcgagcggga cctgcgcagg ctctacagcg
6661 tggacgctca gggcttcctg gacaagccgg gccgggcaga cgagcagtgg cggccctcgg
6721 cggagctggg cagcggggag cctggggagg cgaaggcctg gggccctgag gccgagcccg
6781 ctctgggtgc gcgcagaaag aagaagatga gcccccctg catctcggtg gaacccctg
6841 cggaggacga gggctctgcg cggccctccg cggcagaggg cggcagcacc acactgaggc
6901 gcaggacccc gtcctgtgag gccacgcctc agggactc cctggagccc acagagggct
6961 caggcgccgg gggggaccct gcagccaagg gggagcgctg gggccaggcc tcctgccggg
7021 ctgagcacct gaccgtcccc agctttgcct ttgagccgct ggacctcggg gtccccagtg
7081 gagacccttt cttggacggt agccacagtg tgaccccaga atccagagct tcctcttcag
7141 gggccatagt gccctggaa cccccagaat cagagcctcc catgcccgtc ggtgaccccc
7201 cagagaagag gcgggggctg tacctcacag tcccccagtg tcctctggag aaaccagggt
7261 ccccctcagc caccccctgcc caggggtg gtgcagatga ccccgtgtag ctcggggctt
7321 ggtgccgccc acggctttgg ccctggggtc tggggccccc gctggggtgg aggcccaggc
7381 agaaccctgc atggaccctg acttgggtcc cgtcgtgagc agaaaggccc ggggaggatg
7441 acggcccagg ccctggttct ctgcccagcg aagcaggagt agctgccggg ccccacgagc
7501 ctccatccgt tctggttcgg gtttctccga gttttgctac cagccgaggc tgtgcgggca
7561 actgggtcag cctcccgtca ggagagaagc cgcgtctgtg gacgaagac cgggcacccg
7621 ccagagaggg gaaggtacca ggttgcgtcc tttcaggccc cgcgttgtta caggacactc
7681 gctggggcc ctgtgccctt gccggcggca ggttgcagcc accgcggccc aatgtcacct
7741 tcactcacag tctgagttct tgtccgcctg tcacgccctc accaccctcc ccttccagcc
7801 accaccctt ccgttccgct cgggccttcc cagaagcgtc ctgtgactct gggagaggtg
7861 acacctcact aaggggccga ccccatggag taacgcgc
```

FIG. 19D

MTEGARAADEVRVPLGAPPPGPAALVGASPESPGAPGREAERGS
ELGVSPSESPAAERGAELGADEEQRVPYPALAATVFFCLGQTTRPRSWCLRLVCNPWF
EHVSMLVIMLNCVTLGMFRPCEDVECGSERCNILEAFDAFIFAFFAVEMVIKMVALGL
FGQKCYLGDTWNRLDFFIVVAGMMEYSLDGHNVSLSAIRTVRVLRPLRAINRVPSMRI
LVTLLLDTLPMLGNVLLLCFFVFFIFGIVGVQLWAGLLRNRCFLDSAFVRNNNLTFLR
PYYQTEEGEENPFICSSRRDNGMQKCSHIPGRRELRMPCTLGWEAYTQPQAEGVGAAR
NACINWNQYYNVCRSGDSNPHNGAINFDNIGYAWIAIFQVITLEGWVDIMYYVMDAHS
FYNFIYFILLIIVGSFFMINLCLVVIATQFSETKQRESQLMREQRARHLSNDSTLASF
SEPGSCYEELLKYVGHIFRKVKRRSLRLYARWQSRWRKKVDPSAVQGQPGHRQRRAG
RHTASVHHLVYHHHHHHHHHHYHFSHGSPRRPGPEPGACDTRLVRAGAPPSPPSPGRGP
PDAESVHSIYHADCHIEGPQERARVAHAAATAAASLRLATGLGTMNYPTILPSGVGSG
KGSTSPGPKGKWAGGPPGTGGHGPLSLNSPDPYEKIPHVVGEHGLGQAPGHLSGLSVP
CPLPSPPAGTLTCELKSCPYCTRALEDPEGELSGSESGDSDGRGVYEFTQDVRHGDRW
DPTRPPRATDTPGPGPGSPQRRAQQRAAPGEPGWMGRLWVTFSGKLRRIVDSKYFSRG
IMMAILVNTLSMGVEYHEQPEELTNALEISNIVFTSMFALEMLLKLLACGPLGYIRNP
YNIFDGIIVVISVWEIVGQADGGLSVLRTFRLLRVLKLVRFLPALRRQLVVLVKTMDN
VATFCTLLMLFIFIFSILGMHLFGCKFSLKTDTGDTVPDRKNFDSLLWAIVTVFQILT
QEDWNVVLYNGMASTSSWAALYFVALMTFGNYVLFNLLVAILVEGFQAEGDANRSDTD
EDKTSVHFEEDFHKLRELQTTELKMCSLAVTPNGHLEGRGSLSPPLIMCTAATPMPTP
KSSPFLDAAPSLPDSRRGSSSSGDPPLGDQKPPASLRSSPCAPWGPSGAWSSRRSSWS
SLGRAPSLKRRGQCGERESLLSGEGKGSTDDEAEDGRAAPGPRATPLRRAESLDPRPL
RPAALPPTKCRDRDGQVVALPSDFFLRIDSHREDAAELDDDSEDSCCLRLHKVLEPYK
PQWCRSREAWALYLFSPQNRFRVSCQKVITHKMFDHVVLVFIFLNCVTIALERPDIDP
GSTERVFLSVSNYIFTAIFVAEMMVKVVALGLLSGEHAYLQSSWNLLDGLLVLVSLVD
IVVAMASAGGAKILGVLRVLRLLRTLRPLRVISRAPGLKLVVETLISSLRPIGNIVLI
CCAFFIIFGILGVQLFKGKFYYCEGPDTRNISTKAQCRAAHYRWVRRKYNFDNLGQAL
MSLFVLSSKDGWVNIMYDGLDAVGVDQQPVQNHNPWMLLYFISFLLIVSFFVLNMFVG
VVVENFHKCRQHQEAEEARRREEKRLRRLERRRRSTFPSPEAQRRPYYADYSPTRRSI
HSLCTSHYLDLFITFIICVNVITMSMEHYNQPKSLDEALKYCNYVFTIVFVFEAALKL
VAFGFRRFFKDRWNQLDLAIVLLSLMGITLEEIEMSAALPINPTIIRIMRVLRIARVL
KLLKMATGMRALLDTVVQALPQVGNLGLLFMLLFFIYAALGVELFGRLECSEDNPCEG
LSRHATFSNFGMAFLTLFRVSTGDNWNGIMKDTLRECSREDKHCLSYLPALSPVYFVT
FVLVAQFVLVNVVVAVLMKHLEESNKEAREDAELDAEIELEMAQGPGSARRVDADRPP
LPQESPGARDAPNLVARKVSVSRMLSLPNDSYMFRPVVPASAPHPRPLQEVEMETYGA
GTPLGSVASVHSPPAESCASLQIPLAVSSPARSGEPLHALSPRGTARSPSLSRLLCRQ
EAVHTDSLEGKIDSPRDTLDPAEPGEKTPVRPVTQGGSLQSPPRSPRPASVRTRKHTF
GQHCVSSRPAAPGGEEAEASDPADEEVSHITSSACPWQPTAEPHGPEASPVAGGERDL
RRLYSVDAQGFLDKPGRADEQWRPSAELGSGEPGEAKAWGPEAEPALGARRKKKMSPP
CISVEPPAEDEGSARPSAAEGGSTTLRRRTPSCEATPHRDSLEPTEGSGAGGDPAAKG
ERWGQASCRAEHLTVPSFAFEPLDLGVPSGDPFLDGSHSVTPESRASSSGAIVPLEPP
ESEPPMPVGDPPEKRRGLYLTVPQCPLEKPGSPSATPAPGGGADDPV

FIGURE 20A

```
   1 gcggcggcgg ctgcggcggt ggggccgggc gaggtccgct gcggtcccgg cggctccgtg
  61 gctgctccgc tctgagcgcc tggcgcgccc cgcgccctcc ctgccggggc cgctgggccg
 121 gggatgcacg cggggcccgg gagccatggt ccgcttcggg gacgagctgg gcggccgcta
 181 tggaggcccc ggcggcggag agcgggcccg gggcggcggg gccggcgggg cgggggggccc
 241 gggtcccggg gggctgcagc ccggccagcg ggtcctctac aagcaatcga tcgcgcagcg
 301 cgcgcggacc atggcgctgt acaaccccat cccggtcaag cagaactgct tcaccgtcaa
 361 ccgctcgctc ttcgtcttca gcaggacaa cgtcgtccgc aaatacgcga agcgcatcac
 421 cgagtggcct ccattcgagt atatgatcct ggccaccatc atcgccaact gcatcgtgct
 481 ggccctggag cagcacctcc ctgatgggga caaaacgccc atgtccgagc ggctggacga
 541 cacggagccc tatttcatcg ggatcttttg cttcgaggca gggatcaaaa tcatcgctct
 601 gggctttgtc ttccacaagg gctcttacct gcggaacggc tggaacgtca tggacttcgt
 661 ggtcgtcctc acagggatcc ttgccacggc tggaactgac ttcgacctgc gaacactgag
 721 ggctgtgcgt gtgctgaggc cctgaagct ggtgtctggg attccaagtt gcaggtggt
 781 gctcaagtcc atcatgaagg ccatggttcc actcctgcag attgggctgc ttctcttctt
 841 tgccatcctc atgtttgcca tcattggcct ggagttctac atgggcaagt tccacaaggc
 901 ctgtttcccc aacagcacag atgcggagcc cgtgggtgac ttcccctgtg gcaaggaggc
 961 cccagcccgg ctgtgcgagg gcgacactga gtgccgggag tactggccag gacccaactt
1021 tggcatcacc aactttgaca atatcctgtt tgccatcttg acggtgttcc agtgcatcac
1081 catggagggc tggactgaca tcctctataa tacaaacgat gcggccggca acacctggaa
1141 ctggctctac ttcatccctc tcatcatcat cggctccttc ttcatgctca acctggtgct
1201 gggcgtgctc tcggggagt ttgccaagga gcgagagagg gtggagaacc gccgcgcctt
1261 cctgaagctg cgccggcagc agcagatcga gcgagagctc aacgggtacc tggagtggat
1321 cttcaaggcg gaggaagtca tgctggccga ggaggacagg aatgcagagg agaagtcccc
1381 tttggacgtg ctgaagagag cggccaccaa gaagagcaga aatgacctga tccacgcaga
1441 ggagggagag gaccggtttg cagatctctg tgctgttgga tccccttcg cccgcgccag
1501 cctcaagagc gggaagacag agagctcgtc atacttccgg aggaaggaga agatgttccg
1561 gttttttatc cggcgcatgg tgaaggctca gagcttctac tgggtggtgc tgtgcgtggt
1621 ggccctgaac acactgtgtg tggccatggt gcattacaac cagccgcggc ggcttaccac
1681 gaccctgtat tttgcagagt ttgtttttcct gggtctcttc ctcacagaga tgtccctgaa
1741 gatgtatggc ctggggccca aagctactt ccggtcctcc ttcaactgct tcgactttgg
1801 ggtcatcgtg gggagcgtct ttgaagtggt ctgggcggcc atcaagccgg gaagctcctt
1861 tgggatcagt gtgctgcggg ccctccgcct gctgaggatc ttcaaagtca cgaagtactg
1921 gagctccctg cggaacctgg tggtgtccct gctgaactcc atgaagtcca tcatcagcct
1981 gctcttcttg ctcttcctgt tcattgtggt cttcgccctg ctggggatgc agctgtttgg
2041 gggacagttc aacttccagg atgagactcc cacaaccaac ttcgacacct tccctgccgc
2101 catcctcact gtcttccaga tcctgacggg agaggactgg aatgcagtga tgtatcacgg
2161 gatcgaatcg caaggcggcg tcagcaaagg catgttctcg tccttttact tcattgtcct
2221 gacactgttc ggaaactaca ctctgctgaa tgtctttctg gccatcgctg tggacaacct
2281 ggccaacgcc caagagctga ccaaggatga agaggagatg gaagaagcag ccaatcagaa
2341 gcttgctctg caaaaggcca aagaagtggc tgaagtcagc cccatgtctg ccgcgaacat
2401 ctccatcgcc gccaggcagc agaactcggc caaggcgcgc tcggtgtggg agcagcgggc
2461 cagccagcta cggctgcaga acctgcgggc cagctgcgag gcgctgtaca gcgagatgga
2521 ccccgaggag cggctgcgct tcgccactac gcgccaccct ccggcccgaca tgaagacgca
2581 cctggaccgg ccgctggtgg tggagctggg ccgcgacggc gcgcgggggc cgtgggaggg
2641 caaagcccga cctgaggctg cggaggcccc cgagggcgtc gaccctccgc gcaggcacca
2701 ccggcaccgc gacaaggaca agaccccgc ggcgggggac caggaccgag cagaggcccc
2761 gaaggcggag agcggggagc ccggtgcccg ggaggagcgg ccgcggccgc accgcagcca
2821 cagcaaggag gccgcggggc ccccggaggc gcggagcgag cgcggccgag gcccaggccc
```

FIGURE 20B

```
2881 cgagggcggc cggcggcacc accggcgcgg ctccccggag gaggcggccg agcgggagcc
2941 ccgacgccac cgcgcgcacc ggcaccagga tccgagcaag gagtgcgccg gcgccaaggg
3001 cgagcggcgc gcgcggcacc gcggcggccc ccgagcgggg ccccgggagg cggagagcgg
3061 ggaggagccg gcgcggcggc accgggcccg gcacaaggcg cagcctgctc acgaggctgt
3121 ggagaaggag accacggaga aggaggccac ggagaaggag gctgagatag tggaagccga
3181 caaggaaaag gagctccgga accaccagcc ccgggagcca cactgtgacc tggagaccag
3241 tgggactgtg actgtgggtc ccatgcacac actcccagc acctgtctcc agaaggtgga
3301 ggaacagcca gaggatgcag acaatcagcg gaacgtcact cgcatgggca gtcagccccc
3361 agaccgaac actattgtac atatcccagt gatgctgacg ggccctcttg gggaagccac
3421 ggtcgttccc agtggtaacg tggacctgga aagccaagca gaggggaaga aggaggtgga
3481 agcggatgac gtgatgagga gcggcccccg gcctatcgtc ccatacagct ccatgttctg
3541 tttaagcccc accaacctgc tccgccgctt ctgccactac atcgtgacca tgaggtactt
3601 cgaggtggtc attctcgtgg tcatcgcctt gagcagcatc gccctggctg ctgaggaccc
3661 agtgcgcaca gactcgccca ggaacaacgc tctgaaatac ctggattaca ttttcactgg
3721 tgtctttacc tttgagatgg tgataaagat gatcgacttg ggactgctgc ttcaccctgg
3781 agcctatttc cgggacttgt ggaacattct ggacttcatt gtggtcagtg gcgccctggt
3841 ggcgtttgct ttctcaggat ccaaagggaa agacatcaat accatcaagt ctctgagagt
3901 ccttcgtgtc ctgcggcccc tcaagaccat caaacggctg cccaagctca aggctgtgtt
3961 tgactgtgtg gtgaactccc tgaagaatgt cctcaacatc ttgattgtct acatgctctt
4021 catgttcata tttgccgtca ttgcggtgca gctcttcaaa gggaagtttt tctactgcac
4081 agatgaatcc aaggagctgg agagggactg caggggtcag tatttggatt atgagaagga
4141 ggaagtggaa gctcagccca ggcagtggaa gaaatacgac tttcactacg acaatgtgct
4201 ctgggctctg ctgacgctgt tcacagtgtc cacgggagaa ggctggccca tggtgctgaa
4261 acactccgtg gatgccacct atgaggagca gggtccaagc cctgggtacc gcatggagct
4321 gtccatcttc tacgtggtct actttgtggt ctttccctcc ttcttcgtca acatctttgt
4381 ggctttgatc atcatcacct tccaggagca gggggacaag gtgatgtctg aatgcagcct
4441 ggagaagaac gagagggctt gcattgactt cgccatcagc gccaaacccc tgacacggta
4501 catgccccaa aaccggcagt cgttccagta taagacgtgg acatttgtgg tctccccgcc
4561 ctttgaatac ttcatcatgg ccatgatagc cctcaacact gtggtgctga tgatgaagtt
4621 ctatgatgca ccctatgagt acgagctgat gctgaaatgc ctgaacatcg tgttcacatc
4681 catgttctcc atggaatgcg tgctgaagat catcgccttt ggggtgctga actatttcag
4741 agatgcctgg aatgtctttg actttgtcac tgtgttggga agtattactg atatttttagt
4801 aacagagatt gcggaaacga acaatttcat caacctcagc ttcctccgcc tctttcgagc
4861 tgcgcggctg atcaagctgc tccgccaggg ctacaccatc cgcatcctgc tgtggaccttt
4921 tgtccagtcc ttcaaggccc tgccctacgt gtgtctgctc attgccatgc tgttcttcat
4981 ctacgccatc atcggcatgc aggtgtttgg gaatattgcc ctggatgatg acaccagcat
5041 caaccgccac aacaacttcc ggacgttttt gcaagccctg atgctgctgt tcaggagcgc
5101 cacgggggag gcctggcacg agatcatgct gtcctgcctg agcaaccagg cctgtgatga
5161 gcaggccaat gccaccgagt gtggaagtga ctttgcctac ttctactttg tctccttcat
5221 cttcctgtgc tcctttctga tgttgaacct ctttgtggct gtgatcatgg acaatttga
5281 gtacctcacg cgggactctt ccatcctagg tcctcaccac ttggatgagt tcatccgggt
5341 ctgggctgaa tacgacccgg ctgcgtgtgg gcgcatcagt tacaatgaca tgtttgagat
5401 gctgaaacac atgtccccgc ctctggggct ggggaagaaa tgccctgctc gagttgctta
5461 caagcgcctg gttcgcatga acatgcccat ctccaacgag gacatgactg ttcacttcac
5521 gtccacgctg atggccctca tccggacggc actggagatc aagctggccc cagctgggac
5581 aaagcagcat cagtgtgacg cggagttgag gaaggagatt ccgttgtgt gggccaatct
```

FIG. 20C

```
5641 gccccagaag actttggact tgctggtacc accccataag cctgatgaga tgacagtggg
5701 gaaggtttat gcagctctga tgatatttga cttctacaag cagaacaaaa ccaccagaga
5761 ccagatgcag caggctcctg gaggcctctc ccagatgggt cctgtgtccc tgttccaccc
5821 tctgaaggcc accctggagc agacacagcc ggctgtgctc cgaggagccc gggttttcct
5881 tcgacagaag agttccacct ccctcagcaa tggcggggcc atacaaaacc aagagagtgg
5941 catcaaagag tctgtctcct ggggcactca aaggacccag gatgcacccc atgaggccag
6001 gccacccctg gagcgtggcc actccacaga gatccctgtg gggcggtcag gagcactggc
6061 tgtggacgtt cagatgcaga gcataacccg gaggggccct gatggggagc cccagcctgg
6121 gctggagagc cagggtcgag cggcctccat gccccgcctt gcggccgaga ctcagcccgt
6181 cacagatgcc agccccatga agcgctccat ctccacgctg gcccagcggc ccgtgggac
6241 tcatctttgc agcaccaccc cggaccgccc accccctagc caggcgtcgt cgcaccacca
6301 ccaccaccgc tgccaccgcc gcagggacag gaagcagagg tccctggaga aggggcccag
6361 cctgtctgcc gatatggatg gcgcaccaag cagtgctgtg gggccggggc tgcccccggg
6421 agaggggcct acaggctgcc ggcgggaacg agagcgccgg caggagcggg gccggtccca
6481 ggagcggagg cagccctcat cctcctcctc ggagaagcag cgcttctact cctgcgaccg
6541 ctttggggc cgtgagcccc cgaagcccaa gccctccctc agcagccacc caacgtcgcc
6601 aacagctggc caggagccgg gaccccaccc acagggcagt ggttccgtga atgggagccc
6661 cttgctgtca acatctggtg ctagcacccc cggccgcggt gggcggaggc agctccccca
6721 gacgcccctg actccccgcc ccagcatcac ctacaagacg gccaactcct cacccatcca
6781 cttcgccggg gctcagacca gcctccctgc cttctcccca ggccggctca gccgtgggct
6841 ttccgaacac aacgccctgc tgcagagaga ccccctcagc cagcccctgg ccctggctc
6901 tcgaattggc tctgacccct acctggggca gcgtctggac agtgaggcct ctgtccacgc
6961 cctgcctgag gacacgctca ctttcgagga ggctgtggcc accaactcgg gccgctcctc
7021 caggacttcc tacgtgtcct ccctgacctc ccagtctcac cctctccgcc gcgtgcccaa
7081 cggttaccac tgcaccctgg gactcagctc gggtggccga gcacggcaca gctaccacca
7141 ccctgaccaa gaccactggt gctagctgca ccgtgaccgc tcagacgcct gcatgcagca
7201 ggcgtgtgtt ccagtggatg agttttatca tccacacggg gcagtcggcc ctcgggggag
7261 gccttgccca ccttggtgag gctcctgtgg cccctccctc ccctcctcc cctcttttac
7321 tctagacgac gaataaagcc ctgttgcttg agtgtacgta ccgc
```

FIG. 20D

MVRFGDELGGRYGGPGGGERARGGGAGGAGGPGPGGLQPGQRVL
YKQSIAQRARTMALYNPIPVKQNCFTVNRSLFVFSEDNVVRKYAKRITEWPPFEYMIL
ATIIANCIVLALEQHLPDGDKTPMSERLDDTEPYFIGIFCFEAGIKIIALGFVFHKGS
YLRNGWNVMDFVVVLTGILATAGTDFDLRTLRAVRVLRPLKLVSGIPSLQVVLKSIMK
AMVPLLQIGLLLFFAILMFAIIGLEFYMGKFHKACFPNSTDAEPVGDFPCGKEAPARL
CEGDTECREYWPGPNFGITNFDNILFAILTVFQCITMEGWTDILYNTNDAAGNTWNWL
YFIPLIIIGSFFMLNLVLGVLSGEFAKERERVENRRAFLKLRRQQQIERELNGYLEWI
FKAEEVMLAEEDRNAEEKSPLDVLKRAATKKSRNDLIHAEEGEDRFADLCAVGSPFAR
ASLKSGKTESSSYFRRKEKMFRFFIRRMVKAQSFYWVVLCVVALNTLCVAMVHYNQPR
RLTTTLYFAEFVFLGLFLTEMSLKMYGLGPRSYFRSSFNCFDFGVIVGSVFEVVWAAI
KPGSSFGISVLRALRLLRIFKVTKYWSSLRNLVVSLLNSMKSIISLLFLLFLFIVVFA
LLGMQLFGGQFNFQDETPTTNFDTFPAAILTVFQILTGEDWNAVMYHGIESQGGVSKG
MFSSFYFIVLTLFGNYTLLNVFLAIAVDNLANAQELTKDEEEMEEAANQKLALQKAKE
VAEVSPMSAANISIAARQQNSAKARSVWEQRASQLRLQNLRASCEALYSEMDPEERLR
FATTRHLRPDMKTHLDRPLVVELGRDGARGPVGGKARPEAAEAPEGVDPPRRHHRHRD
KDKTPAAGDQDRAEAPKAESGEPGAREERPRPHRSHSKEAAGPPEARSERGRGPGPEG
GRRHHRRGSPEEAAEREPRRHRAHRHQDPSKECAGAKGERRARHRGGPRAGPREAESG
EEPARRHRARHKAQPAHEAVEKETTEKEATEKEAEIVEADKEKELRNHQPREPHCDLE
TSGTVTVGPMHTLPSTCLQKVEEQPEDADNQRNVTRMGSQPPDPNTIVHIPVMLTGPL
GEATVVPSGNVDLESQAEGKKEVEADDVMRSGPRPIVPYSSMFCLSPTNLLRRFCHYI
VTMRYFEVVILVVIALSSIALAAEDPVRTDSPRNNALKYLDYIFTGVFTFEMVIKMID
LGLLLHPGAYFRDLWNILDFIVVSGALVAFAFSGSKGKDINTIKSLRVLRVLRPLKTI
KRLPKLKAVFDCVVNSLKNVLNILIVYMLFMFIFAVIAVQLFKGKFFYCTDESKELER
DCRGQYLDYEKEEVEAQPRQWKKYDFHYDNVLWALLTLFTVSTGEGWPMVLKHSVDAT
YEEQGPSPGYRMELSIFYVVYFVVFPPFFVNIFVALIIITFQEQGDKVMSECSLEKNE
RACIDFAISAKPLTRYMPQNRQSFQYKTWTFVVSPPFEYFIMAMIALNTVVLMMKFYD
APYEYELMLKCLNIVFTSMFSMECVLKIIAFGVLNYFRDAWNVFDFVTVLGSITDILV
TEIAETNNFINLSFLRLFRAARLIKLLRQGYTIRILLWTFVQSFKALPYVCLLIAMLF
FIYAIIGMQVFGNIALDDDTSINRHNNFRTFLQALMLLFRSATGEAWHEIMLSCLSNQ
ACDEQANATECGSDFAYFYFVSFIFLCSFLMLNLFVAVIMDNFEYLTRDSSILGPHHL
DEFIRVWAEYDPAACGRISYNDMFEMLKHMSPPLGLGKKCPARVAYKRLVRMNMPISN
EDMTVHFTSTLMALIRTALEIKLAPAGTKQHQCDAELRKEISVVWANLPQKTLDLLVP
PHKPDEMTVGKVYAALMIFDFYKQNKTTRDQMQQAPGGLSQMGPVSLFHPLKATLEQT
QPAVLRGARVFLRQKSSTSLSNGGAIQNQESGIKESVSWGTQRTQDAPHEARPPLERG
HSTEIPVGRSGALAVDVQMQSITRRGPDGEPQPGLESQGRAASMPRLAAETQPVTDAS
PMKRSISTLAQRPRGTHLCSTTPDRPPPSQASSHHHHHRCHRRRDRKQRSLEKGPSLS
ADMDGAPSSAVGPGLPPGEGPTGCRRERERRQERGRSQERRQPSSSSSEKQRFYSCDR
FGGREPPKPKPSLSSHPTSPTAGQEPGPHPQGSGSVNGSPLLSTSGASTPGRGGRRQL
PQTPLTPRPSITYKTANSSPIHFAGAQTSLPAFSPGRLSRGLSEHNALLQRDPLSQPL
APGSRIGSDPYLGQRLDSEASVHALPEDTLTFEEAVATNSGRSSRTSYVSSLTSQSHP
LRRVPNGYHCTLGLSSGGRARHSYHHPDQDHWC

FIGURE 21A

```
   1 gcggcggcgg ctgcggcggt ggggccgggc gaggtccgct gcggtcccgg cggctccgtg
  61 gctgctccgc tctgagcgcc tggcgcgccc cgcgccctcc ctgccggggc cgctgggccg
 121 gggatgcacg cggggcccgg gagccatggt ccgcttcggg gacgagctgg gcggccgcta
 181 tggaggcccc ggcggcggag agcgggcccg gggcggcggg gccggcgggg cggggggccc
 241 gggtcccggg gggctgcagc ccggccagcg ggtcctctac aagcaatcga tcgcgcagcg
 301 cgcgcggacc atggcgctgt acaaccccat cccggtcaag cagaactgct tcaccgtcaa
 361 ccgctcgctc ttcgtcttca gcgaggacaa cgtcgtccgc aaatacgcga agcgcatcac
 421 cgagtggcct ccattcgagt atatgatcct ggccaccatc atcgccaact gcatcgtgct
 481 ggccctggag cagcacctcc ctgatgggga caaaacgccc atgtccgagc ggctggacga
 541 cacggagccc tatttcatcg ggatcttttg cttcgaggca gggatcaaaa tcatcgctct
 601 gggctttgtc ttccacaagg gctcttacct gcggaacggc tggaacgtca tggacttcgt
 661 ggtcgtcctc acagggatcc ttgccacggc tggaactgac ttcgacctgc gaacactgag
 721 ggctgtgcgt gtgctgaggc cctgaagct ggtgtctggg attccaagtt tgcaggtggt
 781 gctcaagtcc atcatgaagg ccatggttcc actcctgcag attgggctgc ttctcttctt
 841 tgccatcctc atgtttgcca tcattggcct ggagttctac atgggcaagt tccacaaggc
 901 ctgtttcccc aacagcacag atgcggagcc cgtggtgac ttccctgtg gcaaggaggc
 961 cccagcccgg ctgtgcgagg gcgacactga gtgccgggag tactggccag gacccaactt
1021 tggcatcacc aactttgaca atatcctgtt tgccatcttg acggtgttcc agtgcatcac
1081 catggagggc tggactgaca tcctctataa tacaaacgat gcggccggca cacctggaa
1141 ctggctctac ttcatccctc tcatcatcat cggctccttc ttcatgctca acctggtgct
1201 gggcgtgctc tcgggggagt ttgccaagga gcgagagagg gtggagaacc gccgcgcctt
1261 cctgaagctg cgccggcagc agcagatcga gcgagagctc aacgggtacc tggagtggat
1321 cttcaaggcg gaggaagtca tgctggccga ggaggacagg aatgcagagg agaagtcccc
1381 tttggacgtg ctgaagagag cggccaccaa gaagagcaga atgacctga tccacgcaga
1441 ggagggagag gaccggtttg cagatctctg tgctgttgga tcccccttcg cccgcgccag
1501 cctcaagagc gggaagacag agagctcgtc atacttccgg aggaaggaga agatgttccg
1561 gtttttatc cggcgcatgg tgaaggctca gagcttctac tgggtggtgc tgtgcgtggt
1621 ggccctgaac acactgtgtg tggccatggt gcattacaac cagccgcggc ggcttaccac
1681 gaccctgtat tttgcagagt ttgtttttcct gggtctcttc ctcacagaga tgtccctgaa
1741 gatgtatggc ctggggccca gaagctactt ccggtcctcc ttcaactgct cgactttgg
1801 ggtcatcgtg gggagcgtct ttgaagtggt ctgggcggcc atcaagccgg gaagctcctt
1861 tgggatcagt gtgctgcggg ccctccgcct gctgaggatc ttcaaagtca cgaagtactg
1921 gagctccctg cggaacctgg tggtgtccct gctgaactcc atgaagtcca tcatcagcct
1981 gctcttcttg ctcttcctgt tcattgtggt cttcgccctg ctggggatgc agctgtttgg
2041 gggacagttc aacttccagg atgagactcc cacaaccaac ttcgacacct ccctgccgc
2101 catcctcact gtcttccaga tcctgacggg agaggactgg aatgcagtga tgtatcacgg
2161 gatcgaatcg caaggcggcg tcagcaaagg catgttctcg tccttttact tcattgtcct
2221 gacactgttc ggaaactaca ctctgctgaa tgtctttctg gccatcgctg tggacaacct
2281 ggccaacgcc caagagctga ccaaggatga agaggagatg gaagaagcag ccaatcagaa
2341 gcttgctctg caaaaggcca agaagtggc tgaagtcagc cccatgtctg ccgcgaacat
2401 ctccatcgcc gccaggcagc agaactcggc caaggcgcgc tcggtgtggg agcagcgggc
2461 cagccagcta cggctgcaga acctgcgggc cagctgcgag gcgctgtaca gcgagatgga
2521 ccccgaggag cggctgcgct tgccactac gcgccacctg cggcccgaca tgaagacgca
2581 cctggaccgg ccgctggtgg tggagctggg ccgcgacggc gcgggggc cgtgggagg
2641 caaagcccga cctgaggctg cggaggcccc cgagggcgtc gaccctccgc gcaggcacca
2701 ccggcaccgc gacaaggaca agaccccgc ggcgggggac caggaccgag cagaggcccc
2761 gaaggcggag agcggggagc ccggtgcccg ggaggagcgg ccgcggccgc accgcagcca
```

FIGURE 21B

```
2821 cagcaaggag gccgcggggc ccccggaggc gcggagcgag cgcggccgag gcccaggccc
2881 cgaggcggc cggcggcacc accggcgcgg ctccccggag gaggcggccg agcgggagcc
2941 ccgacgccac cgcgcgcacc ggcaccagga tccgagcaag gagtgcgccg gcgccaaggg
3001 cgagcggcgc gcgcggcacc gcggcggccc ccgagcgggg ccccgggagg cggagagcgg
3061 ggaggagccg gcgcggcggc accgggcccg gcacaaggcg cagcctgctc acgaggctgt
3121 ggagaaggag accacggaga aggaggccac ggagaaggag gctgagatag tggaagccga
3181 caaggaaaag gagctccgga accaccagcc ccgggagcca cactgtgacc tggagaccag
3241 tgggactgtg actgtgggtc ccatgcacac actgcccagc acctgtctcc agaaggtgga
3301 ggaacagcca gaggatgcag acaatcagcg gaacgtcact cgcatgggca gtcagccccc
3361 agacccgaac actattgtac atatcccagt gatgctgacg ggccctcttg gggaagccac
3421 ggtcgttccc agtggtaacg tggacctgga aagccaagca gaggggaaga aggaggtgga
3481 agcggatgac gtgatgagga gcggcccccg gcctatcgtc ccatacagct ccatgttctg
3541 tttaagcccc accaacctgc tccgccgctt ctgccactac atcgtgacca tgaggtactt
3601 cgaggtggtc attctcgtgg tcatcgcctt gagcagcatc gccctggctg ctgaggaccc
3661 agtgcgcaca gactcgccca ggaacaàcgc tctgaaatac ctggattaca ttttcactgg
3721 tgtctttacc tttgagatgg tgataaagat gatcgacttg ggactgctgc ttcaccctgg
3781 agcctatttc cgggacttgt ggaacattct ggacttcatt gtggtcagtg gcgccctggt
3841 ggcgtttgct ttctcaggat ccaaagggaa agacatcaat accatcaagt ctctgagagt
3901 ccttcgtgtc ctgcggcccc tcaagaccat caaacggctg cccaagctca aggctgtgtt
3961 tgactgtgtg gtgaactccc tgaagaatgt cctcaacatc ttgattgtct acatgctctt
4021 catgttcata tttgccgtca ttgcggtgca gctcttcaaa gggaagtttt tctactgcac
4081 agatgaatcc aaggagctgg agagggactg caggggtcag tatttggatt atgagaagga
4141 ggaagtggaa gctcagccca ggcagtggaa gaaatacgac tttcactacg acaatgtgct
4201 ctgggctctg ctgacgctgt tcacagtgtc cacgggagaa ggctggccca tggtgctgaa
4261 acactccgtg gatgccacct atgaggagca gggtccaagc cctgggtacc gcatggagct
4321 gtccatcttc tacgtggtct actttgtggt ctttccttc ttcttcgtca acatctttgt
4381 ggctttgatc atcatcacct tccaggagca gggggacaag gtgatgtctg aatgcagcct
4441 ggagaagaac gagagggctt gcattgactt cgccatcagc gccaaacccc tgacacggta
4501 catgccccaa aaccggcagt cgttccagta taagacgtgg acatttgtgg tctccccgcc
4561 ctttgaatac ttcatcatgg ccatgatagc cctcaacact gtggtgctga tgatgaagtt
4621 ctatgatgca ccctatgagt acgagctgat gctgaaatgc ctgaacatcg tgttcacatc
4681 catgttctcc atggaatgcg tgctgaagat catcgccttt gggtgctga actatttcag
4741 agatgcctgg aatgtctttg actttgtcac tgtgttggga agtattactg atatttagt
4801 aacagagatt gcggaaacga acaatttcat caacctcagc ttcctccgcc tctttcgagc
4861 tgcgcggctg atcaagctgc tccgccaggg ctacaccatc cgcatcctgc tgtggacctt
4921 tgtccagtcc ttcaaggccc tgccctacgt gtgtctgctc attgccatgc tgttcttcat
4981 ctacgccatc atcggcatgc aggtgtttgg gaatattgcc ctggatgatg acaccagcat
5041 caaccgccac aacaacttcc ggacgttttt gcaagccctg atgctgctgt tcaggagcgc
5101 cacgggggag gcctggcacg agatcatgct gtcctgcctg agcaaccagg cctgtgatga
5161 gcaggccaat gccaccgagt gtggaagtga ctttgcctac ttctacttcg tctccttcat
5221 cttcctgtgc tcctttctga tgttgaacct ctttgtggct gtgatcatgg acaatttga
5281 gtacctcacg cgggactctt ccatcctagg tcctcaccac ttggatgagt tcatccgggt
5341 ctgggctgaa tacgacccgg ctgcgtgtgg gcgcatcagt tacaatgaca tgtttgagat
5401 gctgaaacac atgtccccgc ctctgggggct ggggaagaaa tgccctgctc gagttgctta
5461 caagcgcctg gttcgcatga acatgcccat ctccaacgag gacatgactg ttcacttcac
5521 gtccacgctg atggccctca tccggacggc actggagatc aagctggccc cagctgggac
```

FIG. 21C

```
5581 aaagcagcat cagtgtgacg cggagttgag gaaggagatt tccgttgtgt gggccaatct
5641 gccccagaag actttggact tgctggtacc accccataag cctgatgaga tgacagtggg
5701 gaaggtttat gcagctctga tgatatttga cttctacaag cagaacaaaa ccaccagaga
5761 ccagatgcag caggctcctg gaggcctctc ccagatgggt cctgtgtccc tgttccaccc
5821 tctgaaggcc accctggagc agacacagcc ggctgtgctc cgaggagccc gggttttcct
5881 tcgacagaag agttccacct ccctcagcaa tggcggggcc atacaaaacc aagagagtgg
5941 catcaaagag tctgtctcct ggggcactca aaggacccag gatgcacccc atgaggccag
6001 gccacccctg gagcgtggcc actccacaga gatccctgtg gggcggtcag gagcactggc
6061 tgtggacgtt cagatgcaga gcataacccg gaggggccct gatggggagc cccagcctgg
6121 gctggagagc cagggtcgag cggcctccat gccccgcctt gcggccgaga ctcagcccgt
6181 cacagatgcc agccccatga agcgctccat ctccacgctg gcccagcggc cccgtgggac
6241 tcatctttgc agcaccaccc cggaccgccc accccctagc caggcgtcgt cgcaccacca
6301 ccaccaccgc tgccaccgcc gcagggacag gaagcagagg tccctggaga aggggcccag
6361 cctgtctgcc gatatggatg gcgcaccaag cagtgctgtg gggccggggc tgcccccggg
6421 agaggggcct acaggctgcc ggcgggaacg agagcgccgg caggagcggg gccggtccca
6481 ggagcggagg cagccctcat cctcctcctc ggagaagcag cgcttctact cctgcgaccg
6541 ctttgggggc cgtgagcccc cgaagcccaa gccctccctc agcagccacc caacgtcgcc
6601 aacagctggc caggagccgg gacccacccc acaggccggc tcagccgtgg gctttccgaa
6661 cacaacgccc tgctgcagag agacccctc agccagcccc tggcccctgg ctctcgaatt
6721 ggctctgacc cttacctggg gcagcgtctg gacagtgagg cctctgtcca cgccctgcct
6781 gaggacacgc tcactttcga ggaggctgtg gccaccaact cgggccgctc ctccaggact
6841 tcctacgtgt cctccctgac ctcccagtct caccctctcc gccgcgtgcc caacggttac
6901 cactgcaccc tgggactcag ctcgggtggc cgagcacggc acagctacca ccacctgac
6961 caagaccact ggtgctagct gcaccgtgac cgctcagacg cctgcatgca gcaggcgtgt
7021 gttccagtgg atgagtttta tcatccacac ggggcagtcg gccctcgggg gaggccttgc
7081 ccaccttggt gaggctcctg tggcccctcc ctccccctcc tcccctcttt tactctagac
7141 gacgaataaa gccctgttgc ttgagtgtac gtaccgc
```

FIG. 21D

MVRFGDELGGRYGGPGGGERARGGGAGGAGGPGPGGLQPGQRVL
YKQSIAQRARTMALYNPIPVKQNCFTVNRSLFVFSEDNVVRKYAKRITEWPPFEYMIL
ATIIANCIVLALEQHLPDGDKTPMSERLDDTEPYFIGIFCFEAGIKIIALGFVFHKGS
YLRNGWNVMDFVVVLTGILATAGTDFDLRTLRAVRVLRPLKLVSGIPSLQVVLKSIMK
AMVPLLQIGLLLFFAILMFAIIGLEFYMGKFHKACFPNSTDAEPVGDFPCGKEAPARL
CEGDTECREYWPGPNFGITNFDNILFAILTVFQCITMEGWTDILYNTNDAAGNTWNWL
YFIPLIIIGSFFMLNLVLGVLSGEFAKERERVENRRAFLKLRRQQQIERELNGYLEWI
FKAEEVMLAEEDRNAEEKSPLDVLKRAATKKSRNDLIHAEEGEDRFADLCAVGSPFAR
ASLKSGKTESSSYFRRKEKMFRFFIRRMVKAQSFYWVVLCVVALNTLCVAMVHYNQPR
RLTTTLYFAEFVFLGLFLTEMSLKMYGLGPRSYFRSSFNCFDFGVIVGSVFEVVWAAI
KPGSSFGISVLRALRLLRIFKVTKYWSSLRNLVVSLLNSMKSIISLLFLLFLFIVVFA
LLGMQLFGGQFNFQDETPTTNFDTFPAAILTVFQILTGEDWNAVMYHGIESQGGVSKG
MFSSFYFIVLTLFGNYTLLNVFLAIAVDNLANAQELTKDEEEMEEAANQKLALQKAKE
VAEVSPMSAANISIAARQQNSAKARSVWEQRASQLRLQNLRASCEALYSEMDPEERLR
FATTRHLRPDMKTHLDRPLVVELGRDGARGPVGGKARPEAAEAPEGVDPPRRHHRHRD
KDKTPAAGDQDRAEAPKAESGEPGAREERPRPHRSHSKEAAGPPEARSERGRGPGPEG
GRRHHIRRGSPEEAAEREPRRHRAHRHQDPSKECAGAKGERRARHRGGPRAGPREAESG
EEPARRHRARHKAQPAHEAVEKETTEKEAEIVEADKEKELRNHQPREPHCDLE
TSGTVTVGPMHTLPSTCLQKVEEQPEDADNQRNVTRMGSQPPDPNTIVHIPVMLTGPL
GEATVVPSGNVDLESQAEGKKEVEADDVMRSGPRPIVPYSSMFCLSPTNLLRRFCHYI
VTMRYFEVVILVVIALSSIALAAEDPVRTDSPRNNALKYLDYIFTGVFTFEMVIKMID
LGLLLHPGAYFRDLWNILDFIVVSGALVAFAFSGSKGKDINTIKSLRVLRVLRPLKTI
KRLPKLKAVFDCVVNSLKNVLNILIVYMLFMFIFAVIAVQLFKGKFFYCTDESKELER
DCRGQYLDYEKEEVEAQPRQWKKYDFHYDNVLWALLTLFTVSTGEGWPMVLKHSVDAT
YEEQGPSPGYRMELSIFYVVYFVVFPFFFVNIFVALIIITFQEQGDKVMSECSLEKNE
RACIDFAISAKPLTRYMPQNRQSFQYKTWTFVVSPPFEYFIMAMIALNTVVLMMKFYD
APYEYELMLKCLNIVFTSMFSMECVLKIIAFGVLNYFRDAWNVFDFVTVLGSITDILV
TEIAETNNFINLSFLRLFRAARLIKLLRQGYTIRILLWTFVQSFKALPYVCLLIAMLF
FIYAIIGMQVFGNIALDDDTSINRHNNFRTFLQALMLLFRSATGEAWHEIMLSCLSNQ
ACDEQANATECGSDFAYFYFVSFIFLCSFLMLNLFVAVIMDNFEYLTRDSSILGPHHL
DEFIRVWAEYDPAACGRISYNDMFEMLKHMSPPLGLGKKCPARVAYKRLVRMNMPISN
EDMTVHFTSTLMALIRTALEIKLAPAGTKQHQCDAELRKEISVVWANLPQKTLDLLVP
PHKPDEMTVGKVYAALMIFDFYKQNKTTRDQMQQAPGGLSQMGPVSLFHPLKATLEQT
QPAVLRGARVFLRQKSSTSLSNGGAIQNQESGIKESVSWGTQRTQDAPHEARPPLERG
HSTEIPVGRSGALAVDVQMQSITRRGPDGEPQPGLESQGRAASMPRLAAETQPVTDAS
PMKRSISTLAQRPRGTHLCSTTPDRPPPSQASSHHHHHRCHRRRDRKQRSLEKGPSLS
ADMDGAPSSAVGPGLPPGEGPTGCRRERERRQERGRSQERRQPSSSSSEKQRFYSCDR
FGGREPPKPKPSLSSHPTSPTAGQEPGPHPQAGSAVGFPNTTPCCRETPSASPWPLAL
ELALTLTWGSVWTVRPLSTPCLRTRSLSRRLWPPTRAAPPGLPTCPP

FIGURE 22A

```
   1 gatgtcccga gctgctatcc ccggctcggc ccgggcagcc gccttctgag cccccgaccc
  61 gaggcgccga gccgccgccg cccgatgggc tgggccgtgg agcgtctccg cagtcgtagc
 121 tccagccgcc gcgctcccag ccccggcagc ctcagcatca gcggcggcgg cggcggcggc
 181 ggcgtcttcc gcatcgttcg ccgcagcgta acccggagcc ctttgctctt tgcagaatgg
 241 cccgcttcgg agacgagatg ccggcccgct acgggggagg aggctccggg gcagccgccg
 301 gggtggtcgt gggcagcgga ggcgggcgag gagccggggg cagccggcag ggcgggcagc
 361 ccggggcgca aaggatgtac aagcagtcaa tggcgcagag agcgcggacc atggcactct
 421 acaaccccat ccccgtccga cagaactgcc tcacggttaa ccggtctctc ttcctcttca
 481 gcgaagacaa cgtggtgaga aaatacgcca aaaagatcac cgaatggcct cccttctgaat
 541 atatgatttt agccaccatc atagcgaatt gcatcgtcct cgcactggag cagcatctgc
 601 ctgatgatga caagaccccg atgtctgaac ggctggatga cacagaacca tacttcattg
 661 gaatttttg tttcgaggct ggaattaaaa tcattgccct tgggtttgcc ttccacaaag
 721 gctcctactt gaggaatggc tgaatgtca tggactttgt ggtggtgcta acgggcatct
 781 tggcgacagt tgggacggag tttgacctac ggacgctgag ggcagttcga gtgctgcggc
 841 cgctcaagct ggtgtctgga atcccaagtt tacaagtcgt cctgaagtcg atcatgaagg
 901 cgatgatccc tttgctgcag atcggcctcc tcctattttt tgcaatcctt atttttgcaa
 961 tcatagggtt agaattttat atgggaaaat ttcataccac ctgctttgaa gaggggacag
1021 atgacattca gggtgagtct ccggctccat gtgggacaga agagcccgcc cgcacctgcc
1081 ccaatgggac caaatgtcag ccctactggg aagggcccaa caacgggatc actcagttcg
1141 acaacatcct gtttgcagtg ctgactgttt ccagtgcat aaccatggaa gggtggactg
1201 atctcctcta caatagcaac gatgcctcag ggaacacttg gaactggttg tacttcatcc
1261 ccctcatcat catcggctcc ttttttatgc tgaaccttgt gctgggtgtg ctgtcagggg
1321 agtttgccaa agaaagggaa cgggtggaga accggcgggc ttttctgaag ctgaggcggc
1381 aacaacagat tgaacgtgag ctcaatgggt acatggaatg gatctcaaaa gcagaagagg
1441 tgatcctcgc cgaggatgaa actgacgggg agcagaggca tccctttgat ggagctctgc
1501 ggagaaccac cataaagaaa agcaagacag atttgctcaa ccccgaagag gctgaggatc
1561 agctggctga tatagcctct gtgggttctc ccttcgcccg agccagcatt aaaagtgcca
1621 agctggagaa ctcgaccttt tttcacaaaa aggagaggag gatgcgtttc tacatccgcc
1681 gcatggtcaa aactcaggcc ttctactgga ctgtactcag tttggtagct ctcaacacgc
1741 tgtgtgttgc tattgttcac tacaaccagc ccgagtggct ctccgacttc ctttactatg
1801 cagaattcat tttcttagga ctctttatgt ccgaaatgtt tataaaaatg tacgggcttg
1861 ggacgcggcc ttacttccac tcttccttca actgctttga ctgtggggtt atcattggga
1921 gcatcttcga ggtcatctgg gctgtcataa aacctggcac atcctttgga atcagcgtgt
1981 tacgagccct caggttattg cgtattttca agtcacaaa gtactgggca tctctcagaa
2041 acctggtcgt ctctctcctc aactccatga agtccatcat cagcctgttg ttctctcttt
2101 tcctgttcat tgtcgtcttc gcccttttgg gaatgcaact cttcggcggc cagtttaatt
2161 tcgatgaagg gactcctccc accaacttcg atacttttcc agcagcaata atgacggtgt
2221 ttcagatcct gacgggcgaa gactggaacg aggtcatgta cgacgggatc aagtctcagg
2281 ggggcgtgca gggcggcatg gtgttctcca tctatttcat tgtactgacg ctctttggga
2341 actacacccct cctgaatgtg ttcttggcca tcgctgtgga caatctggcc aacgcccagg
2401 agctcaccaa ggtggaggcg gacgagcaag aggaagaaga agcagcgaac cagaaacttg
2461 ccctacagaa agccaaggag gtggcagaag tgagtcctct gtccgcggcc aacatgtcta
2521 tagctgtgaa agagcaacag aagaatcaaa agccagcca gtccgtgtgg gagcagcgga
2581 ccagtgagat gcgaaagcag aacttgctgg ccagccggga ggccctgtat aacgaaatgg
2641 acccggacga gcgctggaag gctgcctaca cgcggcacct gcggccagac atgaagacgc
```

FIGURE 22B

```
2701 acttggaccg gccgctggtg gtggacccgc aggagaaccg caacaacaac accaacaaga
2761 gccgggcggc cgagcccacc gtggaccagc gcctcggcca gcagcgcgcc gaggacttcc
2821 tcaggaaaca ggcccgctac cacgatcggg cccgggaccc cagcggctcg gcgggcctgg
2881 acgcacggag gccctgggcg ggaagccagg aggccgagct gagccgggag ggaccctacg
2941 gccgcgagtc ggaccaccac gcccgggagg gcagcctgga gcaacccggg ttctgggagg
3001 gcgaggccga gcgaggcaag gccggggacc cccaccggag gcacgtgcac cggcaggggg
3061 gcagcaggga gagccgcagc gggtccccgc gcacgggcgc ggacggggag catcgacgtc
3121 atcgcgcgca ccgcaggccc ggggaggagg gtccggagga caaggcggag cggagggcgc
3181 ggcaccgcga gggcagccgg ccggcccggg gcggcgaggg cgagggcgag ggccccgacg
3241 ggggcgagcg caggagaagg caccggcatg gcgctccagc cacgtacgag ggggacgcgc
3301 ggagggagga caaggagcgg aggcatcgga ggaggaaaga gaaccagggc tccggggtcc
3361 ctgtgtcggg ccccaacctg tcaaccaccc ggccaatcca gcaggacctg ggccgccaag
3421 acccacccct ggcagaggat attgacaaca tgaagaacaa caagctggcc accgcggagt
3481 cggccgctcc ccacggcagc cttggccacg ccggcctgcc ccagagccca gccaagatgg
3541 gaaacagcac cgaccccggc cccatgctgg ccatccctgc catggccacc aaccccccaga
3601 acgccgccag ccgccggacg cccaacaacc cggggaaccc atccaatccc ggcccccca
3661 agaccccga gaatagcctt atcgtcacca accccagcgg cacccagacc aattcagcta
3721 agactgccag gaaacccgac cacaccacag tggacatccc cccagcctgc ccaccccccc
3781 tcaaccacac cgtcgtacaa gtgaacaaaa acgccaaccc agacccactg ccaaaaaaag
3841 aggaagagaa gaaggaggag gaggaagacg accgtgggga agacggccct aagccaatgc
3901 ctccctatag ctccatgttc atcctgtcca cgaccaaccc ccttcgccgc ctgtgccatt
3961 acatcctgaa cctgcgctac tttgagatgt gcatcctcat ggtcattgcc atgagcagca
4021 tcgccctggc cgccgaggac cctgtgcagc ccaacgcacc tcggaacaac gtgctgcgat
4081 actttgacta cgtttttaca ggcgtcttca cctttgagat ggtgatcaag atgattgacc
4141 tggggctcgt cctgcatcag ggtgcctact tccgtgacct ctggaatatt ctcgacttca
4201 tagtggtcag tggggccctg gtagcctttg ccttcactgg caatagcaaa ggaaaagaca
4261 tcaacacgat taaatccctc cgagtcctcc gggtgctacg acctcttaaa accatcaagc
4321 ggctgccaaa gctcaaggct gtgtttgact gtgtggtgaa ctcacttaaa aacgtcttca
4381 acatcctcat cgtctacatg ctattcatgt tcatcttcgc cgtggtggct gtgcagctct
4441 tcaaggggaa attcttccac tgcactgacg agtccaaaga gtttgagaaa gattgtcgag
4501 gcaaataccct cctctacgag aagaatgagg tgaaggcgcg agaccgggag tggaagaagt
4561 atgaattcca ttacgacaat gtgctgtggg ctctgctgac cctcttcacc gtgtccacgg
4621 gagaaggctg gccacaggtc tcaagcatt cggtggacgc cacctttgag aaccagggcc
4681 ccagccccgg gtaccgcatg gagatgtcca ttttctacgt cgtctacttt gtggtgttcc
4741 ccttcttctt tgtcaatatc tttgtggcct tgatcatcat cacccttccag gagcaagggg
4801 acaagatgat ggaggaatac agcctggaga aaaatgagag ggcctgcatt gatttcgcca
4861 tcagcgccaa gccgctgacc cgacacatgc cgcagaacaa gcagagcttc cagtaccgca
4921 tgtggcagtt cgtggtgtct ccgccttcg agtacacgat catggccatg atcgccctca
4981 acaccatcgt gcttatgatg aagttctatg gggcttctgt tgcttatgaa aatgccctgc
5041 gggtgttcaa catcgtctc acctccctct tctctctgga atgtgtgctg aaagtcatgg
5101 cttttgggat tctgaattat ttccgcgatg cctggaacat cttcgacttt gtgactgttc
5161 tgggcagcat caccgatatc ctcgtgactg agtttgggaa tccgaataac ttcatcaacc
5221 tgagctttct ccgcctcttc cgagctgccc ggctcatcaa acttctccgt cagggttaca
5281 ccatccgcat tcttctctgg accttgtgc agtccttcaa ggccctgcct tatgtctgtc
5341 tgctgatcgc catgctcttc ttcatctatg ccatcattgg gatgcaggtg tttggtaaca
```

FIG. 22C

```
5401 ttggcatcga cgtggaggac gaggacagtg atgaagatga gttccaaatc actgagcaca
5461 ataacttccg gaccttcttc caggccctca tgcttctctt ccggagtgcc accggggaag
5521 cttggcacaa catcatgctt tcctgcctca gcgggaaacc gtgtgataag aactctggca
5581 tcctgactcg agagtgtggc aatgaatttg cttatttta ctttgtttcc ttcatcttcc
5641 tctgctcgtt tctgatgctg aatctctttg tcgccgtcat catggacaac tttgagtacc
5701 tcacccgaga ctcctccatc ctgggccccc accacctgga tgagtacgtg cgtgtctggg
5761 ccgagtatga ccccgcagct tggggccgca tgccttacct ggacatgtat cagatgctga
5821 gacacatgtc tccgcccctg ggtctgggga agaagtgtcc ggccagagtg gcttacaagc
5881 ggcttctgcg gatggacctg cccgtcgcag atgacaacac cgtccacttc aattccaccc
5941 tcatggctct gatccgcaca gccctggaca tcaagattgc caagggagga gccgacaaac
6001 agcagatgga cgctgagctg cggaaggaga tgatggcgat ttggcccaat ctgtcccaga
6061 agacgctaga cctgctggtc acacctcaca gtccacgga cctcaccgtg gggaagatct
6121 acgcagccat gatgatcatg gagtactacc ggcagagcaa ggccaagaag ctgcaggcca
6181 tgcgcgagga gcaggaccgg acaccccctca tgttccagcg catggagccc ccgtcccaa
6241 cgcaggaagg gggacctggc cagaacgccc tccctccac ccagctggac ccaggaggag
6301 ccctgatggc tcacgaaagc ggcctcaagg agagcccgtc ctgggtgacc cagcgtgccc
6361 aggagatgtt ccagaagacg ggcacatgga gtccggaaca aggccccct accgacatgc
6421 ccaacagcca gcctaactct cagtccgtgg agatgcgaga gatgggcaga gatggctact
6481 ccgacagcga gcactacctc cccatggaag gccagggccg ggctgcctcc atgccccgcc
6541 tccctgcaga gaaccagagg agaaggggcc ggccacgtgg gaataacctc agtaccatct
6601 cagacaccag ccccatgaag cgttcagcct ccgtgctggg cccaaggcc cgacgcctgg
6661 acgattactc gctggagcgg gtcccgcccg aggagaacca gcggcaccac cagcggcgcc
6721 gcgaccgcag ccaccgcgcc tctgagcgct ccctgggccg ctacaccgat gtggacacag
6781 gcttggggac agacctgagc atgaccaccc aatccgggga cctgccgtcg aaggagcggg
6841 accaggagcg gggccggccc aaggatcgga agcatcgaca gcaccaccac caccaccacc
6901 accaccacca tccccgccc cccgacaagg accgctatgc ccaggaacgg ccggaccacg
6961 gccgggcacg ggctcgggac cagcgctggt cccgctcgcc cagcgagggc cgagagcaca
7021 tggcgcaccg gcagggcagt agttccgtaa gtggaagccc agccccctca acatctggta
7081 ccagcactcc gcggcggggc cgccgccagc tccccagac ccctccacc cccggccac
7141 acgtgtccta ttcccctgtg atccgtaagg ccggcggctc ggggcccccg cagcagcagc
7201 agcagcagca gcagcagcag caggcggtgg ccaggccggg ccgggcggcc accagcggcc
7261 ctcggaggta cccaggcccc acggccgagc ctctggccgg agatcggccg cccacggggg
7321 gccacagcag cggccgctcg cccaggatgg agaggcgggt cccaggcccg gcccggagcg
7381 agtcccccag ggcctgtcga cacggcgggg cccggtggcc ggcatctggc ccgcacgtgt
7441 ccgaggggcc cccgggtccc cggcaccatg gctactaccg gggctccgac tacgacgagg
7501 ccgatggccc gggcagcggg gcggcgagg aggccatggc cgggcctac gacgcgccac
7561 cccccgtacg acacgcgtcc tcgggcgcca ccggcgctc gcccaggact ccccgggcct
7621 cgggcccggc ctgcgcctcg ccttctcggc acggccggcg actccccaac ggctactacc
7681 cggcgcacgg actggccagg cccgcggc cgggctccag gaagggcctg cacgaaccct
7741 acagcgagag tgacgatgat tggtgctaag cccgggcgag gtggcgcccg cccggccccc
7801 cacgcacc
```

FIGURE 22D

MARFGDEMPARYGGGGSGAAAGVVVGSGGGRGAGGSRQGGQPGA
QRMYKQSMAQRARTMALYNPIPVRQNCLTVNRSLFLFSEDNVVRKYAKKITEWPPFEY
MILATIIANCIVLALEQHLPDDDKTPMSERLDDTEPYFIGIFCFEAGIKIIALGFAFH
KGSYLRNGWNVMDFVVVLTGILATVGTEFDLRTLRAVRVLRPLKLVSGIPSLQVVLKS
IMKAMIPLLQIGLLLFFAILIFAIIGLEFYMGKFHTTCFEEGTDDIQGESPAPCGTEE
PARTCPNGTKCQPYWEGPNNGITQFDNILFAVLTVFQCITMEGWTDLLYNSNDASGNT
WNWLYFIPLIIIGSFFMLNLVLGVLSGEFAKERERVENRRAFLKLRRQQQIERELNGY
MEWISKAEEVILAEDETDGEQRHPFDGALRRTTIKKSKTDLLNPEEAEDQLADIASVG
SPFARASIKSAKLENSTFFHKKERRMRFYIRRMVKTQAFYWTVLSLVALNTLCVAIVH
YNQPEWLSDFLYYAEFIFLGLFMSEMFIKMYGLGTRPYFHSSFNCFDCGVIIGSIFEV
IWAVIKPGTSFGISVLRALRLLRIFKVTKYWASLRNLVVSLLNSMKSIISLLFLLFLF
IVVFALLGMQLFGGQFNFDEGTPPTNFDTFPAAIMTVFQILTGEDWNEVMYDGIKSQG
GVQGGMVFSIYFIVLTLFGNYTLLNVFLAIAVDNLANAQELTKVEADEQEEEEAANQK
LALQKAKEVAEVSPLSAANMSIAVKEQQKNQKPAKSVWEQRTSEMRKQNLLASREALY
NEMDPDERWKAAYTRHLRPDMKTHLDRPLVVDPQENRNNNTNKSRAAEPTVDQRLGQQ
RAEDFLRKQARYHDRARDPSGSAGLDARRPWAGSQEAELSREGPYGRESDHHAREGSL
EQPGFWEGEAERGKAGDPHRRHVHRQGGSRESRSGSPRTGADGEHRRHRAHRRPGEEG
PEDKAERRARHREGSRPARGGEGEGEGPDGGERRRRHRHGAPATYEGDARREDKERRH
RRRKENQGSGVPVSGPNLSTTRPIQQDLGRQDPPLAEDIDNMKNNKLATAESAAPHGS
LGHAGLPQSPAKMGNSTDPGPMLAIPAMATNPQNAASRRTPNNPGNPSNPGPPKTPEN
SLIVTNPSGTQTNSAKTARKPDHTTVDIPPACPPPLNHTVVQVNKNANPDPLPKKEEE
KKEEEEDDRGEDGPKPMPPYSSMFILSTTNPLRRLCHYILNLRYFEMCILMVIAMSSI
ALAAEDPVQPNAPRNNVLRYFDYVFTGVFTFEMVIKMIDLGLVLHQGAYFRDLWNILD
FIVVSGALVAFAFTGNSKGKDINTIKSLRVLRVLRPLKTIKRLPKLKAVFDCVVNSLK
NVFNILIVYMLFMFIFAVVAVQLFKGKFFHCTDESKEFEKDCRGKYLLYEKNEVKARD
REWKKYEFHYDNVLWALLTLFTVSTGEGWPQVLKHSVDATFENQGPSPGYRMEMSIFY
VVVYFVVFPFFFVNIFVALIIITFQEQGDKMMEEYSLEKNERACIDFAISAKPLTRHMP
QNKQSFQYRMWQFVVSPPFEYTIMAMIALNTIVLMMKFYGASVAYENALRVFNIVFTS
LFSLECVLKVMAFGILNYFRDAWNIFDFVTVLGSITDILVTEFGNPNNFINLSFLRLF
RAARLIKLLRQGYTIRILLWTFVQSFKALPYVCLLIAMLFFIYAIIGMQVFGNIGIDV
EDEDSDEDEFQITEHNNFRTFFQALMLLFRSATGEAWHNIMLSCLSGKPCDKNSGILT
RECGNEFAYFYFVSFIFLCSFLMLNLFVAVIMDNFEYLTRDSSILGPHHLDEYVRVWA
EYDPAAWGRMPYLDMYQMLRHMSPPLGLGKKCPARVAYKRLLRMDLPVADDNTVHFNS
TLMALIRTALDIKIAKGGADKQQMDAELRKEMMAIWPNLSQKTLDLLVTPHKSTDLTV
GKIYAAMMIIMEYYRQSKAKKLQAMREEQDRTPLMFQRMEPPSPTQEGGPGQNALPSTQ
LDPGGALMAHESGLKESPSWVTQRAQEMFQKTGTWSPEQGPPTDMPNSQPNSQSVEMR
EMGRDGYSDSEHYLPMEGQGRAASMPRLPAENQRRRGRPRGNNLSTISDTSPMKRSAS
VLGPKARRLDDYSLERVPPEENQRHHQRRRDRSHRASERSLGRYTDVDTGLGTDLSMT
TQSGDLPSKERDQERGRPKDRKHRQHHHHHHHHHHPPPPDKDRYAQERPDHGRARARD
QRWSRSPSEGREHMAHRQGSSSVSGSPAPSTSGTSTPRRGRRQLPQTPSTPRPHVSYS
PVIRKAGGSGPPQQQQQQQQQQAVARPGRAATSGPRRYPGPTAEPLAGDRPPTGGHS
SGRSPRMERRVPGPARSESPRACRHGGARWPASGPHVSEGPPGPRHHGYYRGSDYDEA
DGPGSGGGEEAMAGAYDAPPPVRHASSGATGRSPRTPRASGPACASPSRHGRRLPNGY
YPAHGLARPRGPGSRKGLHEPYSESDDDWC

FIGURE 23A

```
   1 gatgtcccga gctgctatcc ccggctcggc ccgggcagcc gccttctgag cccccgaccc
  61 gaggcgccga gccgccgccg cccgatgggc tgggccgtgg agcgtctccg cagtcgtagc
 121 tccagccgcc gcgctcccag ccccggcagc ctcagcatca gcggcggcgg cggcggcggc
 181 ggcgtcttcc gcatcgttcg ccgcagcgta acccggagcc ctttgctctt tgcagaatgg
 241 cccgcttcgg agacgagatg ccggcccgct acgggggagg aggctccggg gcagccgccg
 301 gggtggtcgt gggcagcgga ggcgggcgag gagccggggg cagccggcag ggcgggcagc
 361 ccggggcgca aaggatgtac aagcagtcaa tggcgcagag agcgcggacc atggcactct
 421 acaaccccat ccccgtccga cagaactgcc tcacggttaa ccggtctctc ttcctcttca
 481 gcgaagacaa cgtggtgaga aaatacgcca aaaagatcac cgaatggcct cccttgaat
 541 atatgatttt agccaccatc atagcgaatt gcatcgtcct cgcactggag cagcatctgc
 601 ctgatgatga caagacccg atgtctgaac ggctggatga cacagaacca tacttcattg
 661 gaatttttg tttcgaggct ggaattaaaa tcattgccct tgggtttgcc ttccacaaag
 721 gctcctactt gaggaatggc tggaatgtca tggactttgt ggtggtgcta acgggcatct
 781 tggcgacagt tgggacggag tttgacctac ggacgctgag ggcagttcga gtgctgcggc
 841 cgctcaagct ggtgtctgga atcccaagtt tacaagtcgt cctgaagtcg atcatgaagg
 901 cgatgatccc tttgctgcag atcggcctcc tctatttt tgcaatcctt attttgcaa
 961 tcataggggt agaattttat atgggaaaat ttcataccac ctgctttgaa gaggggacag
1021 atgacattca gggtgagtct ccggctccat gtgggacaga agagcccgcc cgcacctgcc
1081 ccaatgggac caaatgtcag ccctactggg aagggcccaa caacgggatc actcagttcg
1141 acaacatcct gtttgcagtg ctgactgttt tccagtgcat aaccatggaa gggtggactg
1201 atctcctcta caatagcaac gatgcctcag ggaacacttg gaactggttg tacttcatcc
1261 ccctcatcat catcggctcc ttttttatgc tgaaccttgt gctgggtgtg ctgtcagggg
1321 agtttgccaa agaaagggaa cgggtggaga accggcgggc tttctgaag ctgaggcggc
1381 aacaacagat tgaacgtgag ctcaatgggt acatggaatg gatctcaaaa gcagaagagg
1441 tgatcctcgc cgaggatgaa actgacgggg agcagaggca tcctttgat ggagctctgc
1501 ggagaaccac cataaagaaa agcaagacag atttgctcaa ccccgaagag gctgaggatc
1561 agctggctga tatagcctct gtgggttctc ccttcgcccg agccagcatt aaaagtgcca
1621 agctggagaa ctcgaccttt tttcacaaaa aggagaggag gatgcgtttc tacatccgcc
1681 gcatggtcaa aactcaggcc ttctactgga ctgtactcag tttggtagct ctcaacacgc
1741 tgtgtgttgc tattgttcac tacaaccagc ccagtggct ctccgacttc ctttactatg
1801 cagaattcat tttcttagga ctctttatgt ccgaaatgtt tataaaaatg tacgggcttg
1861 ggacgcggcc ttacttccac tcttccttca actgctttga ctgtggggtt atcattggga
1921 gcatcttcga ggtcatctgg gctgtcataa aacctggcac atcctttgga atcagcgtgt
1981 tacgagccct caggttattg cgtatttca aagtcacaaa gtactgggca tctctcagaa
2041 acctggtcgt ctctctcctc aactccatga agtccatcat cagcctgttg ttctctcttt
2101 tcctgttcat tgtcgtcttc gccctttgg gaatgcaact cttcggcggc cagtttaatt
2161 tcgatgaagg gactcctccc accaacttcg atacttttcc agcagcaata atgacggtgt
2221 ttcagatcct gacgggcgaa gactggaacg aggtcatgta cgacgggatc aagtctcagg
2281 ggggcgtgca gggcggcatg gtgttctcca tctatttcat tgtactgacg ctctttggga
2341 actacacct cctgaatgtg ttcttggcca tcgctgtgga caatctggcc aacgcccagg
2401 agctcaccaa ggtggaggcg gacgagcaag aggaagaaga agcagcgaac cagaaacttg
2461 ccctacagaa agccaaggag gtggcagaag tgagtcctct gtccgcggcc aacatgtcta
2521 tagctgtgaa agagcaacag aagaatcaaa agccagccaa gtccgtgtgg gagcagcgga
2581 ccagtgagat gcgaaagcag aacttgctgg ccagccggga ggccctgtat aacgaaatgg
2641 acccggacga gcgctggaag gctgcctaca cgcggcacct gcggccagac atgaagacgc
2701 acttggaccg gccgctggtg gtggacccgc aggagaaccg caacaacaac accaacaaga
```

FIGURE 23B

```
2761 gccgggcggc cgagcccacc gtggaccagc gcctcggcca gcagcgcgcc gaggacttcc
2821 tcaggaaaca ggcccgctac cacgatcggg cccgggaccc cagcggctcg gcgggcctgg
2881 acgcacggag gccctgggcg ggaagccagg aggccgagct gagccgggag ggaccctacg
2941 gccgcgagtc ggaccaccac gcccgggagg gcagcctgga gcaacccggg ttctgggagg
3001 gcgaggccga gcgaggcaag gccggggacc cccaccggag gcacgtgcac cggcagggggg
3061 gcagcaggga gagccgcagc gggtccccgc gcacgggcgc ggacggggag catcgacgtc
3121 atcgcgcgca ccgcaggccc ggggaggagg gtccggagga caaggcggag cggagggcgc
3181 ggcaccgcga gggcagccgg ccggcccggg gcggcgaggg cgagggcgag ggccccgacg
3241 ggggcgagcg caggagaagg caccggcatg gcgctccagc cacgtacgag ggggacgcgc
3301 ggagggagga caaggagcgg aggcatcgga ggaggaaaga gaaccagggc tccggggtcc
3361 ctgtgtcggg ccccaacctg tcaaccaccc ggccaatcca gcaggacctg ggccgccaag
3421 acccacccct ggcagaggat attgacaaca tgaagaacaa caagctggcc accgcggagt
3481 cggccgctcc ccacggcagc cttggccacg ccggcctgcc ccagagccca gccaagatgg
3541 gaaacagcac cgaccccggc cccatgctgg ccatccctgc catggccacc aaccccccaga
3601 acgccgccag ccgccggacg cccaacaacc cggggaaccc atccaatccc ggccccccca
3661 agaccccga gaatagcctt atcgtcacca accccagcgg cacccagacc aattcagcta
3721 agactgccag gaaacccgac cacaccacag tggacatccc ccagcctgc ccaccccccc
3781 tcaaccacac cgtcgtacaa gtgaacaaaa acgccaaccc agcccactg ccaaaaaaag
3841 aggaagagaa gaaggaggag gaggaagacg accgtgggga agacggccct aagccaatgc
3901 ctccctatag ctccatgttc atcctgtcca cgaccaaccc ccttcgccgc ctgtgccatt
3961 acatcctgaa cctgcgctac tttgagatgt gcatcctcat ggtcattgcc atgagcagca
4021 tcgccctggc cgccgaggac cctgtgcagc ccaacgcacc tcggaacaac gtgctgcgat
4081 acttttgacta cgttttaca ggcgtcttca cctttgagat ggtgatcaag atgattgacc
4141 tggggctcgt cctgcatcag ggtgcctact tccgtgacct ctggaatatt ctcgacttca
4201 tagtggtcag tgggggccctg gtagcctttg ccttcactgg caatagcaaa ggaaaagaca
4261 tcaacacgat taaatccctc cgagtcctcc gggtgctacg acctcttaaa accatcaagc
4321 ggctgccaaa gctcaaggct gtgtttgact gtgtggtgaa ctcacttaaa aacgtcttca
4381 acatcctcat cgtctacatg ctattcatgt tcatcttcgc cgtggtggct gtgcagctct
4441 tcaagggggaa attcttccac tgcactgacg agtccaaaga gtttgagaaa gattgtcgag
4501 gcaaatacct cctctacgag aagaatgagg tgaaggcgcg agaccgggag tggaagaagt
4561 atgaattcca ttacgacaat gtgctgtggg ctctgctgac cctcttcacc gtgtccacgg
4621 gagaaggctg gccacaggtc ctcaagcatt cggtggacgc cacctttgag aaccagggcc
4681 ccagccccgg gtaccgcatg gagatgtcca ttttctacgt cgtctacttt gtggtgttcc
4741 ccttcttctt tgtcaatatc tttgtggcct tgatcatcat caccttccag gagcaagggg
4801 acaagatgat ggaggaatac agcctggaga aaaatgagag ggcctgcatt gatttcgcca
4861 tcagcgccaa gccgctgacc cgacacatgc gcagaacaa gcagagcttc cagtaccgca
4921 tgtggcagtt cgtggtgtct ccgcctttcg agtacacgat catggccatg atcgccctca
4981 acaccatcgt gctaatgatg aagttctatg gggcttctgt tgcttatgaa aatgccctgc
5041 gggtgttcaa catcgtcttc acctccctct tctctctgga atgtgtgctg aaagtcatgg
5101 cttttgggat tctgaattat ttccgcgatg cctggaacat cttcgacttt gtgactgttc
5161 tgggcagcat caccgatatc ctcgtgactg agtttgggaa tccgaataac ttcatcaacc
5221 tgagctttct ccgcctcttc cgagctgccc ggctcatcaa acttctccgt cagggttaca
5281 ccatccgcat tcttctctgg accttttgtg cagtccttcaa ggccctgcct tatgtctgtc
5341 tgctgatcgc catgctcttc ttcatctatg ccatcattgg gatgcaggtg tttggtaaca
```

FIG. 23C

```
5401 ttggcatcga cgtggaggac gaggacagtg atgaagatga gttccaaatc actgagcaca
5461 ataacttccg gaccttcttc caggccctca tgcttctctt ccggagtgcc accggggaag
5521 cttggcacaa catcatgctt tcctgcctca gcgggaaacc gtgtgataag aactctggca
5581 tcctgactcg agagtgtggc aatgaatttg cttattttta ctttgtttcc ttcatcttcc
5641 tctgctcgtt tctgatgctg aatctctttg tcgccgtcat catggacaac tttgagtacc
5701 tcacccgaga ctcctccatc ctgggccccc accacctgga tgagtacgtg cgtgtctggg
5761 ccgagtatga ccccgcagct tggggccgca tgccttacct ggacatgtat cagatgctga
5821 gacacatgtc tccgcccctg ggtctgggga agaagtgtcc ggccagagtg gcttacaagc
5881 ggcttctgcg gatggacctg cccgtcgcag atgacaacac cgtccacttc aattccaccc
5941 tcatggctct gatccgcaca gccctggaca tcaagattgc caagggagga gccgacaaac
6001 agcagatgga cgctgagctg cggaaggaga tgatggcgat ttggcccaat ctgtcccaga
6061 agacgctaga cctgctggtc acacctcaca agtccacgga cctcaccgtg gggaagatct
6121 acgcagccat gatgatcatg gagtactacc ggcagagcaa ggccaagaag ctgcaggcca
6181 tgcgcgagga gcaggaccgg acacccctca tgttccagcg catggagccc ccgtccccaa
6241 cgcaggaagg gggacctggc cagaacgccc tcccctccac ccagctggac ccaggaggag
6301 ccctgatggc tcacgaaagc ggcctcaagg agagcccgtc ctgggtgacc cagcgtgccc
6361 aggagatgtt ccagaagacg ggcacatgga gtccggaaca aggccccct accgacatgc
6421 ccaacagcca gcctaacact cagtccgtgg agatgcgaga gatgggcaga gatggctact
6481 ccgacagcga gcactacctc cccatggaag gccagggccg ggctgcctcc atgccccgcc
6541 tccctgcaga gaaccagagg agaagggggcc ggccacgtgg gaataacctc agtaccatct
6601 cagacaccag ccccatgaag cgttcagcct ccgtgctggg ccccaaggcc cgacgcctgg
6661 acgattactc gctggagcgg gtcccgcccg aggagaacca gcggcaccac cagcggcgcc
6721 gcgaccgcag ccaccgcgcc tctgagcgct ccctgggccg ctacaccgat gtggacacag
6781 gcttggggac agacctgagc atgaccaccc aatccgggga cctgccgtcg aaggagcggg
6841 accaggagcg gggccggccc aaggatcgga agcatcgaca gcaccaccac caccaccacc
6901 accaccacca tccccccgccc cccgacaagg accgctatgc ccaggaacgg ccggaccacg
6961 gccgggcacg ggctcgggac cagcgctggt cccgctcgcc cagcgagggc cgagagcaca
7021 tggcgcaccg gcagtagttc cgtaagtgga agcccagccc cctcaacatc tggtaccagc
7081 actccgcggc ggggccgccg ccagctcccc cagaccccct ccacccccg gccacacgtg
7141 tcctattccc ctgtgatccg taaggccggc ggctcggggc cccgcagca gcagcagcag
7201 cagcaggcgg tggccaggcc gggccgggcg gccaccagcg gccctcggag gtacccaggc
7261 cccacggccg agcctctggc cggagatcgg ccgcccacgg ggggccacag cagcggccgc
7321 tgcccagga tggagaggcg ggtccaggc ccggccgga gcgagtcccc cagggcctgt
7381 cgacacggcg gggcccggtg gccggcatct ggcccgcacg tgtccgaggg gcccccgggt
7441 cccggcacc atggctacta ccggggctcc gactacgacg aggccgatgg cccgggcagc
7501 gggggcggcg aggaggccat ggccggggcc tacgacgcgc caccccccgt acgacacgcg
7561 tcctcgggcg ccaccgggcg ctcgcccagg actccccggg cctcgggccc ggcctgcgcc
7621 tcgccttctc ggcacggccg gcgactcccc aacggctact accggcgca cggactggcc
7681 aggccccgcg ggccgggctc caggaagggc ctgcacgaac cctacagcga gagtgacgat
7741 gattggtgct aagcccgggc gaggtggcgc ccgcccggcc cccacgcac c
```

FIG. 23D

MARFGDEMPARYGGGGSGAAAGVVVGSGGGRGAGGSRQGGQPGA
QRMYKQSMAQRARTMALYNPIPVRQNCLTVNRSLFLFSEDNVVRKYAKKITEWPPFEY
MILATIIANCIVLALEQHLPDDDKTPMSERLDDTEPYFIGIFCFEAGIKIIALGFAFH
KGSYLRNGWNVMDFVVVLTGILATVGTEFDLRTLRAVRVLRPLKLVSGIPSLQVVLKS
IMKAMIPLLQIGLLLFFAILIFAIIGLEFYMGKFHTTCFEEGTDDIQGESPAPCGTEE
PARTCPNGTKCQPYWEGPNNGITQFDNILFAVLTVFQCITMEGWTDLLYNSNDASGNT
WNWLYFIPLIIIGSFFMLNLVLGVLSGEFAKERERVENRRAFLKLRRQQQIERELNGY
MEWISKAEEVILAEDETDGEQRHPFDGALRRTTIKKSKTDLLNPEEAEDQLADIASVG
SPFARASIKSAKLENSTFFHKKERRMRFYIRRMVKTQAFYWTVLSLVALNTLCVAIVH
YNQPEWLSDFLYYAEFIFLGLFMSEMFIKMYGLGTRPYFHSSFNCFDCGVIIGSIFEV
IWAVIKPGTSFGISVLRALRLLRIFKVTKYWASLRNLVVSLLNSMKSIISLLFLLFLF
IVVFALLGMQLFGGQFNFDEGTPPTNFDTFPAAIMTVFQILTGEDWNEVMYDGIKSQG
GVQGGMVFSIYFIVLTLFGNYTLLNVFLAIAVDNLANAQELTKVEADEQEEEEAANQK
LALQKAKEVAEVSPLSAANMSIAVKEQQKNQKPAKSVWEQRTSEMRKQNLLASREALY
NEMDPDERWKAAYTRHLRPDMKTHLDRPLVVDPQENRNNNTNKSRAAEPTVDQRLGQQ
RAEDFLRKQARYHDRARDPSGSAGLDARRPWAGSQEAELSREGPYGRESDHHAREGSL
EQPGFWEGEAERGKAGDPHRRHVHRQGGSRESRSGSPRTGADGEHRRHRAHRRPGEEG
PEDKAERRARHREGSRPARGGEGEGEGPDGGERRRRHRHGAPATYEGDARREDKERRH
RRRKENQGSGVPVSGPNLSTTRPIQQDLGRQDPPLAEDIDNMKNNKLATAESAAPHGS
LGHAGLPQSPAKMGNSTDPGPMLAIPAMATNPQNAASRRTPNNPGNPSNPGPPKTPEN
SLIVTNPSGTQTNSAKTARKPDHTTVDIPPACPPPLNHTVVQVNKNANPDPLPKKEEE
KKEEEEDDRGEDGPKPMPPYSSMFILSTTNPLRRLCHYILNLRYFEMCILMVIAMSSI
ALAAEDPVQPNAPRNNVLRYFDYVFTGVFTFEMVIKMIDLGLVLHQGAYFRDLWNILD
FIVVSGALVAFAFTGNSKGKDINTIKSLRVLRVLRPLKTIKRLPKLKAVFDCVVNSLK
NVFNILIVYMLFMFIFAVVAVQLFKGKFFHCTDESKEFEKDCRGKYLLYEKNEVKARD
REWKKYEFHYDNVLWALLTLFTVSTGEGWPQVLKHSVDATFENQGPSPGYRMEMSIFY
VVYFVVFPFFFVNIFVALIIITFQEQGDKMMEEYSLEKNERACIDFAISAKPLTRHMP
QNKQSFQYRMWQFVVSPPFEYTIMAMIALNTIVLMMKFYGASVAYENALRVFNIVFTS
LFSLECVLKVMAFGILNYFRDAWNIFDFVTVLGSITDILVTEFGNPNNFINLSFLRLF
RAARLIKLLRQGYTIRILLWTFVQSFKALPYVCLLIAMLFFIYAIIGMQVFGNIGIDV
EDEDSDEDEFQITEHNNFRTFFQALMLLFRSATGEAWHNIMLSCLSGKPCDKNSGILT
RECGNEFAYFYFVSFIFLCSFLMLNLFVAVIMDNFEYLTRDSSILGPHHLDEYVRVWA
EYDPAAWGRMPYLDMYQMLRHMSPPLGLGKKCPARVAYKRLLRMDLPVADDNTVHFNS
TLMALIRTALDIKIAKGGADKQQMDAELRKEMMAIWPNLSQKTLDLLVTPHKSTDLTV
GKIYAAMMIMEYYRQSKAKKLQAMREEQDRTPLMFQRMEPPSPTQEGGPGQNALPSTQ
LDPGGALMAHESGLKESPSWVTQRAQEMFQKTGTWSPEQGPPTDMPNSQPNSQSVEMR
EMGRDGYSDSEHYLPMEGQGRAASMPRLPAENQRRRGRPRGNNLSTISDTSPMKRSAS
VLGPKARRLDDYSLERVPPEENQRHHQRRRDRSHRASERSLGRYTDVDTGLGTDLSMT
TQSGDLPSKERDQERGRPKDRKHRQHHHHHHHHHHHHPPPPDKDRYAQERPDHGRARARD
QRWSRSPSEGREHMAHRQ

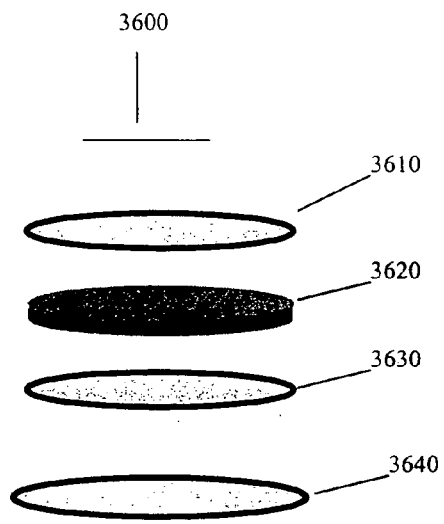
Figure 36A
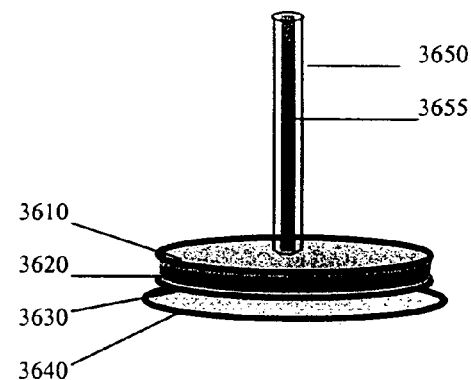
Figure 36B
Figure 36
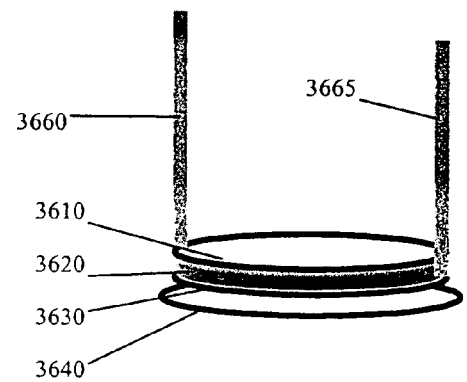
Figure 36C

ELECTRICAL FIELD STIMULATION OF EUKARYOTIC CELLS

CROSS-REFERENCE TO RELATED APPLICATIONS

The subject application is related to co-pending provisional application No. 60/304,955, filed Jul. 12, 2001, to which priority is claimed under 35 USC § 119(e).

STATEMENT REGARDING FEDERALLY-SPONSORED R&D

Not applicable.

REFERENCE TO MICROFICHE APPENDIX

Not applicable.

FIELD OF THE INVENTION

The present invention is directed to methods and associated apparatuses for stimulating eukaryotic cells by the application of electric fields. The electric fields are produced by certain arrangements of electrodes that create an electric potential difference in the environment of the cells, resulting in a change in membrane potential of the cells. The change in membrane potential affects various physiological processes within the cells, including the opening and closing of voltage-gated ion channels. The ability to alter the open/close transitions of voltage-gated ion channels by the application of electric fields as described herein provides for novel methods of screening compounds for the ability to modulate the activity of voltage-gated ion channels.

BACKGROUND OF THE INVENTION

Certain molecular events in eukaryotic cells depend on the existence or magnitude of an electric potential gradient across the plasma (i.e., outer) membrane of the cells. Among the more important of such events is the movement of ions across the plasma membrane through voltage-gated ion channels. Voltage-gated ion channels form transmembrane pores that open in response to changes in cell membrane potential and allow ions to pass through the membrane. Voltage-gated ion channels have many physiological roles. They have been shown to be involved in maintaining cell membrane potentials and controlling the repolarization of action potentials in many types of cells (Bennett et al., 1993, Cardiovascular Drugs & Therapy 7:195-202; Johnson et al., 1999, J. Gen. Physiol. 113:565-580; Bennett & Shin, "Biophysics of voltage-gated sodium channels," in *Cardiac Electrophysiology: From Cell to Bedside*, 3$^{rd}$ edition, D. Zipes & J. Jalife, eds., 2000, W. B. Saunders Co., pp. 67-86; Bennett & Johnson, "Molecular physiology of cardiac ion channels," Chapter 2 in *Basic Cardiac Electrophysiology and Pharmacology*, 1$^{st}$ edition, A. Zasa & M. Rosen, eds., 2000, Harwood Academic Press, pp. 29-57). Moreover, mutations in sodium, calcium, or potassium voltage-gated ion channel genes leading to defective channel proteins have been implicated in a variety of disorders including the congenital long QT syndromes, ataxia, migraine, muscle paralysis, deafness, seizures, and cardiac conduction diseases, to name a few (Bennett et al., 1995, Nature 376:683-685; Roden et al., 1995, J. Cardiovasc. Electrophysiol. 6:1023-1031; Kors et al., 1999, Curr. Opin. Neurol. 12:249-254; Lehmann et al., 1999, Physiol. Rev. 79:1317-1372; Holbauer & Heufelder, 1997, Eur. J. Endocrinol. 136:588-589; Naccarelli & Antzelevitch, 2000, Am. J. Med. 110:573-581).

Several types of voltage-gated ion channels exist. Voltage-gated potassium channels establish the resting membrane potential and modulate the frequency and duration of action potentials in neurons, muscle cells, and secretory cells. Following depolarization of the membrane potential, voltage-gated potassium channels open, allowing potassium efflux and thus membrane repolarization. This behavior has made voltage-gated potassium channels important targets for drug discovery in connection with a variety of diseases. Dysfunctional voltage-gated potassium channels have been implicated in a number of diseases and disorders. Wang et al., 1998, Science 282: 1890-1893 have shown that the voltage-gated potassium channels KCNQ2 and KCNQ3 form a heteromeric potassium ion channel known as the "M-channel." Mutations in KCNQ2 and KCNQ3 in the M-channel are responsible for causing epilepsy (Biervert et al., 1998, Science 279:403-406; Singh et al., 1998, Nature Genet. 18:25-29; Schroeder et al., Nature 1998, 396:687-690).

Voltage-gated sodium channels are transmembrane proteins that are essential for the generation of action potentials in excitable cells (Catterall, 1993, Trends Neurosci. 16:500-506). In mammals, voltage-gated sodium channels consist of a macromolecular assembly of α and β subunits with the α subunit being the pore-forming component. α subunits are encoded by a large family of related genes, with some α subunits being present in the central nervous system (Noda et al., 1986, Nature 322:826-828; Auld et al., 1988, Neuron 1:449-461; Kayano et al., 1988, FEBS Lett. 228:187-194) and others in muscle (Rogart et al., 1989, Proc. Natl. Acad. Sci. USA 86:8170-8174; Trimmer et al., 1989, Neuron 3:33-49).

Voltage-gated calcium channels are transmembrane proteins that in the open configuration allow the passive flux of $Ca^{2+}$ ions across the plasma membrane, down the electrochemical gradient. They mediate various cell functions, including excitation-contraction coupling, signal transduction, and neurotransmitter release.

Current methods of drug discovery often involve assessing the biological activity (i.e., screening) of tens or hundreds of thousands of compounds in order to identify a small number of those compounds having a desired activity. In many high throughput screening programs, it is desirable to test as many as 50,000 to 100,000 compounds per day. Unfortunately, current methods of assaying the activity of voltage-gated ion channels are ill suited to the needs of a high throughput screening program. Current methods often rely on electrophysiological techniques. Standard electrophysiological techniques involve "patching" or sealing against the cell membrane with a glass pipette followed by suction on the glass pipette, leading to rupture of the membrane patch (Hamill et al., 1981, Pflugers Arch. 391: 85-100). This has limitations and disadvantages. Accessing the cell interior may alter the cell's response properties. The high precision optical apparatuses necessary for micromanipulating the cells and the pipettes make simultaneous recording from more than a few cells at a time impossible. Given these difficulties, the throughput that can be achieved with electrophysiological techniques falls far short of that necessary for high throughput screening.

Various techniques have been developed as alternatives to standard methods of electrophysiology. For example, radioactive flux assays have been used in which cells are loaded with a radioactive tracer (e.g., $^{86}Rb^+$, $^{22}Na^+$, $[^{14}C]$-guanidinium) and the efflux of the dye is monitored. Cells loaded with the tracer are exposed to compounds and those compounds that either enhance or diminish the efflux of the tracer are identified as possible activators or inhibitors of ion channels in the cells' membranes.

Assays that measure the change in a cell's membrane potential due to the change in activity of an ion channel have been developed. Such assays often employ voltage sensitive dyes that redistribute between the extracellular environment and the cell's interior based upon a change in membrane potential and that have a different fluorescence spectrum depending on whether they are inside or outside the cell. A related assay method uses a pair of fluorescent dyes capable of fluorescence resonance energy transfer to sense changes in membrane potential. For a description of this technique, see González & Tsien, 1997, Chemistry & Biology 4:269-277. See also González & Tsien, 1995, Biophys. J. 69:1272-1280 and U.S. Pat. No. 5,661,035. Other methods employ ion selective indicators such as calcium dependent fluorescent dyes to monitor changes in $Ca^{2+}$ influx during opening and closing of calcium channels.

Ideally, methods of screening against voltage-gated ion channels require that the transmembrane potential of the cells being assayed be controlled and/or that the ion channels studied be cycled between open and closed states. This has been done in various ways. In standard electrophysiological techniques, the experimental set-up allows for direct manipulation of membrane potential by the voltage clamp method (Hodgkin & Huxley, 1952, J. Physiol. (Lond.) 153:449-544), e.g., changing the applied voltage or injecting various ions into the cell. In other methods, changing the extracellular $K^+$ concentration from a low value (e.g., 5 mM) to a higher value (e.g., 70-80 mM) results in a change in the electrochemical potential for $K^+$ due to the change in the relative proportion of intracellular and extracellular potassium. This results in a change in the transmembrane electrical potential towards a more depolarized state. This depolarization can activate many voltage-gated ion channels, e.g., voltage-gated calcium, sodium, or potassium channels. Alternatively, $Na^+$ channels can be induced into an open conformation by the use of toxins such as veratridine or scorpion venom (Strichartz et al., 1987, Ann. Rev. Neurosci. 10:237-267; Narahashi & Harman, 1992, Meth. Enzymol. 207:620-643). While sometimes effective, such experimental manipulations may alter the channel pharmacology, can be awkward to perform, and can lead to artifactual disturbances in the system being studied.

Electrical field stimulation of cells has been performed on a single cell by sealing a glass microelectrode to the cell membrane. Rupture of the sealed patch of cell membrane resulted in an electrical connection between the interior fluid in the glass microelectrode and the fluid within the cell that was used to stimulate the cell via an electronic pulse generator. The electrophysiological response of the cell was measured via a sensitive electronic amplifier. The disadvantage of this technique is that only one cell at a time was tested and it is a tedious and time consuming operation to seal the microelectrode to an individual cell.

HEK293 cells have been grown on a silicon chip made up of an array of field-effect transistors. Some of the cells were positioned over the gate region of the transistors, thus having portions of their plasma membranes overlying the source and the drain. When a patch pipette in such cells manipulated the intracellular voltage, Maxi-K potassium channels in the cells' plasma membranes were opened. This led to current flow in the region between the cells' membrane and the transistor. This current flow modulated the source-drain current, which could be detected by an appropriate device. The chip plus cells was said to have potential as a sensor and as a prototype for neuroprosthetic devices. See Straub et al., 2001, Nature Biotechnol. 19:121-124; Neher, 2001, Nature Biotechnol. 19:114.

SUMMARY OF THE INVENTION

The present invention is directed to methods of identifying activators and inhibitors of voltage-gated ion channels in which the methods employ electrical field stimulation of the cells via extracellular electrodes in order to manipulate the open/close state transitions of the voltage-gated ion channels. This allows for more convenient, more precise manipulation of these transitions, and, coupled with efficient methods of detecting ion flux or membrane potential, results in methods that are especially suitable for high throughput screening in order to identify substances that are activators or inhibitors of voltage-gated ion channels.

The present invention also provides apparatuses for use in the above-described methods. In particular, modifications of standard multiwell tissue culture plates are provided where the modified multiwell tissue culture plates have electrodes that can alter the transmembrane electric potential of cells in the wells of the plates, thus altering the ratio of open/close states of voltage-gated ion channels in the cells.

BRIEF DESCRIPTION OF THE DRAWINGS

FIG. 4A shows an exploded view of the embodiment containing a well frame 1 the openings 2 of which form the wells on the substrate 3 where the well frame 1 is attached to the substrate 3 (e.g., by gluing it in place), a contact guide plate 5 with a spring loaded contact 6, and a printed circuit board (PCB) 7. The substrate holder 4 is used to hold the assembled device in position on a measuring instrument such as a microscope or fluorescent plate reader (not shown). The PCB 7 contains connections through which the electrodes (not shown) can be linked to a pulse generator (not shown). FIG. 4B shows an assembled view.

FIG. 12A-B shows an embodiment that is similar to the embodiment of FIG. 7 in having one electrode enter from above while the other electrode forms the bottom of the wells. FIG. 12A is a side cross-sectional view that shows a substrate that is a 96-well microtiter plate in which one electrode 1 is a layer of a conductive material such as ITO that forms the bottom of the wells 2. The other electrode 3 enters the wells from above and makes contact with the fluid in the wells (fluid not shown). The electrodes are connected to an electrical pulse generator 4 by leads 5. Either electrode may be the positive or negative electrode. An alternative embodiment, similar to that shown, is to replace the bottom of standard 96, 384, 1536, or 3456 well plates with a conductive material such as ITO, which forms one electrode. The second electrode is lowered into each well from above. Contact to the ITO electrode can be made via electrically conducting silver epoxide or by placing a 3 M KCl (or similar salt solution) in alternate wells as the contact to the ITO bottoms from a platinum wire. FIG. 12B shows a top view of the substrate.

FIG. 13A-B shows an embodiment comprising two multiwell substrates containing virtual wells. FIG. 13A is a side cross-sectional view that shows the top substrate 1 approaching the bottom substrate 2. The top electrode 3 is made of a conducting material such as ITO and forms the bottom of the virtual wells 4 of the top substrate 1. Similarly, the bottom electrode 5 is made of a conducting material such as ITO and forms the bottom of the virtual wells 6 of the bottom substrate 2. A thin layer of TEFLON® or a similar hydrophobic material 11 covers the surfaces of the conducting material on the substrates. Circular areas of the surface of the substrate that lack TEFLON® are relatively hydrophilic and form the virtual wells. The TEFLON® layer is about 0.5 μm to 100 μm thick. The top 3 and bottom 5 electrodes are connected to an electrical pulse generator 6 by leads 7. The left most wells of the apparatus are shown containing fluid drops. The top drop 8 might contain a substance such as a drug or a compound to be tested while the bottom drop 9 might contain cells expressing a voltage-gated ion channel. FIG. 13B shows the apparatus after the top 1 and bottom 2 substrates have moved close enough together so that the top 8 and bottom 9 drops have mixed. 10 is a spacer (not shown in FIG. 13A) that helps to align the top 1 and bottom 2 substrates and keeps the substrates the proper distance apart for mixing of the drops.

FIG. 16B shows a side cut-away view of this embodiment that illustrates how the positive 2 and negative 4 electrodes might be connected to a pulse generator 11. Also shown is the transparent conductive layer 6 coating the transparent substrate 7. FIG. 16C shows a top view of the embodiment that illustrates the alternating pattern of positive and negative electrodes.

FIG. 18A-B shows a nucleotide sequence encoding the human PN3 sodium channel (SEQ.ID.NO.:1). FIG. 18C shows the corresponding amino acid sequence (SEQ.ID.NO.:2). From GenBank accession no. AF117907.

FIG. 19A-C shows a nucleotide sequence encoding the α1H subunit of the human T-type calcium channel (SEQ.ID.NO.:3). FIG. 19D shows the corresponding amino acid sequence (SEQ.ID.NO.:4). From GenBank accession no. AF073931.

FIG. 20A-C shows a nucleotide sequence encoding a splice variant of the α1B subunit of the human N-type calcium channel (SEQ.ID.NO.:5). FIG. 20D shows the corresponding amino acid sequence (SEQ.ID.NO.:6). From GenBank accession no. M94172.

FIG. 21A-C shows a nucleotide sequence encoding a splice variant of the α1B subunit of the human N-type calcium channel (SEQ.ID.NO.:7). FIG. 21D shows the corresponding amino acid sequence (SEQ.ID.NO.:8). From GenBank accession no. M94173.

FIG. 22A-C shows a nucleotide sequence encoding the human calcium channel α1A isoform 1A-1 subunit (SEQ.ID.NO.:9). FIG. 22D shows the corresponding amino acid sequence (SEQ.ID.NO.:10). From GenBank accession no. AF004884.

FIG. 23A-C shows a nucleotide sequence encoding the human calcium channel α1A isoform 1A-2 subunit (SEQ.ID.NO.:11). FIG. 23D shows the corresponding amino acid sequence (SEQ.ID.NO.:12). From GenBank accession no. AF004883.

FIG. 32 shows an electrode head similar to that shown in FIG. 25, and a copper electrode plate. This embodiment is especially adapted for use with Caco-2 multiscreens (Millipore, Beford, Mass.).

FIG. 36 depicts a novel electrode embodiment that comprises a dielectric disc sandwiched between two conductive discs. FIG. 36A shows an expanded view of the novel electrode embodiment. FIG. 36B shows the novel electrode embodiment electrically connected to a concentric lead. FIG. 36C shows the novel electrode embodiment electrically connected to edge leads.

DETAILED DESCRIPTION OF THE INVENTION

Figure 1:
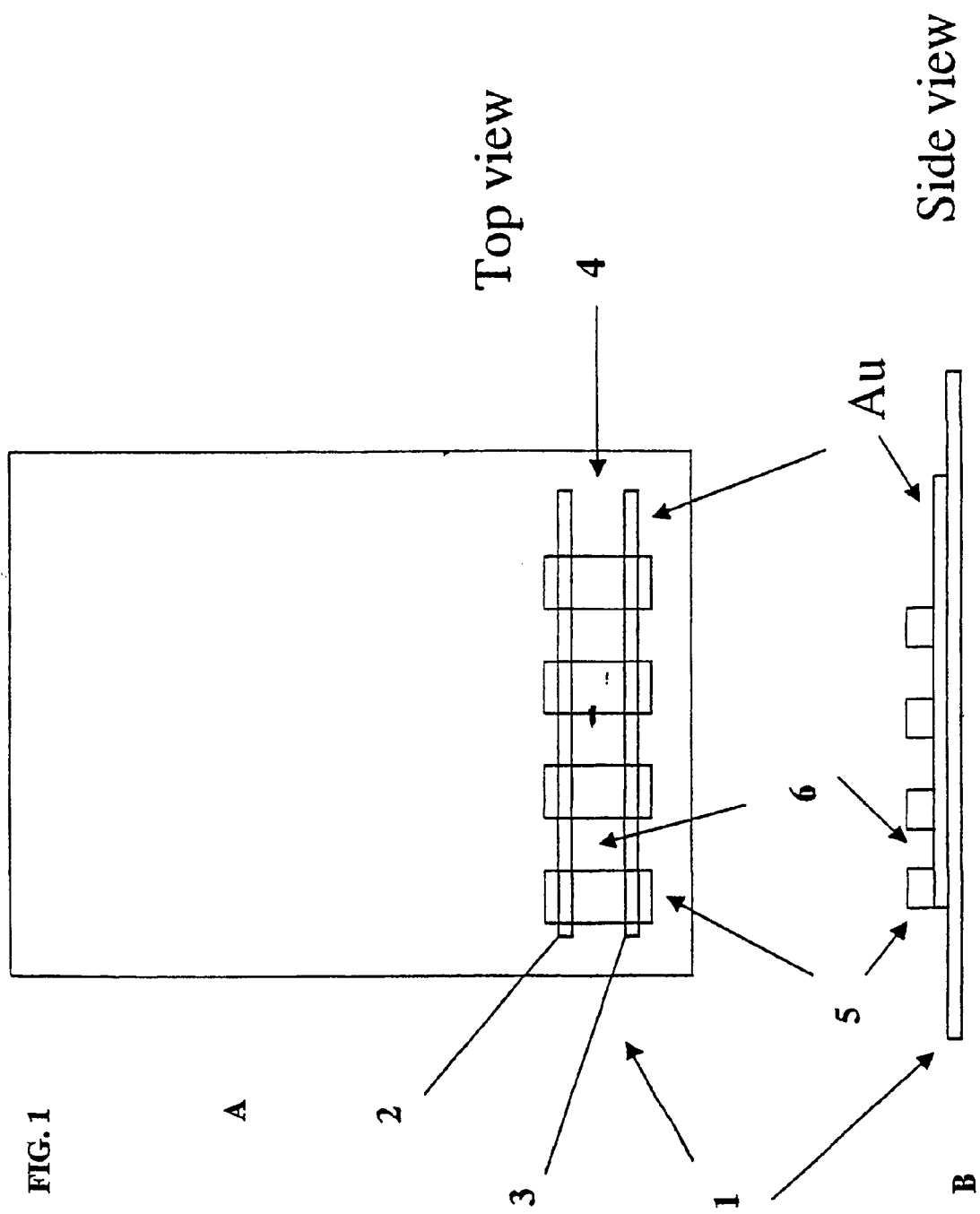
FIG. 1A shows a top view of one embodiment of the present invention. This embodiment comprises a glass slide 1 in which or upon which are a gold positive electrode 2 and a gold negative electrode 3 spaced such that a gap 4 of about 25 μm to 100 μm exists between the electrodes. The electrodes together with spacers 5 (here shown as plastic strips) arranged generally at right angles to the electrodes define a series of wells 6 about 100 μm deep into which cells can be placed and/or grown.
FIG. 1B shows a cross-sectional side view of the embodiment of FIG. 1A. In this embodiment, the identities of the positive and negative electrodes can be interchanged, if desired. The electrodes need not be made from gold; other conductive materials may be used. Also, the spacers need not be plastic; other non-conductive materials may be used.

The present invention provides equipment and techniques to implement electric field stimulation (EFS) of cells while monitoring a biological response of the cells. Preferably, the biological response is monitored by fluorescence detection. The cells are grown and/or attached to specially designed substrates such as, e.g., glass slides which contain preferably transparent, electrically conductive electrodes or multiwell tissue culture plates containing electrodes so disposed that when a preselected voltage is applied across the electrodes the transmembrane potential of cells within the wells of the multiwell tissue culture plates is altered.

In general terms, the present invention involves providing a substrate upon which living eukaryotic cells, preferably mammalian cells, are present where the cells express voltage-gated ion channels in their plasma membranes. Positive and negative electrodes are positioned either on or near the substrate so that when a voltage is applied through the electrodes the voltage-gated ion channels either open or close, thereby modulating the flow of at least one type of ion through the plasma membranes of the cells. This modulation of ion flow, or a change in membrane potential that results from the modulation of ion flow, is detected, either directly or indirectly, preferably by the use of fluorescent indicator compounds in the cells. Collections of substances, e.g., combinatorial libraries of small organic molecules, natural products, phage display peptide libraries, etc., are brought into contact with the voltage-gated ion channels in the plasma membranes of the cells and those substances that are able to affect the modulation of ion flow are identified. In this way, the present invention provides methods of screening for activators and inhibitors of voltage-gated ion channels. Such activators and inhibitors are expected to be useful as pharmaceuticals or as lead compounds from which pharmaceuticals can be developed by the usual processes of drug development, e.g., medicinal chemistry.

During an applied extracellular electrical field, the cell membrane electrical capacitance will charge or discharge depending upon the polarity and orientation of the cell relative to the field. This results in a transient change in the transmembrane potential in a given patch of membrane. These transient changes in transmembrane potential will vary continuously around each cell depending upon the orientation of each patch of membrane relative to the applied field and the existing transmembrane potential. In each membrane patch, membrane potential will be perturbed away from the resting value by the applied external field. This change in membrane potential will in turn affect the proportion of open and closed voltage-gated ion channels in each local patch of membrane, which will affect the conductance of the voltage-gated ion channels and thus change the membrane potential further. This process is expected to vary around each cell such that, in any given cell, different patches of membrane and the embedded voltage-gated ion channels will experience different membrane potentials. In general, the membrane potential in a given patch of membrane will change at a rate that is proportional to its resistance (1/conductance) and its capacitance ($C_m$) such that $dV/dt=I/C_m$ where I is the total current flow (I=V/R) across the patch of membrane.

Figure 14:
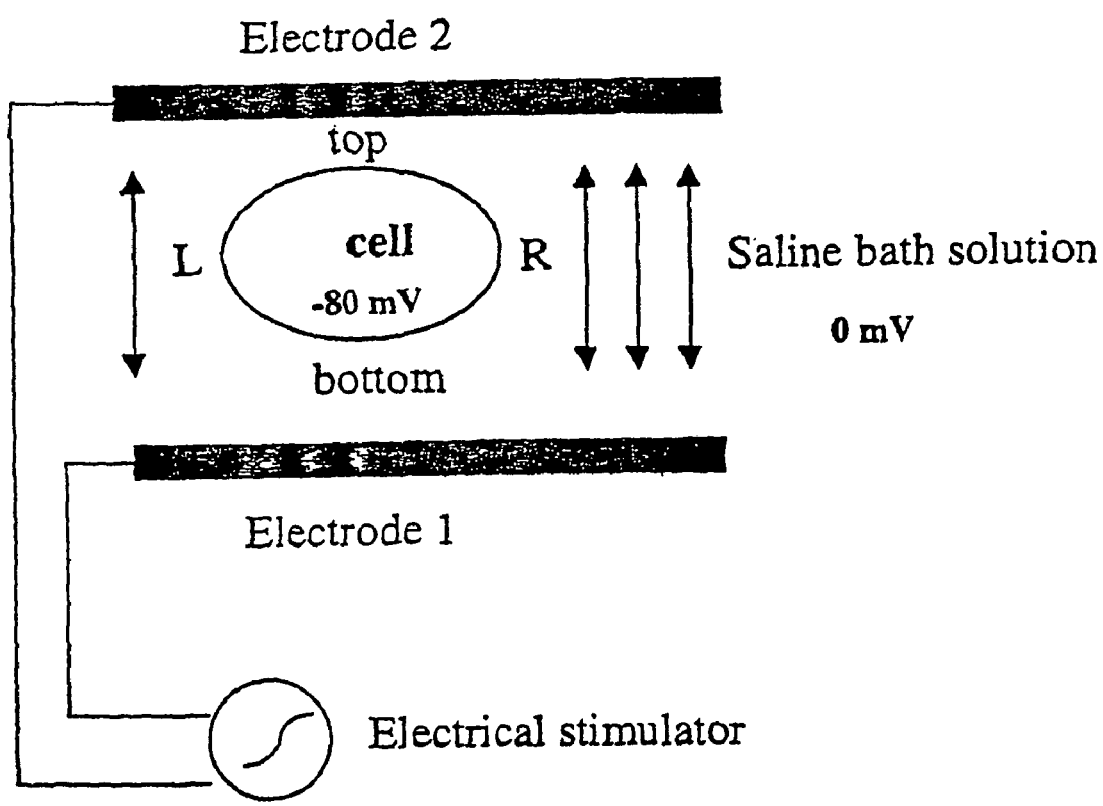
FIG. 14 illustrates the principles of electrical field stimulation of cells.

FIG. 14 illustrates these concepts. For the sake of simplicity, the plasma membrane of the cell shown in FIG. 14 is divided into four patches: left, top, right, and bottom. Current will flow between the electrodes if a voltage difference is applied. This will alter the cell membrane potential. If electrode 1 is positive and electrode 2 is negative, the membrane patch at the bottom of the cell will be hyperpolarized but the top patch will be depolarized. The left and right patches will "see" no change in membrane potential. If polarity is reversed, the opposite will occur.

In reality, of course, the cell's plasma membrane is a continuum of individual patches rather the simplified system of four patches depicted in FIG. 14. The applied voltage alters the membrane potentials of the various patches to many different values such that the embedded voltage-gated ion channels "sample" the many different potentials and are driven through their various conformational states. These include open states, closed states, high affinity drug bound states, and low affinity drug bound states.

Accordingly, the present invention provides a method for identifying modulators of the activity of a voltage-gated ion channel comprising:

(a) altering the transmembrane potential of at least a portion of the membrane of a cell expressing the voltage-gated ion channel by applying a voltage to the cells through extracellular electrodes while monitoring ion flow through the voltage-gated ion channel;

(b) exposing the cell in step (a) to a substance and monitoring ion flow through the voltage-gated ion channel;

(c) comparing the ion flow through the voltage-gated ion channel in step (a) and step (b);

where a difference in the ion flow through the voltage-gated ion channel in step (a) and step (b) indicates that the substance is a modulator of the voltage-gated ion channel.

A variation of the method comprises:

(a) dividing a plurality of cells expressing the voltage-gated ion channel into a control portion and a test portion;

(b) altering the transmembrane potential of the control portion of cells by applying a voltage to the cells through extracellular electrodes while monitoring ion flow through the voltage-gated ion channel;

(c) altering the transmembrane potential of the test portion of cells by applying the voltage to the cells through extracellular electrodes in the presence of a substance while monitoring ion flow through the voltage-gated ion channel;

(d) comparing the ion flow through the voltage-gated ion channel in step (b) and step (c);

where a difference in the ion flow through the voltage-gated ion channel in step (b) and step (c) indicates that the substance is modulator of the voltage-gated ion channel.

For the sake of simplicity, the above methods are described in terms of "a" voltage-gated ion channel although those skilled in the art will understand that in actual practice the cells will express a plurality of the voltage-gated ion channels for which modulators are sought. Generally, each cell will express at least $10^2$, $10^3$, $10^4$, $10^5$, $10^6$ or more molecules of the voltage-gated ion channel. Also, ion flow will be monitored through the plurality of the voltage-gated ion channels rather than through a single voltage-gated ion channel. Similarly, the methods will generally be practiced by employing a plurality of cells, even though the methods are described above in terms of "a" cell.

Generally, the methods of the present invention will be carried out on a substrate that is a modified version of a standard multiwell tissue culture plate or microtiter plate. Such substrates will have a place for the cells to be tested (generally the wells of the tissue culture plate or microtiter plate) and will have positive and negative electrodes (either built into the plate or nearby) in such an orientations with respect to the cells that the electrodes can deliver a voltage potential that causes an alteration in the open/close state of the voltage-gated ion channels in the cells. The electrodes are extracellular, i.e., they do not penetrate into or across the plasma membranes of the cells although they may touch the outside of the plasma membranes in certain embodiments. Extracellular electrodes do not include electrodes which form a continuous connection with a cell's interior, e.g., patch/clamp electrodes.

Therefore, the present invention provides a method of identifying activators of a voltage-gated ion channel comprising:

(a) providing a substrate upon which are living eukaryotic cells that express a plurality of the voltage-gated ion channels in their plasma membranes;

(b) providing positive and negative electrodes positioned either on or near the substrate such that when a preselected voltage is applied through the positive and negative electrodes the transmembrane electrical potential of the cells is altered such that at least a portion of the voltage-gated ion channels are closed;

(c) applying the preselected voltage through the positive and negative electrodes;

(d) determining a control value for the flow of ions through the voltage-gated ion channels of the cells in step (c);

(e) exposing the cells of step (c) to a substance for a period sufficient and under conditions such that a detectable number of the portion of the voltage-gated ion channels that are closed become open and allow ion flow through the detectable number of voltage-gated ion channels if the substance is an activator of the voltage-gated ion channels;

(f) determining a test value for the flow of ions through the voltage-gated ion channels of the cells of step (e);

(g) comparing the control value to the test value;

where if the control value is less than the test value, then the substance is an activator of the voltage-gated ion channel.

The above-described method can be easily modified to provide a method for identifying inhibitors of the voltage-gated ion channel. The voltage applied through the electrodes is preselected such that it alters the electrical field around the cells and consequently alters the transmembrane electrical field. This in turn changes the states of the embedded voltage-gated ion channels such that instead of the voltage-gated ion channels being closed, the voltage-gated ion channels may open. Substances are then screened for the ability to close or inhibit the channels.

Accordingly, the present invention provides a method of identifying inhibitors of a voltage-gated ion channel comprising:

(a) providing a substrate upon which are living eukaryotic cells that express a plurality of the voltage-gated ion channels in their plasma membranes;

(b) providing positive and negative electrodes positioned either on or near the substrate such that when a preselected voltage is applied through the positive and negative electrodes the transmembrane electrical potential of the cells is altered such that at least a portion of the voltage-gated ion channels are open;

(c) applying the preselected voltage through the positive and negative electrodes;

(d) determining a control value for the flow of ions through the voltage-gated ion channels of the cells in step (c);

(e) exposing the cells of step (c) to a substance for a period sufficient and under conditions such that a detectable number of the portion of the voltage-gated ion channels that are open become closed and restrict ion flow through the detectable number of voltage-gated ion channels if the substance is an inhibitor of the voltage-gated ion channels;

(f) determining a test value for the flow of ions through the voltage-gated ion channels of the cells of step (e);

(g) comparing the control value to the test value;

where if the control value is greater than the test value, then the substance is an inhibitor of the voltage-gated ion channel.

In the above-described method for identifying activators, the terms "a portion of the voltage-gated ion channels are closed" and "a detectable number" are related and have relative rather than absolute values. Similarly, in the above-described method for identifying inhibitors, the terms "a portion of the voltage-gated ion channels are open" and "a detectable number" are also related and have relative rather than absolute values. What is meant is that a portion of the voltage-gated ion channels will be open or closed such that when the substance acts on the channels, a change in the open/closed state of a sufficient number of channels (i.e., "a detectable number") occurs such that a difference in ion flow that is large enough to be measured by the detection system employed takes place. There is no need to determine the actual number of ion channels that constitutes the "portion" of voltage-gated ion channels that are closed or open or the "detectable number" so long as the difference in ion flow can be measured. The actual portion of channels that will be open or closed as well as the actual value of "detectable number" in order for the methods to be practiced will depend on such variables as the channel that is being studied, the concentrations of the substances tested, the nature of the detection system for ion flow, and so forth. Adjusting the voltage applied through the electrodes to take into account such variables so that control and test values can be obtained is a matter of routine experimentation in which the skilled artisan will be guided by knowledge in the art such as, e.g., the known voltage dependence of the open/close transition of the voltage-gated ion channel under study, the nature and sensitivity of the detection system employed to monitor the flow of ions, the level of expression of the ion channel in the cells, and so forth.

The electrodes can be arranged in a variety of ways in order to provide for the proper stimulus. A number of arrangements are described herein and illustrated in the accompanying figures. These include arrangements where the cells are present in wells in the substrate and:

(a) both a positive and negative electrode is present in each well;

(b) one electrode is present in the well and the other electrode enters the fluid medium in the well from above without touching the sides or bottom of the well;

(c) the electrodes form part of the sides or bottom of the wells;

(d) a pattern of interdigitating electrodes has been formed on the surface of the substrate and at least some of the cells are positioned between the interdigitating branches of the positive and negative electrodes.

The skilled person will recognize that it is generally beneficial to run controls together with the methods described herein. For example, it will usually be helpful to have a control in which the substances are tested in the methods against cells that preferably are essentially identical to the cells that are used in the methods except that these cells would not express the voltage-gated ion channels of interest. In this way it can be determined that substances which are identified by the methods are really exerting their effects through the voltage-gated ion channels of interest rather than through some unexpected non-specific mechanism. One possibility for such control cells would be to use non-recombinant parent cells where the cells of the actual experiment express the voltage-gated ion channels of interest due to the recombinant expression of those voltage-gated ion channels of interest.

Other types of controls would involve taking substances that are identified by the methods of the present invention as activators or inhibitors of voltage-gated ion channels of interest and testing those substances in the methods of the prior art in order to confirm that those substances are also activators and inhibitors when tested in those prior art methods.

One skilled in the art would recognize that, where the present invention involves comparing control values for the flow of ions to test values for the flow of ions and determining whether the control values are greater or less than the test values, a non-trivial difference is sought. For example, if in the methods of identifying inhibitors, the control value were found to be 1% greater than the test value, this would not indicate that the substance is an inhibitor. Rather, one skilled in the art would attribute such a small difference to normal experimental variance. What is looked for is a significant difference between control and test values. For the purposes of this invention, a significant difference fulfills the usual requirements for a statistically valid measurement of a biological signal. For example, depending upon the details of the experimental arrangement, a significant difference might be a difference of at least 10%, preferably at least 20%, more preferably at least 50%, and most preferably at least 100%.

One skilled in the art would understand that the cells that give rise to the control values need not be physically the same cells that give rise to the test values, although that is possible. What is necessary is that the cells that give rise to the control values be substantially the same type of cell as the cells that give rise to the test values. A cell line that has been transfected with and expresses a certain voltage-gated ion channel could be used for both the control and test cells. Large numbers of such cells could be grown and a portion of those cells could be exposed to the substance and thus serve as the cells giving rise to the test value for ion flow while a portion would not be exposed to the substance and would thus serve as the cells giving rise to the control value for ion flow. No individual cell itself would be both control and test cell but the virtual identity of all the cells in the cell line ensures that the methods would nevertheless be reliable.

Accordingly, the present invention provides a method of identifying activators of a voltage-gated ion channel comprising:

(a) providing a substrate upon which are living eukaryotic cells that express a plurality of the voltage-gated ion channels in their plasma membranes;

(b) providing positive and negative electrodes positioned either on or near the substrate such that when a preselected voltage is applied through the positive and negative electrodes the transmembrane electrical potential of the cells is altered such that at least a portion of the voltage-gated ion channels are closed;

(c) applying the preselected voltage through the positive and negative electrodes to a control sample of the cells;

(d) determining a control value for the flow of ions through the voltage-gated ion channels of the control sample of the cells in step (c);

(e) applying the preselected voltage through the positive and negative electrodes to a test sample of the cells while exposing the test sample of the cells to a substance for a period sufficient and under conditions such that a detectable number of the portion of the voltage-gated ion channels that are closed in the test sample become open and allow ion flow through the detectable number of voltage-gated ion channels if the substance is an activator of the voltage-gated ion channels;

(f) determining a test value for the flow of ions through the voltage-gated ion channels of the test sample of cells of step (e);

(g) comparing the control value to the test value;

where if the control value is less than the test value, then the substance is an activator of the voltage-gated ion channel.

Similarly, the present invention provides a method of identifying inhibitors of a voltage-gated ion channel comprising:

(a) providing a substrate upon which are living eukaryotic cells that express a plurality of the voltage-gated ion channels in their plasma membranes;

(b) providing positive and negative electrodes positioned either on or near the substrate such that when a preselected voltage is applied through the positive and negative electrodes the transmembrane electrical potential of the cells is altered such that at least a portion of the voltage-gated ion channels are open;

(c) applying the preselected voltage through the positive and negative electrodes to a control sample of the cells;

(d) determining a control value for the flow of ions through the voltage-gated ion channels of the control sample of the cells in step (c);

(e) applying the preselected voltage through the positive and negative electrodes to a test sample of the cells while exposing the test sample of the cells to a substance for a period sufficient and under conditions such that a detectable number of the portion of the voltage-gated ion channels that are open in the test sample become closed and restrict ion flow through the detectable number of voltage-gated ion channels if the substance is an inhibitor of the voltage-gated ion channels;

(f) determining a test value for the flow of ions through the voltage-gated ion channels of the test sample of cells of step (e);

(g) comparing the control value to the test value;

where if the control value is greater than the test value, then the substance is an inhibitor of the voltage-gated ion channel.

"Substances" can be any substances that are generally screened in the pharmaceutical industry during the drug development process. For example, substances may be low molecular weight organic compounds (e.g., having a molecular weight of less than about 1,000 daltons); RNA, DNA, antibodies, peptides, or proteins.

The conditions under which cells are exposed to substances in the methods described herein are conditions that are typically used in the art for the study of protein-ligand interactions: e.g., physiological pH; salt conditions such as those represented by such commonly used buffers as PBS or in tissue culture media; a temperature of about 4° C. to about 55° C.; incubation times of from several seconds to several hours. Generally, the cells are present in wells in the substrate and the substances are added directly to the wells, optionally after first washing away the media in the wells.

Determining the values of ion flow in the methods of the present invention can be accomplished through the use of fluorescent indicator compounds. One type of fluorescent indicator compound is sensitive to the level of intracellular calcium ions in the cells used in the present invention. This type of fluorescent indicator compound can be used when the methods are directed to those voltage-gated ion channels whose activity results in a change in intracellular calcium levels. Such voltage-gated ion channels include not only voltage-gated calcium channels but also other types of voltage-gated ion channels where the activity of those channels is naturally or can be coupled to changes in intracellular calcium levels. Many types of voltage-gated potassium channels can be so coupled. When using this approach to study a voltage-gated ion channel of interest that is not a voltage-gated calcium channel, it may be desirable to engineer the cells employed so as to recombinantly express voltage-gated calcium channels that are coupled to the voltage-gated ion channel of interest.

Fluorescent indicator compounds suitable for measuring intracellular calcium levels include various calcium indicator dyes (e.g., fura-2, fluo-3, indo-1, Calcium Green; see Veliçelebi et al., 1999, Meth. Enzymol. 294:2047).

Calcium indicator dyes are substances which show a change in a fluorescent characteristic upon binding calcium, e.g., greatly increased intensity of fluorescence and/or a change in fluorescent spectra (i.e., a change in emission or excitation maxima). Fluo-3, fura-2, and indo-1 are commonly used calcium indicator dyes that were designed as structural analogs of the highly selective calcium chelators ethylene glycol-bis(β-aminoethyl ether) N,N,N',N'-tetraacetic acid (EGTA) and 1,2-bis(2-aminophenoxy) ethane-N,N,N',N'-tetraacetic acid (BAPTA). The fluorescence intensity from fluo-3 increases by more than 100-fold upon binding of calcium. While the unbound dye exhibits very little fluorescence, calcium-bound fluo-3 shows strong fluorescence emission at 526 nm. Fura-2 is an example of a dye that exhibits a change in its fluorescence spectrum upon calcium binding. In the unbound state, fura-2 has an excitation maximum of 362 nm. This excitation maximum shifts to 335 nm upon calcium binding, although there is no change in emission maximum. Binding of calcium to fura-2 can be monitored by excitation at the two excitation maxima and determining the ratio of the amount of fluorescence emission following excitation at 362 nm compared to the amount of fluorescence emission following excitation at 335 nm. A smaller ratio (i.e., less emission following excitation at 362 nm) indicates that more fura-2 is bound to calcium, and thus a higher internal calcium concentration in the cell.

The use of calcium indicator dyes entails loading cells with the dye, a process which can be accomplished by exposing cells to the membrane-permeable acetoxymethyl esters of the dyes. Once inside the plasma membrane of the cells, intracellular esterases cleave the esters, exposing negative charges in the free dyes. This prevents the free dyes from crossing the plasma membrane and thus leaves the free dyes trapped in the cells. Measurements of fluorescence from the dyes are then made, the cells are treated in such a way that the internal calcium concentration is changed (e.g., by exposing cells to an activator or inhibitor of a voltage-gated ion channel), and fluorescence measurements are again taken.

Fluorescence from the indicator dyes can be measured with a luminometer or a fluorescence imager. One preferred detection instrument is the Fluorometric Imaging Plate Reader (FLIPR) (Molecular Devices, Sunnyvale, Calif.). The FLIPR is well suited to high throughput screening using the methods of the present invention as it incorporates integrated liquid handling capable of simultaneously pipetting to 96 or 384 wells of a microtiter plate and rapid kinetic detection using a argon laser coupled to a charge-coupled device imaging camera.

A typical protocol for use of calcium indicator dyes would entail plating cells expressing a voltage-gated ion channel of interest into an appropriate substrate (e.g., clear, flat-bottom, black-wall 96 well plates that have a suitable arrangement of positive and negative electrodes) and allowing the cells to grow overnight in standard tissue culture conditions (e.g., 5% $CO_2$, 37° C.). The cells are generally plated at a density of about 10,000 to 100,000 cells per well in appropriate growth medium. On the day of the assay, growth medium is removed and dye loading medium is added to the wells.

If the calcium indicator dye is fluo-3, e.g., dye loading medium could be prepared by solubilizing 50 μg of fluo-3-AM ester (Molecular Probes F-1242) in 22 μl DMSO to give a 2 mM dye stock. Immediately before loading the cells, 22 μl 20% pluronic acid (Molecular Probes P-3000) is added to the dye. The tube containing the dye is mixed with a vortex mixer and 42 ml of the dye/pluronic acid solution is added to 10.5 ml of Hanks Balanced Salt Solution (Gibco/BRL Cat # 14025-076) with 20 mM HEPES (Gibco/BRL Cat # 1560-080), 2.5 mM probenecid (Sigma Cat # P-8761), and 1% fetal bovine serum (Gibco/BRL Cat # 26140-087; not BSA)). The dye and the loading medium are mixed by repeated inversion (final dye concentration about 4 μM).

Growth medium can be removed from the cells by washing (wash medium is Hanks Balanced Salt Solution (Gibco/BRL Cat # 14025-076) with 20 mM HEPES (Gibco/BRL Cat # 1560-080), 2.5 mM probenecid (Sigma Cat # P-8761), and 0.1% bovine serum albumin (Sigma Cat # A-9647; not FBS) three times, leaving 100 μl residual medium in the wells after the fourth wash. Then 100 μl of the dye in the loading medium is added to each well. The cells are then incubated for 60 minutes to allow for dye loading.

Following dye loading, fluorescent measurements of the cells are taken prior to exposure of the cells to substances that are to be tested. The cells are then exposed to the substances and those substances that cause a change in a fluorescent characteristic of the dye are identified. The measuring instrument can be a fluorescent plate reader such as the FLIPR (Molecular Devices). Substances that cause a change in a fluorescent characteristic in the test cells but not the control cells are possible activators or inhibitors of the voltage-gated ion channel.

The exact details of the procedure outlined above are meant to be illustrative. One skilled in the art would be able to optimize experimental parameters (cell number, dye concentration, dye loading time, temperature of incubations, cell washing conditions, ionic composition of the bath solution and instrument settings, etc.) by routine experimentation depending on the particular relevant experimental variables (e.g., type of cell used, identity of dye used). Several examples of experimental protocols that can be used are described in Veliçelebi et al., 1999, Meth. Enzymol. 294:2047. Other suitable instrumentation and methods for measuring transmembrane potential changes via optical methods includes microscopes, multiwell plate readers and other instrumentation that is capable of rapid, sensitive fluorescence detection. For example, the VIPR (Aurora Biosciences, San Diego, Calif.) is an integrated liquid handler and kinetic fluorescence reader for 96-well and greater multiwell plates. The VIPR reader integrates an eight channel liquid handler, a multiwell positioning stage and a fiber-optic illumination and detection system. The system is designed to measure fluorescence from a column of eight wells simultaneously before, during and after the introduction of liquid sample obtained from another microtiter plate or trough. The VIPR reader excites and detects emission signals from the bottom of a multiwell plate by employing eight trifurcated optical bundles (one bundle for each well). One leg of the trifurcated fiber is used as an excitation source, the other two legs of the trifurcated fiber being used to detect fluorescence emission. A ball lens on the end of the fiber increases the efficiency of light excitation and collection. The bifurcated emission fibers allow the reader to detect two emission signals simultaneously and are compatible with rapid signals generated by the FRET-based voltage dyes.

Photomultiplier tubes then detect emission fluorescence, enabling sub-second emission ratio detection.

In particular embodiments, the calcium indicator dye is selected from the group consisting of: fluo-3, fura-2, fluo-4, fluo-5, calcium green-1, Oregon green, 488 BAPTA, SNARF-1, and indo-1.

In particular embodiments, the change in fluorescent characteristic is an increase in intensity of a fluorescence emission maximum. In other embodiments, the change in fluorescent characteristic is a shift in the wavelength of an absorption maximum.

In particular embodiments, the cells naturally express the voltage-gated ion channel of interest and/or calcium channels. In other embodiments, the cells do not naturally express the voltage-gated ion channel of interest and/or calcium channels but instead have been transfected with expression vectors that encode the voltage-gated ion channel of interest and/or calcium channels so that the cells recombinantly express the voltage-gated ion channel of interest and/or calcium channels. Transfection is meant to include any method known in the art for introducing expression vectors into the cells. For example, transfection includes calcium phosphate or calcium chloride mediated transfection, lipofection, infection with a retroviral construct, and electroporation.

An alternative to the use of calcium indicator dyes is the use of the aequorin system. The aequorin system makes use of the protein apoaequorin, which binds to the lipophilic chromophore coelenterazine forming a combination of apoaequorin and coelenterazine that is known as aequorin. Apoaequorin has three calcium binding sites and, upon calcium binding, the apoaequorin portion of aequorin changes its conformation. This change in conformation causes coelenterazine to be oxidized into coelenteramide, $CO_2$, and a photon of blue light (466 nm). This photon can be detected with suitable instrumentation.

Since the gene encoding apoaequorin has been cloned (U.S. Pat. Nos. 5,541,309; 5,422,266; 5,744,579; Inouye et al., 1985, Proc. Natl. Acad. Sci. USA 82:3154-3158; Prasher et al., 1985, Biochem. Biophys. Res. Comm. 126:1259-1268), apoaequorin can be recombinantly expressed in cells in which it is desired to measure the intracellular calcium concentration. Alternatively, existing cells that stably express recombinant apoaequorin can be used. Such cells derived from HEK293 cells and CHO-K1 cells are described in Button & Brownstein, 1993, Cell Calcium 14:663-671. For example, the HEK293/aeq17 cell line can be used as follows.

The HEK293/aeq17 cells are grown in Dulbecco's Modified Medium (DMEM, GIBCO-BRL, Gaithersburg, Md., USA) with 10% fetal bovine serum (heat inactivated), 1 mM sodium pyruvate, 500 μg/ml Geneticin, 100 μg/ml streptomycin, 100 units/ml penicillin. Expression vectors encoding the voltage-gated ion channel of interest as well as, optionally, the desired voltage-gated calcium channel subunits ($\alpha_{1A}$, $\alpha_{1B}$, $\alpha_{1C}$, $\alpha_{1D}$, $\alpha_{1E}$, $\alpha_{1G}$, $\alpha_{1H}$, $\alpha_{1I}$, $\alpha_2\delta$, $\beta_1$, $\beta_2$, $\beta_3$, $\beta_4$, etc.) can be transfected into the HEK293/aeq17 cells by standard methods in order to express the desired voltage-gated ion channel subunits and voltage-gated calcium channel subunits in the HEK293/aeq17 cells. The cells are washed once with DMEM plus 0.1% fetal bovine serum, and then charged for one hour at 37° C./5% $CO_2$ in DMEM containing 8 μM coelenterazine cp (Molecular Probes, Eugene, Oreg., USA) and 30 µM glutathione. The cells are then washed once with Versene (GIBCO-BRL, Gaithersburg, Md., USA), detached using Enzyme-free cellissociation buffer (GIBCO-BRL, Gaithersburg, Md., USA), diluted into ECB (Ham's F12 nutrient mixture (GIBCO-BRL) with 0.3 mM $CaCl_2$, 25 mM HEPES, pH7.3, 0.1% fetal bovine serum). The cell suspension is centrifuged at 500×g for 5 min. The supernatant is removed, and the pellet is resuspended in 10 ml ECB. The cell density is determined by counting with a hemacytometer and adjusted to 500,000 cells/ml in ECB. The substances to be tested are diluted to the desired concentrations in ECB and aliquoted into the assay plates, preferably in triplicate, at 0.1 ml/well. The cell suspension is injected at 0.1 ml/well, read and integrated for a total of 400 readings using a luminometer (Luminoskan Ascent, Labsystems Oy, Helsinki, Finland). Alternatively, the cells may first be placed into the assay plates and then the substances added. Data are analyzed using the software GraphPad Prism Version 3.0 (GraphPad Software, Inc., San Diego, Calif., USA).

It will be understood by those skilled in the art that the procedure outlined above is a general guide in which the various steps and variables can be modified somewhat to take into account the specific details of the particular assay that is desired to be run. For example, one could use semisynthetic coelenterazine (Shimomura, 1989, Biochem. J. 261:913-920; Shimomura et al., 1993, Cell Calcium 14:373-378); the time of incubation of the cells with coelenterazine can be varied somewhat; somewhat greater or lesser numbers of cells per well can be used; and so forth.

For reviews on the use of aequorin, see Créton et al., 1999, Microscopy Research and Technique 46:390-397; Brini et al., 1995, J. Biol. Chem. 270:9896-9903; Knight & Knight, 1995, Meth. Cell. Biol. 49:201-216. Also of interest may be U.S. Pat. No. 5,714,666 which describes methods of measuring intracellular calcium in mammalian cells by the addition of coelenterazine co-factors to mammalian cells that express apoaequorin.

Another way to measure ion flow is to monitor changes in transcription that result from the activity of voltage-gated ion channels by the use of transcription based assays. Transcription-based assays involve the use of a reporter gene whose transcription is driven by an inducible promoter whose activity is regulated by a particular intracellular event such as, e.g., changes in intracellular calcium levels, that are caused by the activity of a voltage-gated ion channel. Transcription-based assays are reviewed in Rutter et al., 1998, Chemistry & Biology 5:R285-R290. Transcription-based assays of the present invention rely on the expression of reporter genes whose transcription is activated or repressed as a result of intracellular events that are caused by the interaction of a activator or inhibitor with a voltage-gated ion channel.

An extremely sensitive transcription-based assay is disclosed in Zlokarnik et al., 1998, Science 279:84-88 (Zlokarnik) and also in U.S. Pat. No. 5,741,657. The assay disclosed in Zlokarnik and U.S. Pat. No. 5,741,657 employs a plasmid encoding β-lactamase under the control of an inducible promoter. This plasmid is transfected into cells together with a plasmid encoding a receptor for which it is desired to identify agonists. The inducible promoter on the β-lactamase is chosen so that it responds to at least one intracellular signal that is generated when an agonist binds to the receptor. Thus, following such binding of agonist to receptor, the level of β-lactamase in the transfected cells increases. This increase in β-lactamase is measured by treating the cells with a cell-permeable dye that is a substrate for cleavage by β-lactamase. The dye contains two fluorescent moieties. In the intact dye, the two fluorescent moieties are physically linked, and thus close enough to one another that fluorescence resonance energy transfer (FRET) can take place between them. Following cleavage of the dye into two parts by β-lactamase, the two fluorescent moieties are located on different parts, and thus can diffuse apart. This increases the distance between the fluorescent moieties, thus decreasing the amount of FRET that can occur between them. It is this decrease in FRET that is measured in the assay.

The assay described in Zlokarnik and U.S. Pat. No. 5,741,657 can be modified for use in the methods of the present invention by using an inducible promoter to drive β-lactamase where the promoter is activated by an intracellular signal generated by the opening or closing of a voltage-gated ion channel. Cells expressing a voltage-gated ion channel and the inducible promoter-driven β-lactamase are placed in the apparatus of the present invention, where the open or closed state of the voltage-gated ion channels can be controlled. The cells are exposed to the cell-permeable dye and then exposed to substances suspected of being activators or inhibitors of the voltage-gated ion channel. Those substances that cause a change in the open or closed state of the voltage-gated ion channel are identified by their effect on the inducible promoter-driven β-lactamase and thus on FRET. The inducible promoter-driven β-lactamase is engineered with a suitable promoter so that β-lactamase is induced when the substance is either an activator or an inhibitor, depending upon the nature of the assay.

The flow of ions through voltage-gated ion channels can also be measured by measuring changes in membrane potential via the use of fluorescent voltage sensitive dyes. The changes in membrane potential will depend on the ion channels in the cell membrane. The resultant membrane potential will depend on the net properties of all the channels and the change caused by inhibiting (through a substance that is an inhibitor or antagonist) or activating (through a substance that is an activator or an agonist) the voltage-gated ion channel of interest. One knowledgeable in cellular and membrane biophysics and electrophysiology will understand the directions of the changes in membrane potential since those changes depend on the ion channels present and the inhibition or activation of those channels by test substances. In many cases when using fluorescent voltage sensitive dyes, the experimental system can be calibrated by using known activators or inhibitors of the voltage-gated ion channel of interest.

The present invention therefore includes assays that monitor changes in ion flow caused by activators or inhibitors of voltage-gated ion channels based upon FRET between a first and a second fluorescent dye where the first dye is bound to one side of the plasma membrane of a cell expressing a voltage-gated ion channel of interest and the second dye is free to move from one face of the membrane to the other face in response to changes in membrane potential. In certain embodiments, the first dye is impenetrable to the plasma membrane of the cells and is bound predominately to the extracellular surface of the plasma membrane. The second dye is trapped within the plasma membrane but is free to diffuse within the membrane. At normal (i.e., negative) resting potentials of the membrane, the second dye is bound predominately to the inner surface of the extracellular face of the plasma membrane, thus placing the second dye in close proximity to the first dye. This close proximity allows for the generation of a large amount of FRET between the two dyes. Following membrane depolarization, the second dye moves from the extracellular face of the membrane to the intracellular face, thus increasing the distance between the dyes. This increased distance results in a decrease in FRET, with a corresponding increase in fluorescent emission derived from the first dye and a corresponding decrease in the fluorescent emission from the second dye. See FIG. 1 of González & Tsien, 1997, Chemistry & Biology 4:269-277. See also González & Tsien, 1995, Biophys. J. 69:1272-1280 and U.S. Pat. No. 5,661,035.

In certain embodiments, the first dye is a fluorescent lectin or a fluorescent phospholipid that acts as the fluorescent donor. Examples of such a first dye are: a coumarin-labeled phosphatidylethanolamine (e.g., N-(6-chloro-7-hydroxy-2-oxo-2H-1-benzopyran-3-carboxamidoacetyl)-dimyristoylphosphatidylethanolamine) or N-(7-nitrobenz-2-oxa-1, 3-diazol-4-yl)-dipalmitoylphosphatidylethanolamine); a fluorescently-labeled lectin (e.g., fluorescein-labeled wheat germ agglutinin). In certain embodiments, the second dye is an oxonol that acts as the fluorescent acceptor. Examples of such a second dye are: bis(1,3-dialkyl-2-thiobarbiturate) trimethineoxonols (e.g., bis(1,3-dihexyl-2-thiobarbiturate) trimethineoxonol) or pentamethineoxonol analogues (e.g., bis(1,3-dihexyl-2-thiobarbiturate)pentamethineoxonol; or bis(1,3-dibutyl-2-thiobarbiturate)pentamethineoxonol). See González & Tsien, 1997, Chemistry & Biology 4:269-277 for methods of synthesizing various dyes suitable for use in the present invention. In certain embodiments, the assay may comprise a natural carotenoid, e.g., astaxanthin, in order to reduce photodynamic damage due to singlet oxygen.

The use of such fluorescent dyes capable of moving from one face of the plasma membrane to the other is especially appropriate when the methods of the present invention are directed to inwardly rectifying potassium channels. Activation of inwardly rectifying potassium channels results in increased potassium current flow across the plasma membrane. This increased current flow results in a hyperpolarization of the cell membrane that can be detected by use of the technique described above since such hyperpolarization will result in greater FRET.

A large number of possible combinations of types of substrates and electrodes; physical arrangement of electrodes; number, shape, and arrangement of wells for holding the cells are suitable for use in the present invention.

FIG. 1 illustrates an embodiment of the invention where the electrodes are generally parallel wires or strips of conductive material such as gold. The electrodes lie on the surface of a glass substrate and, together with the spacers, form the walls of the wells. For clarity, only a single series of wells is shown in FIG. 1. Generally, substantially the entire surface of the glass substrate would be covered by wells formed in the manner shown. Cells are placed in the wells and grown in suitable media until an appropriate number of cells is present in the wells. Alternatively, an appropriate number of cells may be placed into the wells and used without further growth.

Figure 2A:
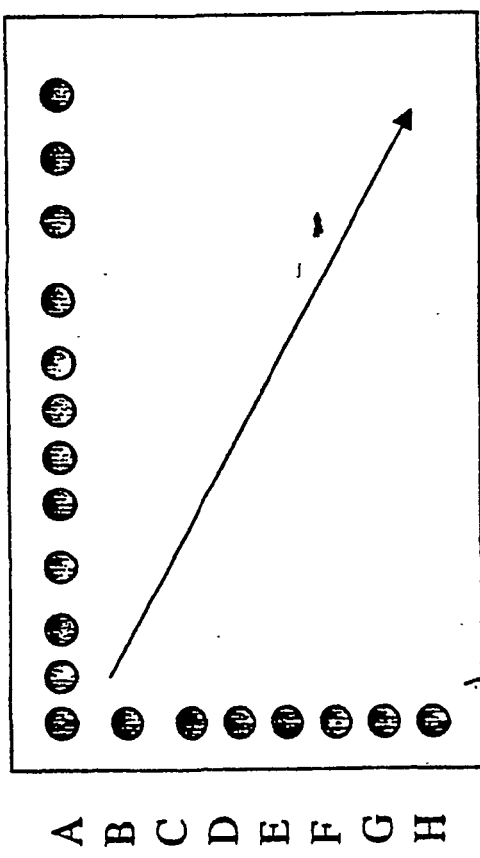
FIG. 2A shows a top view of an embodiment of the present invention in which a typical 96 well plate contains electrodes within each well.
Figure 2B:
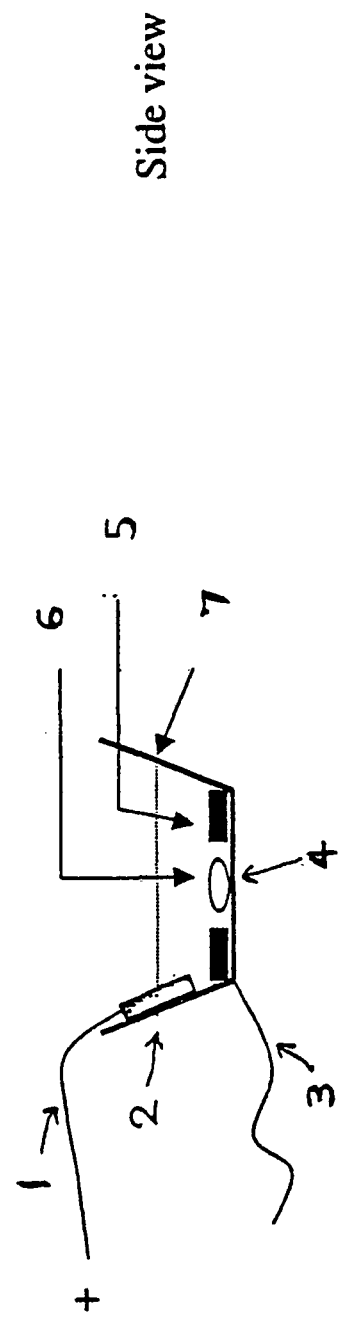
FIG. 2B shows a cross-sectional side view of one of the wells in FIG. 2A. The well has a first electrode 1 (here shown as a positive electrode) on the side 2 of the well, a second electrode 3 (here shown as a negative electrode) on the bottom 4 of the well, a strip of an optional insulating material 5 on the bottom of the well, and a cell 6 at the bottom of the well. A single cell is shown merely for convenience of illustration; in most cases a plurality of cells would be in the bottom of the well. The sides 2 of the well are made of a non-conducting material such as plastic and the bottom of the well is made from a conducting material such as indium tin oxide (ITO). The well is shown with a fluid level 7 sufficient to completely cover the cell 6 and the second electrode 3 at the bottom 4 of the well and to reach the first electrode 1 on the side 2 of the well. The well is not drawn to scale with respect to FIG. 2A.

FIG. 2B illustrates an embodiment of the invention where the wells are cavities or depressions in the surface of the substrate, as in typical multiwell tissue culture plates. Each well has an electrode at the bottom of the well and another electrode that is aligned along a side of the well. The cells are shown in FIG. 2B as attached at the bottom of the well but in certain embodiments the cells may be suspension cells dispersed in the fluid in the well.

Figure 2C:
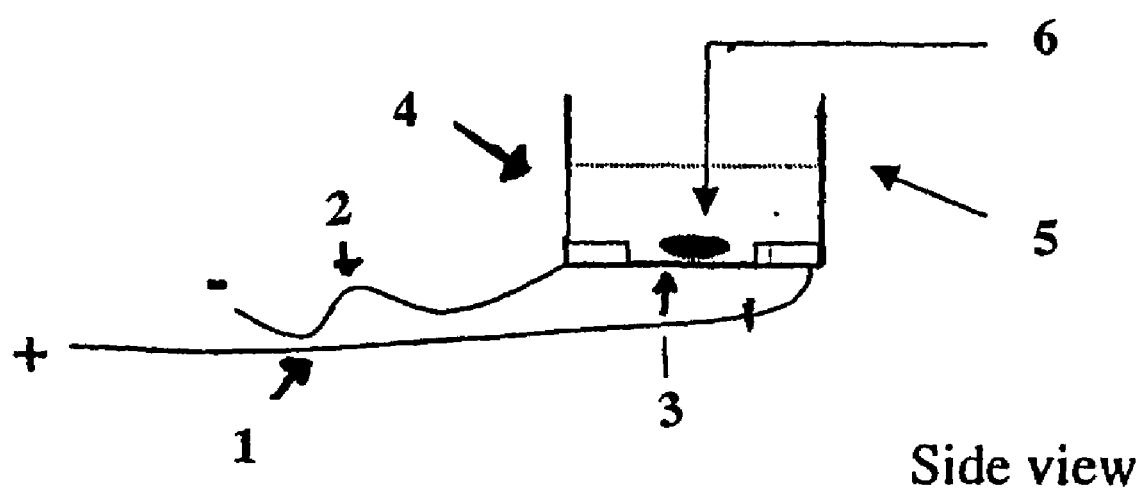
FIG. 2C shows an alternative arrangement of electrodes in a well. In this embodiment, both the positive electrode 1 and the negative electrode 2 are in the bottom 3 of the well. In this embodiment, the sides 4 and bottom 3 of the well are made of non-conducting material such as plastic. The fluid level 5 is such as to cover the cells 6 as well as the positive 1 and negative 2 electrodes.

FIG. 2C illustrates an embodiment of the invention similar to that shown in FIG. 2B except that in FIG. 2C both electrodes are at the bottom of the wells.

Figure 3:
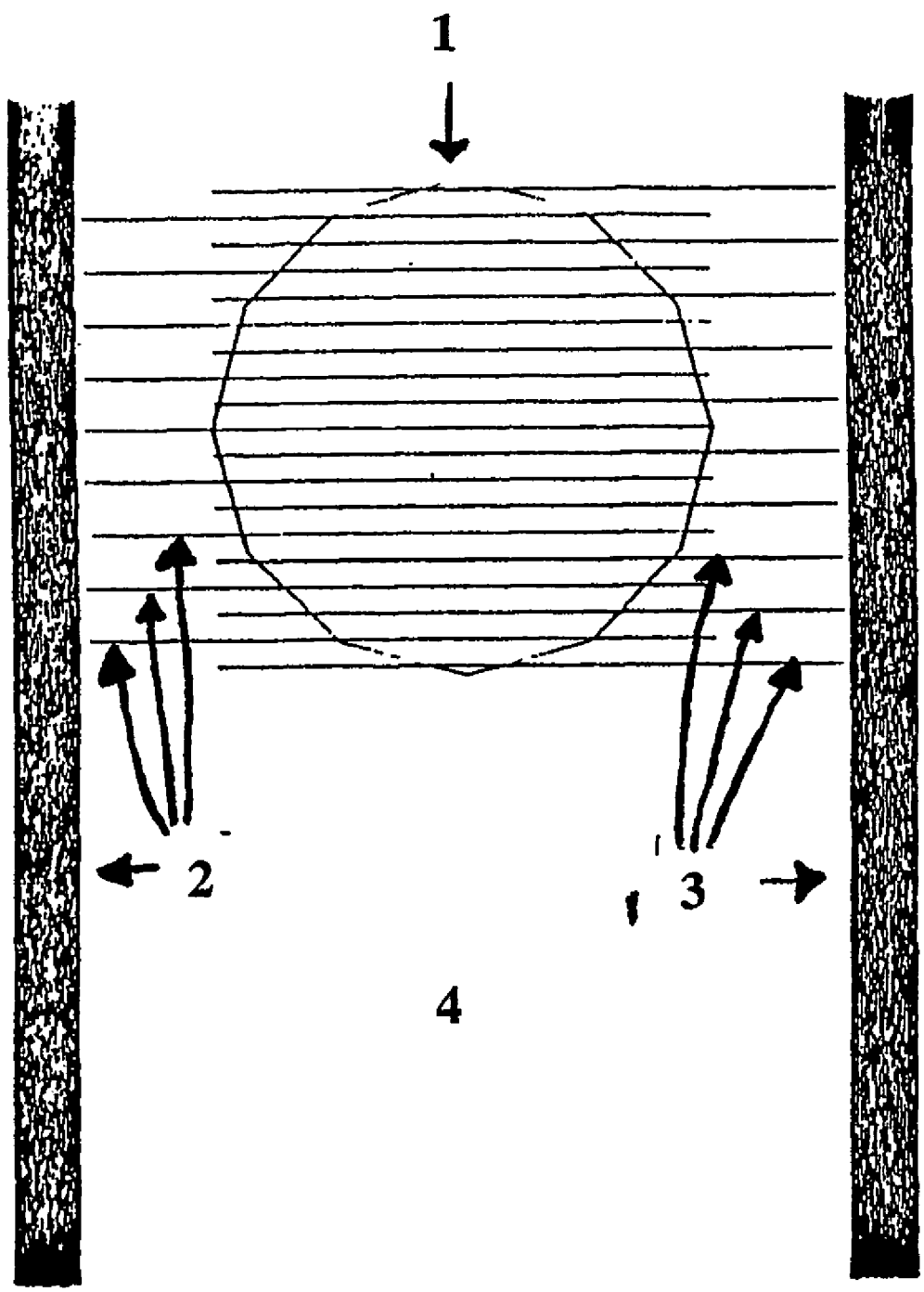
FIG. 3 shows a single well 1 from an embodiment of the invention where first 2 and second 3 electrodes are interdigitating and have been chemically etched on a layer of conductive material on the surface of a glass substrate 4. The well is generally circular with a 3 mm diameter. The electrodes are 10 μm wide and have a spacing of 160 μm. Either the first 2 or the second 3 electrodes may function as the positive electrode. The width of the electrodes and the spacing between the electrodes can be varied. The width is preferably between 1 and 10 μm; the spacing between the electrodes is preferably 5 μm to 160 μm. In particularly preferred embodiments, the spacing between the electrodes is at least as great as a typical diameter of a eukaryotic cell (i.e., about 40 μm to 50 μm).

FIG. 3 illustrates an embodiment of the invention where an array of interdigitating transparent electrodes has been chemically etched onto the surface of a glass substrate. The electrode array, comprising a comb of positive and negative electrodes, has been chemically etched onto an indium tin oxide (ITO) coated glass plate. The thin layer of ITO (about 200 Å to 2,000 Å, or 500 Å to 1,500 Å, preferably 1,200 Å thick) forms a transparent conductive coating on the surface of the glass. Although not essential, it is preferred that the layer of ITO be thin enough to be transparent. The chemical etching process removes the ITO from selected areas, resulting in an array of transparent ITO electrodes bonded to the glass. Multiple reaction wells may be contained on a single glass plate by forming fluid retention wells at the different electrode array sites. The wells can be formed by attaching (e.g., gluing) a well frame to the glass substrate or by forming virtual wells on the glass plate by a method such as screening hydrophobic ink onto the plate.

Figure 4A:
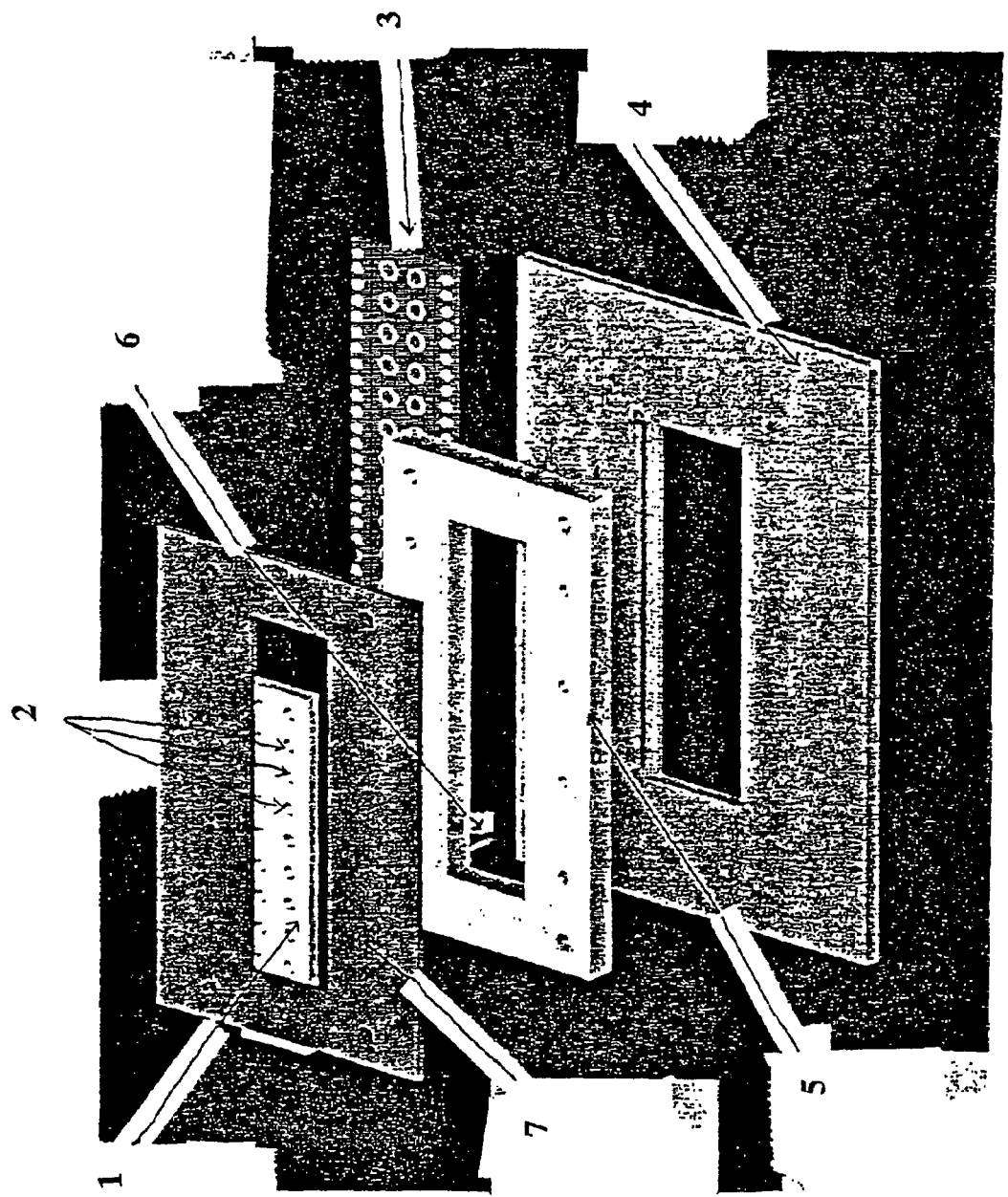
FIGS. 4A and 4B illustrates an embodiment in which wells are formed by attaching a well frame onto the substrate.
Figure 4B:
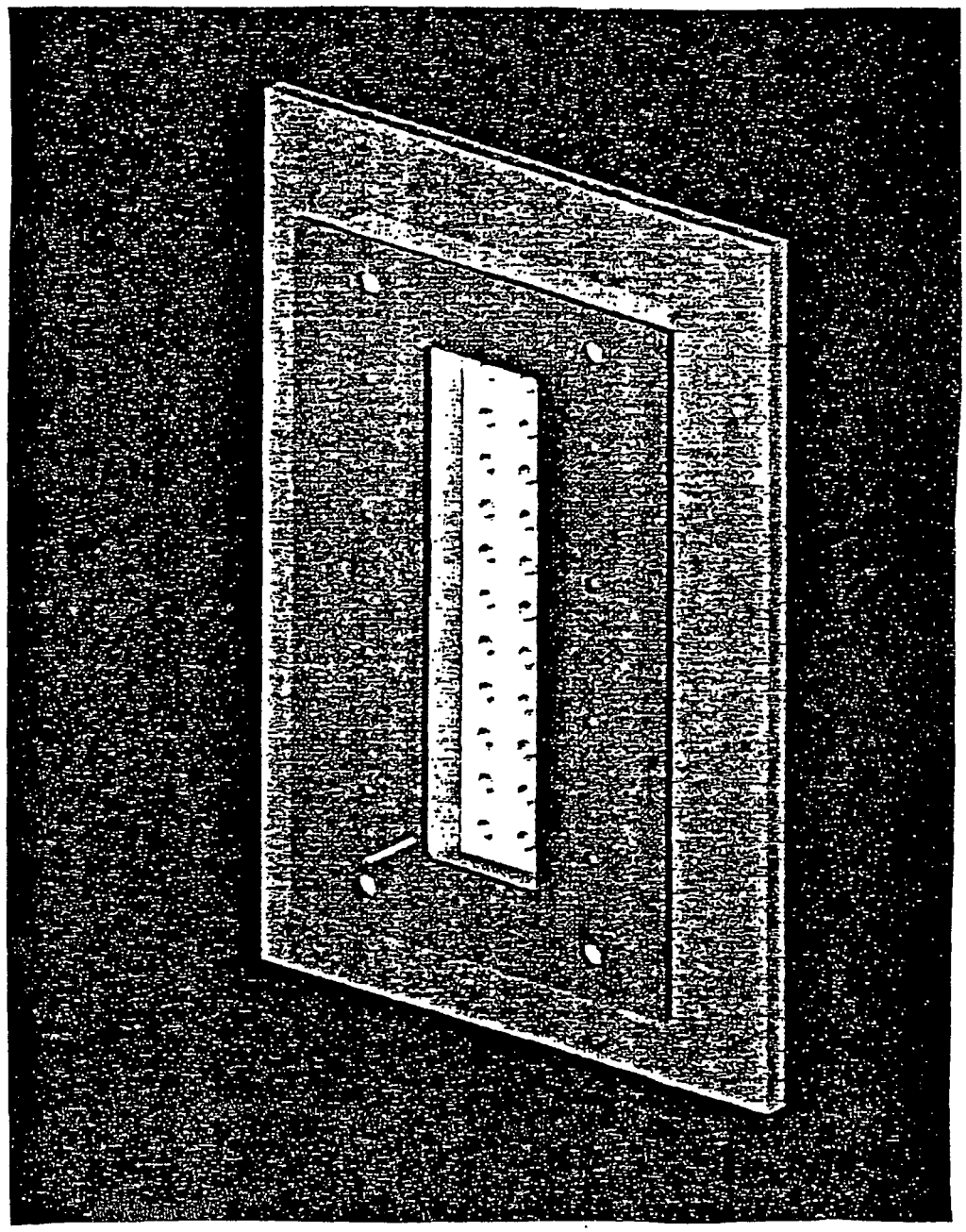

FIGS. 4A and 4B illustrates an embodiment in which wells are formed by attaching a well frame onto the substrate.

Figure 6:
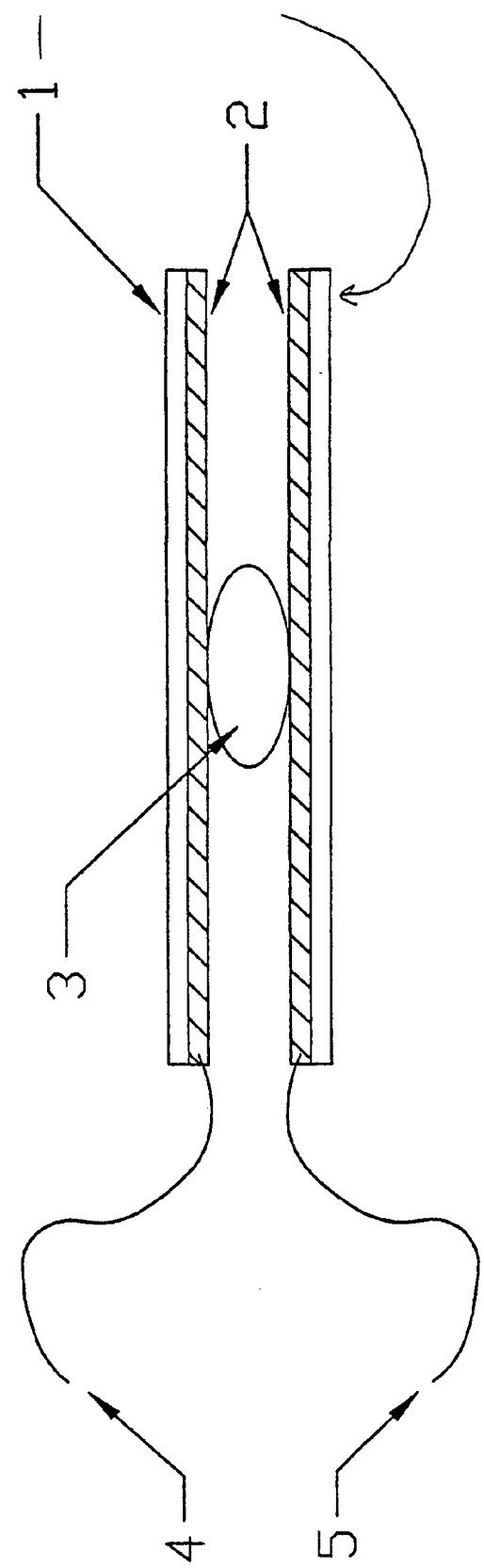
FIG. 6 shows a single well from an embodiment of the invention where two substantially parallel plates 1 have their opposing surfaces coated with conductive layers 2 between which is sandwiched a droplet of fluid containing the cells to be tested 3. One conductive layer is a positive electrode (here the upper conductive layer 4) while the other conductive layer is a negative electrode (here the lower conductive layer 5). Of course, the identity of the electrodes could be reversed, with the upper conductive layer being the negative electrode and the lower conductive layer being the positive electrode). In particular versions of this embodiment, the plates are glass and the conductive layer is indium tin oxide (ITO). The conductive layer preferably has a thickness of about 200 Å to 2,000 Å, or 500 Å to 1,500 Å, or 800 Å to 1,200 Å.

FIG. 6 illustrates an embodiment in which a droplet of fluid containing cells that express a voltage-gated ion channel is sandwiched between two plates. The plates, which can be glass plates, are each coated with a thin layer of conductive material such as indium tin oxide (ITO). The layers of conductive material are connected to a pulse generator such that one layer functions as a positive electrode and the other layer functions as a negative electrode.

Figure 7:
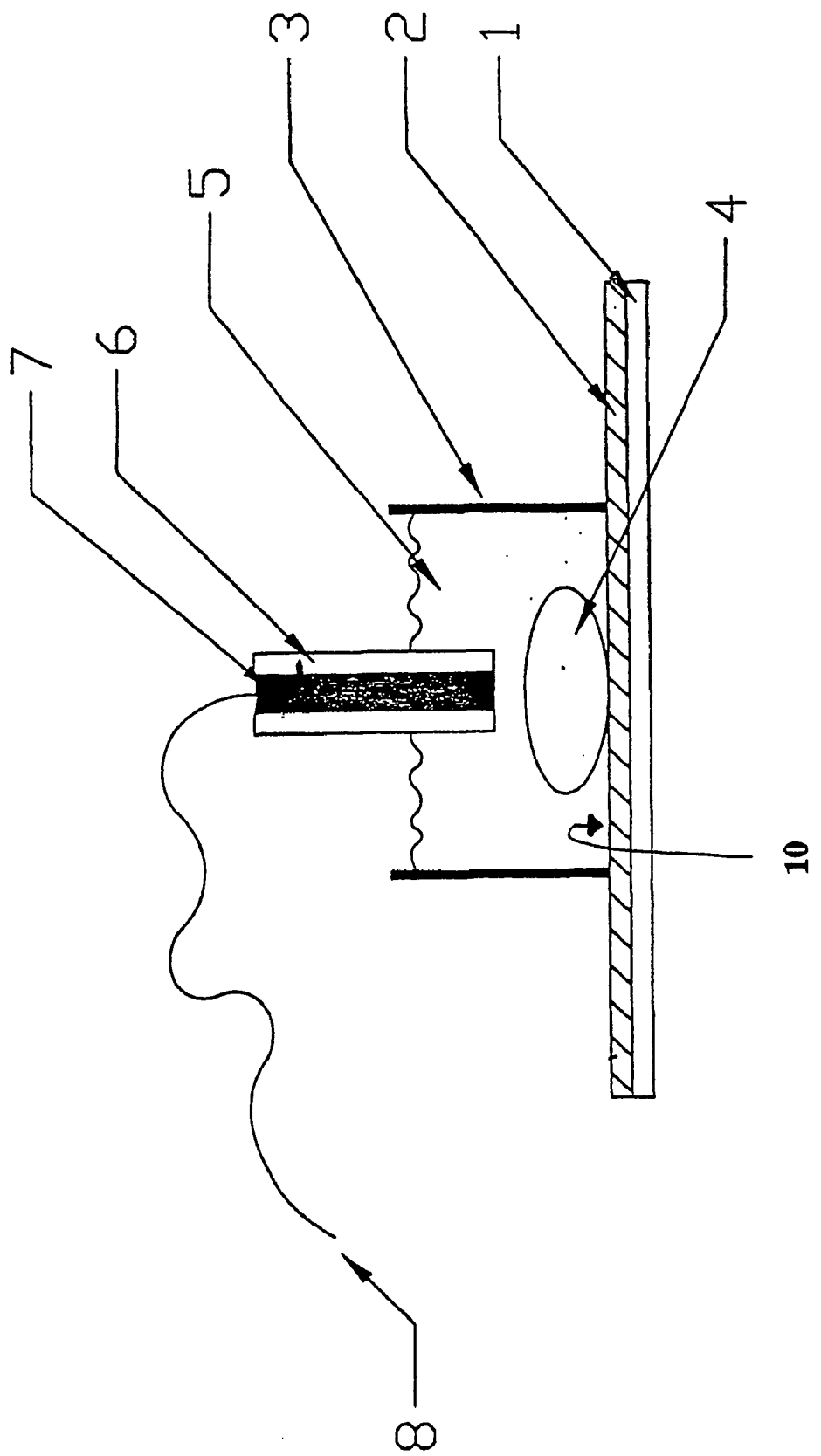
FIG. 7 shows a single well 3 from an embodiment of the invention where one of the electrodes is a thin coating of conductive material 2 on the surface of a flat substrate 1 and forms the bottom 10 of the well. The other electrode 7 enters the well 3 from above and makes contact with the fluid 5 within the well 3. Electrode 7 is shown in cut-away view. Electrode 7 contains a central conductive material portion 8 that is surrounded by an insulator 6. For the sake of simplicity, a single cell 4 is shown in the well. Generally, at least $10^5$ cells would be present in the well. The conductive layer preferably has a thickness of about 200 Å to 2,000 Å, or 500 Å to 1,500 Å, or 800 Å to 1,200 Å.
Figure 8:
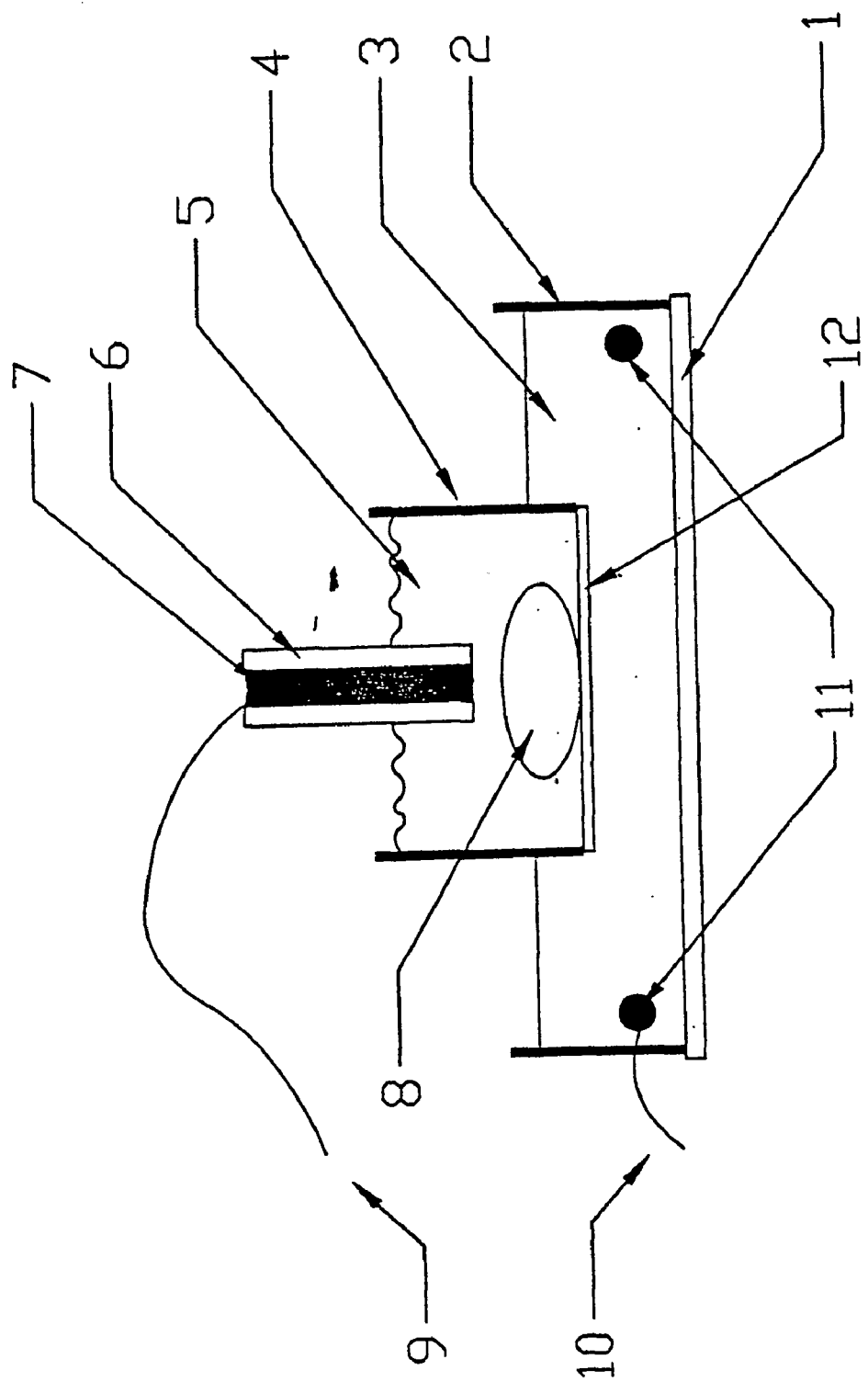
FIG. 8 shows a single well 4 from an embodiment of the invention where the bottom of the well 4 is a filter membrane 12 upon which cells can be grown. For simplicity, a single cell 8 is shown on the filter membrane 12. The well 4 is located in a trough 2 having a glass bottom 1 and filled with a first fluid 3. One electrode 7 enters the well 4 from above and makes contact with a second fluid 5 within the well 4. Electrode 7 contains a central conductive material portion that is surrounded by an insulator 6 and is connected to a pulse generator (not shown) by a first lead 9. A second electrode 11 is positioned within the first fluid 3 and is connected to the pulse generator by a second lead 10. The second electrode 11 is shown in cut-away view. The second electrode 11 actually forms a circle in the bottom of the well 4. Either the first electrode 7 is the positive electrode while the second electrode 11 is the negative electrode or the first electrode 7 is the negative electrode while the second electrode 11 is the positive electrode.
Figure 9:
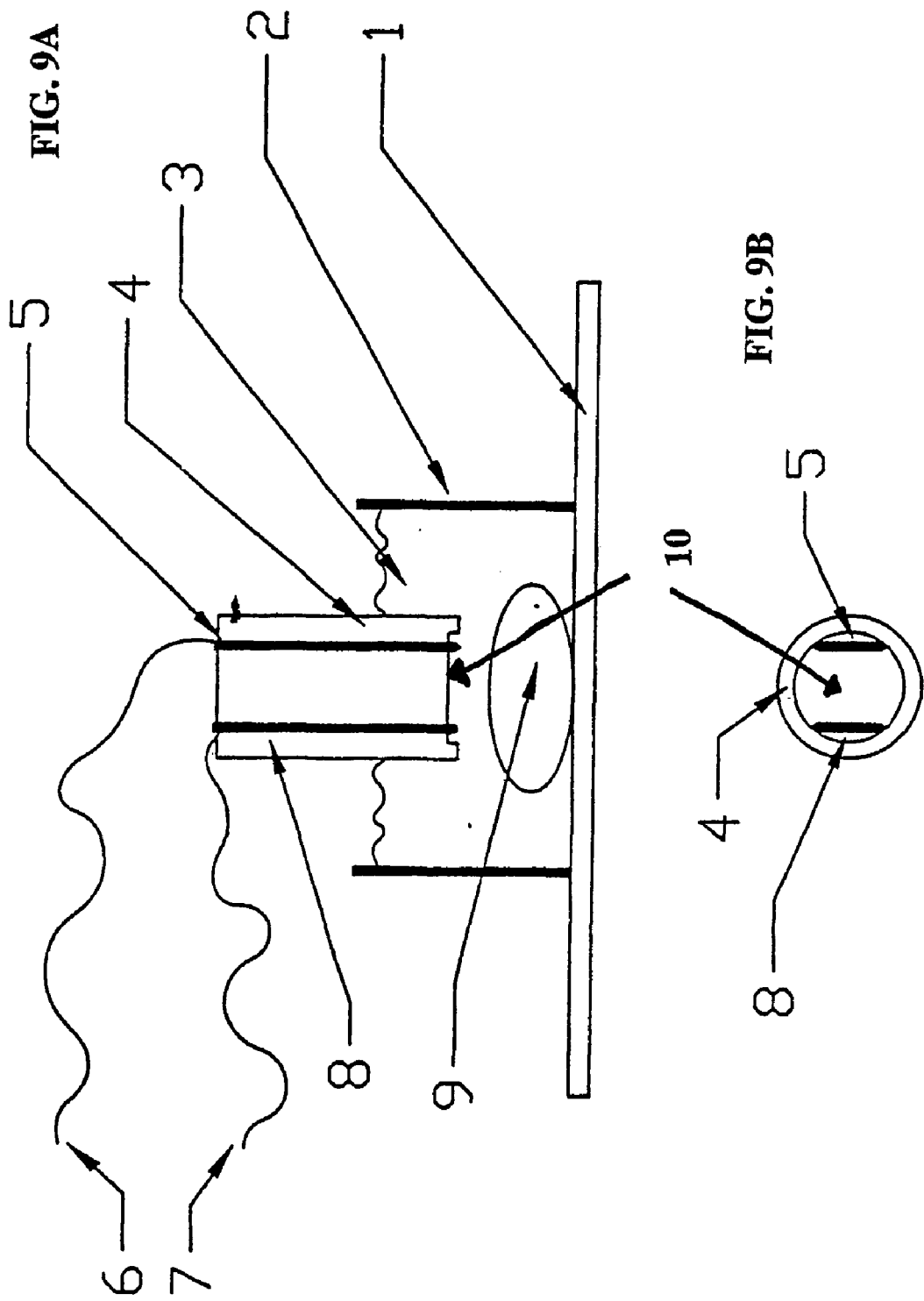
FIG. 9A shows a single well 2 from an embodiment of the invention where both the positive 5 and negative 8 electrodes enter the well 2 from above. The well 2 contains fluid 3 in which a single cell 9 is shown, although generally a plurality of cells will be present in the well 2. The positive electrode 5 is connected to a pulse generator (not shown) by a positive lead 6. The negative electrode 8 is connected to the pulse generator by a negative lead 7. Both electrodes are embedded in an insulator 4. The positive 5 and negative 8 electrodes traverse the interior of the insulator 4 such that the positive 5 and negative 8 electrodes are generally perpendicular to a glass plate 1 that forms the bottom of the well 2. However, when the positive 5 and negative 8 electrodes exit the bottom 10 of the insulator 4, the positive 5 and negative 8 electrodes are each bent into a 90° angle so that they lie on and parallel to the bottom 10 of the insulator 4.
FIG. 9B is a view looking up from the glass plate 1 that forms the bottom of the well 2 and shows the arrangement of the bent portion of the positive 5 and negative 8 electrodes lying on bottom of the insulator 4.
Figure 10:
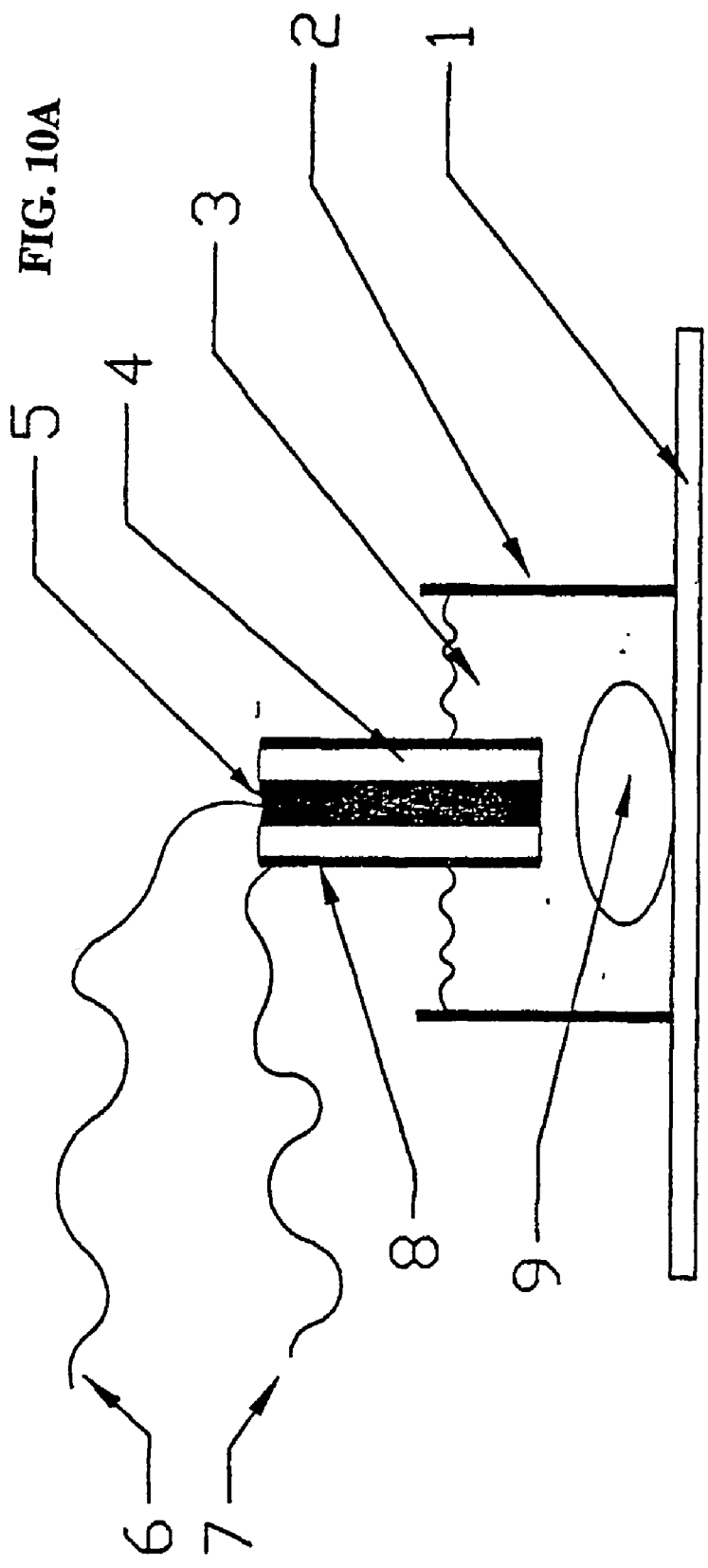
FIG. 10A shows an embodiment of the invention where both the positive 5 and negative 8 electrodes enter the well 2 from above and the positive 5 and negative 8 electrodes are arranged in a manner similar to that of a co-axial cable. The positive electrode 5 is embedded in an insulator 4 with the negative electrode 8 coating the outside of the insulator 4. The positive electrode 5 is connected to a pulse generator (not shown) by a positive lead 6. The negative electrode 8 is connected to the pulse generator by a negative lead 7. The well 2 contains fluid 3 in which a single cell 9 is shown, although generally a plurality of cells will be present in the well 2. A glass plate 1 forms the bottom of the well 2.
FIG. 10B shows a view looking up from below the positive 5 and negative 8 electrodes.
Figure 11:
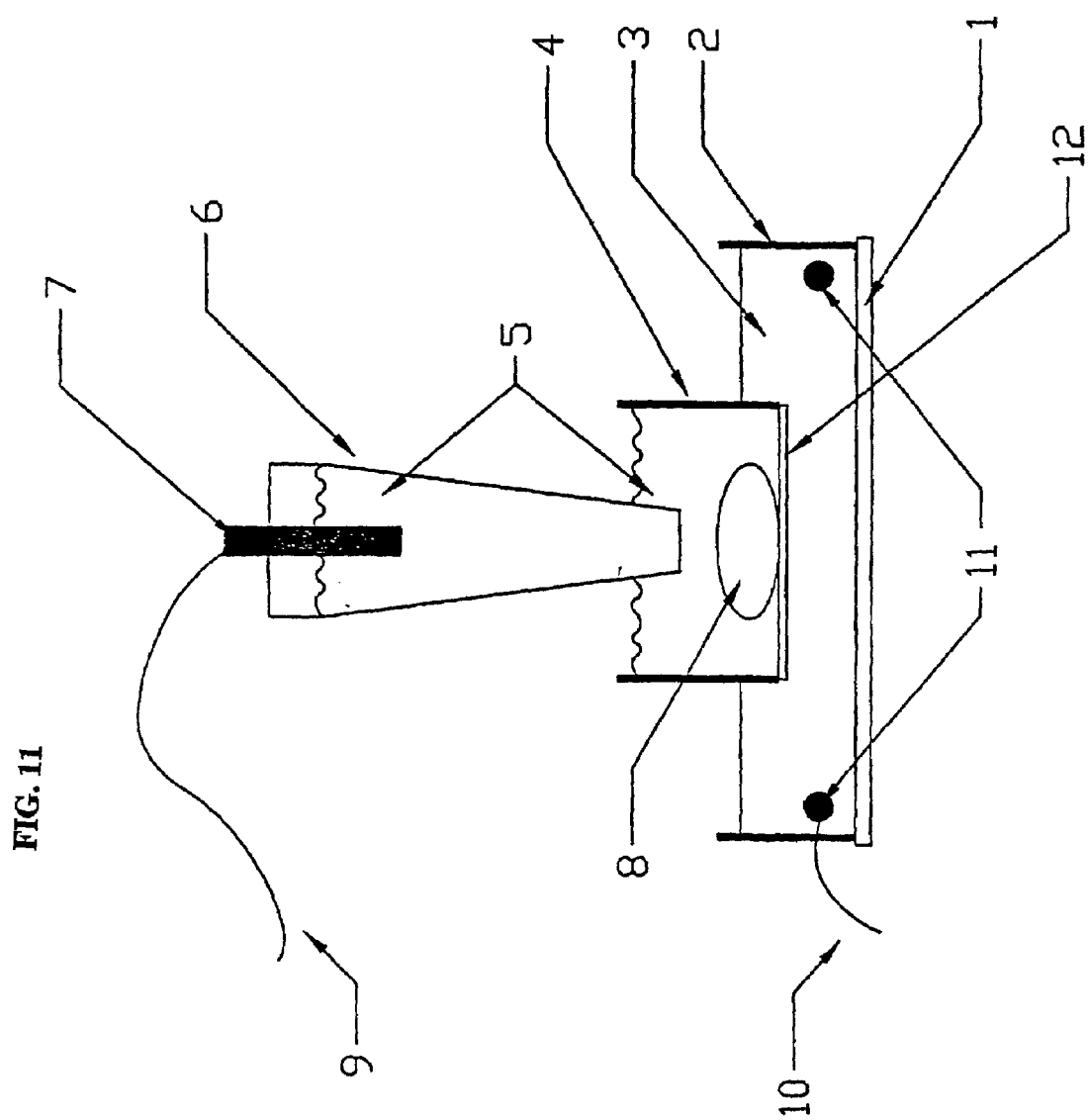
FIG. 11 shows an embodiment of the invention similar to the embodiment shown in FIG. 8 except that in FIG. 11 the electrode 7 that enters the well from above is not surrounded by an insulator but instead is within a pipette tip 6 and makes contact with a first fluid 5 also within the pipette tip 6 that is co-extensive with the first fluid 5 in the well 4. This arrangement has the advantage of minimizing the formation of bubbles in the first fluid 5 in the area at the end of the electrode 7. The bottom of the well 4 is a filter membrane 12 upon which cells can be grown. For simplicity, a single cell 8 is shown on the filter membrane 12. The well 4 sits in a trough 2 having a glass bottom 1 and filled with a second fluid 3. Electrode 7 is connected to a pulse generator (not shown) by a first lead 9. A second electrode 11 is positioned within the second fluid 3 and is connected to the pulse generator by a second lead 10. The second electrode 11 is shown in cut-away view. The second electrode 11 actually forms a circle in the bottom of the well 4. Either electrode can be the positive or negative electrode.

FIGS. 7 and 8 illustrate embodiments in which one of the electrodes enters the well from above. In FIGS. 9 and 10, both electrodes enter from above.

Figure 5:
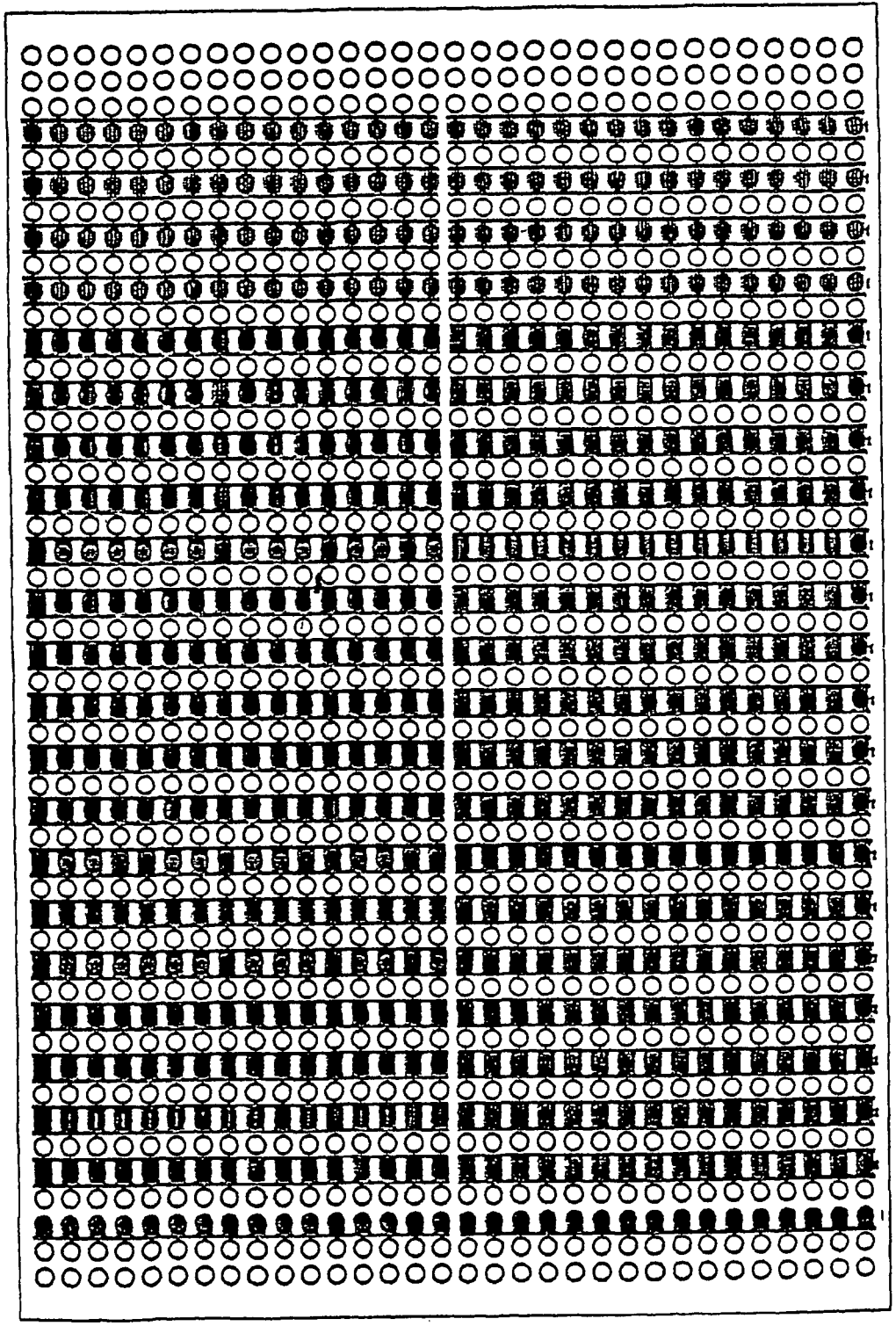
FIG. 5 shows an arrangement of interdigitating electrodes formed upon a substrate that contains virtual wells. Virtual wells are described further herein.

The substrates for use in the present invention may contain virtual wells. Virtual wells are formed when a surface is patterned to have relatively hydrophilic domains within relatively hydrophobic fields so that an aqueous sample is physically constrained by surface tension to the more hydrophilic domains by the edges of the more hydrophobic fields. The hydrophilic domains can be small circles that form a pattern similar to the wells of a conventional microtiter plate. Virtual wells provide a location in which samples can be confined without the deep indentations found in conventional microtiter plates. FIG. 5 illustrates a surface for use in the present invention that is a derivatized glass surface upon which virtual wells have been formed and upon which a pattern of interdigitated electrodes has also been formed. FIG. 3 shows an individual well from this surface. International Patent Publication WO 99/39829 describes virtual wells and how they can be made.

"Interdigitating" refers to an arrangement of positive and negative electrodes where the positive and negative electrodes contain branches that are arranged such that, if a line were drawn from one branch of a positive electrode to the adjacent branch of the positive electrode, the line would cross a branch of the negative electrode. Similarly, if a line were drawn from one branch of a negative electrode to the adjacent branch of the negative electrode, the line would cross a branch of the positive electrode. Generally, each interdigitating positive or negative electrode has at least 2, or at least 4, or at least 10, or at least 20 interdigitating branches. An example of interdigitating electrodes is shown in FIG. 3.

Various additional arrangements of electrodes formed from conductive materials on glass substrates are possible. One arrangement has the positive and negative electrodes formed on two parallel glass substrates. For example, instead of having the positive and negative electrodes on a single glass substrate, two ITO coated glass substrates can be utilized by placing the glass substrates parallel to one another and placing the biologic fluid containing the cells in the gap between the glass substrates. In this arrangement, one conductive glass substrate serves as the positive electrode while the second glass substrate serves as the negative electrode. The electrode field is formed at a right angle to the surface of the plates. This arrangement would allow fluid containing the cells to be either dispensed in between the plates or drawn into the gap via capillary action. The detector's light beam would enter perpendicular to the glass substrates and pass into the gap between the glass substrates, illuminating the fluid and cells. The fluorescence transmission from the cells would be collected by the detector in a similar manner. FIG. 6 illustrates one version of this arrangement. Another version is shown in FIG. 13 where an embodiment comprising two ITO-coated plates each containing multiple virtual wells is depicted. The ITO forms the bottom of the wells as well as the electrodes.

Figure 15:
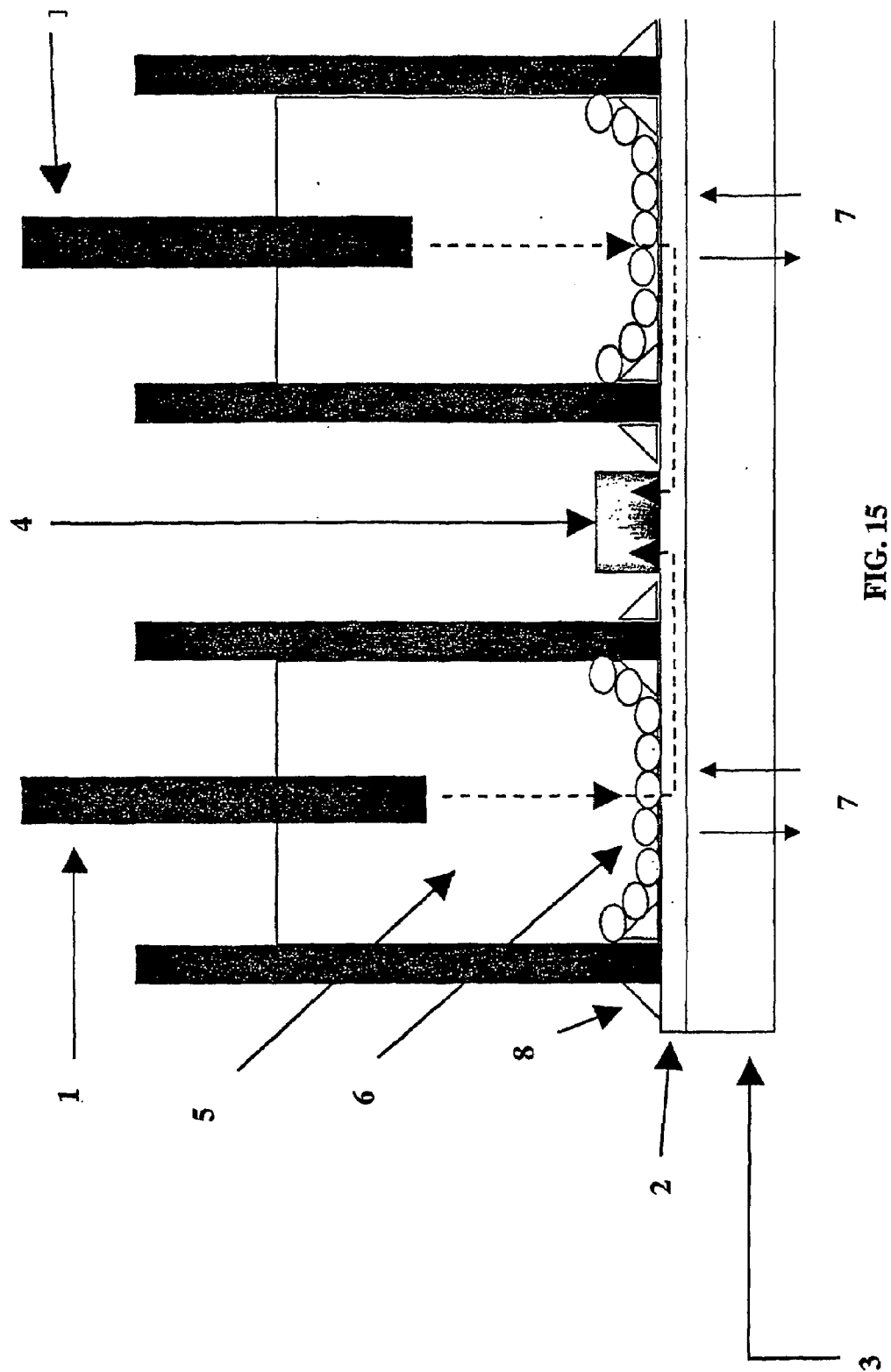
FIG. 15 shows two wells from an embodiment where one electrode enters the wells from above 1 while the second electrode is formed from the transparent ITO-coated bottom 2 of the transparent substrate 3 that is in contact with a highly conductive metal grounding grid 4. The dashed lines with arrowheads illustrate how current flows from the electrodes that enter from above 1 through a buffered salt solution 5 and the cells 6 and through the ITO layer 2 and the metal grounding grid 4. Arrows 7 within the substrate 3 illustrate how light from a source used in the detection system (not shown) would pass in the upward direction through the transparent substrate 3 and the ITO layer 2 into the cells 6 and then be re-emitted by the cells 6 as fluorescence and pass downward to a detector (not shown). Optional adhesive seals 8 that can be used to attach the wells to the ITO-coated substrate 3 are shown. The thickness of the ITO layer is preferably about 200 Å to 2,000 Å, or 500 Å to 1,500 Å, or 800 Å to 1,200 Å.

Another arrangement has the positive and negative electrodes formed by a single glass substrate and a reference electrode. This arrangement utilizes a single glass substrate coated with a conductive material such as ITO as one electrode. A well holding the biological fluid and cells is formed on the surface of the conductive material coating the glass substrate. A wire or similar conducting member placed into the well serves as the second electrode. FIG. 7 illustrates a single well of a version of this arrangement. FIG. 12 depicts this type of arrangement as it is usually practiced, in a multiwell format. FIG. 15 shows a modification of this arrangement where one electrode is a highly conductive metal grid that is in contact with the ITO layer.

Figure 16A:
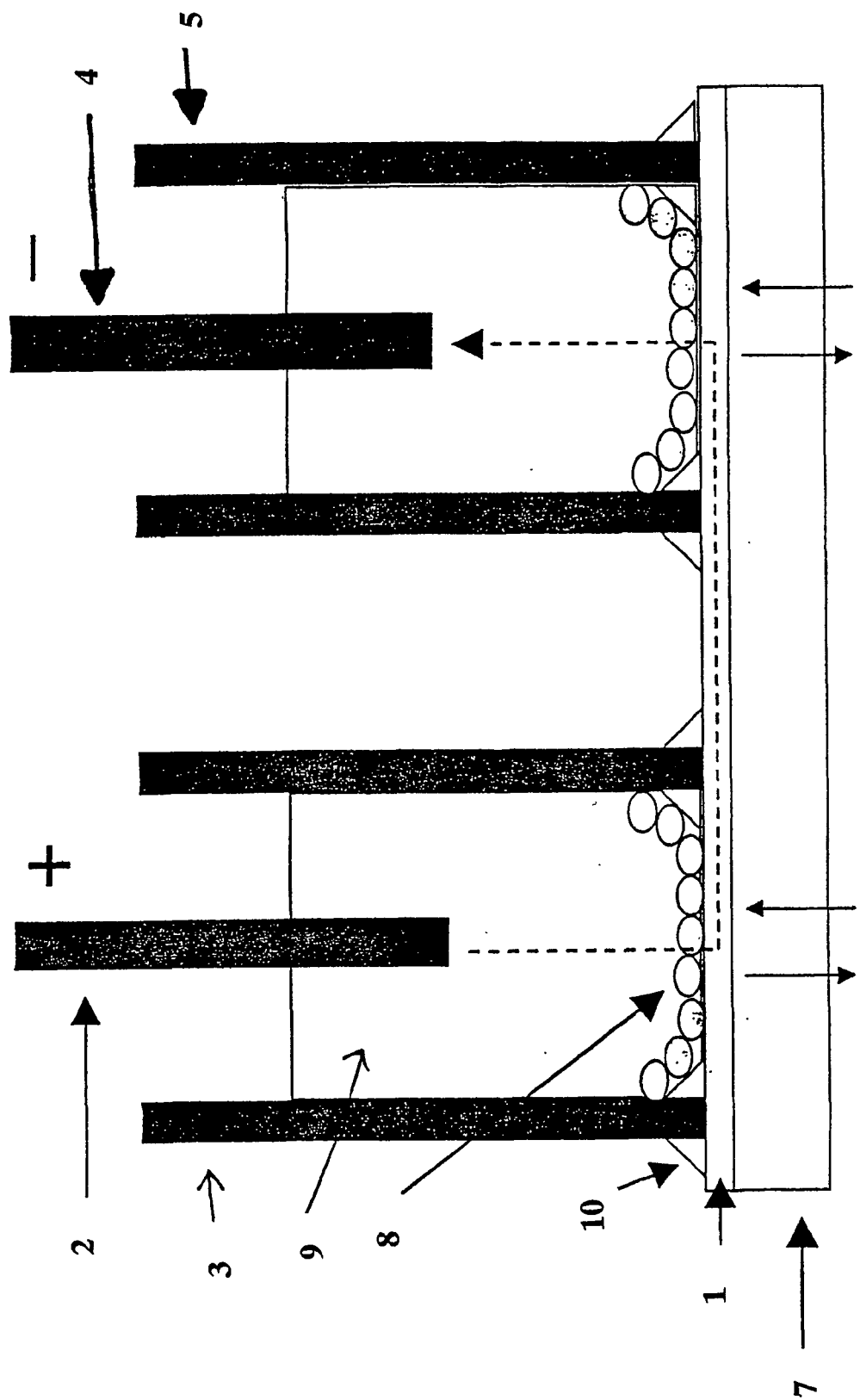
FIG. 16A shows two wells of a multiwell embodiment having a conductive layer 1 such as ITO that forms the bottom of the wells. The positive electrode 2 enters the left well 3 from above while the negative electrode 4 enters the right well 5 from above. The transparent layer of a conductive material 1 such as ITO coats a transparent substrate 7 such as glass. The dotted line with an arrowhead shows the path of current flow. Of course, the identity of the positive and negative electrodes could be reversed. Cells 8 are shown in fluid 9 within the wells. Optional adhesive seals 10 that can be used to attach the wells to the ITO-coated substrate 7 are shown. Light path is indicated by arrows in the substrate.
Figure 16D:
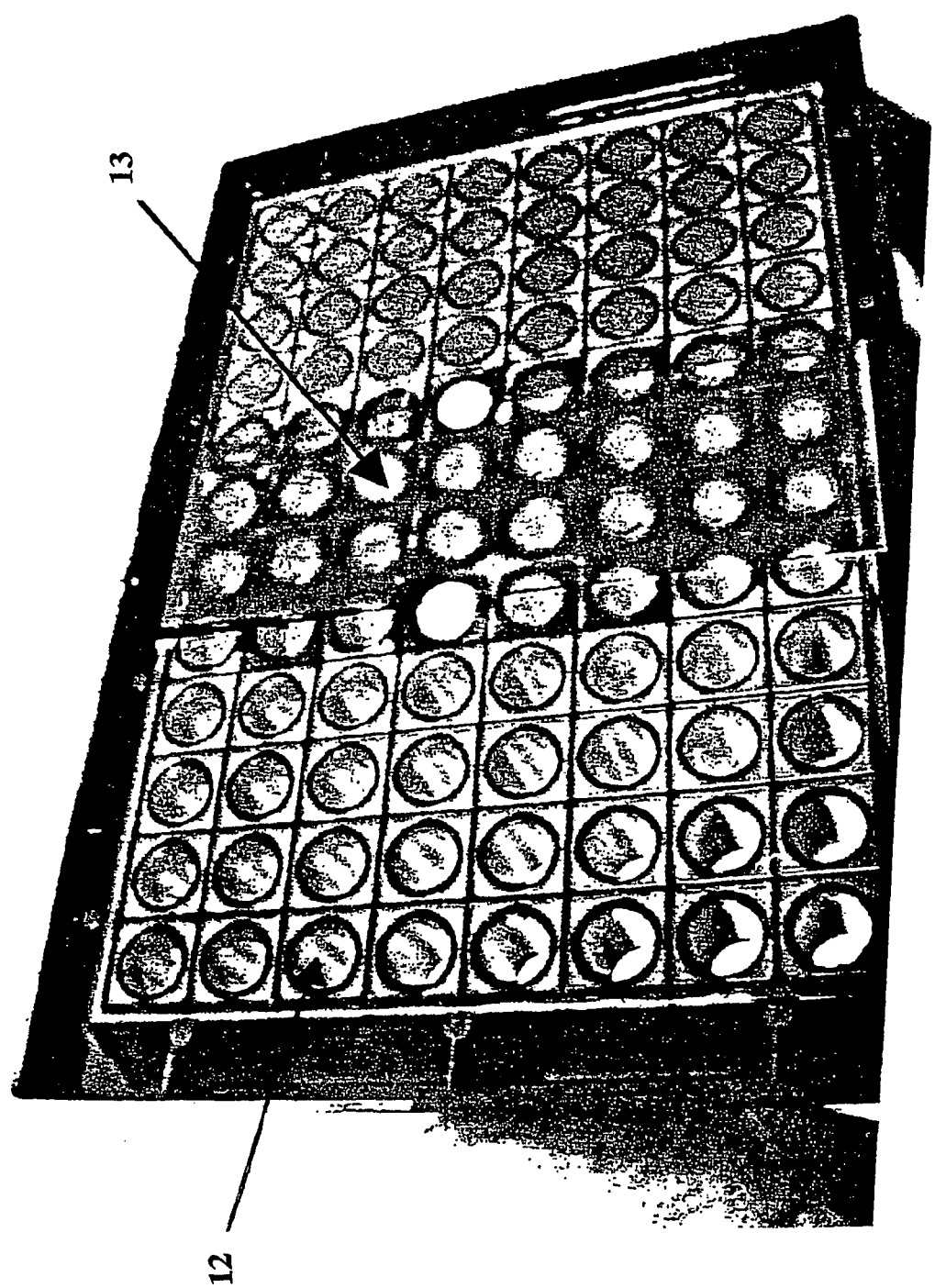
FIG. 16D is a photograph of this embodiment that has been partially disassembled. The wells are formed by a well frame 12 that is attached to the glass substrate 13 that is has been coated with ITO. During normal operation, the substrate will cover all the wells. For the purpose of illustration, this view shows only part of the substrate.
Figure 17:
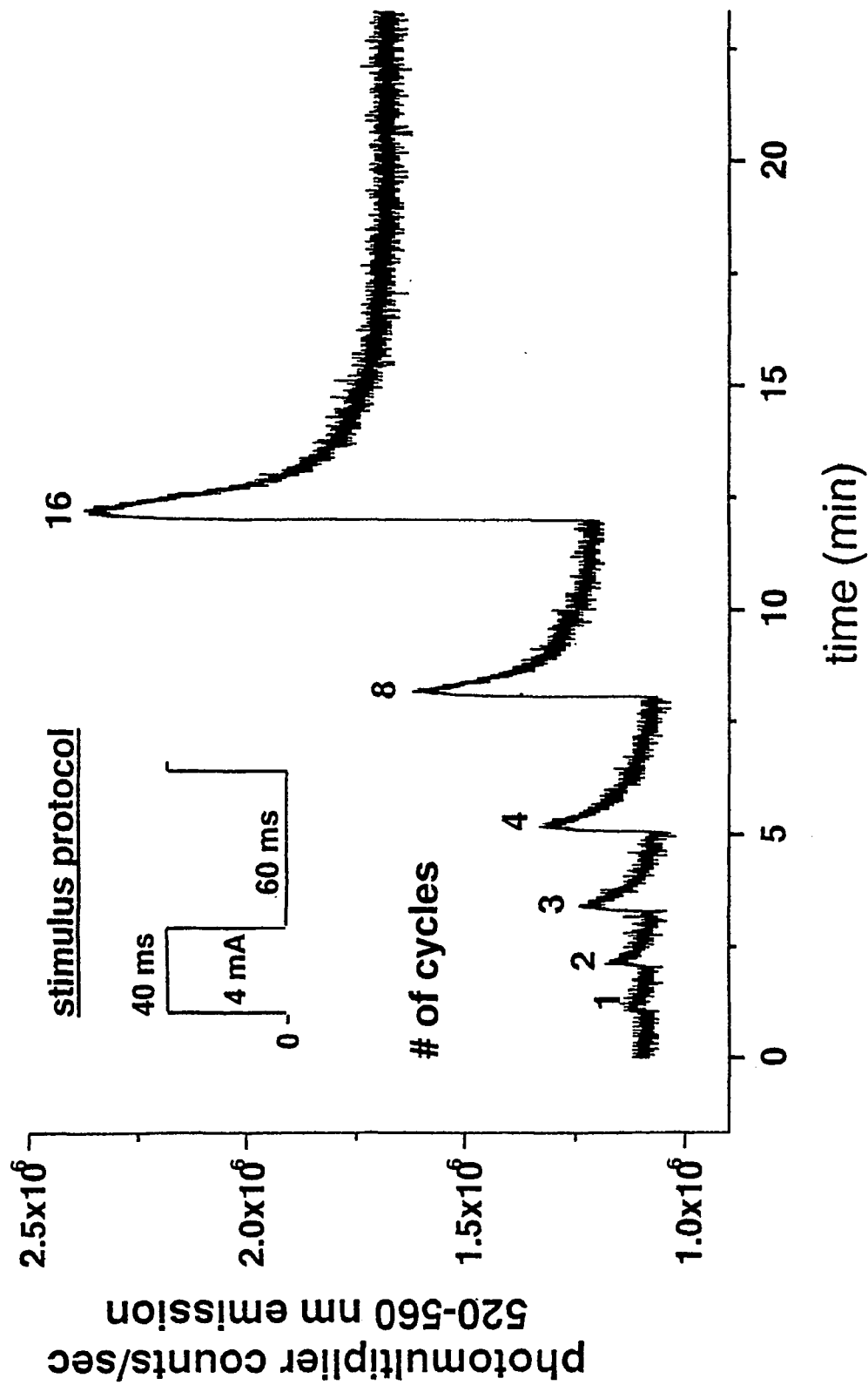
FIG. 17 shows a graphical representation of data obtained from an embodiment of the invention similar to that depicted in FIG. 16. The data represent $Ca^{2+}$ influx into HEK293 cells that have been transfected to express the human α1H T-type voltage-gated calcium channel (GenBank accession no. AF073931). $Ca^{2+}$ influx occurred when the T-type channels opened and was measured by detecting fluorescent emission at 520-560 nm of the calcium indicator dye Fluo4 that had been excited at 480 nm. At the time points indicated, a preselected voltage was applied through the electrodes. This resulted in the opening of a portion of the T-type channels, allowing $Ca^{2+}$ influx. This caused a spike in the fluorescent emission at 520-560 nm by the calcium indicator dye Fluo4. The spice gradually decayed, as shown.

Another arrangement has the single conductive glass substrate acting as the conductor to the current generated by a positive and negative electrode pair placed in adjacent wells. See FIG. 16A-D. This arrangement does not use a grounding grid. The current flows from a first electrode in a first well through the ITO bottom of the first well to the ITO bottom of an adjacent second well and through a second electrode in the second well. Adjacent electrodes are alternately positive and negative. See FIGS. 16A and 16C.

In certain embodiments using interdigitating electrodes, the spacing and width of the branches of the electrodes are on the same order of magnitude as the size of individual cells. Cells may be grown and attached to the substrate in such a manner that, if a cell attaches between a pair of positive and negative electrode branches, a lower applied stimulus pulse can be utilized. The advantage of this close electrode spacing is that it results in less shunting of the stimulus current pulse through the fluid medium and less fluid heating while stimulating the cells. The use of transparent interdigitating electrodes offers the advantage of passing light from a fluorescent emission light source through the preferably glass substrate and transparent electrodes onto the cell and light passage of the fluorescence signal back to the light detector. While making the electrodes from a transparent material such as indium tin oxide (ITO) has advantages in certain embodiments, the electrodes may also be made from non-transparent conductive materials such as platinum, silver, or gold. If the electrode material is not transparent, fluorescence measurements are still possible because light can pass through the glass in between the electrodes.

Regardless of the arrangement of electrodes, stimulus pulses are generated by a pulse generator and applied to either a single well electrode array or to multiple well electrode arrays. Various commercial pulse generators can be utilized that permit waveform generation and amplitude adjustment. Constant voltage or constant current waveforms can be applied to the electrodes. Commercially available power supplies that can be used in the present invention include the STG 1004 or STG 1008 Stimulus Generator or the National Instruments PCI 6713 8 channel pcb.

In using the pulse generator to stimulate the cells, particular attention should be paid to the amplitude, pulse width, and polarity used. For certain extreme field strengths, electroporation of the biological membrane can occur, and this should be avoided. When changing the external electrical field, the desired goal is a change in the trans-membrane field (Vm) by less than approximately ±100 mV. As such the amount of charge added or removed from the cell membrane capacitance is critical. Adjustment of the pulse amplitude and duration is necessary to ensure a change in Vm without electroporation of the cells. Typically the voltage changes across the electrodes may be on the order of ±10 volts, preferably less than ±5 volts, and if possible less than ±1 volt. These values can be adjusted empirically, by routine experimentation, in order to optimize the cellular membrane potential change without electroporation of the cell membrane. In general, the amount of charge change on the cell membrane will depend upon the local field changes, which depend upon the electrical current. Adjusting the area (the current-time integral) of the applied current as determined by the change in external electric field can be readily optimized empirically. In general, if the goal is to stimulate a cellular action potential, the pulse duration will be kept brief and the amplitude will be increased up to a point that exceeds the threshold for action potential generation. This will be affected by the relative levels of ion channels expressed in the cells and will vary accordingly, requiring empirical adjustment. A typical value might be a pulse duration of 1 millisecond and a pulse amplitude of 5 volts; this might be varied to increase the duration to 2 milliseconds and decrease the amplitude to 2.5 volts, or to decrease the duration and increase the amplitude, etc. In general, there is an inverse parabolic relationship between the duration and the amplitude of the applied pulse, where the area of the applied current-time integral remains constant. Because ion channel kinetics and action potentials can be rapid and brief, minimizing the pulse duration is useful. These parameters will also depend upon the manufactured electrodes, their capacitance and resistance, the geometrical relationship to the cells, the ionic strength and composition of the solutions used, and the electrical coupling to the cells. Because of these many variables, an empirical approach based upon the above guidelines is best.

Electrode arrangements can be adapted to 12-well, 24-well, 96-well, 384-well, 1,536-well, 3,456-well, and other plate formats, permitting the present invention to be used in high throughput screening applications.

In embodiments of the invention such as that illustrated in FIG. 12 where multiple wells are present in the substrate and each well has an electrode associated with it, the stimulus delivered to each well through the electrodes can be individually controlled by the application of suitable software that governs the pulse generator. Such software is well known in the art or can be readily designed by one skilled in the art.

Particular embodiments of the present invention employ an arrangement of electrodes and wells on a substrate such that the substrate has the same form factor as a typical multiwell tissue culture plate that is used for high throughput screening, e.g., a 96 well plate. The spacing of the wells on the substrate can be such that the center-to-center distances of the wells on the substrate is the same as the typical center-to-center distances between wells on typical 96 well plates that are used for high throughput screening. This facilitates the use of the present invention with current equipment used in high throughput screening such as plate handlers, detectors, automatic pipettors, etc. Substrates can be manufactured by modifying the well-known manufacturing processes generally used to make multiwell tissue culture plates by adding electrodes to the plates according to one of the configurations of electrodes disclosed herein.

In particular embodiments of the present invention, the substrate is not silicon or a field effect transistor.

In particular embodiments of the present invention, cells are utilized that have been transfected with expression vectors comprising DNA that encodes a voltage-gated ion channel. Preferably, the cells do not naturally express corresponding voltage-gated ion channels. For example, if the expression vectors direct the expression of a voltage-gated calcium channel, the cells will not naturally express voltage-gated calcium channels. Alternatively, if the cells naturally express corresponding voltage-gated ion channels, those corresponding voltage-gated ion channels can be distinguished from the transfected voltage-gated ion channels in some manner, e.g., by the use of appropriate inhibitors, by manipulation of membrane potential. A preferred cell line for use in the present invention is the HEK293 cell line (ATCC 1573) since this cell line naturally expresses endogenous potassium channels, which may be beneficial for electrical field stimulation experiments with channels that cause membrane potential depolarization (e.g., sodium or calcium channels).

Cells are generally eukaryotic cells, preferably mammalian cells. The cells may be grown to the appropriate number on the substrates or they may be placed on the substrate and used without further growth. The cells may be attached to the substrate or, in those embodiments where the cells are placed or grown in wells, the cells may be suspension cells that are suspended in the fluid in the wells. Primary cells or established cell lines may be used.

Suitable cells for transfection with expression vectors that direct the expression of voltage-gated ion channels include but are not limited to cell lines of human, bovine, porcine, monkey and rodent origin. The cells may be adherent or non-adherent. Cells and cell lines which are suitable and which are widely available, include but are not limited to: L cells L-M(TK⁻) (ATCC CCL 1.3), L cells L-M (ATCC CCL 1.2), BEK293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), CPAE (ATCC CCL 209), Saos-2 (ATCC HTB-85), ARPE-19 human retinal pigment epithelium (ATCC CRL-2302), GH3 cells, and primary cardiac myocytes.

A variety of voltage-gated ion channels may be used in the present invention. For example, voltage-gated sodium channels, voltage-gated potassium channels, and voltage-gated calcium channels are suitable.

In certain embodiments of the present invention, the cells used do not naturally express the voltage-gated ion channel of interest. Instead, DNA encoding the voltage-gated ion channel is transfected into cells in order to express the voltage-gated ion channel in the plasma membrane of the cells. DNA encoding voltage-gated ion channels can be obtained by methods well known in the art. For example, a cDNA fragment encoding a voltage-gated ion channel can be isolated from a suitable cDNA library by using the polymerase chain reaction (PCR) employing suitable primer pairs. The cDNA fragment encoding the voltage-gated ion channel can then be cloned into a suitable expression vector. Primer pairs can be selected based upon the known DNA sequence of the voltage-gated ion channel it is desired to obtain. Suitable cDNA libraries can be made from cellular or tissue sources known to contain mRNA encoding the voltage-gated ion channel.

One skilled in the art would know that for certain voltage-gated ion channels, it is desirable to transfect, and thereby express, more than one subunit in order to obtain a functional voltage-gated ion channel. For example, N-type calcium channels are composed of a multisubunit complex containing at least an α1B, an α2δ, and a β1 subunit. On the other hand, T-type calcium channels are functional with only a single subunit, e.g., α1G, α1H, or α1I. Common knowledge in the art of the subunit composition of a voltage-gated ion channel of interest will lead the skilled artisan to express the correct subunits in the transfected cells.

One skilled in the art could use published voltage-gated ion channel sequences to design PCR primers and published studies of voltage-gated ion channel expression to select the appropriate sources from which to make cDNA libraries in order to obtain DNA encoding the voltage-gated ion channels. The following publications may be of use in this regard:

U.S. Pat. No. 5,380,836 describes nucleic acid sequences encoding a rat cardiac voltage-gated sodium channel;

U.S. Pat. No. 6,030,810 describes a number of voltage-gated, tetrodotoxin-sensitive sodium channels;

U.S. Pat. No. 6,184,349 B1 discloses a human tetrodotoxin-resistant peripheral nerve voltage-gated sodium channel known as PN3; see also GenBank accession no. AF117907;

Isom et al., 1994, Neuron 12:1183-1194 discloses a rat voltage-gated sodium channel β subunit;

McClatchey et al., 1993, Hum. Molec. Gen. 2:745-749 discloses a human voltage-gated sodium channel β1 subunit (hSCNβ1);

Isom et al., Science, 1992, 256:839-842 discloses a rat brain voltage-gated sodium channel β1 subunit (rSCNβ1);

Misgeld et al., 1995, Prog. Neurobiol. 46:423-462; North, 1989, Br. J. Pharmacol. 98:13-23; Gahwiler et al., 1985, Proc. Natl. Acad. Sci USA 82:1558-1562; and Andrade et al., 1986, Science 234:1261-1265 disclose inwardly rectifying voltage-gated potassium channels that are suitable for use in the methods of the present invention.

U.S. Pat. Nos. 5,874,236 and 5,429,921 describe various α1 and β subunits of human voltage-gated calcium channels;

U.S. Pat. Nos. 5,407,820 and 5,710,250 describe α2 subunits of human voltage-gated calcium channels;

International Patent Publication WO 98/13490 describes a brain-specific P/Q-type human voltage-gated calcium channel involved in familial hemiplagic migraine;

Table 1 provides a list of ion channel genes that are suitable for use in the present invention.

TABLE 1

Some ion channel genes of interest for EFS experiments

| Symbol | Full Name | Cytogenetic Location | MIM Number | PubMed ID |
|---|---|---|---|---|
| SCN1 | symbol withdrawn, see SCN1A | | | |
| SCN1A | sodium channel, voltage-gated, type I, alpha polypeptide | 2q24 | 182389 | 8062593 |
| SCN1B | sodium channel, voltage-gated, type I, beta polypeptide | 19 | 600235 | 8394762 |
| SCN2A1 | sodium channel, voltage-gated, type II, alpha 1 polypeptide | 2q22-q23 | 182390 | 1317301 |
| SCN2A2 | sodium channel, voltage-gated, type II, alpha 2 polypeptide | 2q23-q24 | 601219 | 1317301 |
| SCN2A | symbol withdrawn, see SCN2A1 | — | | |
| SCN2B | sodium channel, voltage-gated, type II, beta polypeptide | 11q22-qter | 601327 | 10198179 |
| SCN3A | sodium channel, voltage-gated, type III, alpha polypeptide | 2q24 | 182391 | 9589372 |
| SCN4A | sodium channel, voltage-gated, type IV, alpha polypeptide | 17q23-q25.3 | 603967 | 1654742 |
| SCN4B | sodium channel, voltage-gated, type IV, beta polypeptide | reserved | | |
| SCN5A | sodium channel, voltage-gated, type V, alpha polypeptide (long (electrocardiographic) QT syndrome 3) | 3p21 | 600163 | |
| SCN6A | sodium channel, voltage-gated, type VI, alpha polypeptide | 2q21-q23 | 182392 | 10198179 |
| SCN7A | symbol withdrawn, see SCN6A | — | | |
| SCN8A | sodium channel, voltage gated, type VIII, alpha polypeptide | 12q13.1 | 600702 | 7670495 |
| SCN9A | sodium channel, voltage-gated, type IX, alpha polypeptide | 2q24 | 603415 | 7720699 |
| SCN10A | sodium channel, voltage-gated, type X, alpha polypeptide | 3p21-p22 | 604427 | 9839820 |
| SCN11A | sodium channel, voltage-gated, type XI, alpha polypeptide | 3p21-p24 | 604385 | 10444332 |
| SCN12A | sodium channel, voltage-gated, type XII, alpha polypeptide | 3p23-p21.3 | | 10623608 |
| SCNN1 | symbol withdrawn, see SCNN1A | — | | |
| SCNN1A | sodium channel, nonvoltage-gated 1 alpha | 12p13 | 600228 | 7896277 |
| SCNN1B | sodium channel, nonvoltage-gated 1, beta (Liddle syndrome) | 16p12.2-p12.1 | | 600760 |
| SCNN1D | sodium channel, nonvoltage-gated 1, delta | 1p36.3-p36.2 | 601328 | 8661065 |
| SCNN1G | sodium channel, nonvoltage-gated 1, gamma | 16p12 | 600761 | 7490094 |
| CACNA1A | calcium channel, voltage-dependent, P/Q type, alpha 1A subunit | 19p13 | 601011 | 8825650 |
| CACNA1B | calcium channel, voltage-dependent, L type, alpha 1B subunit | 9q34 | 601012 | 8825650 |
| CACNA1C | calcium channel, voltage-dependent, L type, alpha 1C subunit | 12pter-p13.2 | 114205 | 1650913 |
| CACNA1D | calcium channel, voltage-dependent, L type, alpha 1D subunit | 3p14.3 | 114206 | 1664412 |
| CACNA1E | calcium channel, voltage-dependent, alpha 1E subunit | 1q25-q31 | 601013 | 8388125 |
| CACNA1F | calcium channel, voltage-dependent, alpha 1F subunit | Xp11.23-p11.22 | 300110 | 9344658 |
| CACNA1G | calcium channel, voltage-dependent, alpha 1G subunit | 17q22 | 604065 | 9495342 |
| CACNA1H | calcium channel, voltage-dependent, alpha 1H subunit | 16p13.3 | | 9670923 |
| CACNA1I | calcium channel, voltage-dependent, alpha 1I subunit | 22q12.3-13.2 | | 10454147 |
| CACNA1S | calcium channel, voltage-dependent, L type, alpha 1S subunit | 1q31-q32 | 114208 | 7916735 |
| CACNA2 | symbol withdrawn, see CACNA2D1 | — | | |
| CACNA2D1 | calcium channel, voltage-dependent, alpha 2/delta subunit 1 | 7q21-q22 | 114204 | 8188232 |
| CACNA2D2 | calcium channel, voltage-dependent, alpha 2/delta subunit 2 | reserved | | |
| CACNB1 | calcium channel, voltage-dependent, beta 1 subunit | 17q21-q22 | 114207 | 8381767 |
| CACNB2 | calcium channel, voltage-dependent, beta 2 subunit | 10p12 | 600003 | 9254841 |
| CACNB3 | calcium channel, voltage-dependent, beta 3 subunit | 12q13 | 601958 | 8119293 |
| CACNB4 | calcium channel, voltage-dependent, beta 4 subunit | 2q22-q31 | 601949 | 9628818 |

TABLE 1-continued

Some ion channel genes of interest for EFS experiments

| Symbol | Full Name | Cytogenetic Location | MIM Number | PubMed ID |
|---|---|---|---|---|
| CACNG1 | calcium channel, voltage-dependent, gamma subunit 1 | 17q24 | 114209 | 8395940 |
| CACNG2 | calcium channel, voltage-dependent, gamma subunit 2 | reserved | 602911 | |
| CACNG3 | calcium channel, voltage-dependent, gamma subunit 3 | reserved | | |
| CACNG4 | calcium channel, voltage-dependent, gamma subunit 4 | 17q24 | | 10613843 |
| CACNG5 | calcium channel, voltage-dependent, gamma subunit 5 | 17q24 | | 10613843 |
| CACNG6 | calcium channel, voltage-dependent, gamma subunit 6 | 19q13.4 | | 11170751 |
| CACNG7 | calcium channel, voltage-dependent, gamma subunit 7 | 19q13.4 | | 11170751 |
| CACNG8 | calcium channel, voltage-dependent, gamma subunit 8 | 19q13.4 | | 11170751 |
| KCNA1 | potassium voltage-gated channel, shaker-related subfamily, member 1 (episodic ataxia with myokymia) | 12p13 | 176260 | 1349297 |
| KCNA1B | literature alias, see KCNAB1 | — | | |
| KCNA2 | potassium voltage-gated channel, shaker-related subfamily, member 2 | 12 | 176262 | |
| KCNA2B | literature alias, see KCNAB2 | — | | |
| KCNA3 | potassium voltage-gated channel, shaker-related subfamily, member 3 | 1p13.3 or 13 | 176263 | 2251283 |
| KCNA3B | literature alias, see KCNAB3 | — | | |
| KCNA4 | potassium voltage-gated channel, shaker-related subfamily, member 4 | 11p14 | 176266 | 2263489 |
| KCNA4L | potassium voltage-gated channel, shaker-related subfamily, member 4-like | 11q14 | | 8449523 |
| KCNA5 | potassium voltage-gated channel, shaker-related subfamily, member 5 | 12 | 176267 | |
| KCNA6 | potassium voltage-gated channel, shaker-related subfamily, member 6 | reserved | 176257 | |
| KCNA7 | potassium voltage-gated channel, shaker-related subfamily, member 7 | 19 | 176268 | |
| KCNA8 | literature alias, see KCNQ1 | — | | |
| KCNA9 | symbol withdrawn, see KCNQ1 | — | | |
| KCNA10 | potassium voltage-gated channel, shaker-related subfamily, member 10 | reserved | 602420 | |
| KCNAB1 | potassium voltage-gated channel, shaker-related subfamily, beta member 1 | 3q26.1 | 601141 | 8838324 |
| KCNAB2 | potassium voltage-gated channel, shaker-related subfamily, beta member 2 | 1p36.3 | 601142 | 8838324 |
| KCNAB3 | potassium voltage-gated channel, shaker-related subfamily, beta member 3 | 17p13.1 | 604111 | 9857044 |
| KCNB1 | potassium voltage-gated channel, Shab-related subfamily, member 1 | 20q13.2 | 600397 | 7774931 |
| KCNB2 | potassium voltage-gated channel, Shab-related subfamily, member 2 | 8 | | 9612272 |
| KCNC1 | potassium voltage-gated channel, Shaw-related subfamily, member 1 | 11p15 | 176258 | 8449507 |
| KCNC2 | potassium voltage-gated channel, Shaw-related subfamily, member 2 | 12 and 19q13.4 | 176256 | 8111118 |
| KCNC3 | potassium voltage-gated channel, Shaw-related subfamily, member 3 | 19 | 176264 | 1740329 |
| KCNC4 | potassium voltage-gated channel, Shaw-related subfamily, member 4 | 1p21 | 176265 | 1920536 |
| KCND1 | potassium voltage-gated channel, Shal-related subfamily, member 1 | Xp11.23-p11.3 | 300281 | 10729221 |
| KCND2 | potassium voltage-gated channel, Shal-related subfamily, member 2 | 7q31-32 | 605410 | 10551270 |
| KCND3 | potassium voltage-gated channel, Shal-related subfamily, member 3 | 1p13.2 | 605411 | 10942109 |
| KCNE1 | potassium voltage-gated channel, Isk-related family, member 1 | 21q22.1-q22.2 | 176261 | 8432548 |
| KCNE1L | potassium voltage-gated channel, Isk-related family, member 1-like | Xq22.3 | 300328 | 10493825 |
| KCNE2 | potassium voltage-gated channel, Isk-related family, member 2 | 21q22.1 | 603796 | 10219239 |
| KCNE3 | potassium voltage-gated channel, Isk-related family, member 3 | reserved | 604433 | 10219239 |
| KCNE4 | potassium voltage-gated channel, Isk-related family, member 4 | reserved | | 10219239 |

TABLE 1-continued

Some ion channel genes of interest for EFS experiments

| Symbol | Full Name | Cytogenetic Location | MIM Number | PubMed ID |
|---|---|---|---|---|
| KCNF1 | potassium voltage-gated channel, subfamily F, member 1 | 2p25 | 603787 | 9434767 |
| KCNF2 | literature alias, see KCNG2 | — | | |
| KCNF | symbol withdrawn, see KCNF1 | — | | |
| KCNG1 | potassium voltage-gated channel, subfamily G, member 1 | 20q13 | 603788 | 9434767 |
| KCNG2 | potassium voltage-gated channel, subfamily G, member 2 | 18q22-18q23 | 605696 | 10551266 |
| KCNG | symbol withdrawn, see KCNG1 | — | | |
| KCNH1 | potassium voltage-gated channel, subfamily H (eag-related), member 1 | 1q32-41 | 603305 | 9738473 |
| KCNH2 | potassium voltage-gated channel, subfamily H (eag-related), member 2 | 7q35-q36 | 152427 | 7842012 |
| KCNH3 | potassium voltage-gated channel, subfamily H (eag-related), member 3 | 12q13 | 604527 | 10455180 |
| KCNH4 | potassium voltage-gated channel, subfamily H (eag-related), member 4 | reserved | 604528 | 10455180 |
| KCNH5 | potassium voltage-gated channel, subfamily H (eag-related), member 5 | 14 | 605716 | 9738473 |
| KCNIP1 | Kv channel interacting protein 1 | reserved | | 10676964 |
| KCNIP2 | Kv channel-interacting protein 2 | 10 | | 10676964 |
| KCNIP3 | literature alias, see CSEN | — | | |
| KCNJ1 | potassium inwardly-rectifying channel, subfamily J, member 1 | 11q24 | 600359 | 7680431 |
| KCNJ2 | potassium inwardly-rectifying channel, subfamily J, member 2 | 17q23.1-q24.2 | 600681 | 7696590 |
| KCNJ3 | potassium inwardly-rectifying channel, subfamily J, member 3 | 2q24.1 | 601534 | 8088798 |
| KCNJ4 | potassium inwardly-rectifying channel, subfamily J, member 4 | 22q13.1 | 600504 | 8016146 |
| KCNJ5 | potassium inwardly-rectifying channel, subfamily J, member 5 | 11q24 | 600734 | |
| KCNJ6 | potassium inwardly-rectifying channel, subfamily J, member 6 | 21q22.1 | 600877 | 7796919 |
| KCNJ7 | symbol withdrawn, see KCNJ6 | — | | |
| KCNJ8 | potassium inwardly-rectifying channel, subfamily J, member 8 | 12p11.23 | 600935 | 8595887 |
| KCNJ9 | potassium inwardly-rectifying channel, subfamily J, member 9 | 1q21-1q23 | 600932 | 8575783 |
| KCNJ10 | potassium inwardly-rectifying channel, subfamily J, member 10 | 1q | 602208 | 9367690 |
| KCNJ11 | potassium inwardly-rectifying channel, subfamily J, member 11 | 11p15.1 | 600937 | 7502040 |
| KCNJ12 | potassium inwardly-rectifying channel, subfamily J, member 12 | 17p11.1 | 602323 | 7859381 |
| KCNJ13 | potassium inwardly-rectifying channel, subfamily J, member 13 | 2q37 | 603208 | 9878260 |
| KCNJ14 | potassium inwardly-rectifying channel, subfamily J, member 14 | 19q13 | 603953 | 9592090 |
| KCNJ15 | potassium inwardly-rectifying channel, subfamily J, member 15 | 21q22.2 | 602106 | 9299242 |
| KCNJ16 | potassium inwardly-rectifying channel, subfamily J, member 16 | 17q23.1-q24.2 | 605722 | 11240146 |
| KCNJN1 | channel, subfamily J, inhibitor 1 | 17p11.2-p11.1 | 602604 | 8647284 |
| KCNK1 | potassium channel, subfamily K, member 1 (TWIK-1) | 1q42-q43 | 601745 | 8661042 |
| KCNK2 | potassium channel, subfamily K, member 2 (TREK-1) | 1q41 | 603219 | 9721223 |
| KCNK3 | potassium channel, subfamily K, member 3 (TASK-1) | 2p23 | 603220 | 9312005 |
| KCNK4 | potassium inwardly-rectifying channel, subfamily K, member 4 | 11q13 | 605720 | 10767409 |
| KCNK5 | potassium channel, subfamily K, member 5 (TASK-2) | 6p21 | 603493 | 9812978 |
| KCNK6 | potassium channel, subfamily K, member 6 (TWIK-2) | 19q13.1 | 603939 | 10075682 |
| KCNK7 | potassium channel, subfamily K, member 7 | 11q13 | 603940 | 10206991 |
| KCNK9 | potassium channel, subfamily K, member 9 (TASK-3) | 8 | 605874 | 10734076 |
| KCNK10 | potassium channel, subfamily K, member 10 | reserved | 605873 | |
| KCNK12 | potassium channel, subfamily K, member 12 | 2p22-2p21 | | |

TABLE 1-continued

Some ion channel genes of interest for EFS experiments

| Symbol | Full Name | Cytogenetic Location | MIM Number | PubMed ID |
|---|---|---|---|---|
| KCNK13 | potassium channel, subfamily K, member 13 | 14q24.1-14q24.3 | | 11060316 |
| KCNK14 | potassium channel, subfamily K, member 14 | 2p22-2p21 | | 11060316 |
| KCNK15 | potassium channel, subfamily K, member 15 | reserved | | |
| KCNMA1 | potassium large conductance calcium-activated channel, subfamily M, alpha member 1 | 10 | 600150 | 7987297 |
| KCNMB1 | potassium large conductance calcium-activated channel, subfamily M, beta member 1 | 5q34 | 603951 | 8799178 |
| KCNMB2 | symbol withdrawn, see KCNMB3 | — | | |
| KCNMB2 | potassium large conductance calcium-activated channel, subfamily M, beta member 2 | reserved | 605214 | 10097176 |
| KCNMB2L | symbol withdrawn, see KCNMB3L | — | | |
| KCNMB3 | potassium large conductance calcium-activated channel, subfamily M beta member 3 | 3q26.3-q27 | 605222 | 10585773 |
| KCNMB3L | potassium large conductance calcium-activated channel, subfamily M, beta member 3-like | 22q11 | | 10585773 |
| KCNMB4 | potassium large conductance calcium-activated channel, subfamily M, beta member 4 | reserved | 605223 | |
| KCNMBL | symbol withdrawn, see KCNMB3 | — | | |
| KCNMBLP | symbol withdrawn, see KCNMB3L | — | | |
| KCNN1 | potassium intermediate/small conductance calcium-activated channel, subfamily N, member 1 | 19p13.1 | 602982 | 8781233 |
| KCNN2 | potassium intermediate/small conductance calcium-activated channel, subfamily N, member 2 | reserved | 605879 | |
| KCNN3 | potassium intermediate/small conductance calcium-activated channel, subfamily N, member 3 | 22q11-q13.1 | 602983 | 9491810 |
| KCNN4 | potassium intermediate/small conductance calcium-activated channel, subfamily N, member 4 | 19q13.2 | 602754 | 9380751 |
| KCNQ1 | potassium voltage-gated channel, KQT-like subfamily, member 1 | 11p15.5 | 192500 | 8528244 |
| KCNQ1OT1 | KCNQ1 overlapping transcript 1 | 11p15.5 | 604115 | 10220444 |
| KCNQ2 | potassium voltage-gated channel, KQT-like subfamily, member 2 | 20q13.3-20q13.3 | 121200 | 9425895 |
| KCNQ3 | potassium voltage-gated channel, KQT-like subfamily, member 3 | 8q24 | 121201 | 9425900 |
| KCNQ4 | potassium voltage-gated channel, KQT-like subfamily, member 4 | 1p34 | 603537 | 10025409 |
| KCNQ5 | potassium voltage-gated channel, KQT-like subfamily, member 5 | 6q14 | | 10787416 |
| KCNS1 | potassium voltage-gated channel, delayed-rectifier, subfamily S, member 1 | reserved | 602905 | 9305895 |
| KCNS2 | potassium voltage-gated channel, delayed-rectifier, subfamily S, member 2 | 8q22 | 602906 | 9305895 |
| KCNS3 | potassium voltage-gated channel, delayed-rectifier, subfamily S, member 3 | reserved | 603888 | 10484328 |

PCR reactions can be carried out with a variety of thermostable enzymes including but not limited to AmpliTaq, AmpliTaq Gold, or Vent polymerase. For AmpliTaq, reactions can be carried out in 10 mM Tris-Cl, pH 8.3, 2.0 mM $MgCl_2$, 200 µM of each dNTP, 50 mM KCl, 0.2 µM of each primer, 10 ng of DNA template, 0.05 units/µl of AmpliTaq. The reactions are heated at 95° C. for 3 minutes and then cycled 35 times using suitable cycling parameters, including, but not limited to, 95° C., 20 seconds, 62° C., 20 seconds, 72° C., 3 minutes. In addition to these conditions, a variety of suitable PCR protocols can be found in *PCR Primer, A Laboratory Manual*, edited by C. W. Dieffenbach and G. S. Dveksler, 1995, Cold Spring Harbor Laboratory Press; or *PCR Protocols: A Guide to Methods and Applications*, Michael et al., eds., 1990, Academic Press.

It is desirable to sequence the DNA encoding voltage-gated ion channels obtained by the herein-described methods, in order to verify that the desired voltage-gated ion channel has in fact been obtained and that no unexpected changes have been introduced into its sequence by the PCR reactions. The DNA can be cloned into suitable cloning vectors or expression vectors, e.g., the mammalian expression vector pcDNA3.1 (Invitrogen, San Diego, Calif.) or other expression vectors known in the art or described herein.

A variety of expression vectors can be used to recombinantly express DNA encoding voltage-gated ion channels for use in the present invention. Commercially available expression vectors which are suitable include, but are not limited to, pMC1neo (Stratagene), pSG5 (Stratagene), pcD-NAI and pcDNAIamp, pcDNA3, pcDNA3.1, pCR3.1 (Invitrogen, San Diego, Calif.), EBO-pSV2-neo (ATCC 37593), pBPV-1(8-2) (ATCC 37110), pdBPV-MMTneo(342-12) (ATCC 37224), pRSVgpt (ATCC 37199), pRSVneo (ATCC 37198), pCI.neo (Promega), pTRE (Clontech, Palo Alto, Calif.), pV1Jneo, pIRESneo (Clontech, Palo Alto, Calif.), pCEP4 (Invitrogen, San Diego, Calif.), pSC11, and pSV2-dhfr (ATCC 37146). The choice of vector will depend upon cell type in which it is desired to express the voltage-gated ion channels, as well as on the level of expression desired, and the like.

The expression vectors can be used to transiently express or stably express the voltage-gated ion channels. The transient expression or stable expression of transfected DNA is well known in the art. See, e.g., Ausubel et al., 1995, "Introduction of DNA into mammalian cells," in *Current Protocols in Molecular Biology*, sections 9.5.1-9.5.6 (John Wiley & Sons, Inc.).

As an alternative to the above-described PCR methods, cDNA clones encoding ion channels can be isolated from cDNA libraries using as a probe oligonucleotides specific for the desired voltage-gated ion channels and methods well known in the art for screening cDNA libraries with oligonucleotide probes. Such methods are described in, e.g., Sambrook et al., 1989, *Molecular Cloning: A Laboratory Manual*; Cold Spring Harbor Laboratory, Cold Spring Harbor, N.Y.; Glover, D. M. (ed.), 1985, *DNA Cloning: A Practical Approach*, MRL Press, Ltd., Oxford, U.K., Vol. I, II. Oligonucleotides that are specific for particular voltage-gated ion channels and that can be used to screen cDNA libraries can be readily designed based upon the known DNA sequences of the voltage-gated ion channels and can be synthesized by methods well-known in the art.

The present invention also provides apparatuses for use with the methods disclosed herein. For example, the present invention provides a multiwell tissue culture plate where a plurality of the wells of the plate contain a pair of electrodes disposed such that when a preselected voltage is applied across the electrodes the transmembrane potential of cells within the wells is altered.

In certain embodiments, the multiwell tissue culture plate contains one of the pair of electrodes on the bottom of the wells and the other of the pair of electrodes on the side of the wells. This embodiment is depicted in FIG. 2B.

In other embodiments, the multiwell tissue culture plate contains both of the pair of electrodes on the bottom of the wells. This embodiment is depicted in FIG. 2C.

In other embodiments of the multiwell tissue culture plate, one of the pair of electrodes is a layer of conductive material that forms the bottom of the wells and the other of the pair of electrodes enters the wells from above. This embodiment is depicted in FIGS. 7, 12, and 16.

In other embodiments of the multiwell tissue culture plate, both of the pair of electrodes are embedded in an insulator and enter the wells from above. This embodiment is depicted in FIGS. 9 and 10.

In other embodiments of the multiwell tissue culture plate, the electrode that enters the wells from above has a central conductive material portion that is surrounded by an insulator. This embodiment is depicted in FIG. 8.

In other embodiments of the multiwell tissue culture plate, one of the pair of electrodes forms the bottom of the wells and the other of the pair of electrodes enters the wells from above. This embodiment is depicted in FIGS. 7 and 10.

In other embodiments of the multiwell tissue culture plate, the pairs of electrodes form an alternating pattern of positive and negative electrodes in the wells. This embodiment is depicted in FIG. 16.

In other embodiments of the multiwell tissue culture plate, the layer of conductive material that forms the bottom of the wells is a layer of indium tin oxide that overlays a glass substrate. Preferably, the layer of conductive material and the glass substrate are transparent.

In other embodiments of the multiwell tissue culture plate, a plurality of the wells of the plate contain interdigitating electrodes. This embodiment is depicted in FIGS. 3 and 5.

The present invention provides a multiwell tissue culture plate where:
  the bottom of the wells is a filter membrane upon which cells can be grown;
  the wells are located in a trough that can contain fluid;
  the trough contains a first electrode;
  a second electrode enters the wells from above;

where the first and second electrodes are so disposed that when a preselected voltage is applied across the electrodes the transmembrane potential of cells within the wells is altered. This embodiment is depicted in FIG. 8.

The present invention also provides a combination of the multiwell tissue culture plates disclosed herein and a fluorescent imager where the multiwell tissue culture plate and the fluorescent imager are positioned relative to one another such that the fluorescent imager can obtain fluorescent readings from the wells of the multiwell tissue culture plate.

The present invention also provides a combination of a top substrate and a bottom substrate where the top and bottom substrates each contain:
  a plurality of virtual wells; and
  a layer of conductive material that forms the bottoms of the virtual wells; where the layers of conductive material in the top and bottom substrates are connected to a pulse generator such that the layers of conductive material function as electrodes such that when a preselected voltage is applied across the electrodes the transmembrane potential of cells within the virtual wells is altered. Such a combination is depicted in FIGS. 6 and 13.

The present invention also provides a substrate having square or rectangular wells formed by a plurality of generally parallel positive and negative electrodes and a plurality of spacers arranged generally at right angles to the electrodes, where:
one wall of the wells is formed by a positive electrode and
  the opposite wall of the well is formed by a negative electrode;
the spacers form the walls of the wells that are at right angles
  to the walls formed by the electrodes;
where the electrodes are so disposed that when a preselected
  voltage is applied across the electrodes the transmembrane potential of cells within the wells is altered. Such a
  substrate is depicted in FIG. 1.

An example of another embodiment of the present invention comprises:
  a substrate having an upper surface upon which are present at least $10^3$ living eukaryotic cells which have a voltage-gated ion channel of interest in their plasma membranes;
  a plurality of positive electrodes and a plurality of negative electrodes positioned either on or near the substrate such that when a voltage is applied through the positive and negative electrodes the transmembrane potential of the cells is altered;

at least one substance that is suspected of being an activator or an inhibitor of the voltage-gated ion channel;

where the cells contain a fluorescent indicator compound.

An example of another embodiment of the present invention comprises:

a multiwell tissue culture plate having a plurality of wells in which are present at least $10^3$ living eukaryotic cells per well of the plurality which cells have a voltage-gated ion channel of interest in their plasma membranes;

a plurality of positive electrodes and a plurality of negative electrodes positioned such that when a preselected voltage is applied through the positive and negative electrodes, the transmembrane potential of the cells is altered;

at least one substance that is suspected of being an activator or an inhibitor of the voltage-gated ion channel in at least one of the plurality of the wells;

where the cells contain a fluorescent indicator compound or a voltage sensitive membrane dye.

The following non-limiting examples are presented to better illustrate the invention.

EXAMPLE 1

Figure 24:
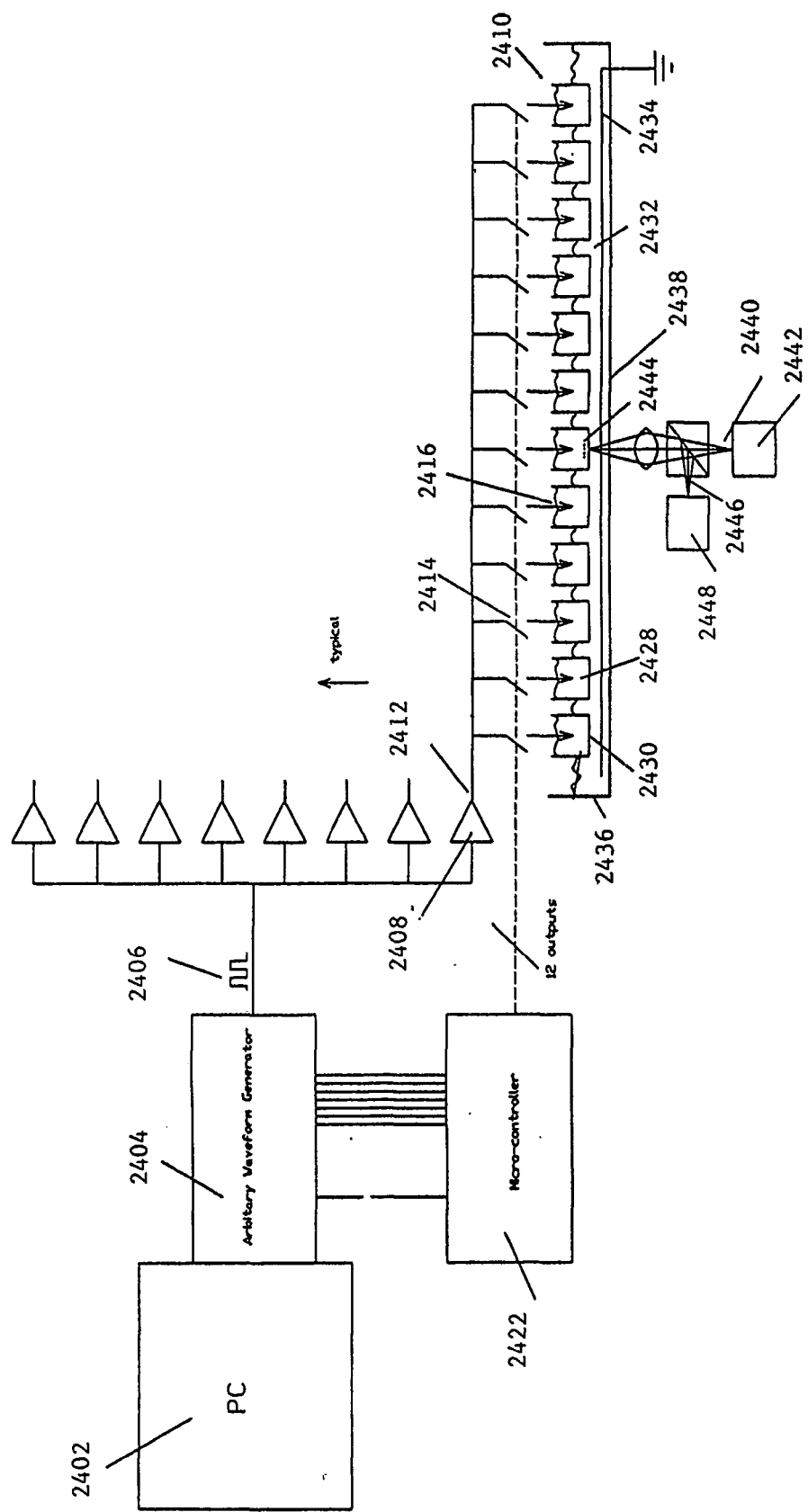
FIG. 24 shows a schematic diagram of one embodiment of a EFS system utilizing a computer, voltage generator, amplifier, membrane bottom wells, common trough, and fluorescence detector, inter alia.

In FIG. 24, a preferred system for conducting high throughput screening using EFS stimulation is shown. The system consist of a computer 2402 that comprises an arbitrary waveform generator card 2404 electronically associated with the computer 2402. Custom software was written on the computer 2402 which causes the arbitrary generator card 2404 to generate a pulse voltage waveform (2406) of the appropriate electrical stimulus. The voltage waveform (2406) is applied to the input of eight constant current amplifiers 2408. Each constant current amplifier 2408 services a row on the 96-well sample filter plate 2410. The outputs from the amplifiers 2412 pass through the contacts of electrical relays 2414 allowing the current pulse to be applied to the electrodes 2416.

The waveform generator card 2404 also generates a 7-bit binary transistor-transistor logic TL value (2418) that represents the address of the well to be excited by the stimulus. In addition, a trigger pulse 2420 is generated. Microprocessor controller 2422, waits for the trigger pulse 2420, interprets the binary value (2418) and then switches on the appropriate relay 2414 which then directs the constant current pulse (2424) to the particular electrode 2416 or electrodes, via electrode connecting wire(s) 2417 in the sample well 2426. Current flows from the amplifier's output (2424), through the relay contact 2414 through the electrode 2416 the liquid in the well 2428, through the well's membrane 2430 and returns via fluid 2432 beneath the membrane 2430 and a return wire 2434. One large common current return trough 2436 services all 96-electrodes. Other arrangements are possible where each sample well has its own isolated current return trough and return wire. See Example 2 below.

The current return trough 2436 beneath the membranes 2430 has a clear glass bottom 2438 that permits excitation light (2440) from a light source 2442 to pass through the glass bottom 2438, through the transparent membrane 2430 and illuminate cells 2444 adhered to the membrane 2430. Fluorescent light (2446) from the cells 2444 returns back through the membrane 2430 and the glass bottom 2438 entering into the detector 2448. Suitable detectors include those described supra. The preferred detector is the FLIPR (Molecular Devices) fluorescence imager or the VIPR (Aurura biosciences).

When the pulse sequence is completed, the microprocessor controller 2422 switches off the relays 2414 isolating the constant current amplifiers' pulses (2424) from the electrodes 2416.

Figure 25:
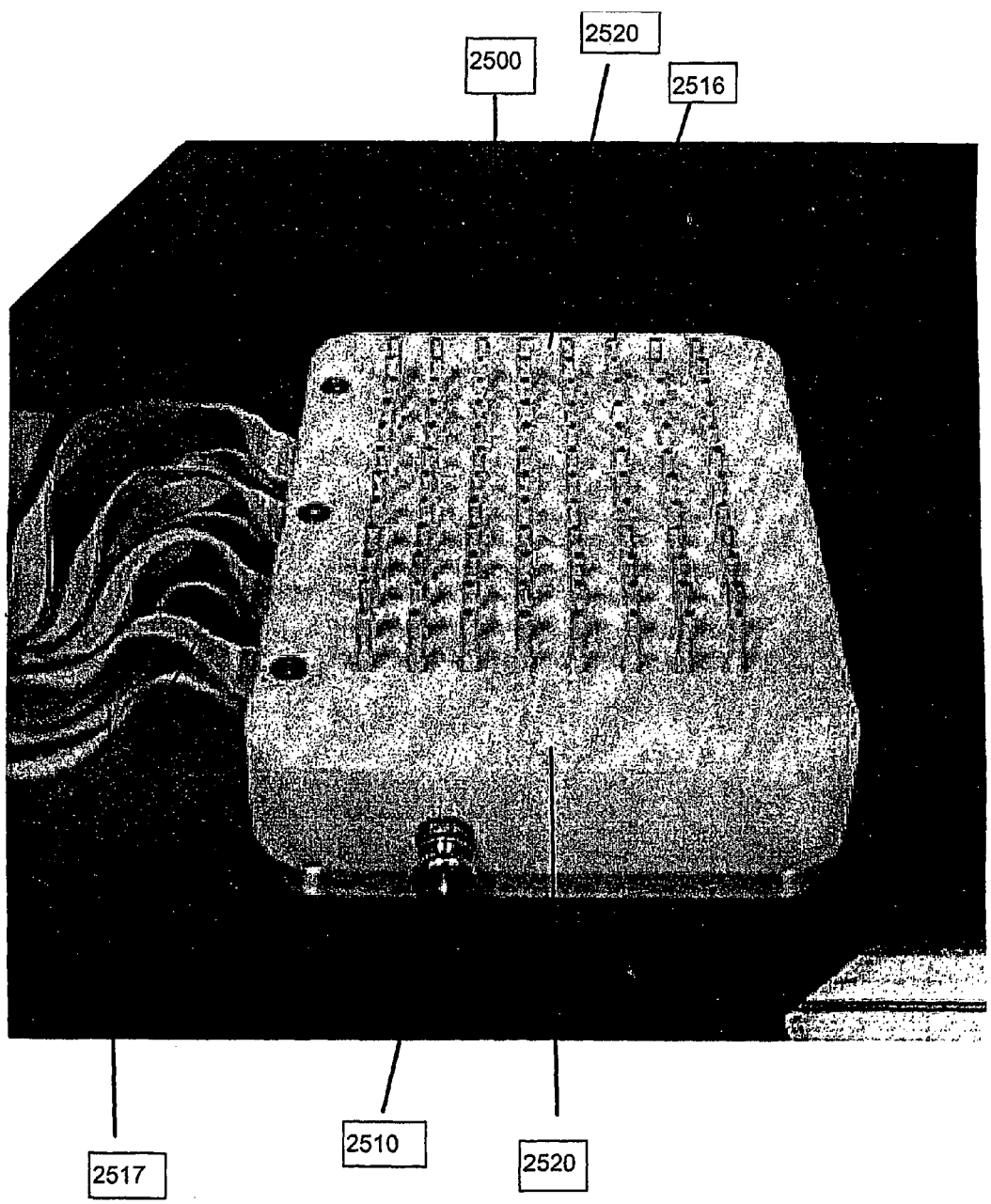
FIG. 25 is a photograph showing an electrode head embodiment especially adapted for use with a 96 well tray.
Figure 26:
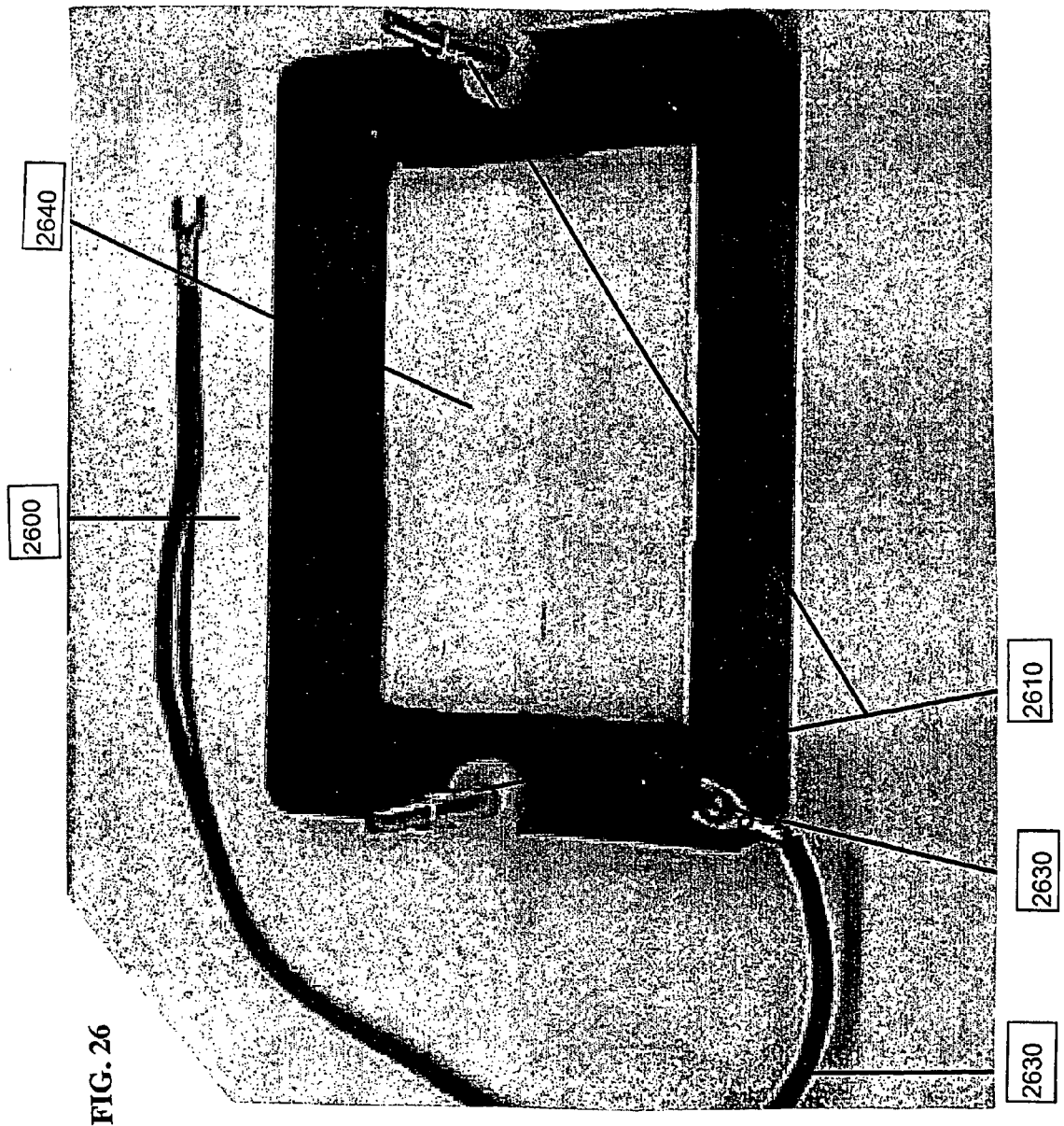
FIG. 26 is a photograph showing a trough embodiment for use in conjunction with the electrode head embodiment shown in FIG. 25.

Turning to FIGS. 25 and 26, FIG. 25 represents a photograph of an electrode head 2500 embodiment comprising top electrodes 2516 and first electrode connecting wires 2517. The electrode head comprises a ground contact rod 2510. FIG. 26 represents a photograph of a trough embodiment 2600 for use in conjunction with the electrode head 2500 embodiment shown in FIG. 25. The trough 2600 comprises bracing posts 2610 to assist in aligning and attachment of the electrode head through apertures 2520 in the electrode head 2500 (see FIG. 28). A bottom electrode wire (hidden) is positioned in the trough which when submerged in the salt/buffer solution, upon assembly of the EFS system (see FIG. 28) acts as bottom electrode for each of the wells. The bottom electrode wire is in electrical communication with a return connection wire 2620 at position 2630. The return connection wire is secured to the ground contact rod 2510 upon assembly of the EFS system. The trough 2600 also comprises a transparent bottom portion 2640 preferably made of glass.

Figure 27:
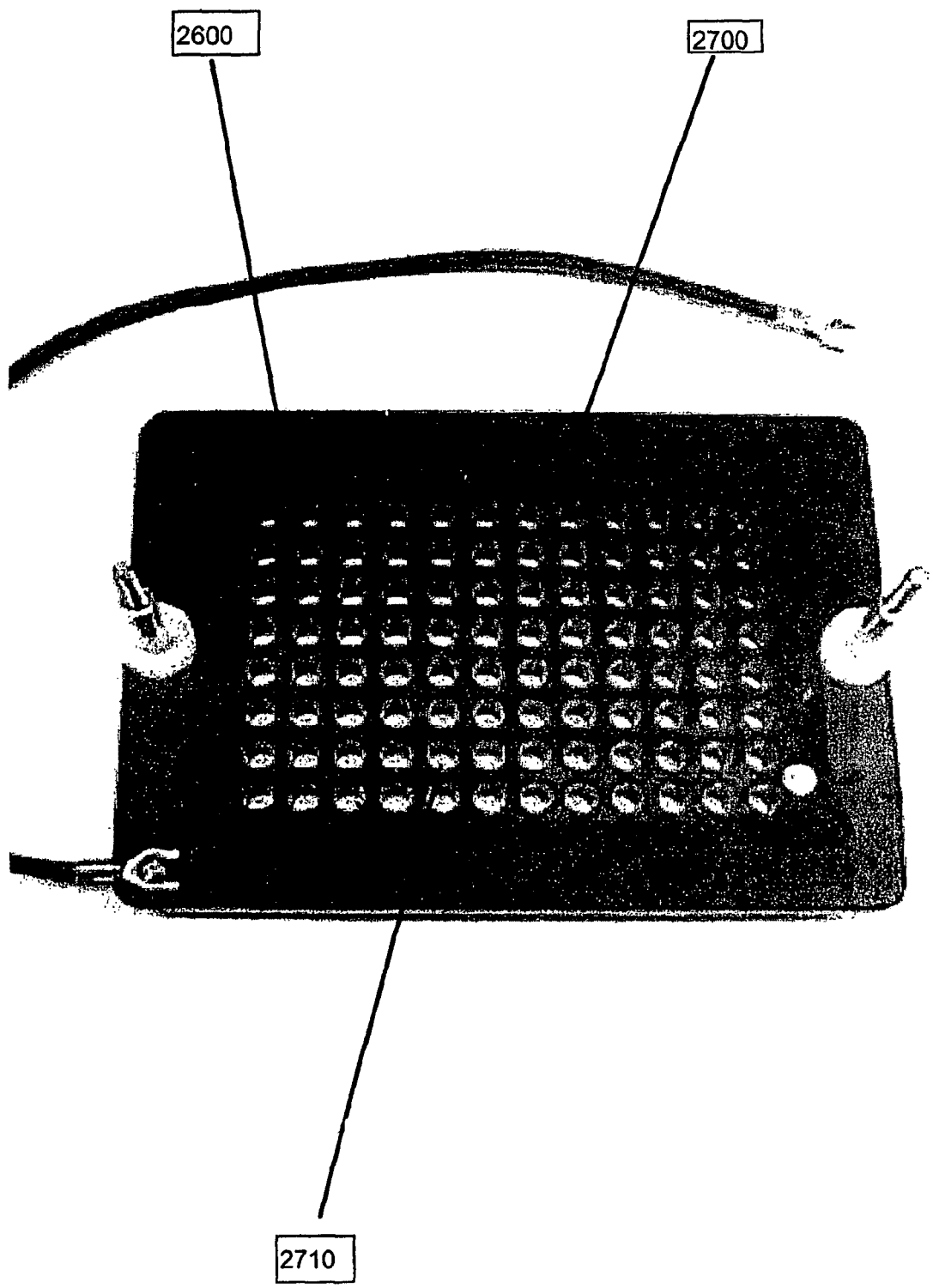
FIG. 27 is a photograph showing the trough embodiment of FIG. 26 with a multi-screen well tray positioned therein.

FIG. 27 represents a photograph of the trough embodiment 2600 wherein a Multiscreen™-Black CM 96 wellplate 2700, with 96 wells 2710, is positioned in the trough 2600. Information concerning Millipore's multiscreen plates and biopore membranes is found, e.g., at http://www.millipore.com/catalogue.nsf/docs/C7781 and http://www.millipore.com/publications.nsf/docs/tn062.

Figure 28:
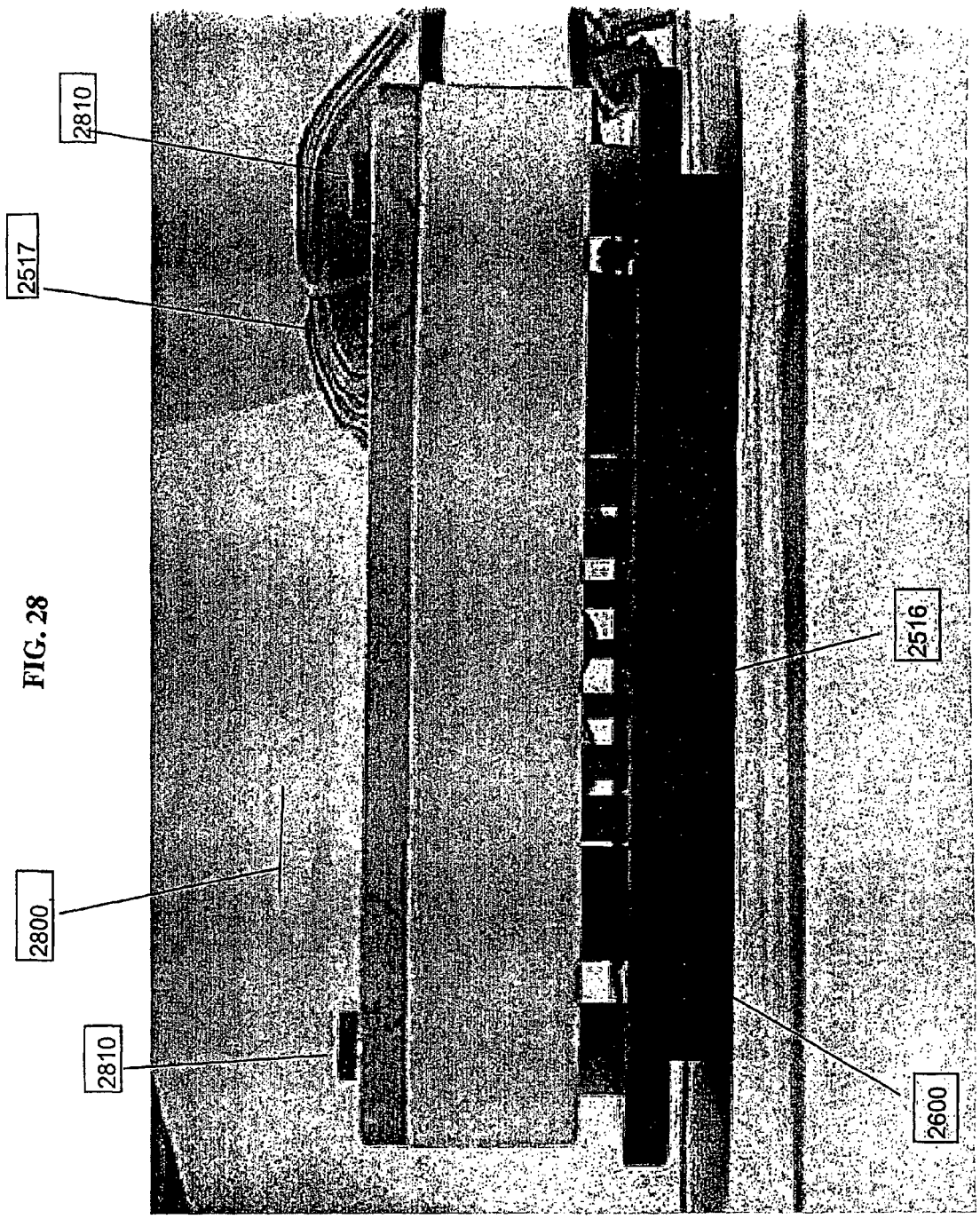
FIG. 28 is a photograph showing the assembled electrode head, trough and multiscreen.

FIG. 28 is a photograph of the assembled EFS system 2800 comprising the trough 2600 with well plate 2700 in place. The electrode head 2500 is secured to the top of the trough 2600 such that the electrodes 2416 are inserted into the wells 2710, one electrode per well. The electrode head 2500 is secured down onto bracing posts 2610 (hidden) by fasteners 2810. The fasteners are preferable threaded nuts. Preferably, prior to assembly, each well 2710 (hidden) has been loaded with cells which have been cultured to canvas the bottom of the wells 2710 (hidden). After cells have been cultured under standard and known conditions, and before assembly of the EFS unit 2800, each well is preferably washed to remove cell media and then loaded with the predetermined buffer solution as discussed above.

Figure 29:
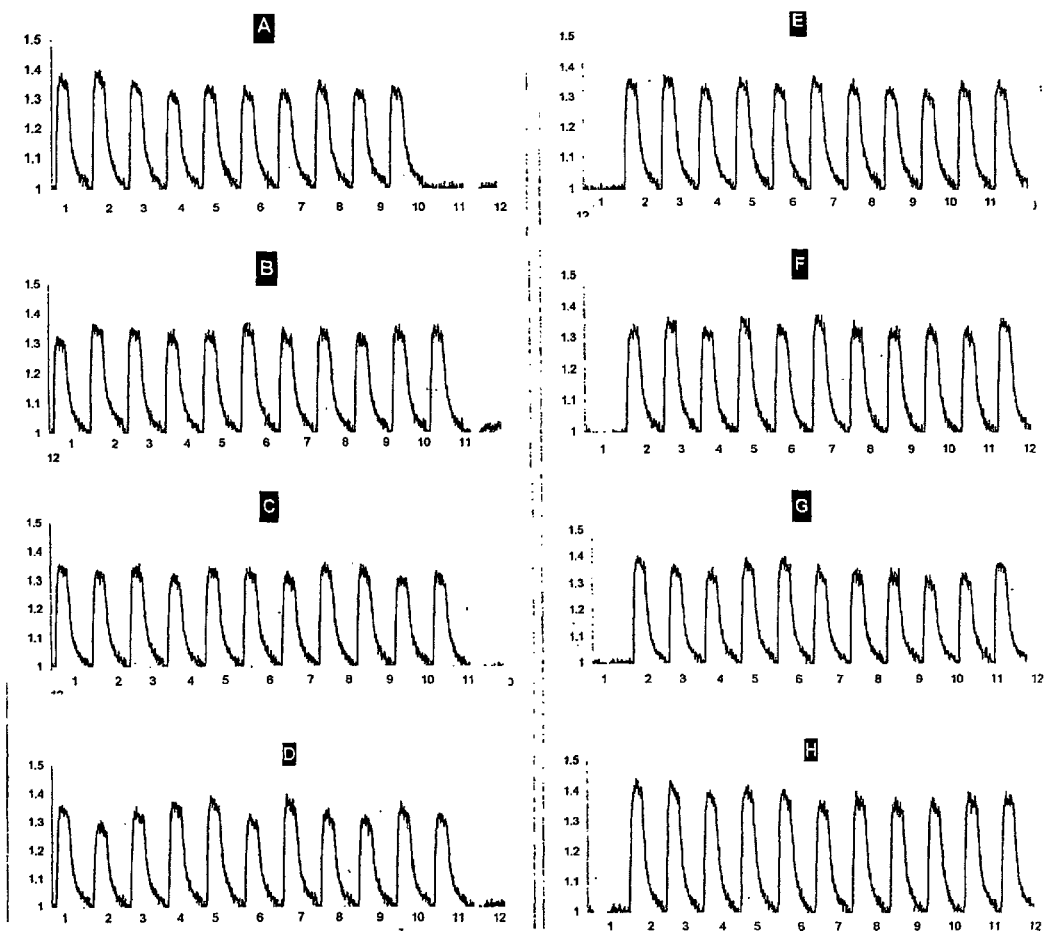
FIG. 29 shows a graphical representation of data obtained from an embodiment of the invention similar to that depicted in FIG. 28. The data represent a membrane potential change in HEK293 cells that have been transfected to express human PN1 voltage-gated sodium channel. Each plot represents a row (12 wells) A-H of a 96-well plate. Each column of the 96-well plate data was acquired for 15 seconds on a VIPR™. Stimulation pulse protocol was applied during the data acquisition as follows; 2 s baseline was followed with a 2 ms square pulse, Amplitude=20 mA, Frequency=10 Hz, Duration=5 s.

FIG. 29 shows a graphical representation of data obtained from an embodiment of the invention similar to that depicted in FIG. 28. The data represent a membrane potential change in HEK293 cells that have been transfected to express human PN1 voltage-gated sodium channel. Each plot represents a row (12 wells) A-H of a 96-well plate. Each column of the 96-well plate data was acquired for 15 seconds on a VIPR™. Stimulation pulse protocol was applied during the data acquisition as follows; 2 s baseline was followed with a 2 ms square pulse, Amplitude=20 mA, Frequency=10 Hz, Duration=5 s. Those skilled in the art will readily appreciate, in view of the teachings herein, that the subject system may generate a pulse between 1 μs to 1 s. Preferably, the pulse generated is between about 0.1 ms and about 100 ms.

Figure 30:
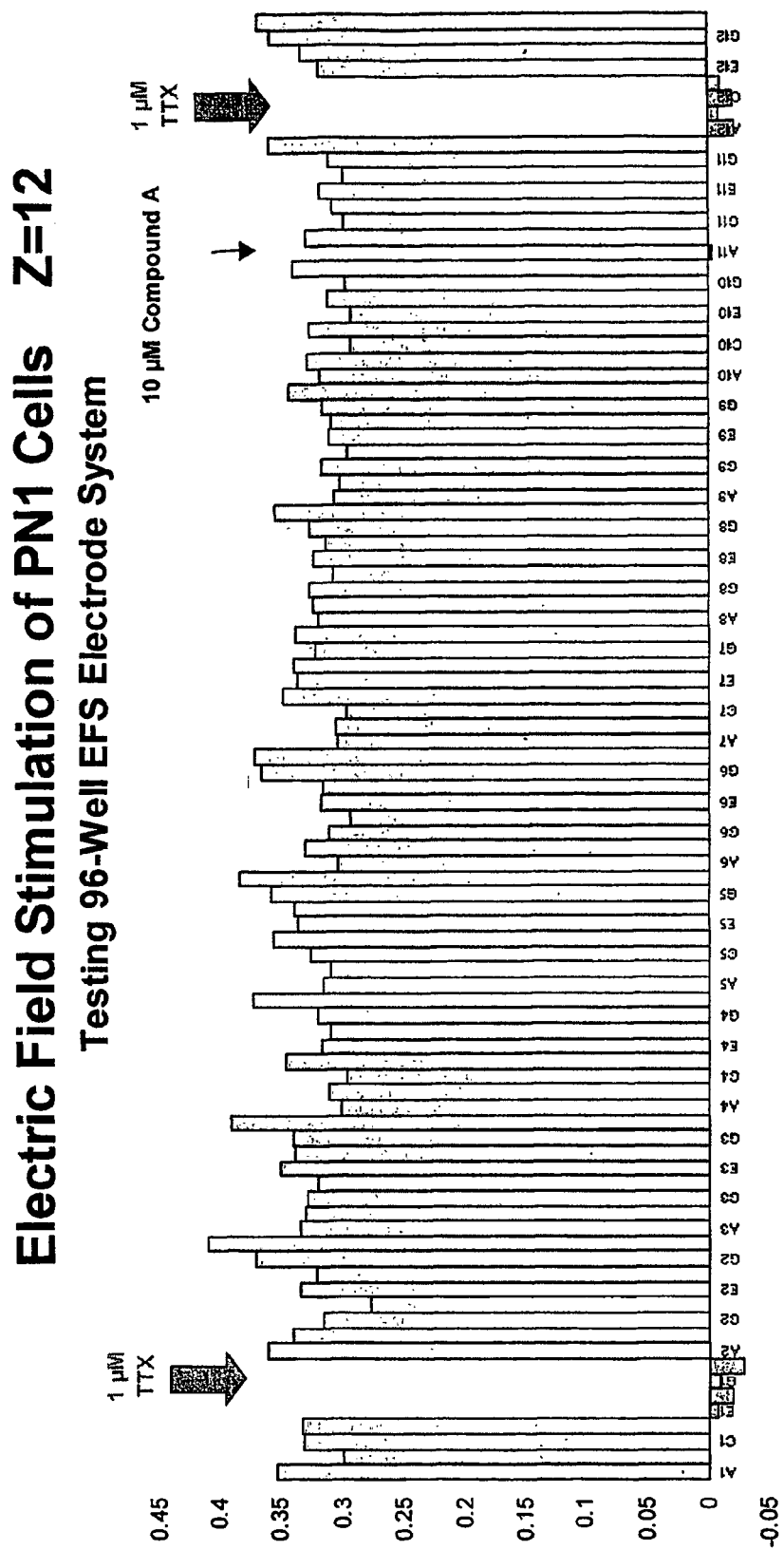
FIG. 30 is a bar graph representation of the peak ration change of data depicted in FIG. 29. 1 µM TTX a specific and potent blocker of tetrodotoxin (TTX)-sensitive voltage-gated sodium channels is present in wells E1, F1, G1, H1, A12, B12, C12 and D12. In addition well A11 contains an internal standard for blocking TTX-sensitive voltage-gated sodium channels. Z-score is a measure of the difference in the uninhibited and inhibited signal divided by the sum of the standard deviations.

FIG. 30 is a bar graph representation of the peak ratio change of data depicted in FIG. 29. 1 μM TTX a specific and potent blocker of tetrodotoxin (TTX)-sensitive voltage-gated sodium channels is present in wells E1, F1, G1, H1, A12, B12, C12 and D12. In addition well A11 contains an internal standard for blocking TTX-sensitive voltage-gated sodium channels. Z-score is a measure of the difference in the uninhibited and inhibited signal divided by the sum of the standard deviations of the uninhibited and inhibited signals.

Figure 31:
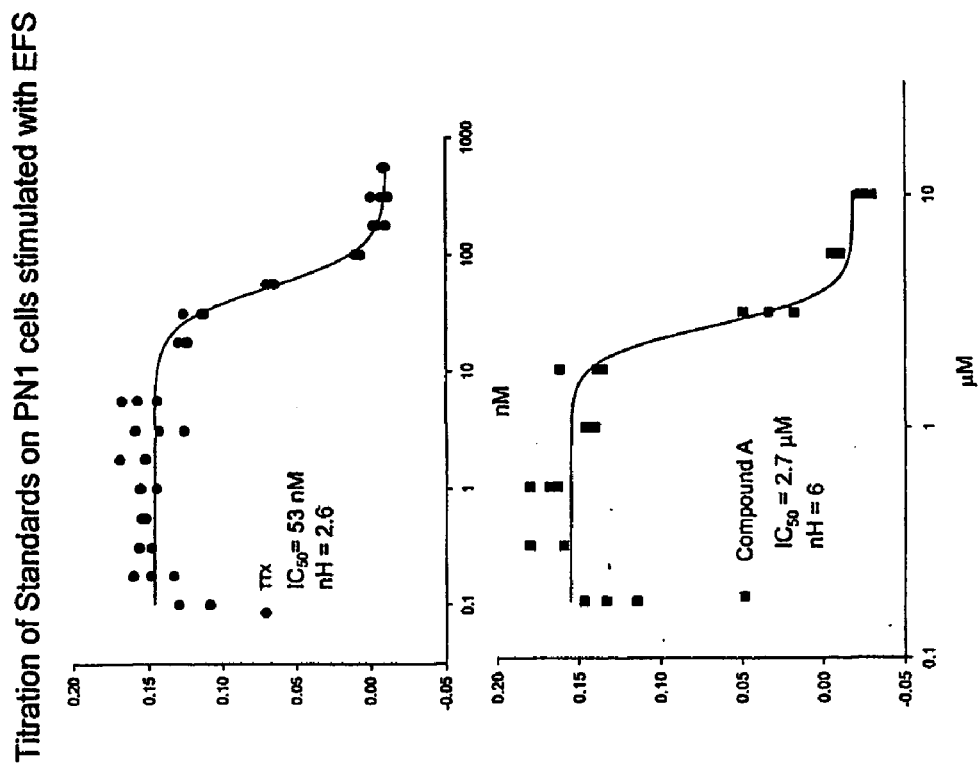
FIG. 31 shows the effects of increasing concentrations of TTX (upper panel) and of Compound A (lower panel) on the EFS-stimulated depolarization signal in HEK293/PN1 cells. The $IC_{50}$s obtained in these experiments are comparable to those obtained through other techniques. The high Hill coefficients, nH, result from the threshold nature of the stimulation protocol.

FIG. 31 shows the effects of increasing concentrations of TTX (upper panel) and of Compound A (lower panel) on the EFS-stimulated depolarization signal in HEK293/PN1 cells. The $IC_{50}$s obtained in these experiments are comparable to those obtained through other techniques. The high Hill coefficients, nH, result from the threshold nature of the stimulation protocol and the nonlinear relation between ion channel activity and membrane potential.

EXAMPLE 2

Figure 32:
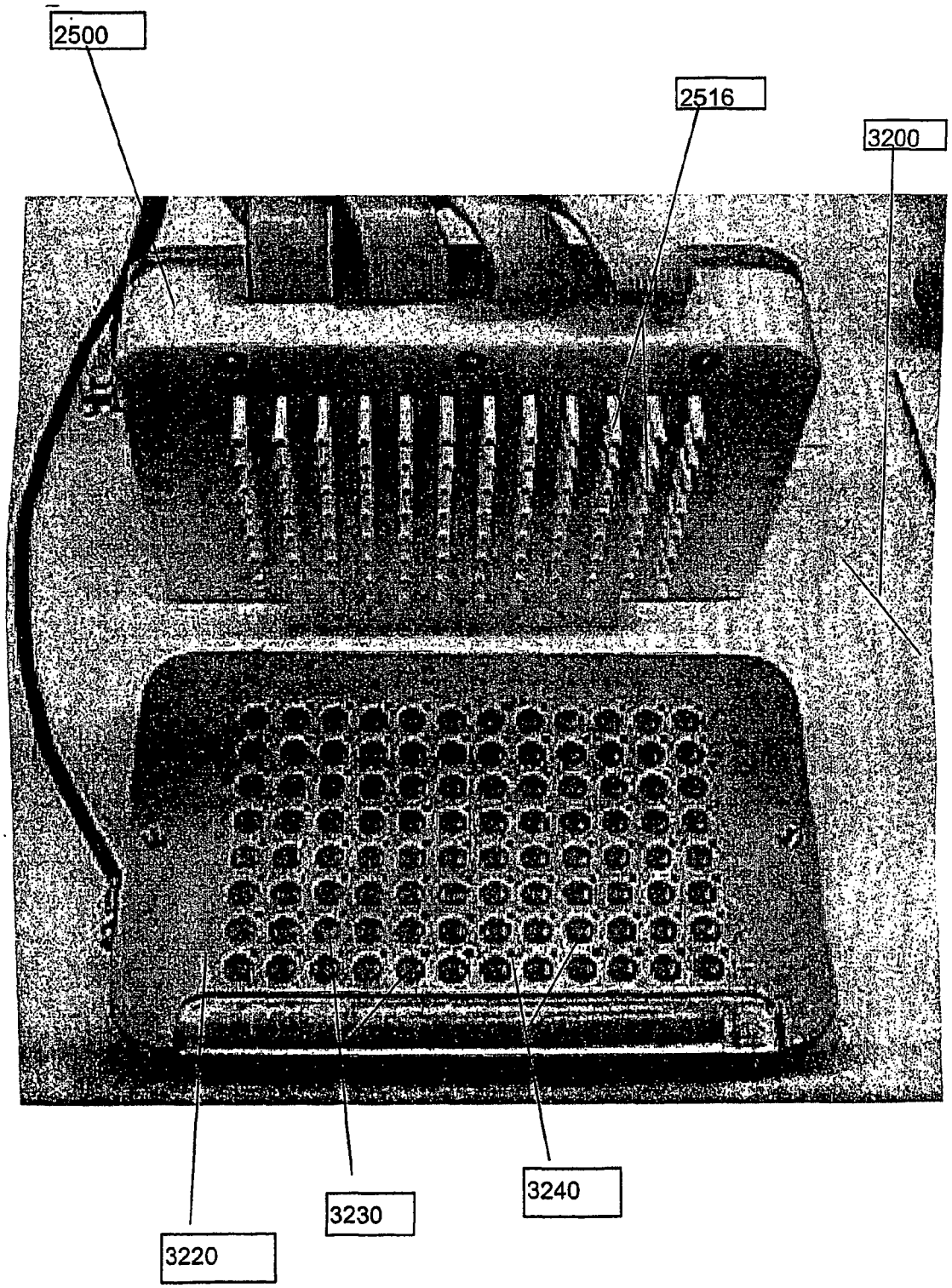
FIG. 32 is a photograph showing an alternative embodiment.

FIG. 32 represents a photograph of an EFS embodiment 3200 pertaining to an alternative EFS system configuration. The electrode head 2500 is similar to that described above in FIG. 25. However, the configurations of the electrodes, wells and trough are configured differently to further isolate the electrical fields. This reduces cross-talk and interference between wells. For this embodiment, the inventors have adapted Millipore's Multiscreen™ Caco-2 Assay System for use as a EFS system. Information concerning the Multiscreen™ Caco-2 Assay System can be found at http://www.millipore.com/publications.nsf/docs/PF1780EN00.
The standard commercially available Caco-2 plate system comprises two plates: a membrane-bottom cell growth plate and a 96-well receiver tray. One of the unique characteristics of the Caco-2 system is that it each well has an individual corresponding trough that is accessed basolaterally to each well. Therefore, it supplants the need for a common trough into which all of the wells sit. According to this embodiment, the top electrodes 2516 are disposed into each of the wells in the membrane-bottom cell growth plate (hidden). To establish the bottom electrode for each well, a conductive electrode plate 3220 is provided. The conductive electrode plate 3220 comprise a series of well apertures 3230, providing access of the top electrodes 2410 into the individual wells during assembly. The conductive electrode plate 3220 also comprises a series of conductive pins (hidden) secured thereto and extending downward at positions 3240. These conductive pins are inserted through the basolateral access port of the membrane-bottom cell growth plate (not shown).

Figure 33:
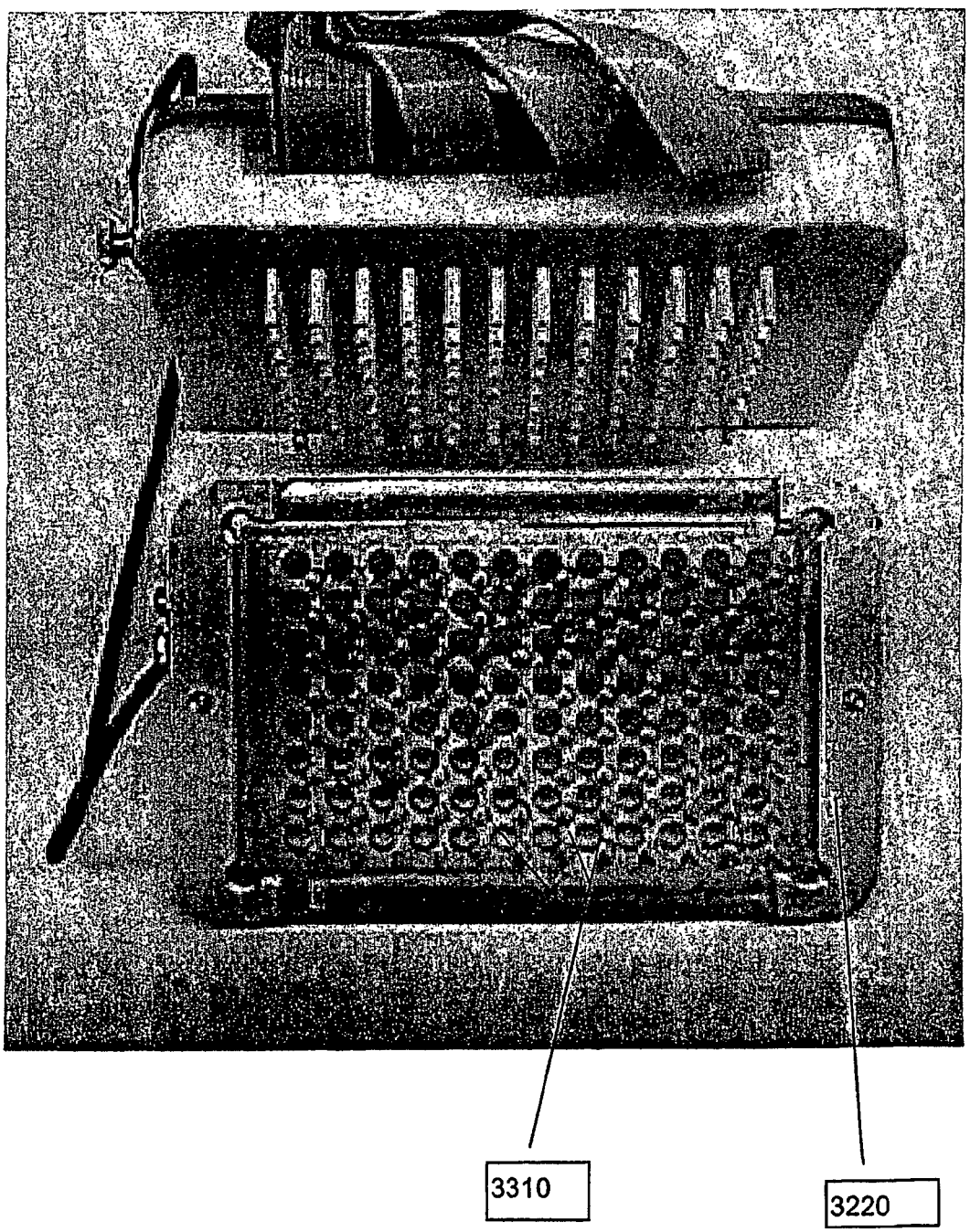
FIG. 33 is a photograph similar to that shown in FIG. 32 except that the copper electrode plate has been turned over to show conducting pins (note: pins extend out of page toward reader).
Figure 34:
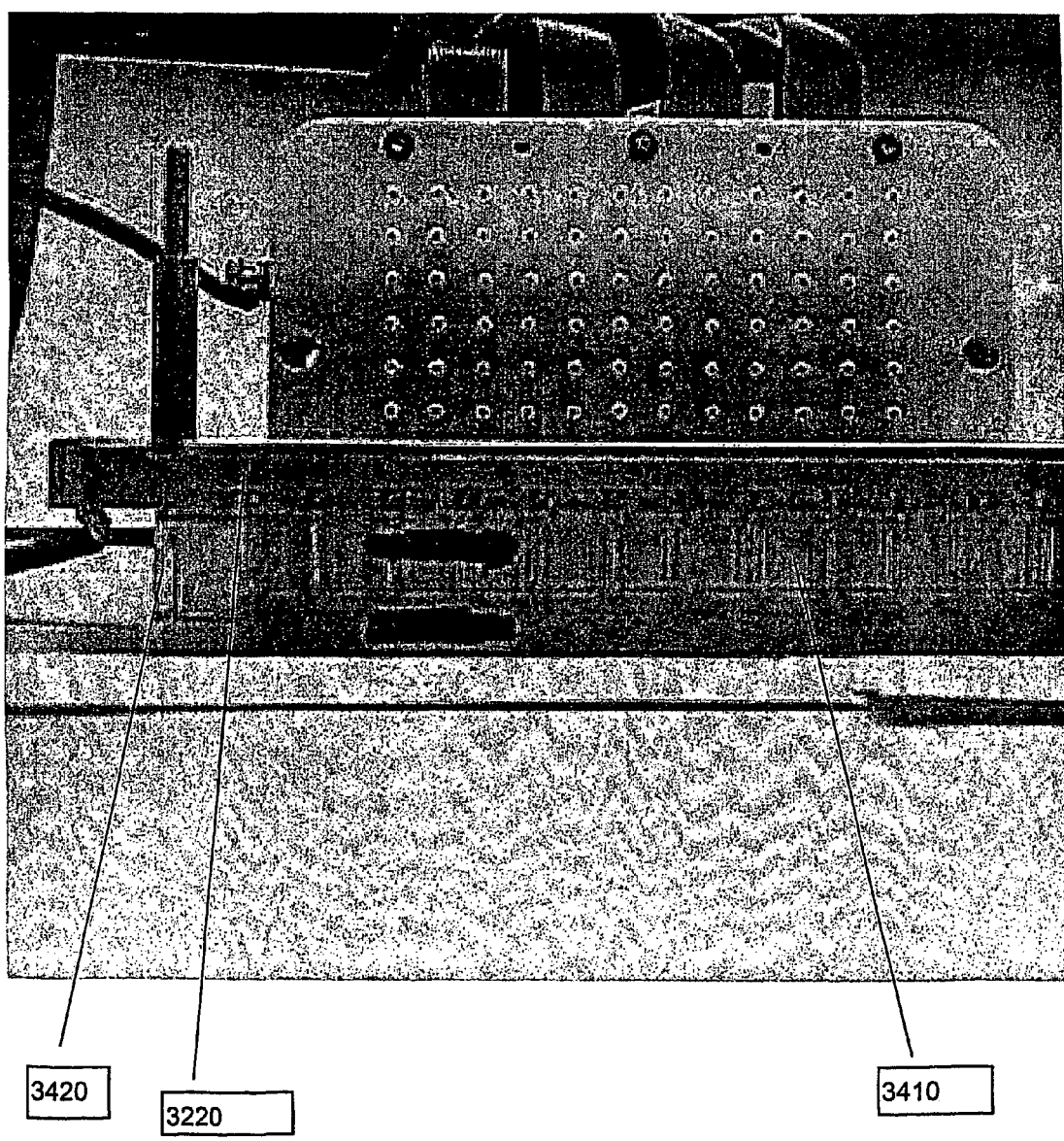
FIG. 34 is a photograph showing the copper electrode plate placed on top of an assembled Caco-2 membrane bottom well and receiver tray.
Figure 35:
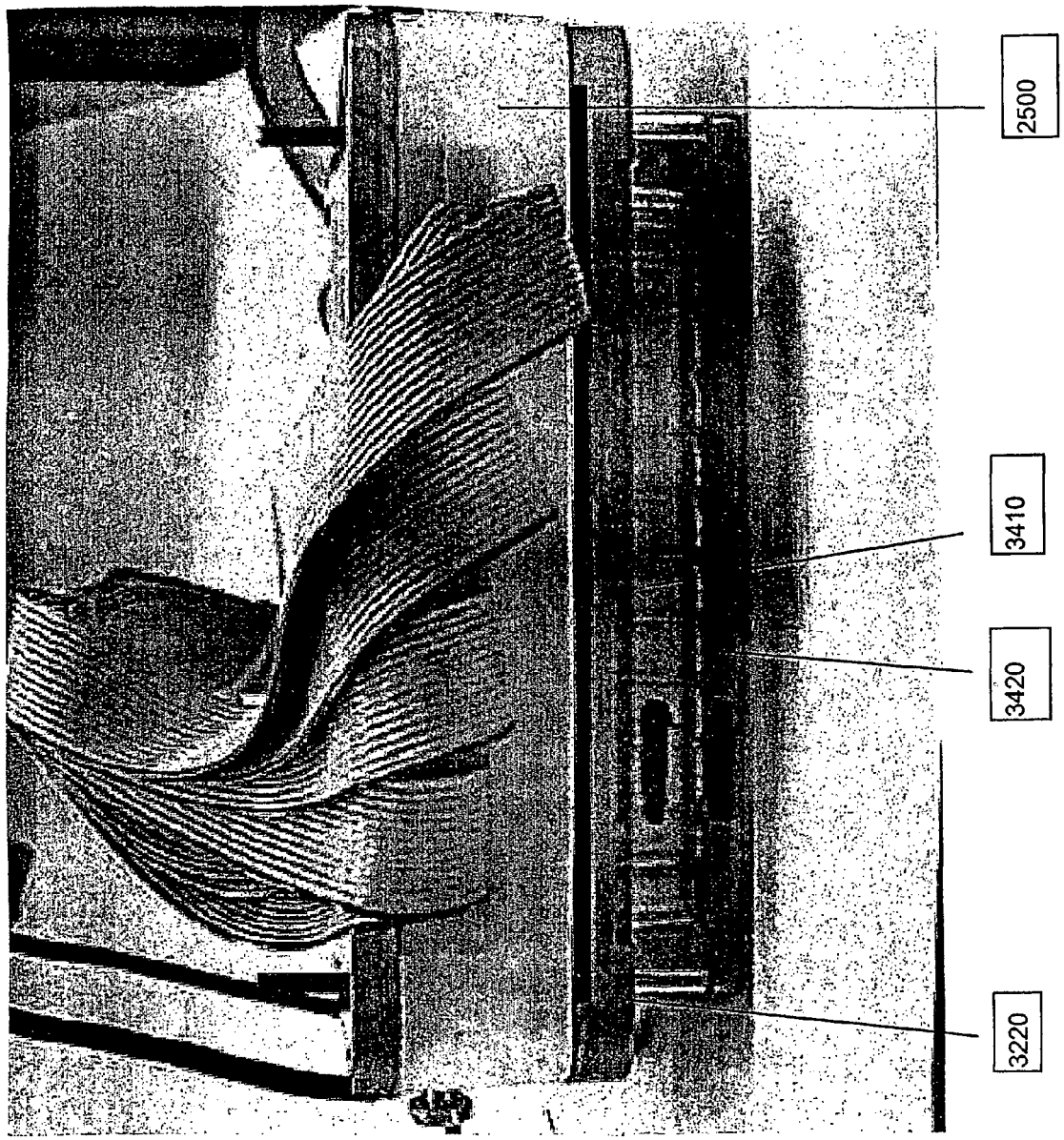
FIG. 35 is a photograph showing the assembled embodiment of FIG. 34, i.e., electrode head, copper electrode plate with pins, Caco-2 membrane bottom well, and Caco-2 receiver tray.

FIG. 33 is a depiction of the bottom of the conductive electrode plate 3220 and shows the conductive pins 3310, which are extending out of the page toward the reader. FIG. 34 shows a side-view of the conductive electrode plate 3220 properly positioned atop of the membrane-bottom cell growth plate 3410 and 96 well receiver tray 3420. When the electrode conductive plate 3220 is properly positioned on top of the membrane-bottom cell growth plate 3410, the conductive pins 3310 are inserted through the basolateral access port (not shown) into the individual trough area (not shown) of the 96 well receiver tray. When the individual trough area is filled with the appropriate solution it contacts the bottom of each well and individual pin. Therefore, when the well and trough area are filled with solution, current may flow from the top electrode to the bottom electrode during operation. FIG. 35 is a side-view of the assembled EFS system. The assembled system comprises the membrane-bottom cell growth plate 3410 positioned in the 96 well tray 3420. The electrode plate 3220 is mounted on top of the membrane bottom well plate 3410. The electrode head 2500 is shown mounted on top of the electrode plate 3220.

One clear advantage to the EFS systems described in Examples 1 and 2 above, and elsewhere in the present application, is the ability to generate a uniform field across the cells, as opposed to tangential to the cells. Generating an electrical field across the cells is made possible by the novel "top to bottom" placement of the electrodes in a multiwell format.

EXAMPLE 3

FIG. 36 shows a novel electrode embodiment 3600. FIG. 36A depicts an expanded view of the electrode 3600. The electrode 3600 comprises two parallel plates 3610 and 3630 with a low dielectric plate or disc 3620 between them. Optionally, the electrode may be coated with an insulating material. Potential advantages of this design are that special multiwell plates are not required, i.e., any plate that the cells will stick to and that the stimulation and emission light will pass through may be used. There is no filter in the well that may absorb compound or pass compound during long incubations. In the case of the coated electrode, very little current is used and ohmic heating is diminished, even for dc current and even for extended periods of stimulation. The capacitance current is low enough that this advantage applies to ac current as well. The sealed electrode permits placement very close to the cell layer for more uniform stimulation.

Not to be bound by any theory, it is believed that the more uniform the electrical field presented to the cells is, a more accurate indication of potential modulation to the cells will be achieved. In other words, the more uniform the electrical field is, the potential modulation as observed by any of the methods presented herein, e.g., fluorescence, will more directly correlate to actual modulation of ion channels in the cell membrane, and less correlate with background noise in the system caused by cross-interference, cross-illumination, dye effects, dye leaching or any other interference in the system. One way to increase the uniformity of the electrical field applied to the cells is to present one or more of the electrodes in close proximity to, or in contact with, the cells. However, this can affect the cells in deleterious ways leading to failure in the system. Some of the problems associated with close proximity or contact of the electrode(s) to the cells are caused by, for example, ohmic heating, oxidation and formation of bubbles on the electrode. The embodiments of the present invention as taught in FIGS. 8, 11, 24-28 and 32-35 are particularly preferred because they achieve a uniform electrical field across the cells without putting the electrodes in contact with or close proximity to the cells. Furthermore, the novel electrode design shown in FIG. 36 achieves a uniform electrical field, by allowing close proximity of the electrode to the cells, without creating the problems of ohmic heating, oxidation, or bubbling of the cells.

It is believed that the subject EFS system embodiments produce substantially uniform fields, where the one or more electrical fields vary over an area of observation by no more than about 30% from the mean electrical field at any one time. Percentages are determined by measurements in two dimensions; or preferably, variation is calculated in three dimensions. In a more preferred embodiment, the one or more electrical fields vary over an area of observation by no more than about 15% from the mean electrical field at any one time. In an even more preferred embodiment, the one or more electrical fields vary over an area of observation by no more than 10% from the mean electrical field at any one time. In an optimal embodiment, the variation is no more than 5% from the mean.

The similarity to a capacitor is obvious, but the low dielectric 3620 between the plates 3610 and 3630 reduces the amount of current required to initially charge the plates with only a miniscule current required to maintain the charge between the plates. An external electric field is generated that can be used to depolarize the cells. The external electric field density is reduced by a high dielectric between the plates as is used with an authentic capacitor and is maximal with a low dielectric such as teflon or mylar or no dielectric. The external field density is further enhanced by placing the plates very close together, but the optimal separation may be determined empirically.

FIG. 36B shows an embodiment comprising a concurrent lead design. The concurrent lead comprises an internal wire 3655 and an external wire 3650. The internal wire passes through the top plate 3610 and dielectric plate 3620 and is attached or integral to the bottom plate 3630. The external wire is attached or integral to the top plate 3610. Those skilled in the art will recognize that the foregoing arrangement of the leads may be reversed. FIG. 36C shows an embodiment comprising edge leads 3660 and 3665. Edge lead 3660 is attached or integral to top plate 3610 and edge lead 3665 is attached or integral to bottom plate 3630.

Some of the embodiments of the subject invention include the following:

A method of characterizing the biological activity of a candidate compound comprising.

exposing one or more cells to said compound; repetitively exposing said one or more cells to one or more electric fields so as to effect a controlled change in transmembrane potential of said one or more cells; and monitoring, without using a patch clamp, changes in the transmembrane potential of said one or more cells.

The above method, where the monitoring comprises detecting fluorescence emission from an area of observation containing said one or more cells.

The above method, where the electric fields are biphasic.

The above method, additionally comprising limiting spatial variation in electric field intensity so as to minimize irreversible cell electroporation.

The above method, where one or more electrical fields may cause an ion channel of interest to cycle between different voltage dependent states.

The above method, where the one or more electrical fields cause an ion channel of interest to open.

The above method, where the one or more electrical fields cause an ion channel of interest to be released from inactivation.

The above method, where the one or more cells comprise a voltage sensor selected from the group consisting of a FRET based voltage sensor, an electrochromic transmembrane potential dye, a transmembrane potential redistribution dye, an ion sensitive fluorescent or luminescent molecule and a radioactive ion.

The above method, where the one or more cells comprise a voltage regulated ion channel.

The above method, where the voltage regulated ion channel is selected from the group consisting of a potassium channel, a calcium channel, a chloride channel and a sodium channel.

The above method, where the electric field exhibits limited spatial variation in intensity in the area of observation of less than about 25% from. a mean intensity in that area.

The above method, where the one or more electrical fields varies over an area of observation by no more than about 15% from the mean electrical field at any one time.

The above method, where the one or more electrical fields varies over an area of observation by no more than about 5% from the mean electrical field at any one time.

The above method, where the one or more electrical fields comprises stimulation with either a square wave-form, a sinusoidal wave-form or a saw tooth wave-form.

The above method, where the one or more electrical fields have an amplitude within the range of about 10 V/cm to about 100 V/cm.

The above method, where the one or more electrical fields have an amplitude within the range of about 20 V/cm to about 80 V/cm.

The above method, where the one or more electrical fields are repeated at a frequency of stimulation that is greater than or equal to the reciprocal of the transmembrane time constant of said one or more cells.

The above method, where the one or more electrical fields are repeated at a frequency of stimulation within the range of zero to 1 kHz.

The above method, where the one or more electrical fields have a pulse duration within the range of about 100 microseconds to about 20 milliseconds.

The above method, where the transmembrane potential is developed across the plasma membrane of said one or more cells.

A method of assaying the biochemical activity of a compound against a target ion channel comprising.

selecting a cell line having a normal resting transmembrane potential corresponding to a selected voltage dependent state of said target ion channel; expressing said target ion channel in a population of cells of said selected cell line; exposing said population of cells to said compound; repetitively exposing said population of cells to one or more electric fields so as to effect a controlled change in transmembrane potential of said one or more cells; and monitoring changes in the transmembrane potential of said one or more cells.

The above method, where the target ion channel is exogenously expressed in said cell line.

The above method, where the cell line is transfected with nucleic acid encoding said target ion channel.

The above method, where the cell line expresses insignificant levels of other ion channels.

The above method, where the cell line is selected from the group consisting of CUL,LTK(−), and CHO-M.

The above method, where the target ion channel is a sodium channel, and wherein said population of cells is selected from the group consisting of CHL cells, LTK(−) cells, and CHO-K1 cells.

The above method, where the target ion channel is a sodium channel, and wherein said population of cells is selected from the group consisting of HEK-293 cells, RBL cells, F11 cells, and HL5 cells.

The above method, where the target ion channel is a potassium channel, and wherein said population of cells is selected from the group consisting of CHL cells, LTK(−) cells, and CHO-K1 cells.

The above method, where the target ion channel is a calcium channel, and wherein said population of cells is selected from the group consisting of CHL cells, LTK(−) cells, and CHO-K1 cells.

A method of assaying ion channel activity comprising.

exposing at least one cell to a plurality of electric field pulses so as to create a controlled change in transmembrane potential and so as to activate an ion channel of interest; and detecting ion channel activity by detecting one or more changes in transmembrane potential without using a patch clamp.

The above method, where the at least one cell comprises a voltage sensor selected from the group consisting of a FRET based voltage sensor, an electrochromic transmembrane potential dye, a transmembrane potential redistribution dye, an ion sensitive fluorescent or luminescent molecule and a radioactive ion.

The above method, where the voltage sensor comprises a FRET based voltage sensor.

The above method, where the ion channel of interest is a voltage regulated ion channel.

The above method, where the plurality of electric field pulses cause said ion channel of interest to cycle between different voltage dependent states.

The above method, where the at least one cell is an eukaryotic cell.

The above method, where the at least one cell is a non-excitable cell.

The above method, where the at least one cell is a prokaryotic cell.

The above method, where the at least one cell is a tissue culture cell.

The above method, where the at least one cell is a primary cell line.

The above method, where the at least one cell is part of an intact living organism.

A method of assaying ion channel activity comprising.

expressing a selected target ion channel in at least one cell; expressing a selected counter ion channel in said at least one cell; exposing said at least one cell to a plurality of electric field pulses so as to create a controlled change in transmembrane potential and so as to activate said counter ion channel; and monitoring the transmembrane potential of said at least one cell.

The above method, where a transmembrane potential change is detected when said ion channel of interest is blocked.

The above method, where the ion channel of interest comprises a ligand gated ion channel.

The above method, where the counter channel comprises a sodium channel.

A method of modifying the transmembrane potential of a cell comprising repetitively applying biphasic electric field pulses to said cell, wherein said pulses have a maximum amplitude of less than approximately 90 V/cm, wherein said pulses are applied at a rate of at least about 1 per second, and wherein the total duration of each pulse is at least about 1 millisecond.

The above method, where the maximum amplitude is approximately 20 to 40 V/cm.

The above method, where the pulse duration is approximately 2 to 10 milliseconds per phase.

The above method, where the pulses are applied at a rate of approximately 20 to 100 pulses per second.

A method of characterizing the biological activity of a candidate compound comprising.

placing one or more cells into an area of observation in a sample well; exposing said one or more cells to said compound; repetitively exposing said one or more cells to a series of biphasic electric fields at a rate of approximately 20 to 100 pulses per second, wherein said electric fields exhibit limited spatial variation in intensity in the area of observation of less than about 25% from a mean intensity in that area, and wherein said electric fields produce a controlled change in transmembrane potential of said one or more cells; and monitoring changes in the transmembrane potential of said one or more cells by detecting fluorescence emission of a FRET based voltage sensor from, an area of observation containing said one or more cells.

The above method, where the one or more electrical fields cause an ion channel of interest to open.

The above method, where the one or more electrical fields cause an ion channel of interest to be released from inactivation.

The above method, where the one or more cells comprise a voltage regulated ion channel.

The above method, where the voltage regulated ion channel is selected from the group consisting of a potassium channel, a calcium channel, a chloride channel and a sodium channel.

The above method, where the one or more electrical fields likely vary over an area of observation by no more than about 15% from the mean electrical field at any one time.

The above method, where the one or more electrical fields varies over an area of observation by no more than about 5% from the mean electrical field at any one time.

The above method, where the one or more electrical fields are selected from a square wave-form, a sinusoidal wave-form or a saw tooth wave-form.

A high throughput screening system comprising.

a plurality of wells having a high transmittance portion through which cells present in said wells are optically observable in an area of observation; two electrodes in each of said plurality of wells; an optical detector configured to detect light emanating from said wells through said high transmittance portion; a power supply connected to said electrodes; wherein said power supply and said electrodes are configured to apply a series of electric fields to cells within said area of observation, said electric fields having a spatial variation of less than about 25% of a mean field intensity within said area of observation, said electric fields being effective to controllably alter the transmembrane potential of a portion of said cells; a data processing unit configured to interpret said light emanating from said wells, through said high transmittance portion as ion channel activity resulting from said transmembrane potential alterations.

The above high throughput screening system, where the pluarality of wells are located in a multiwell plate.

The above high throughput screening system, where the high transmittance portion is made from a material selected from the group consisting of glass, quartz, cycloolefin, Aclar, polypropylene, polyethylene and polystyrene.

The above high throughput screening system, where the high transmittance portion exhibits less fluorescence when excited with UV light in the range of 250 nm to 400 nm than polystyrene.

The above high throughput screening system, where the electrodes are located in a well of said plurality of wells.

The above high throughput screening system, where the electrodes are located in a bottom layer of said plurality of wells.

The above high throughput screening system, where the multiwell plate comprises up to 96 wells.

The above high throughput screening system, where the multiwell plate comprises greater than 96 wells.

The above high throughput screening system, where the multiwell plate comprises greater than 384 wells.

The above high throughput screening system, where the electrodes are made of a material selected from the group consisting of gold, platinum, palladium, chromium, molybdenum, iridium, tungsten, tantalum and titanium.

The above high throughput screening system, where the multiwell plate comprises optically opaque materials or pigments to reduce the transmission of light.

The above high throughput screening system, where the electrodes are separated by a gap within the range of about 1 to 4 mm.

The above high throughput screening system, where the electrodes are separated by a gap within the range of about 0.1 to 1 mm.

1.0 The above high throughput screening system, where the electrodes are separated by a gap within the range of about 0.01 to 0.1 mm.

The above high throughput screening system, where the electrodes are charged to create an electrical field intensity of between 5 to 100 V/cm across said gap, and wherein the total charge transferred across the surface area of the electrically conductive material, in fluidic connection with the interior of the well is less than or equal to 100 µC/mm2.

The above high throughput screening system, where the plurality of wells further comprise an insulator orientated and configured so as to create an area of observation within said well in which. the electrical field intensity varies by no more than 10% from the mean electrical field intensity when said at least two strips of electrically conductive material are charged to create an electrical field intensity of between 5 to 100 V/cm across said gap, and. wherein the total charge transferred across the surface area of the electrically conductive material, in fluidic connection with the interior of the well is less than or equal to looptC/mm2.

The above high throughput screening system, where the plurality of wells further comprise at least two satellite electrical conductors.

A high throughput screening system comprising.

sample wells; liquid handling stations for adding reagents and/or cells to said sample wells; and means for controlling the transmembrane potential of cells in said sample wells so as to selectively cause ion channel activity.

means for optically monitoring changes in said transmembrane potential.

The above high throughput screening system, where the means comprises electrodes configured to create an electric field having a spatial variation of less than about 25% of a mean field intensity within an area of observation.

The above high throughput screening system, where the means for controlling the transmembrane potential comprise an electrode array assembly.

The above high throughput screening system, where the electrode assembly array comprises 8 electrode assemblies.

The above high throughput screening system, where the electrode assembly array comprises 96 electrode assemblies.

The above-high throughput screening system, where the electrode assembly array comprises greater than 96 electrode assemblies.

The above high throughput screening system, where the system further comprises means for retractably moving said electrode assembly into and out of the wells of a multiwell plate.

The above high throughput screening system, where the means for controlling the transmembrane potential comprises electrical conductors with two substantially parallel planar surfaces.

The above high throughput screening system, where the electrical conductors are separated by a gap within the range of 1 to 4 mm.

The above high throughput screening system, where the electrical conductors are separated 5 by a gap within the range of 0.1 to 1 mm.

The above high throughput: screening system, where the electrical conductors further comprise a first insulator.

The above high throughput screening system, where the first insulator comprises two planar surfaces orientated perpendicular to said substantially parallel planar surfaces of said electrical conductors and substantially parallel with respect to each other.

The above high throughput: screening system, where the electrical conductors further comprise a second insulator attached to said at least two electrical conductors, wherein said second insulator is interposed in said gap between said at least two electrical conductors to define the depth of said aqueous solution between said at least two electrical conductors.

The above high throughput: screening system, where the first insulator is composed of allow fluorescence material, wherein. said low fluorescence material exhibits less fluorescence when excited with UV light in the range 250 nm to 400 nm than polystyrene of comparable size.

The above high throughput screening system, where the second insulator is composed of a low fluorescence material, wherein said low fluorescence material exhibits less fluorescence when excited with UV light in the range 250 nm to 400 nm than polystyrene of comparable size.

The above high throughput screening system, where the first insulator comprises an insulator selected from the group consisting of plastic, glass and ceramic.

The above high throughput screening system, where the plastic is selected from the group consisting of nylon, polystyrene, Teflon (tetrafluoroethylene), polypropylene, polyethylene, poly-vinyl chloride, and cycloolefin.

The above high throughput screening system, where the electrical conductors comprise a conductor selected from the group consisting of gold, platinum, titanium, tungsten, molybdenum, iridium, vandium, Nb, Ta, stainless steel and graphite.

The above high throughput screening system, where the electrical conductors comprise a surface treatment to reduce electrolysis.

The above high throughput screening system, where the surface treatment to reduce electrolysis comprises platinum black, gold black, iridium/iridium oxide, titanium/titanium nitride or polypyrrole films.

The above high throughput screening system, where the electrical field intensity varies by no more than 10% from the mean electrical field intensity when said at least two electrical conductors are charged to create an electrical field intensity of between 5 to 100 V/cm across said gap, wherein the total charge transferred across the surface area of the electrical conductors in contact with said aqueous solution is less than or equal to 100 µC/mm2.

The above high throughput screening system, where the electrical field intensity varies by no more than 5% from the mean electrical field intensity when said at least two electrical conductors are charged to create an electrical field intensity of between 5 to 100 V/cm across said gap, wherein the total charge transferred across the surface area of the electrical conductors in contact with said aqueous solution is less than or equal to 100 µC/mm2.

A method of screening a plurality of drug candidate compounds against a target ion channel comprising.

expressing said target ion channel in a population of host cells; placing a plurality of said host cells into each of a plurality of sample wells; adding a candidate drug compound to at least: one of said plurality of sample wells; and modulating the transmembrane potential of host cells in said plurality of sample wells with a repetitive application of electric fields so as to set said transmembrane potential to a level corresponding to a pre-selected voltage dependent state of said target ion channel.

The above method, additionally comprising selecting a host: cell line having a normal resting transmembrane potential corresponding to a second pre-selected voltage dependent state of said target ion channel.

The above method, where the electric fields are biphasic.

The above method, where electric fields cause an ion channel of interest to cycle between different voltage dependent states.

The above method, where the electric fields cause an ion channel of interest to open.

The above method, where the electric fields cause an ion channel of interest to be released from inactivation.

The above method, where the one or more cells comprise a voltage sensor selected from the group consisting of a FRET based voltage sensor, an electrochromic transmembrane potential dye, a transmembrane potential redistribution dye, an ion sensitive fluorescent or luminescent molecule and a radioactive ion.

The above method, where the target ion channel is selected from the group consisting of a potassium channel, a calcium channel, a chloride channel and a sodium channel.

The above method, where the one or more electrical fields comprises stimulation with either a square wave-form, a sinusoidal wave-form or a saw tooth wave-form.

The above method, where the one or more electrical fields have an amplitude within the range of about 10 V/cm to about 100 V/cm.

The above method, where the one or more electrical fields have an amplitude within the range of about 20 V/cm to, about 80 V/cm.

An assay plate and electrode assembly comprising at least one sample well having electrodes placed therein, wherein said electrodes are positioned with respect to the bottom surface of the well to provide an electric field adjacent to said bottom surface that varies by less than about 10% from a mean field intensity over at least about 20% of the surface area of said bottom surface.

The above assembly, where the electrodes comprise plate electrodes extending down into said well such that bottom ends of said electrodes are adjacent to but not in contact with said bottom surface.

The above assembly, comprising two electrodes per sample well. The above assembly, comprising more than two electrodes per sample well.

The above assembly, where the electrodes are plated onto said bottom surface of said well. The above assembly, where the bottom surface comprises a high optical transmittance portion.

The above assembly, where the high transmittance portion is made from a material selected from the group consisting of glass, quartz, cycloolefin, Aclar, polypropylene, polyethylene and polystyrene.

The above assembly, where the high transmittance portion exhibits less fluorescence when excited with UV light in the range of 250 nm to 400 nm than polystyrene.

The above assembly, where the electrodes are located in a wall of said plurality of wells.

The above assembly, where the plate comprises up to 96 wells.

The above assembly, where the plate comprises greater than 96 wells.

The above assembly, where the plate comprises greater than 384 wells.

The above assembly, where the electrodes are made of a material selected from the group consisting of gold, platinum, palladium, chromium, molybdenum, iridium, tungsten, tantalum and titanium.

The above assembly, where the electrodes are separated by a gap within the range of about 1 to 4 mm.

The above assembly, where the electrodes are separated by a gap within the range of about 0.1 to 1 mm.

The above assembly, where the electrodes are separated by a gap within the range of about 0.01 to 0.1 mm.

A bottom panel for a multi-well plate comprising.

at least one row of high transmittance regions with positions corresponding to well locations; a first: strip of conductive material extending along said row and overlapping a first portion of said well locations; and a second strip of conductive material extending along said row and overlapping a second portion of said well locations.

The above bottom panel, additionally comprising a first: electrical contact proximate to an end of said first strip and a second electrical contact proximate to an end of said second strip.

An assay apparatus comprising.

a sample well; a first pair of electrodes positioned within said sample well; at least one additional satellite electrode positioned within said sample well.

The above assay apparatus, where the at least one additional satellite electrode comprises second and third pairs of electrodes.

The above assay apparatus, where the satellite electrodes are charged to a potential less than that of the first pair of electrodes.

The above assay apparatus, where the electrodes are positioned with respect to the bottom surface of the well to provide an electric field adjacent to said bottom surface that varies by less than about 10% from a mean field intensity over at least about 20% of the surface area of said bottom surface.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties. Furthermore, for general information, PCT Publication No. PCT/US01/21652 is incorporated herein in its entirety to the extent it is accurate and not inconsistent with the teachings herein. All patents, patent applications, publications, texts and references discussed or cited herein are understood to be incorporated by reference to the same extent as if each individual publication or patent application was specifically and individually set forth in its entirety. In addition, all references, patents, applications, and other documents cited in an Invention Disclosure Statement, Examiner's Summary of Cited References, or otherwise entered into the file history of this application are taken to be incorporated by reference into this specification for the benefit of later applications claiming priority to this application. Finally, all terms not specifically defined are first taken to have the meaning given through usage in this disclosure, and if no such meaning is inferable, their normal meaning.

What is claimed is:

1. A system for applying electrical field stimulation to cells, said system comprising:
   (a) a multiwell tissue culture plate, wherein the bottom of the wells is comprised of an optically transparent filter membrane upon which cells can be grown;
   (b) a trough suitable for containing fluid and configured such that said multiwell tissue culture plate may sit therein;
   (c) at least one first electrode disposed in said trough; and
   (d) an electrode head comprising a plurality of second electrodes in an amount corresponding to the number of wells in said multiwell tissue culture plate, wherein said electrode head and said plurality of electrodes are configured such that said electrodes are disposed in the wells of the multiwell tissue culture plate upon positioning said electrode head onto said multiwell tissue culture plate; and
   wherein said first electrode and said plurality of second electrodes are so disposed that when a pre-selected voltage is applied across the electrodes the transmembrane potential of cells within the wells is altered.

2. The system of claim 1 further comprising a waveform generator that is in electrical communication with said first electrode or said plurality of second electrodes, or both, whereby electric pulse signals are generated by said waveform generator.

3. The system of claim 2 further comprising a computer electrically connected to said waveform generator, said computer comprising software for coordinating said pulse signals produced by said waveform generator.

4. The system of claim 2 wherein said waveform generator generates a binary value that represents the address of the well to be excited by said pulse signals.

5. The system of claim 2 further comprising electrical relays upstream of said plurality of second electrodes.

6. The system of claim 5 further comprising a microcontroller in electrical communication with said waveform generator and said electrical relays so disposed such that upon receiving a trigger pulse and a particular binary value from said waveform generator, said microcontroller switches on the appropriate relay thereby directing a pulse to the particular electrode corresponding to the said particular binary value.

7. The system of claim 1 wherein:
   said trough comprises a plurality of individual troughs suitable for containing fluid, where the number of plurality of troughs corresponds to the number of wells in said multiwell tissue culture plate, where the plurality of troughs are so disposed to individually contain each well of said multiwell tissue culture plate; and where said plurality of troughs may be accessed by a port defined in said multiwell tissue culture plate and disposed laterally to each well; and
   said conductive electrode head comprises a conductive electrode plate configured to be mounted above said multiwell tissue culture plate, wherein said electrode plate comprises a plurality of apertures configured to allow the wells of the multiwell tissue culture plate to pass through said electrode plate, where said electrode plate comprises a plurality of conductive pins integral or attached to said electrode plate, and where the individual pins of said plurality of conductive pins pass through said port to be disposed in individual troughs upon mounting said electrode plate on top of said multiwell tissue culture plate.

* * * * *

SEQUENCE LISTING

<160> NUMBER OF SEQ ID NOS: 12

<210> SEQ ID NO 1
<211> LENGTH: 5874
<212> TYPE: DNA
<213> ORGANISM: Homo Sapiens

<400> SEQUENCE: 1

| | | | | | | |
|---|---|---|---|---|---|---|
| atggaattcc | ccattggatc | cctcgaaact | aacaacttcc | gtcgctttac | tccggagtca | 60 |
| ctggtggaga | tagagaagca | aattgctgcc | aagcagggaa | caaagaaagc | cagagagaag | 120 |
| catagggagc | agaaggacca | agaagagaag | cctcggcccc | agctggactt | gaaagcctgc | 180 |
| aaccagctgc | ccaagttcta | tggtgagctc | ccagcagaac | tgatcgggga | gcccctggag | 240 |
| gatctagatc | cgttctacag | cacacaccgg | acatttatgg | tgctgaacaa | agggaggacc | 300 |
| atttcccggt | ttagtgccac | tcgggccctg | tggctattca | gtcctttcaa | cctgatcaga | 360 |
| agaacggcca | tcaaagtgtc | tgtccactcg | tggttcagtt | tatttattac | ggtcactatt | 420 |
| ttggttaatt | gtgtgtgcat | gacccgaact | gaccttccag | agaaaattga | atatgtcttc | 480 |
| actgtcattt | acacctttga | agccttgata | aagatactgg | caagaggatt | ttgtctaaat | 540 |
| gagttcacgt | acctgagaga | tccttggaac | tggctggatt | ttagcgtcat | taccctggca | 600 |
| tatgttggca | cagcaataga | tctccgtggg | atctcaggcc | tgcggacatt | cagagttctt | 660 |
| agagcattaa | aaacagtttc | tgtgatccca | ggcctgaagg | tcattgtggg | ggccctgatt | 720 |
| cactcagtga | agaaactggc | tgatgtgacc | atcctcacca | tcttctgcct | aagtgttttt | 780 |
| gccttggtgg | ggctgcaact | cttcaagggc | aacctcaaaa | ataaatgtgt | caagaatgac | 840 |
| atggctgtca | atgagacaac | caactactca | tctcacagaa | aaccagatat | ctacataaat | 900 |
| aagcgaggca | cttctgaccc | cttactgtgt | ggcaatggat | ctgactcagg | ccactgccct | 960 |
| gatggttata | tctgccttaa | aacttctgac | aacccggatt | ttaactacac | cagctttgat | 1020 |
| tcctttgctt | gggcttttct | ctcactgttc | cgcctcatga | cacaggattc | ctgggaacgc | 1080 |
| ctctaccagc | agaccctgag | gacttctggg | aaaatctata | tgatcttttt | tgtgctcgta | 1140 |
| atcttcctgg | gatctttcta | cctggtcaac | ttgatcttgg | ctgtagtcac | catggcgtat | 1200 |
| gaggagcaga | accaggcaac | cactgatgaa | attgaagcaa | aggagaagaa | gttccaggag | 1260 |
| gccctcgaga | tgctccggaa | ggagcaggag | gtgctagcag | cactagggat | tgacacaacc | 1320 |
| tctctccact | cccacaatgg | atcacctta | acctccaaaa | atgccagtga | gagaaggcat | 1380 |
| agaataaagc | caagagtgtc | agagggctcc | acagaagaca | caaatcacc | ccgctctgat | 1440 |
| ccttacaacc | agcgcaggat | gtcttttcta | ggcctcgcct | ctggaaaacg | ccgggctagt | 1500 |
| catggcagtg | tgttccattt | ccggtcccct | ggccgagata | tctcactccc | tgagggagtc | 1560 |
| acagatgatg | gagtctttcc | tggagaccac | gaaagccatc | gggctctct | gctgctgggt | 1620 |
| gggggtgctg | gccagcaagg | ccccctccct | agaagccctc | ttcctcaacc | cagcaaccct | 1680 |
| gactccaggc | atgagaaga | tgaacaccaa | ccgccgccca | ctagtgagct | tgcccctgga | 1740 |
| gctgtcgatg | tctcggcatt | cgatgcagga | caaaagaaga | cttcttgtc | agcagaatac | 1800 |
| ttagatgaac | ctttccgggc | ccaaagggca | atgagtgttg | tcagtatcat | aacctccgtc | 1860 |
| cttgaggaac | tcgaggagtc | tgaacagaag | tgcccaccct | gcttgaccag | cttgtctcag | 1920 |
| aagtatctga | tctgggattg | ctgccccatg | tgggtgaagc | tcaagacaat | tctctttggg | 1980 |
| cttgtgacgg | atccctttgc | agagctcacc | atcaccttgt | gcatcgtggt | gaacaccatc | 2040 |

```
ttcatggcca tggagcacca tggcatgagc cctaccttcg aagccatgct ccagataggc    2100
aacatcgtct ttaccatatt ttttactgct gaaatggtct tcaaaatcat tgccttcgac    2160
ccatactatt atttccagaa gaagtggaat atctttgact gcatcatcgt cactgtgagt    2220
ctgctagagc tgggcgtggc caagaaggga agcctgtctg tgctgcggag cttccgcttg    2280
ctgcgcgtat tcaagctggc caaatcctgg cccaccttaa acacactcat caagatcatc    2340
ggaaactcag tgggggcact ggggaacctc accatcatcc tggccatcat tgtctttgtc    2400
tttgctctgg ttggcaagca gctcctaggg gaaaactacc gtaacaaccg aaaaaatatc    2460
tccgcgcccc atgaagactg gccccgctgg cacatgcacg acttcttcca ctctttcctc    2520
attgtcttcc gtatcctctg tggagagtgg attgagaaca tgtgggcctg catggaagtt    2580
ggccaaaaat ccatatgcct catccttttc ttgacggtga tggtgctagg gaacctggtg    2640
gtgcttaacc tgttcatcgc cctgctattg aactctttca gtgctgacaa cctcacagcc    2700
ccggaggacg atggggaggt gaacaacctg caggtggccc tggcacggat ccaggtcttt    2760
ggccatcgta ccaaacaggc tctttgcagc ttcttcagca ggtcctgccc attccccag    2820 cccaaggcag agcctgagct ggtggtgaaa ctcccactct ccagctccaa ggctgagaac    2880
cacattgctg ccaacactgc caggggagc tctggagggc tccaagctcc cagaggcccc    2940
agggatgagc acagtgactt catcgctaat ccgactgtgt gggtctctgt gcccattgct    3000
gagggtgaat ctgatcttga tgacttggag gatgatggtg gggaagatgc tcagagcttc    3060
cagcaggaag tgatccccaa aggacagcag gagcagctgc agcaagtcga gaggtgtggg    3120
gaccacctga cacccaggag cccaggcact ggaacatctt ctgaggacct ggctccatcc    3180
ctgggtgaga cgtggaaaga tgagtctgtt cctcaggccc ctgctgaggg agtggacgac    3240
acaagctcct ctgagggcag cacggtggac tgcctagatc ctgaggaaat cctgaggaag    3300
atccctgagc tggcagatga cctggaagaa ccagatgact gcttcacaga aggatgcatt    3360
cgccactgtc cctgctgcaa actggatacc accaagagtc catgggatgt gggctggcag    3420
gtgcgcaaga cttgctaccg tatcgtggag cacagctggt tgagagctt catcatcttc    3480 atgatcctgc tcagcagtgg atctctggcc tttgaagact attacctgga ccagaagccc    3540
acggtgaaag ctttgctgga gtacactgac agggtcttca cctttatctt tgtgttcgag    3600
atgctgctta agtgggtggc ctatggcttc aaaaagtact tcaccaatgc ctggtgctgg    3660
ctggacttcc tcattgtgaa tatctcactg ataagtctca cagcgaagat tctgaatat    3720 tctgaagtgg ctcccatcaa agcccttcga acccttcgcg ctctgcggcc actgcgggct    3780
ctttctcgat ttgaaggcat gcgggtggtg gtggatgccc tggtgggcgc catcccatcc    3840
atcatgaatg tcctcctcgt ctgcctcatc ttctggctca tcttcagcat catgggtgtg    3900
aacctcttcg cagggaagtt ttggaggtgc atcaactata ccgatggaga gttttccctt    3960
gtacctttgt cgattgtgaa taacaagtct gactgcaaga ttcaaaactc cactggcagc    4020
ttcttctggg tcaatgtgaa agtcaacttt gataatgttg caatgggtta ccttgcactt    4080
ctgcaggtgg caacctttaa aggctggatg gacattatgt atgcagctgt tgattccgg    4140 gaggtcaaca tgcaacccaa gtgggaggac aacgtgtaca tgtatttgta ctttgtcatc    4200
ttcatcattt ttggaggctt cttcacactg aatctctttg ttgggggtcat aattgacaac    4260 ttcaatcaac agaaaaaaaa gttagggggc caggacatct tcatgacaga ggagcagaag    4320
aaatactaca atgccatgaa gaagttgggc tccaagaagc cccagaagcc catcccacgg    4380
```

```
cccctgaaca agttccaggg ttttgtcttt gacatcgtga ccagacaagc ttttgacatc    4440
accatcatgg tcctcatctg cctcaacatg atcaccatga tggtggagac tgatgaccaa    4500
agtgaagaaa agacgaaaat tctgggcaaa atcaaccagt tctttgtggc cgtcttcaca    4560
ggcgaatgtg tcatgaagat gttcgctttg aggcagtact acttcacaaa tggctggaat    4620
gtgtttgact tcattgtggt ggttctctcc attgcgagcc tgattttttc tgcaattctt    4680
aagtcacttc aaagttactt ctccccaacg ctcttcagag tcatccgcct ggcccgaatt    4740
ggccgcatcc tcagactgat ccgagcggcc aagggatcc gcacactgct ctttgccctc    4800
atgatgtccc tgcctgccct cttcaacatc gggctgttgc tattccttgt catgttcatc    4860
tactccatct tcggtatgtc cagctttccc catgtgaggt gggaggctgg catcgacgac    4920
atgttcaact tccagacctt cgccaacagc atgctgtgcc tcttccagat taccacgtcg    4980
gccggctggg atggcctcct cagccccatc ctcaacacag gccccccta ctgtgacccc    5040 aatctgccca cagcaatgg caccagaggg gactgtggga gcccagccgt aggcatcatc    5100
ttcttcacca cctacatcat catctccttc ctcatcgtgg tcaacatgta cattgcagtg    5160
attctgagaa acttcaatgt ggccacggag gagagcactg agcctctgag tgaggacgac    5220
tttgacatgt tctatgagac ctgggagaag tttgacccag aggccactca gtttattacc    5280
ttttctgctc tctcggactt tgcagacact ctctctggtc ccctgagaat cccaaaaccc    5340
aatcgaaata tactgatcca gatggacctg cctttggtcc ctggagataa gatccactgc    5400
ttggacatcc tttttgcttt caccaagaat gtcctaggag aatccgggga gttggattct    5460
ctgaaggcaa atatggagga gaagtttatg gcaactaatc tttcaaaatc atcctatgaa    5520
ccaatagcaa ccactctccg atggaagcaa gaagacattt cagccactgt cattcaaaag    5580
gcctatcgga gctatgtgct gcaccgctcc atggcactct ctaacacccc atgtgtgccc    5640
agagctgagg aggaggctgc atcactccca gatgaaggtt ttgttgcatt cacagcaaat    5700
gaaaattgtg tactcccaga caaatctgaa actgcttctg ccacatcatt cccaccgtcc    5760
tatgagagtg tcactagagg ccttagtgat agagtcaaca tgaggacatc tagctcaata    5820
caaaatgaag atgaagccac cagtatggag ctgattgccc tgggcccta gtga          5874
```

<210> SEQ ID NO 2
<211> LENGTH: 1956
<212> TYPE: PRT
<213> ORGANISM: Homo Sapiens

<400> SEQUENCE: 2

```
Met Glu Phe Pro Ile Gly Ser Leu Glu Thr Asn Asn Phe Arg Arg Phe
 1               5                  10                  15

Thr Pro Glu Ser Leu Val Glu Ile Glu Lys Gln Ile Ala Ala Lys Gln
             20                  25                  30

Gly Thr Lys Lys Ala Arg Glu Lys His Arg Glu Gln Lys Asp Gln Glu
         35                  40                  45

Glu Lys Pro Arg Pro Gln Leu Asp Leu Lys Ala Cys Asn Gln Leu Pro
     50                  55                  60

Lys Phe Tyr Gly Glu Leu Pro Ala Glu Leu Ile Gly Glu Pro Leu Glu
 65                  70                  75                  80

Asp Leu Asp Pro Phe Tyr Ser Thr His Arg Thr Phe Met Val Leu Asn
                 85                  90                  95

Lys Gly Arg Thr Ile Ser Arg Phe Ser Ala Thr Arg Ala Leu Trp Leu
            100                 105                 110
```

```
Phe Ser Pro Phe Asn Leu Ile Arg Arg Thr Ala Ile Lys Val Ser Val
        115                 120                 125

His Ser Trp Phe Ser Leu Phe Ile Thr Val Thr Ile Leu Val Asn Cys
        130                 135                 140

Val Cys Met Thr Arg Thr Asp Leu Pro Glu Lys Ile Glu Tyr Val Phe
145                 150                 155                 160

Thr Val Ile Tyr Thr Phe Glu Ala Leu Ile Lys Ile Leu Ala Arg Gly
                165                 170                 175

Phe Cys Leu Asn Glu Phe Thr Tyr Leu Arg Asp Pro Trp Asn Trp Leu
        180                 185                 190

Asp Phe Ser Val Ile Thr Leu Ala Tyr Val Gly Thr Ala Ile Asp Leu
        195                 200                 205

Arg Gly Ile Ser Gly Leu Arg Thr Phe Arg Val Leu Arg Ala Leu Lys
        210                 215                 220

Thr Val Ser Val Ile Pro Gly Leu Lys Val Ile Val Gly Ala Leu Ile
225                 230                 235                 240

His Ser Val Lys Lys Leu Ala Asp Val Thr Ile Leu Thr Ile Phe Cys
                245                 250                 255

Leu Ser Val Phe Ala Leu Val Gly Leu Gln Leu Phe Lys Gly Asn Leu
        260                 265                 270

Lys Asn Lys Cys Val Lys Asn Asp Met Ala Val Asn Glu Thr Thr Asn
        275                 280                 285

Tyr Ser Ser His Arg Lys Pro Asp Ile Tyr Ile Asn Lys Arg Gly Thr
        290                 295                 300

Ser Asp Pro Leu Leu Cys Gly Asn Gly Ser Asp Ser Gly His Cys Pro
305                 310                 315                 320

Asp Gly Tyr Ile Cys Leu Lys Thr Ser Asp Asn Pro Asp Phe Asn Tyr
                325                 330                 335

Thr Ser Phe Asp Ser Phe Ala Trp Ala Phe Leu Ser Leu Phe Arg Leu
        340                 345                 350

Met Thr Gln Asp Ser Trp Glu Arg Leu Tyr Gln Gln Thr Leu Arg Thr
        355                 360                 365

Ser Gly Lys Ile Tyr Met Ile Phe Phe Val Leu Val Ile Phe Leu Gly
        370                 375                 380

Ser Phe Tyr Leu Val Asn Leu Ile Leu Ala Val Val Thr Met Ala Tyr
385                 390                 395                 400

Glu Glu Gln Asn Gln Ala Thr Thr Asp Glu Ile Glu Ala Lys Glu Lys
                405                 410                 415

Lys Phe Gln Glu Ala Leu Glu Met Leu Arg Lys Glu Gln Glu Val Leu
        420                 425                 430

Ala Ala Leu Gly Ile Asp Thr Thr Ser Leu His Ser His Asn Gly Ser
        435                 440                 445

Pro Leu Thr Ser Lys Asn Ala Ser Glu Arg Arg His Arg Ile Lys Pro
        450                 455                 460

Arg Val Ser Glu Gly Ser Thr Glu Asp Asn Lys Ser Pro Arg Ser Asp
465                 470                 475                 480

Pro Tyr Asn Gln Arg Arg Met Ser Phe Leu Gly Leu Ala Ser Gly Lys
                485                 490                 495

Arg Arg Ala Ser His Gly Ser Val Phe His Phe Arg Ser Pro Gly Arg
        500                 505                 510

Asp Ile Ser Leu Pro Glu Gly Val Thr Asp Asp Gly Val Phe Pro Gly
        515                 520                 525

Asp His Glu Ser His Arg Gly Ser Leu Leu Leu Gly Gly Gly Ala Gly
```

-continued

```
            530                 535                 540
Gln Gln Gly Pro Leu Pro Arg Ser Pro Leu Pro Gln Pro Ser Asn Pro
545                 550                 555                 560

Asp Ser Arg His Gly Glu Asp Glu His Gln Pro Pro Thr Ser Glu
                565                 570                 575

Leu Ala Pro Gly Ala Val Asp Val Ser Ala Phe Asp Ala Gly Gln Lys
                580                 585                 590

Lys Thr Phe Leu Ser Ala Glu Tyr Leu Asp Glu Pro Phe Arg Ala Gln
                595                 600                 605

Arg Ala Met Ser Val Val Ser Ile Ile Thr Ser Val Leu Glu Glu Leu
            610                 615                 620

Glu Glu Ser Glu Gln Lys Cys Pro Pro Cys Leu Thr Ser Leu Ser Gln
625                 630                 635                 640

Lys Tyr Leu Ile Trp Asp Cys Cys Pro Met Trp Val Lys Leu Lys Thr
                645                 650                 655

Ile Leu Phe Gly Leu Val Thr Asp Pro Phe Ala Glu Leu Thr Ile Thr
                660                 665                 670

Leu Cys Ile Val Val Asn Thr Ile Phe Met Ala Met Glu His His Gly
            675                 680                 685

Met Ser Pro Thr Phe Glu Ala Met Leu Gln Ile Gly Asn Ile Val Phe
            690                 695                 700

Thr Ile Phe Phe Thr Ala Glu Met Val Phe Lys Ile Ile Ala Phe Asp
705                 710                 715                 720

Pro Tyr Tyr Tyr Phe Gln Lys Lys Trp Asn Ile Phe Asp Cys Ile Ile
                725                 730                 735

Val Thr Val Ser Leu Leu Glu Leu Gly Val Ala Lys Lys Gly Ser Leu
                740                 745                 750

Ser Val Leu Arg Ser Phe Arg Leu Leu Arg Val Phe Lys Leu Ala Lys
                755                 760                 765

Ser Trp Pro Thr Leu Asn Thr Leu Ile Lys Ile Ile Gly Asn Ser Val
                770                 775                 780

Gly Ala Leu Gly Asn Leu Thr Ile Ile Leu Ala Ile Ile Val Phe Val
785                 790                 795                 800

Phe Ala Leu Val Gly Lys Gln Leu Leu Gly Glu Asn Tyr Arg Asn Asn
                805                 810                 815

Arg Lys Asn Ile Ser Ala Pro His Glu Asp Trp Pro Arg Trp His Met
                820                 825                 830

His Asp Phe Phe His Ser Phe Leu Ile Val Phe Arg Ile Leu Cys Gly
                835                 840                 845

Glu Trp Ile Glu Asn Met Trp Ala Cys Met Glu Val Gly Gln Lys Ser
                850                 855                 860

Ile Cys Leu Ile Leu Phe Leu Thr Val Met Val Leu Gly Asn Leu Val
865                 870                 875                 880

Val Leu Asn Leu Phe Ile Ala Leu Leu Leu Asn Ser Phe Ser Ala Asp
                885                 890                 895

Asn Leu Thr Ala Pro Glu Asp Asp Gly Glu Val Asn Asn Leu Gln Val
                900                 905                 910

Ala Leu Ala Arg Ile Gln Val Phe Gly His Arg Thr Lys Gln Ala Leu
                915                 920                 925

Cys Ser Phe Phe Ser Arg Ser Cys Pro Phe Pro Gln Pro Lys Ala Glu
                930                 935                 940

Pro Glu Leu Val Val Lys Leu Pro Leu Ser Ser Ser Lys Ala Glu Asn
945                 950                 955                 960
```

```
His Ile Ala Ala Asn Thr Ala Arg Gly Ser Ser Gly Gly Leu Gln Ala
            965                 970                 975

Pro Arg Gly Pro Arg Asp Glu His Ser Asp Phe Ile Ala Asn Pro Thr
            980                 985                 990

Val Trp Val Ser Val Pro Ile Ala Glu Gly Glu Ser Asp Leu Asp Asp
            995                1000                1005

Leu Glu Asp Asp Gly Gly Glu Asp Ala Gln Ser Phe Gln Gln Glu Val
        1010                1015                1020

Ile Pro Lys Gly Gln Gln Glu Gln Leu Gln Gln Val Glu Arg Cys Gly
1025                1030                1035                1040

Asp His Leu Thr Pro Arg Ser Pro Gly Thr Gly Thr Ser Ser Glu Asp
            1045                1050                1055

Leu Ala Pro Ser Leu Gly Glu Thr Trp Lys Asp Glu Ser Val Pro Gln
            1060                1065                1070

Ala Pro Ala Glu Gly Val Asp Asp Thr Ser Ser Ser Glu Gly Ser Thr
            1075                1080                1085

Val Asp Cys Leu Asp Pro Glu Glu Ile Leu Arg Lys Ile Pro Glu Leu
            1090                1095                1100

Ala Asp Asp Leu Glu Glu Pro Asp Asp Cys Phe Thr Glu Gly Cys Ile
1105                1110                1115                1120

Arg His Cys Pro Cys Cys Lys Leu Asp Thr Thr Lys Ser Pro Trp Asp
            1125                1130                1135

Val Gly Trp Gln Val Arg Lys Thr Cys Tyr Arg Ile Val Glu His Ser
            1140                1145                1150

Trp Phe Glu Ser Phe Ile Ile Phe Met Ile Leu Leu Ser Ser Gly Ser
            1155                1160                1165

Leu Ala Phe Glu Asp Tyr Tyr Leu Asp Gln Lys Pro Thr Val Lys Ala
            1170                1175                1180

Leu Leu Glu Tyr Thr Asp Arg Val Phe Thr Phe Ile Phe Val Phe Glu
1185                1190                1195                1200

Met Leu Leu Lys Trp Val Ala Tyr Gly Phe Lys Lys Tyr Phe Thr Asn
            1205                1210                1215

Ala Trp Cys Trp Leu Asp Phe Leu Ile Val Asn Ile Ser Leu Ile Ser
            1220                1225                1230

Leu Thr Ala Lys Ile Leu Glu Tyr Ser Glu Val Ala Pro Ile Lys Ala
            1235                1240                1245

Leu Arg Thr Leu Arg Ala Leu Arg Pro Leu Arg Ala Leu Ser Arg Phe
            1250                1255                1260

Glu Gly Met Arg Val Val Asp Ala Leu Val Gly Ala Ile Pro Ser
1265                1270                1275                1280

Ile Met Asn Val Leu Leu Val Cys Leu Ile Phe Trp Leu Ile Phe Ser
            1285                1290                1295

Ile Met Gly Val Asn Leu Phe Ala Gly Lys Phe Trp Arg Cys Ile Asn
            1300                1305                1310

Tyr Thr Asp Gly Glu Phe Ser Leu Val Pro Leu Ser Ile Val Asn Asn
            1315                1320                1325

Lys Ser Asp Cys Lys Ile Gln Asn Ser Thr Gly Ser Phe Phe Trp Val
            1330                1335                1340

Asn Val Lys Val Asn Phe Asp Asn Val Ala Met Gly Tyr Leu Ala Leu
1345                1350                1355                1360

Leu Gln Val Ala Thr Phe Lys Gly Trp Met Asp Ile Met Tyr Ala Ala
            1365                1370                1375
```

```
Val Asp Ser Arg Glu Val Asn Met Gln Pro Lys Trp Glu Asp Asn Val
            1380                1385                1390

Tyr Met Tyr Leu Tyr Phe Val Ile Phe Ile Ile Phe Gly Gly Phe Phe
        1395                1400                1405

Thr Leu Asn Leu Phe Val Gly Val Ile Ile Asp Asn Phe Asn Gln Gln
        1410                1415                1420

Lys Lys Lys Leu Gly Gly Gln Asp Ile Phe Met Thr Glu Glu Gln Lys
1425                1430                1435                1440

Lys Tyr Tyr Asn Ala Met Lys Lys Leu Gly Ser Lys Lys Pro Gln Lys
            1445                1450                1455

Pro Ile Pro Arg Pro Leu Asn Lys Phe Gln Gly Phe Val Phe Asp Ile
            1460                1465                1470

Val Thr Arg Gln Ala Phe Asp Ile Thr Ile Met Val Leu Ile Cys Leu
            1475                1480                1485

Asn Met Ile Thr Met Met Val Glu Thr Asp Asp Gln Ser Glu Glu Lys
            1490                1495                1500

Thr Lys Ile Leu Gly Lys Ile Asn Gln Phe Phe Val Ala Val Phe Thr
1505                1510                1515                1520

Gly Glu Cys Val Met Lys Met Phe Ala Leu Arg Gln Tyr Tyr Phe Thr
            1525                1530                1535

Asn Gly Trp Asn Val Phe Asp Phe Ile Val Val Leu Ser Ile Ala
            1540                1545                1550

Ser Leu Ile Phe Ser Ala Ile Leu Lys Ser Leu Gln Ser Tyr Phe Ser
            1555                1560                1565

Pro Thr Leu Phe Arg Val Ile Arg Leu Ala Arg Ile Gly Arg Ile Leu
            1570                1575                1580

Arg Leu Ile Arg Ala Ala Lys Gly Ile Arg Thr Leu Leu Phe Ala Leu
1585                1590                1595                1600

Met Met Ser Leu Pro Ala Leu Phe Asn Ile Gly Leu Leu Leu Phe Leu
            1605                1610                1615

Val Met Phe Ile Tyr Ser Ile Phe Gly Met Ser Ser Phe Pro His Val
            1620                1625                1630

Arg Trp Glu Ala Gly Ile Asp Asp Met Phe Asn Phe Gln Thr Phe Ala
            1635                1640                1645

Asn Ser Met Leu Cys Leu Phe Gln Ile Thr Thr Ser Ala Gly Trp Asp
            1650                1655                1660

Gly Leu Leu Ser Pro Ile Leu Asn Thr Gly Pro Pro Tyr Cys Asp Pro
1665                1670                1675                1680

Asn Leu Pro Asn Ser Asn Gly Thr Arg Gly Asp Cys Gly Ser Pro Ala
            1685                1690                1695

Val Gly Ile Ile Phe Phe Thr Thr Tyr Ile Ile Ser Phe Leu Ile
            1700                1705                1710

Val Val Asn Met Tyr Ile Ala Val Ile Leu Glu Asn Phe Asn Val Ala
            1715                1720                1725

Thr Glu Glu Ser Thr Glu Pro Leu Ser Glu Asp Asp Phe Asp Met Phe
            1730                1735                1740

Tyr Glu Thr Trp Glu Lys Phe Asp Pro Glu Ala Thr Gln Phe Ile Thr
1745                1750                1755                1760

Phe Ser Ala Leu Ser Asp Phe Ala Asp Thr Leu Ser Gly Pro Leu Arg
            1765                1770                1775

Ile Pro Lys Pro Asn Arg Asn Ile Leu Ile Gln Met Asp Leu Pro Leu
            1780                1785                1790

Val Pro Gly Asp Lys Ile His Cys Leu Asp Ile Leu Phe Ala Phe Thr
```

-continued

```
                  1795                1800                1805
Lys Asn Val Leu Gly Glu Ser Gly Glu Leu Asp Ser Leu Lys Ala Asn
    1810                1815                1820

Met Glu Glu Lys Phe Met Ala Thr Asn Leu Ser Lys Ser Ser Tyr Glu
1825                1830                1835                1840

Pro Ile Ala Thr Thr Leu Arg Trp Lys Gln Glu Asp Ile Ser Ala Thr
                1845                1850                1855

Val Ile Gln Lys Ala Tyr Arg Ser Tyr Val Leu His Arg Ser Met Ala
                    1860                1865                1870

Leu Ser Asn Thr Pro Cys Val Pro Arg Ala Glu Glu Ala Ala Ser
        1875                1880                1885

Leu Pro Asp Glu Gly Phe Val Ala Phe Thr Ala Asn Glu Asn Cys Val
    1890                1895                1900

Leu Pro Asp Lys Ser Glu Thr Ala Ser Ala Thr Ser Phe Pro Pro Ser
1905                1910                1915                1920

Tyr Glu Ser Val Thr Arg Gly Leu Ser Asp Arg Val Asn Met Arg Thr
                1925                1930                1935

Ser Ser Ser Ile Gln Asn Glu Asp Glu Ala Thr Ser Met Glu Leu Ile
                    1940                1945                1950

Ala Pro Gly Pro
        1955

<210> SEQ ID NO 3
<211> LENGTH: 7898
<212> TYPE: DNA
<213> ORGANISM: Homo Sapiens

<400> SEQUENCE: 3
cgaggccgcc gccgtcgcct ccgccgggcg agccggagcc ggagtcgagc cgcggccggg        60
agccgggcgg gctggggacg cgggccgggg gcggaggcgc tggggccgg ggccggggcc       120 gggggcggag gcgctggggg ccggggccgg ggccgggcgc cgagcggggt ccgcggtgac       180
cgcgccgccc gggcgatgcc cgcggggacg ccgccggcca gcagagcgag gtgctgccgg       240
ccgccaccat gaccgagggc gcacgggccg ccgacgaggt ccgggtgccc ctgggcgcgc       300 cgcccctgg ccctgcggcg ttggtggggg cgtccccgga gagccccggg gcgccgggac        360
gcgaggcgga gcggggtcc gagctcggcg tgtcaccctc cgagagcccg gcggccgagc        420
gcggcgcgga gctgggtgcc gacgaggagc agcgcgtccc gtacccggcc ttggcggcca       480
cggtcttctt ctgcctcggt cagaccacgc ggccgcgcag ctggtgcctc cggctggtct       540
gcaacccatg gttcgagcac gtgagcatgc tggtaatcat gctcaactgc gtgaccctgg       600
gcatgttccg gccctgtgag gacgttgagt gcggctccga gcgctgcaac atcctggagg       660
cctttgacgc cttcatttc gccttttttg cggtggagat ggtcatcaag atggtggcct       720 tgggctgtt cgggcagaag tgttacctgg gtgacacgtg aacaggctg gatttcttca        780 tcgtcgtggc gggcatgatg gagtactcgt tggacggaca caacgtgagc ctctcggcta       840
tcaggaccgt gcgggtgctg cggccccctcc gcgccatcaa ccgcgtgcct agcatgcgga       900
tcctggtcac tctgctgctg gatacgctgc ccatgctcgg gaacgtcctt ctgctgtgct       960
tcttcgtctt cttcatttc ggcatcgttg cgtccagct ctgggctggc ctcctgcgga      1020
accgctgctt cctggacagt gcctttgtca ggaacaacaa cctgaccttc ctgcggccgt      1080
actaccagac ggaggagggc gaggagaacc cgttcatctg ctcctcacgc cgagacaacg      1140
gcatgcagaa gtgctcgcac atccccggcc gccgcgagct gcgcatgccc tgcacccctgg     1200
```

-continued

```
gctgggaggc ctacacgcag ccgcaggccg agggggtggg cgctgcacgc aacgcctgca    1260
tcaactggaa ccagtactac aacgtgtgcc gctcgggtga ctccaacccc cacaacggtg    1320
ccatcaactt cgacaacatc ggctacgcct ggattgccat cttccaggtg atcacgctgg    1380
aaggctgggt ggacatcatg tactacgtca tggacgccca ctcattctac aacttcatct    1440
atttcatcct gctcatcatc gtgggctcct tcttcatgat caacctgtgc ctggtggtga    1500
ttgccacgca gttctcggag acgaagcagc gggagagtca gctgatgcgg gagcagcggg    1560
cacgccacct gtccaacgac agcacgctgg ccagcttctc cgagcctggc agctgctacg    1620
aagagctgct gaagtacgtg ggccacatat ccgcaaggt caagcggcgc agcttgcgcc    1680
tctacgcccg ctggcagagc cgctggcgca agaaggtgga ccccagtgct gtgcaaggcc    1740
agggtcccgg gcaccgccag cgccgggcag gcaggcacac agcctcggtg caccacctgg    1800
tctaccacca ccatcaccac caccaccacc actaccattt cagccatggc agccccccgca    1860 ggcccggccc cgagccaggc gcctgcgaca ccaggctggt ccgagctggc gcgccccct    1920 cgccaccttc cccaggccgc ggaccccccg acgcagagtc tgtgcacagc atctaccatg    1980
ccgactgcca catagagggg ccgcaggaga gggcccgggt ggcacatgcc gcagccactg    2040
ccgctgccag cctcaggctg gccacagggc tgggcaccat gaactacccc acgatcctgc    2100 cctcagggt gggcagcggc aaaggcagca ccagcccccgg acccaagggg aagtgggccg    2160
gtggaccgcc aggcaccggg gggcacggcc cgttgagctt gaacagccct gatccctacg    2220
agaagatccc gcatgtggtc ggggagcatg gactgggcca ggcccctggc catctgtcgg    2280
gcctcagtgt gccctgcccc ctgcccagcc ccccagcggg cacactgacc tgtgagctga    2340
agagctgccc gtactgcacc cgtgccctgg aggacccgga gggtgagctc agcggctcgg    2400
aaagtggaga ctcagatggc cgtggcgtct atgaattcac gcaggacgtc cggcacggtg    2460
accgctggga ccccacgcga ccaccccgtg cgacggacac accaggccca ggcccaggca    2520
gcccccagcg gcgggcacag cagagggcag ccccgggcga gccaggctgg atgggccgcc    2580
tctgggttac cttcagcggc aagctgcgcc gcatcgtgga cagcaagtac ttcagccgtg    2640
gcatcatgat ggccatcctt gtcaacacgc tgagcatggg cgtggagtac catgagcagc    2700
ccgaggagct gactaatgct ctggagatca gcaacatcgt gttcaccagc atgtttgccc    2760
tggagatgct gctgaagctg ctggcctgcg gccctctggg ctacatccgg aacccgtaca    2820
acatcttcga cggcatcatc gtggtcatca gcgtctggga gatcgtgggg caggcggacg    2880
gtggcttgtc tgtgctgcgc accttccggc tgctgcgtgt gctgaagctg gtgcgctttc    2940
tgccagccct gcgcgccag ctcgtggtgc tggtgaagac catggacaac gtggctacct    3000
tctgcacgct gctcatgctc ttcattttca tcttcagcat cctgggcatg cacctttcg    3060 gctgcaagtt cagcctgaag acagacaccg gagacaccgt gcctgacagg aagaacttcg    3120
actccctgct gtgggccatc gtcaccgtgt tccagatcct gacccaggag gactggaacg    3180
tggtcctgta caacggcatg gcctccacct cctcctgggc cgccctctac ttcgtggccc    3240
tcatgacctt cggcaactat gtgctcttca acctgctggt ggccatcctc gtggagggct    3300
tccaggcgga gggcgatgcc aacagatccg acacggacga ggacaagacg tcggtccact    3360
tcgaggagga cttccacaag ctcagagaac tccagaccac agagctgaag atgtgttccc    3420
tggccgtgac ccccaacggg cacctggagg acgaggcag cctgtcccct cccctcatca    3480
tgtgcacagc tgccacgccc atgcctaccc ccaagagctc accattcctg gatgcagccc    3540
```

```
ccagcctccc agactctcgg cgtggcagca gcagctccgg ggacccgcca ctgggagacc      3600
agaagcctcc ggccagcctc cgaagttctc cctgtgcccc ctggggcccc agtggcgcct      3660
ggagcagccg cgcgctccagc tggagcagcc tgggccgtgc ccccagcctc aagcgccgcg     3720
gccagtgtgg ggaacgtgag tccctgctgt ctggcgaggg caagggcagc accgacgacg     3780
aagctgagga cggcagggcc cgcccgggc cccgtgccac cccactgcgg cgggccgagt       3840
ccctggaccc acggcccctg cggccggccg ccctcccgcc taccaagtgc cgcgatcgcg     3900
acgggcaggt ggtggccctg cccagcgact tcttcctgcg catcgacagc caccgtgagg     3960
atgcagccga gcttgacgac gactcggagg acagctgctg cctccgcctg cataaagtgc     4020
tggagcccta caagcccag tggtgccgga ccgcgaggc ctgggccctc tacctcttct       4080
ccccacagaa ccggttccgc gtctcctgcc agaaggtcat cacacacaag atgtttgatc     4140
acgtggtcct cgtcttcatc ttcctcaact gcgtcaccat cgccctggag aggcctgaca     4200
ttgaccccgg cagcaccgag cgggtcttcc tcagcgtctc caattacatc ttcacggcca     4260
tcttcgtggc ggagatgatg gtgaaggtgg tggccctggg gctgctgtcc ggcgagcacg     4320
cctacctgca gagcagctgg aacctgctgg atgggctgct ggtgctggtg tccctggtgg     4380
acattgtcgt ggccatggcc tcggctggtg gcgccaagat cctgggtgtt ctgcgcgtgc     4440
tgcgtctgct gcggacccctg cggcctctaa gggtcatcag ccgggccccg ggcctcaagc    4500
tggtggtgga gacgctgata tcgtcgctca ggcccattgg gaacatcgtc ctcatctgct     4560
gcgccttctt catcattttt ggcatcttgg gtgtgcagct cttcaaaggg aagttctact     4620
actgcgaggg ccccgacacc aggaacatct ccaccaaggc acagtgccgg gccgcccact     4680
accgctgggt gcgacgcaag tacaacttcg acaacctggg ccaggccctg atgtcgctgt     4740
tcgtgctgtc atccaaggat ggatgggtga acatcatgta cgacgggctg gatgccgtgg     4800
gtgtcgacca gcagcctgtg cagaaccaca cccctggat gctgctgtac ttcatctcct      4860
tcctgctcat cgtcagcttc ttcgtgctca acatgttcgt gggcgtcgtg gtcgagaact     4920
tccacaagtg ccggcagcac caggaggcgg aggaggcgcg gcggcgagag agaagcggc      4980 tgcggcgcct agagaggagg cgcaggagca ctttccccag cccagaggcc cagcgccggc     5040
cctactatgc cgactactcg cccacgcgcc gctccattca ctcgctgtgc accagccact     5100
atctcgacct cttcatcacc ttcatcatct gtgtcaacgt catcaccatg tccatggagc     5160
actataacca acccagtcg ctggacgagg ccctcaagta ctgcaactac gtcttcacca      5220
tcgtgtttgt cttcgaggct gcactgaagc tggtagcatt tgggttccgt cggttcttca     5280
aggacaggtg gaaccagctg gacctggcca tcgtgctgct gtcactcatg ggcatcacgc     5340
tggaggagat agagatgagc gccgcgctgc ccatcaaccc caccatcatc cgcatcatgc     5400
gcgtgcttcg cattgcccgt gtgctgaagc tgctgaagat ggctacgggc atgcgcgccc     5460
tgctggacac tgtggtgcaa gctctccccc aggtggggaa cctgggccctt cttttcatgc   5520 tcctgttttt tatctatgct gcgctgggag tggagctgtt cgggaggctg gagtgcagtg     5580
aagacaaccc ctgcgagggc ctgagcaggc acgccacctt cagcaacttc ggcatggcct     5640
tcctcacgct gttccgcgtg tccacggggg acaactggaa cgggatcatg aaggacacgc     5700
tgcgcgagtc ctcccgtgag acaagcact gcctgagcta cctgccggcc ctgtcgcccg      5760
tctacttcgt gaccttcgtg ctggtggccc agttcgtgct ggtgaacgtg gtggtggccg     5820
tgctcatgaa gcacctggag gagagcaaca aggaggcacg ggaggatgcg gagctggacg     5880
ccgagatcga gctggagatg gcgcagggcc ccgggagtgc acgccgggtg gacgcggaca     5940
```

-continued

```
ggcctcccttgccccaggagagtccgggcgccagggatgccccaaacctggttgcacgca    6000
aggtgtccgtgtccaggatgctctcgctgcccaacgacagctacatgttcaggcccgtgg    6060
tgcctgcctcggcgcccacccccgccgctgcaggaggtggagatggagacctatgggg     6120
ccggcaccccttgggctccgttgcctctgtgcactctccgcccgcagagtcctgtgcct    6180
ccctccagatcccactggctgtgtcgtcccagccaggagcggcgagccctccacgccc    6240
tgtccctcggggcacagccgctcccccagtctcagccggctgctctgcagacaggagg     6300
ctgtgcacaccgattccttgaagggaagattgacagccctagggacaccctggatcctg    6360
cagagcctggtgagaaaaccccggtgaggccggtgacccaggggggctccctgcagtccc    6420
caccacgctccccacggcccgccagcgtccgcactcgtaagcataccttcggacagcact    6480
gcgtctccagccggccggcgccccaggcgagaggaggccgaggcctcgacccagccg     6540
acgaggaggtcagccacatcaccagctccgcctgcccctggcagcccacagccgagcccc    6600
atggccccgaagcctctccggtggccggcggcgagcgggacctgcgcaggctctacagcg    6660
tggacgctcagggcttcctggacaagccggccgggcagacgagcagtggcggccctcgg    6720
cggagctgggcagcggggagcctggggaggcgaaggcctggggccctgaggccgagcccg    6780
ctctgggtgcgcgcagaaaggaagaagatgagccccccctgcatctcggtgaaccccctg    6840
cggaggacgagggctctgcgcggccctccggcagagggcggcagcaccacactgaggc    6900
gcaggaccccgtcctgtgaggccacgcctcacagggactcctggagcccacagagggct    6960
caggcgccgggggggaccctgcagccaagggggagcgctggggccaggcctcctgccggg    7020
ctgagcacctgaccgtccccagctttgccttgagccgctggacctcggggtccccagtg    7080
gagacccttcttggacggtagccacagtgtgaccccagatccagagcttcctcttcag    7140
ggccatagtgcccctggaaccccagaatcagagcctccatgcccgtcggtgacccc     7200
cagagaagagcgggggctgtacctcacagtcccccagtgtcctctggagaaaccagggt    7260
cccctcagccacccctgccccaggggtggtgcagatgacccgtgtagctcggggctt     7320
ggtgccgcccacggctttggccctgggtctgggggccccgctggggtggaggcccaggc    7380
agaaccctgcatggaccctgacttgggtccgtcgtgagcagaaaggcccggggaggatg    7440
acggcccagccctggttctctgcccagcgaagcaggagtagctgccggggccccacgagc    7500
ctccatccgttctggttcggttttctccgagttttgctacagccgaggctgtgcgggca    7560
actgggtcagcctcccgtcaggagagaagcgcgtctgtggacgaagacgggcacccg     7620
ccagagagggaaggtaccaggttgcgtcctttcaggcccgcgttgttacaggacactc    7680
gctgggggcctgtgcccttgccggcggcaggttgcagccaccgcggcccaatgtcacct    7740
tcactcacagtctgagttctgtccgcctgtcacgccctcaccaccctccccttccagcc    7800
accacccttccgttccgctcgggccttccagaagcgtcctgtgactctgggagaggtg     7860
acacctcactaaggggccgacccccatggagtaacgcgc                        7898
```

<210> SEQ ID NO 4
<211> LENGTH: 2353
<212> TYPE: PRT
<213> ORGANISM: Homo Sapiens

<400> SEQUENCE: 4

Met Thr Glu Gly Ala Arg Ala Ala Asp Glu Val Arg Val Pro Leu Gly
1               5                   10                  15

Ala Pro Pro Pro Gly Pro Ala Ala Leu Val Gly Ala Ser Pro Glu Ser

```
                    20                  25                  30
Pro Gly Ala Pro Gly Arg Glu Ala Glu Arg Gly Ser Glu Leu Gly Val
            35                  40                  45
Ser Pro Ser Glu Ser Pro Ala Ala Glu Arg Gly Ala Glu Leu Gly Ala
    50                  55                  60
Asp Glu Glu Gln Arg Val Pro Tyr Pro Ala Leu Ala Ala Thr Val Phe
65                  70                  75                  80
Phe Cys Leu Gly Gln Thr Thr Arg Pro Arg Ser Trp Cys Leu Arg Leu
                85                  90                  95
Val Cys Asn Pro Trp Phe Glu His Val Ser Met Leu Val Ile Met Leu
            100                 105                 110
Asn Cys Val Thr Leu Gly Met Phe Arg Pro Cys Glu Asp Val Glu Cys
        115                 120                 125
Gly Ser Glu Arg Cys Asn Ile Leu Glu Ala Phe Asp Ala Phe Ile Phe
        130                 135                 140
Ala Phe Phe Ala Val Glu Met Val Ile Lys Met Val Ala Leu Gly Leu
145                 150                 155                 160
Phe Gly Gln Lys Cys Tyr Leu Gly Asp Thr Trp Asn Arg Leu Asp Phe
                165                 170                 175
Phe Ile Val Val Ala Gly Met Met Glu Tyr Ser Leu Asp Gly His Asn
            180                 185                 190
Val Ser Leu Ser Ala Ile Arg Thr Val Arg Val Leu Arg Pro Leu Arg
        195                 200                 205
Ala Ile Asn Arg Val Pro Ser Met Arg Ile Leu Val Thr Leu Leu Leu
    210                 215                 220
Asp Thr Leu Pro Met Leu Gly Asn Val Leu Leu Leu Cys Phe Phe Val
225                 230                 235                 240
Phe Phe Ile Phe Gly Ile Val Gly Val Gln Leu Trp Ala Gly Leu Leu
                245                 250                 255
Arg Asn Arg Cys Phe Leu Asp Ser Ala Phe Val Arg Asn Asn Asn Leu
            260                 265                 270
Thr Phe Leu Arg Pro Tyr Tyr Gln Thr Glu Glu Gly Glu Glu Asn Pro
        275                 280                 285
Phe Ile Cys Ser Ser Arg Arg Asp Asn Gly Met Gln Lys Cys Ser His
        290                 295                 300
Ile Pro Gly Arg Arg Glu Leu Arg Met Pro Cys Thr Leu Gly Trp Glu
305                 310                 315                 320
Ala Tyr Thr Gln Pro Gln Ala Glu Gly Val Gly Ala Ala Arg Asn Ala
                325                 330                 335
Cys Ile Asn Trp Asn Gln Tyr Tyr Asn Val Cys Arg Ser Gly Asp Ser
            340                 345                 350
Asn Pro His Asn Gly Ala Ile Asn Phe Asp Asn Ile Gly Tyr Ala Trp
        355                 360                 365
Ile Ala Ile Phe Gln Val Ile Thr Leu Glu Gly Trp Val Asp Ile Met
    370                 375                 380
Tyr Tyr Val Met Asp Ala His Ser Phe Tyr Asn Phe Ile Tyr Phe Ile
385                 390                 395                 400
Leu Leu Ile Ile Val Gly Ser Phe Phe Met Ile Asn Leu Cys Leu Val
                405                 410                 415
Val Ile Ala Thr Gln Phe Ser Glu Thr Lys Gln Arg Glu Ser Gln Leu
            420                 425                 430
Met Arg Glu Gln Arg Ala Arg His Leu Ser Asn Asp Ser Thr Leu Ala
        435                 440                 445
```

```
Ser Phe Ser Glu Pro Gly Ser Cys Tyr Glu Glu Leu Leu Lys Tyr Val
    450                 455                 460

Gly His Ile Phe Arg Lys Val Lys Arg Arg Ser Leu Arg Leu Tyr Ala
465                 470                 475                 480

Arg Trp Gln Ser Arg Trp Arg Lys Lys Val Asp Pro Ser Ala Val Gln
                485                 490                 495

Gly Gln Gly Pro Gly His Arg Gln Arg Arg Ala Gly Arg His Thr Ala
                500                 505                 510

Ser Val His His Leu Val Tyr His His His His His His His His His
            515                 520                 525

Tyr His Phe Ser His Gly Ser Pro Arg Arg Pro Gly Pro Glu Pro Gly
        530                 535                 540

Ala Cys Asp Thr Arg Leu Val Arg Ala Gly Ala Pro Pro Ser Pro Pro
545                 550                 555                 560

Ser Pro Gly Arg Gly Pro Pro Asp Ala Glu Ser Val His Ser Ile Tyr
                565                 570                 575

His Ala Asp Cys His Ile Glu Gly Pro Gln Glu Arg Ala Arg Val Ala
                580                 585                 590

His Ala Ala Ala Thr Ala Ala Ala Ser Leu Arg Leu Ala Thr Gly Leu
            595                 600                 605

Gly Thr Met Asn Tyr Pro Thr Ile Leu Pro Ser Gly Val Gly Ser Gly
    610                 615                 620

Lys Gly Ser Thr Ser Pro Gly Pro Lys Gly Lys Trp Ala Gly Gly Pro
625                 630                 635                 640

Pro Gly Thr Gly Gly His Gly Pro Leu Ser Leu Asn Ser Pro Asp Pro
                645                 650                 655

Tyr Glu Lys Ile Pro His Val Val Gly His Gly Leu Gly Gln Ala
                660                 665                 670

Pro Gly His Leu Ser Gly Leu Ser Val Pro Cys Pro Leu Pro Ser Pro
            675                 680                 685

Pro Ala Gly Thr Leu Thr Cys Glu Leu Lys Ser Cys Pro Tyr Cys Thr
    690                 695                 700

Arg Ala Leu Glu Asp Pro Glu Gly Glu Leu Ser Gly Ser Glu Ser Gly
705                 710                 715                 720

Asp Ser Asp Gly Arg Gly Val Tyr Glu Phe Thr Gln Asp Val Arg His
                725                 730                 735

Gly Asp Arg Trp Asp Pro Thr Arg Pro Pro Arg Ala Thr Asp Thr Pro
                740                 745                 750

Gly Pro Gly Pro Gly Ser Pro Gln Arg Arg Ala Gln Gln Arg Ala Ala
                755                 760                 765

Pro Gly Glu Pro Gly Trp Met Gly Arg Leu Trp Val Thr Phe Ser Gly
    770                 775                 780

Lys Leu Arg Arg Ile Val Asp Ser Lys Tyr Phe Ser Arg Gly Ile Met
785                 790                 795                 800

Met Ala Ile Leu Val Asn Thr Leu Ser Met Gly Val Glu Tyr His Glu
                805                 810                 815

Gln Pro Glu Glu Leu Thr Asn Ala Leu Glu Ile Ser Asn Ile Val Phe
            820                 825                 830

Thr Ser Met Phe Ala Leu Glu Met Leu Leu Lys Leu Leu Ala Cys Gly
        835                 840                 845

Pro Leu Gly Tyr Ile Arg Asn Pro Tyr Asn Ile Phe Asp Gly Ile Ile
    850                 855                 860
```

```
Val Val Ile Ser Val Trp Glu Ile Val Gly Gln Ala Asp Gly Gly Leu
865                 870                 875                 880

Ser Val Leu Arg Thr Phe Arg Leu Leu Arg Val Leu Lys Leu Val Arg
                885                 890                 895

Phe Leu Pro Ala Leu Arg Arg Gln Leu Val Val Leu Val Lys Thr Met
            900                 905                 910

Asp Asn Val Ala Thr Phe Cys Thr Leu Leu Met Leu Phe Ile Phe Ile
        915                 920                 925

Phe Ser Ile Leu Gly Met His Leu Phe Gly Cys Lys Phe Ser Leu Lys
    930                 935                 940

Thr Asp Thr Gly Asp Thr Val Pro Asp Arg Lys Asn Phe Asp Ser Leu
945                 950                 955                 960

Leu Trp Ala Ile Val Thr Val Phe Gln Ile Leu Thr Gln Glu Asp Trp
                965                 970                 975

Asn Val Val Leu Tyr Asn Gly Met Ala Ser Thr Ser Ser Trp Ala Ala
            980                 985                 990

Leu Tyr Phe Val Ala Leu Met Thr Phe Gly Asn Tyr Val Leu Phe Asn
        995                 1000                1005

Leu Leu Val Ala Ile Leu Val Glu Gly Phe Gln Ala Glu Gly Asp Ala
    1010                1015                1020

Asn Arg Ser Asp Thr Asp Glu Asp Lys Thr Ser Val His Phe Glu Glu
1025                1030                1035                1040

Asp Phe His Lys Leu Arg Glu Leu Gln Thr Thr Glu Leu Lys Met Cys
                1045                1050                1055

Ser Leu Ala Val Thr Pro Asn Gly His Leu Glu Gly Arg Gly Ser Leu
            1060                1065                1070

Ser Pro Pro Leu Ile Met Cys Thr Ala Ala Thr Pro Met Pro Thr Pro
        1075                1080                1085

Lys Ser Ser Pro Phe Leu Asp Ala Ala Pro Ser Leu Pro Asp Ser Arg
1090                1095                1100

Arg Gly Ser Ser Ser Gly Asp Pro Pro Leu Gly Asp Gln Lys Pro
1105                1110                1115                1120

Pro Ala Ser Leu Arg Ser Pro Cys Ala Pro Trp Gly Pro Ser Gly
            1125                1130                1135

Ala Trp Ser Ser Arg Arg Ser Ser Trp Ser Ser Leu Gly Arg Ala Pro
        1140                1145                1150

Ser Leu Lys Arg Arg Gly Gln Cys Gly Glu Arg Glu Ser Leu Leu Ser
    1155                1160                1165

Gly Glu Gly Lys Gly Ser Thr Asp Asp Glu Ala Glu Asp Gly Arg Ala
1170                1175                1180

Ala Pro Gly Pro Arg Ala Thr Pro Leu Arg Arg Ala Glu Ser Leu Asp
1185                1190                1195                1200

Pro Arg Pro Leu Arg Pro Ala Ala Leu Pro Pro Thr Lys Cys Arg Asp
                1205                1210                1215

Arg Asp Gly Gln Val Val Ala Leu Pro Ser Asp Phe Leu Arg Ile
            1220                1225                1230

Asp Ser His Arg Glu Asp Ala Ala Glu Leu Asp Asp Asp Ser Glu Asp
        1235                1240                1245

Ser Cys Cys Leu Arg Leu His Lys Val Leu Glu Pro Tyr Lys Pro Gln
    1250                1255                1260

Trp Cys Arg Ser Arg Glu Ala Trp Ala Leu Tyr Leu Phe Ser Pro Gln
1265                1270                1275                1280

Asn Arg Phe Arg Val Ser Cys Gln Lys Val Ile Thr His Lys Met Phe
```

-continued

```
                1285                1290                1295
Asp His Val Val Leu Val Phe Ile Phe Leu Asn Cys Val Thr Ile Ala
            1300                1305                1310
Leu Glu Arg Pro Asp Ile Asp Pro Gly Ser Thr Glu Arg Val Phe Leu
            1315                1320                1325
Ser Val Ser Asn Tyr Ile Phe Thr Ala Ile Phe Val Ala Glu Met Met
            1330                1335                1340
Val Lys Val Val Ala Leu Gly Leu Leu Ser Gly Glu His Ala Tyr Leu
1345                1350                1355                1360
Gln Ser Ser Trp Asn Leu Leu Asp Gly Leu Leu Val Leu Val Ser Leu
            1365                1370                1375
Val Asp Ile Val Val Ala Met Ala Ser Ala Gly Gly Ala Lys Ile Leu
            1380                1385                1390
Gly Val Leu Arg Val Leu Arg Leu Leu Arg Thr Leu Arg Pro Leu Arg
            1395                1400                1405
Val Ile Ser Arg Ala Pro Gly Leu Lys Leu Val Val Glu Thr Leu Ile
            1410                1415                1420
Ser Ser Leu Arg Pro Ile Gly Asn Ile Val Leu Ile Cys Cys Ala Phe
1425                1430                1435                1440
Phe Ile Ile Phe Gly Ile Leu Gly Val Gln Leu Phe Lys Gly Lys Phe
            1445                1450                1455
Tyr Tyr Cys Glu Gly Pro Asp Thr Arg Asn Ile Ser Thr Lys Ala Gln
            1460                1465                1470
Cys Arg Ala Ala His Tyr Arg Trp Val Arg Arg Lys Tyr Asn Phe Asp
            1475                1480                1485
Asn Leu Gly Gln Ala Leu Met Ser Leu Phe Val Leu Ser Ser Lys Asp
            1490                1495                1500
Gly Trp Val Asn Ile Met Tyr Asp Gly Leu Asp Ala Val Gly Val Asp
1505                1510                1515                1520
Gln Gln Pro Val Gln Asn His Asn Pro Trp Met Leu Leu Tyr Phe Ile
            1525                1530                1535
Ser Phe Leu Leu Ile Val Ser Phe Phe Val Leu Asn Met Phe Val Gly
            1540                1545                1550
Val Val Val Glu Asn Phe His Lys Cys Arg Gln His Gln Glu Ala Glu
            1555                1560                1565
Glu Ala Arg Arg Arg Glu Glu Lys Arg Leu Arg Arg Leu Glu Arg Arg
            1570                1575                1580
Arg Arg Ser Thr Phe Pro Ser Pro Glu Ala Gln Arg Arg Pro Tyr Tyr
1585                1590                1595                1600
Ala Asp Tyr Ser Pro Thr Arg Arg Ser Ile His Ser Leu Cys Thr Ser
            1605                1610                1615
His Tyr Leu Asp Leu Phe Ile Thr Phe Ile Ile Cys Val Asn Val Ile
            1620                1625                1630
Thr Met Ser Met Glu His Tyr Asn Gln Pro Lys Ser Leu Asp Glu Ala
            1635                1640                1645
Leu Lys Tyr Cys Asn Tyr Val Phe Thr Ile Val Phe Val Phe Glu Ala
            1650                1655                1660
Ala Leu Lys Leu Val Ala Phe Gly Phe Arg Arg Phe Phe Lys Asp Arg
1665                1670                1675                1680
Trp Asn Gln Leu Asp Leu Ala Ile Val Leu Leu Ser Leu Met Gly Ile
            1685                1690                1695
Thr Leu Glu Glu Ile Glu Met Ser Ala Ala Leu Pro Ile Asn Pro Thr
            1700                1705                1710
```

```
Ile Ile Arg Ile Met Arg Val Leu Arg Ile Ala Arg Val Leu Lys Leu
            1715                1720                1725

Leu Lys Met Ala Thr Gly Met Arg Ala Leu Leu Asp Thr Val Val Gln
        1730                1735                1740

Ala Leu Pro Gln Val Gly Asn Leu Gly Leu Leu Phe Met Leu Leu Phe
1745                1750                1755                1760

Phe Ile Tyr Ala Ala Leu Gly Val Glu Leu Phe Gly Arg Leu Glu Cys
            1765                1770                1775

Ser Glu Asp Asn Pro Cys Glu Gly Leu Ser Arg His Ala Thr Phe Ser
            1780                1785                1790

Asn Phe Gly Met Ala Phe Leu Thr Leu Phe Arg Val Ser Thr Gly Asp
            1795                1800                1805

Asn Trp Asn Gly Ile Met Lys Asp Thr Leu Arg Glu Cys Ser Arg Glu
            1810                1815                1820

Asp Lys His Cys Leu Ser Tyr Leu Pro Ala Leu Ser Pro Val Tyr Phe
1825                1830                1835                1840

Val Thr Phe Val Leu Val Ala Gln Phe Val Leu Val Asn Val Val Val
            1845                1850                1855

Ala Val Leu Met Lys His Leu Glu Glu Ser Asn Lys Glu Ala Arg Glu
            1860                1865                1870

Asp Ala Glu Leu Asp Ala Glu Ile Glu Leu Glu Met Ala Gln Gly Pro
            1875                1880                1885

Gly Ser Ala Arg Arg Val Asp Ala Asp Arg Pro Pro Leu Pro Gln Glu
            1890                1895                1900

Ser Pro Gly Ala Arg Asp Ala Pro Asn Leu Val Ala Arg Lys Val Ser
1905                1910                1915                1920

Val Ser Arg Met Leu Ser Leu Pro Asn Asp Ser Tyr Met Phe Arg Pro
            1925                1930                1935

Val Val Pro Ala Ser Ala Pro His Pro Arg Pro Leu Gln Glu Val Glu
            1940                1945                1950

Met Glu Thr Tyr Gly Ala Gly Thr Pro Leu Gly Ser Val Ala Ser Val
            1955                1960                1965

His Ser Pro Pro Ala Glu Ser Cys Ala Ser Leu Gln Ile Pro Leu Ala
    1970                1975                1980

Val Ser Ser Pro Ala Arg Ser Gly Glu Pro Leu His Ala Leu Ser Pro
1985                1990                1995                2000

Arg Gly Thr Ala Arg Ser Pro Ser Leu Ser Arg Leu Leu Cys Arg Gln
            2005                2010                2015

Glu Ala Val His Thr Asp Ser Leu Glu Gly Lys Ile Asp Ser Pro Arg
            2020                2025                2030

Asp Thr Leu Asp Pro Ala Glu Pro Gly Glu Lys Thr Pro Val Arg Pro
            2035                2040                2045

Val Thr Gln Gly Gly Ser Leu Gln Ser Pro Arg Ser Pro Arg Pro
            2050                2055                2060

Ala Ser Val Arg Thr Arg Lys His Thr Phe Gly Gln His Cys Val Ser
2065                2070                2075                2080

Ser Arg Pro Ala Ala Pro Gly Gly Glu Glu Ala Glu Ala Ser Asp Pro
            2085                2090                2095

Ala Asp Glu Glu Val Ser His Ile Thr Ser Ser Ala Cys Pro Trp Gln
            2100                2105                2110

Pro Thr Ala Glu Pro His Gly Pro Glu Ala Ser Pro Val Ala Gly Gly
            2115                2120                2125
```

-continued

Glu Arg Asp Leu Arg Arg Leu Tyr Ser Val Asp Ala Gln Gly Phe Leu
    2130                2135                2140

Asp Lys Pro Gly Arg Ala Asp Glu Gln Trp Arg Pro Ser Ala Glu Leu
2145                2150                2155                2160

Gly Ser Gly Glu Pro Gly Glu Ala Lys Ala Trp Gly Pro Glu Ala Glu
            2165                2170                2175

Pro Ala Leu Gly Ala Arg Arg Lys Lys Lys Met Ser Pro Pro Cys Ile
            2180                2185                2190

Ser Val Glu Pro Pro Ala Glu Asp Glu Gly Ser Ala Arg Pro Ser Ala
        2195                2200                2205

Ala Glu Gly Gly Ser Thr Thr Leu Arg Arg Arg Thr Pro Ser Cys Glu
    2210                2215                2220

Ala Thr Pro His Arg Asp Ser Leu Glu Pro Thr Glu Gly Ser Gly Ala
2225                2230                2235                2240

Gly Gly Asp Pro Ala Ala Lys Gly Glu Arg Trp Gly Gln Ala Ser Cys
            2245                2250                2255

Arg Ala Glu His Leu Thr Val Pro Ser Phe Ala Phe Glu Pro Leu Asp
            2260                2265                2270

Leu Gly Val Pro Ser Gly Asp Pro Phe Leu Asp Gly Ser His Ser Val
        2275                2280                2285

Thr Pro Glu Ser Arg Ala Ser Ser Ser Gly Ala Ile Val Pro Leu Glu
    2290                2295                2300

Pro Pro Glu Ser Glu Pro Pro Met Pro Val Gly Asp Pro Glu Lys
2305                2310                2315                2320

Arg Arg Gly Leu Tyr Leu Thr Val Pro Gln Cys Pro Leu Glu Lys Pro
            2325                2330                2335

Gly Ser Pro Ser Ala Thr Pro Ala Pro Gly Gly Ala Asp Asp Pro
        2340                2345                2350

Val

<210> SEQ ID NO 5
<211> LENGTH: 7364
<212> TYPE: DNA
<213> ORGANISM: Homo Sapiens

<400> SEQUENCE: 5
gcggcggcgg ctgcggcggt ggggccgggc gaggtccgct gcggtcccgg cggctccgtg      60
gctgctccgc tctgagcgcc tggcgcgccc cgcgccctcc ctgccggggc cgctgggccg     120
gggatgcacg cggggcccgg gagccatggt ccgcttcggg gacgagctgg gcggccgcta     180
tggaggcccc ggcggcggag agcgggcccg gggcggcggg gccggcgggg cgggggccc      240 gggtcccggg gggctgcagc ccggccagcg ggtcctctac aagcaatcga tcgcgcagcg     300
cgcgcggacc atggcgctgt acaaccccat cccggtcaag cagaactgct tcaccgtcaa     360
ccgctcgctc ttcgtcttca gcgaggacaa cgtcgtccgc aaatacgcga agcgcatcac     420
cgagtggcct ccattcgagt atatgatcct ggccaccatc atcgccaact gcatcgtgct     480
ggccctggag cagcacctcc ctgatgggga caaaacgccc atgtccgagc ggctggacga     540
cacggagccc tatttcatcg ggatcttttg cttcgaggca gggatcaaaa tcatcgctct     600
gggctttgtc ttccacaagg ctcttacct gcggaacggc tggaacgtca tggacttcgt     660
ggtcgtcctc acagggatcc ttgccacggc tggaactgac ttcgacctgc gaacactgag     720
ggctgtgcgt gtgctgaggc ccctgaagct ggtgtctggg attccaagtt tgcaggtggt     780
gctcaagtcc atcatgaagg ccatggttcc actcctgcag attgggctgc ttctcttctt     840

```
tgccatcctc atgtttgcca tcattggcct ggagttctac atgggcaagt tccacaaggc    900
ctgtttcccc aacagcacag atgcggagcc cgtgggtgac ttcccctgtg caaggaggc    960
cccagcccgg ctgtgcgagg cgacactga gtgccgggag tactggccag acccaactt   1020
tggcatcacc aactttgaca atatcctgtt tgccatcctg acggtgttcc agtgcatcac   1080
catggagggc tggactgaca tcctctataa tacaaacgat gcggccggca acacctggaa   1140
ctggctctac ttcatccctc tcatcatcat cggctccttc ttcatgctca acctggtgct   1200
gggcgtgctc tcgggggagt ttgccaagga gcgagagagg gtggagaacc gccgcgcctt   1260
cctgaagctg cgccggcagc agcagatcga gcgagagctc aacgggtacc tggagtggat   1320
cttcaaggcg gaggaagtca tgctggccga ggaggacagg aatgcagagg agaagtcccc   1380
tttggacgtg ctgaagagag cggccaccaa gaagagcaga aatgacctga tccacgcaga   1440
ggagggagag gaccggtttg cagatctctg tgctgttgga tccccttcg cccgcgccag   1500
cctcaagagc gggaagacag agagctcgtc atacttccgg aggaaggaga agatgttccg   1560
gttttttatc cggcgcatgg tgaaggctca gagcttctac tgggtggtgc tgtgcgtggt   1620
ggccctgaac acactgtgtg tggccatggt gcattacaac cagccgcggc ggcttaccac   1680
gaccctgtat tttgcagagt ttgtttttcct gggtctcttc ctcacagaga tgtccctgaa   1740
gatgtatggc ctgggccca gaagctactt ccggtcctcc ttcaactgct tcgactttgg   1800
ggtcatcgtg gggagcgtct ttgaagtggt ctgggcggcc atcaagccgg gaagctcctt   1860
tgggatcagt gtgctgcggg ccctccgcct gctgaggatc ttcaaagtca cgaagtactg   1920
gagctccctg cggaacctgg tggtgtccct gctgaactcc atgaagtcca tcatcagcct   1980
gctcttcttg ctcttcctgt tcattgtggt cttcgccctg ctggggatgc agctgtttgg   2040
gggacagttc aacttccagg atgagactcc cacaaccaac ttcgacacct tccctgccgc   2100
catcctcact gtcttccaga tcctgacggg agaggactgg aatgcagtga tgtatcacgg   2160
gatcgaatcg caaggcggcg tcagcaaagg catgttctcg tccttttact tcattgtcct   2220
gacactgttc ggaaactaca ctctgctgaa tgtctttctg gccatcgctg tggacaacct   2280
ggccaacgcc aagagctga ccaaggatga agaggagatg gaagaagcag ccaatcagaa   2340
gcttgctctg caaaaggcca agaagtggtg tgaagtcagc cccatgtctg ccgcgaacat   2400
ctccatcgcc gccaggcagc agaactcggc caaggcgcgc tcggtgtggg agcagcgggc   2460
cagccagcta cggctgcaga acctgcgggc cagctgcgag gcgctgtaca gcgagatgga   2520
ccccgaggag cggctgcgct tcgccactac gcgccacctg cggcccgaca tgaagacgca   2580
cctggaccgg ccgctggtgg tggagctggg ccgcgacggc gcgcggggc cgtgggagg   2640
caaagcccga cctgaggctg cggaggcccc cgagggcgtc gaccctccgc gcaggcacca   2700
ccggcaccgc gacaaggaca agaccccgc ggcgggggac caggaccgag cagaggcccc   2760
gaaggcggag agcggggagc ccggtgcccg ggaggagcgg ccgcggccgc accgcagcca   2820
cagcaaggag gccgcggggc ccccggaggc gcggagcgag cgcggccgag gcccaggccc   2880
cgagggcggc cggcggcacc accggcgcgg ctccccggag gaggcggccg agcgggagcc   2940
ccgacgccac cgcgcgcacc ggcaccagga tccgagcaag gagtgcgccg gcgccaaggg   3000
cgagcggcgc gcgcggcacc gcggcggccc ccgagcgggg ccccgggagg cggagagcgg   3060
ggaggagccg gcgcggcggc accgggcccg gcacaaggcg cagcctgctc acgaggctgt   3120
ggagaaggag accacggaga aggaggccac ggagaaggag gctgagatag tggaagccga   3180
```

```
caaggaaaag gagctccgga accaccagcc ccgggagcca cactgtgacc tggagaccag   3240
tgggactgtg actgtgggtc ccatgcacac actgcccagc acctgtctcc agaaggtgga   3300
ggaacagcca gaggatgcag acaatcagcg aacgtcact cgcatgggca gtcagccccc   3360
agacccgaac actattgtac atatcccagt gatgctgacg ggccctcttg gggaagccac   3420
ggtcgttccc agtggtaacg tggacctgga agccaagca gaggggaaga aggaggtgga   3480
agcggatgac gtgatgagga gcggcccccg gcctatcgtc ccatacagct ccatgttctg   3540
tttaagcccc accaacctgc tccgccgctt ctgccactac atcgtgacca tgaggtactt   3600
cgaggtggtc attctcgtgg tcatcgcctt gagcagcatc gccctggctg ctgaggaccc   3660
agtgcgcaca gactcgccca ggaacaacgc tctgaaatac ctggattaca ttttcactgg   3720
tgtctttacc tttgagatgg tgataaagat gatcgacttg ggactgctgc ttcaccctgg   3780
agcctatttc cgggacttgt ggaacattct ggacttcatt gtggtcagtg gcgccctggt   3840
ggcgtttgct ttctcaggat ccaaagggaa agacatcaat accatcaagt ctctgagagt   3900
ccttcgtgtc ctgcggcccc tcaagaccat caaacggctg cccaagctca aggctgtgtt   3960
tgactgtgtg gtgaactccc tgaagaatgt cctcaacatc ttgattgtct acatgctctt   4020
catgttcata tttgccgtca ttgcggtgca gctcttcaaa gggaagtttt tctactgcac   4080
agatgaatcc aaggagctgg agagggactg caggggtcag tatttggatt atgagaagga   4140
ggaagtggaa gctcagccca ggcagtggaa gaaatacgac tttcactacg acaatgtgct   4200
ctgggctctg ctgacgctgt tcacagtgtc cacgggagaa ggctggccca tggtgctgaa   4260
acactccgtg gatgccacct atgaggagca gggtccaagc cctgggtacc gcatggagct   4320
gtccatcttc tacgtggtct actttgtggt cttccccttc ttcttcgtca acatcttcgt   4380
ggctttgatc atcatcacct tccaggagca ggggacaag gtgatgtctg aatgcagcct   4440
ggagaagaac gagagggctt gcattgactt cgccatcagc gccaaacccc tgacacggta   4500 catgcccaa aaccggcagt cgttccagta taagacgtgg acatttgtgg tctccccgcc   4560
ctttgaatac ttcatcatgg ccatgatagc cctcaacact gtggtgctga tgatgaagtt   4620
ctatgatgca ccctatgagt acgagctgat gctgaaatgc tgaacatcg tgttcacatc   4680 catgttctcc atggaatgcg tgctgaagat catcgccttt gggtgctga actatttcag   4740 agatgcctgg aatgtctttg actttgtcac tgtgttggga agtattactg atatttagt   4800 aacagagatt gcgaaacga acaattcat caacctcagc ttcctccgcc tctttcgagc   4860
tgcgcggctg atcaagctgc tccgccaggg ctacaccatc cgcatcctgc tgtggaccttt   4920 tgtccagtcc ttcaaggccc tgccctacgt gtgtctgctc attgccatgc tgttcttcat   4980
ctacgccatc atcggcatgc aggtgtttgg gaatattgcc ctggatgatg acaccagcat   5040
caaccgccac aacaacttcc ggacgttttt gcaagccctg atgctgctgt tcaggagcgc   5100 cacggggag gcctggcacg agatcatgct gtcctgcctg agcaaccagg cctgtgatga   5160
gcaggccaat gccaccgagt gtggaagtga ctttgcctac ttctacttcg tctccttcat   5220
cttcctgtgc tccttctga tgttgaacct ctttgtggct gtgatcatgg acaatttga   5280 gtacctcacg cgggactctt ccatcctagg tcctcaccac ttggatgagt tcatccgggt   5340
ctgggctgaa tacgacccgg ctgcgtgtgg gcgcatcagt tacaatgaca tgtttgagat   5400
gctgaaacac atgtccccgc ctctggggct ggggaagaaa tgccctgctc gagttgctta   5460
caagcgcctg gttcgcatga acatgccat tccaacgag gacatgactg ttcacttcac   5520
gtccacgctg atggccctca tccggacggc actggagatc aagctggccc cagctgggac   5580
```

-continued

```
aaagcagcat cagtgtgacg cggagttgag gaaggagatt tccgttgtgt gggccaatct    5640
gccccagaag actttggact tgctggtacc accccataag cctgatgaga tgacagtggg    5700
gaaggtttat gcagctctga tgatatttga cttctacaag cagaacaaaa ccaccagaga    5760
ccagatgcag caggctcctg gaggcctctc ccagatgggt cctgtgtccc tgttccaccc    5820
tctgaaggcc accctggagc agacacagcc ggctgtgctc cgaggagccc gggttttcct    5880
tcgacagaag agttccacct ccctcagcaa tggcggggcc atacaaaacc aagagagtgg    5940
catcaaagag tctgtctcct ggggcactca aggacccag gatgcacccc atgaggccag     6000
gccacccctg gagcgtggcc actccacaga gatccctgtg gggcggtcag gagcactggc    6060
tgtggacgtt cagatgcaga gcataacccg gaggggccct gatggggagc ccagcctgg     6120 gctggagagc cagggtcgag cggcctccat gccccgcctt gcggccgaga ctcagcccgt    6180
cacagatgcc agcccatga agcgctccat ctccacgctg gcccagcggc ccgtgggac     6240 tcatctttgc agcaccaccc cggaccgccc accccctagc caggcgtcgt cgcaccacca    6300
ccaccaccgc tgccaccgcc gcagggacag gaagcagagg tccctggaga aggggcccag    6360
cctgtctgcc gatatggatg cgcaccaag cagtgctgtg gggccggggc tgccccgg      6420 agagggcct acaggctgcc ggcgggaacg agagcgccgg caggagcggg gccggtccca    6480
ggagcggagg cagccctcat cctcctcctc ggagaagcag cgcttctact cctgcgaccg    6540 cttgggggc cgtgagcccc cgaagcccaa gccctccctc agcagccacc caacgtcgcc    6600
aacagctggc caggagccgg gacccccacc acagggcagt ggttccgtga atgggagccc    6660
cttgctgtca acatctggtg ctagcacccc cggccgcggt gggcggaggc agctcccca    6720 gacgcccctg actccccgcc ccagcatcac ctacaagacg ccaactcct cacccatcca    6780 cttcgccggg gctcagacca gcctccctgc cttctcccca ggccggctca gccgtgggct    6840
ttccgaacac aacgccctgc tgcagagaga ccccctcagc cagcccctgg ccctggctc    6900 tcgaattggc tctgacccctt acctggggca gcgtctggac agtgaggcct ctgtccacgc    6960
cctgcctgag gacacgctca ctttcgagga ggctgtggcc accaactcgg ccgctcctc    7020 caggacttcc tacgtgtcct ccctgacctc ccagtctcac cctctccgcc gcgtgcccaa    7080
cggttaccac tgcaccctgg gactcagctc gggtggccga gcacggcaca gctaccacca    7140
ccctgaccaa gaccactggt gctagctgca ccgtgaccgc tcagacgcct gcatgcagca    7200
ggcgtgtgtt ccagtggatg agttttatca tccacacggg gcagtcggcc ctcggggggag    7260 gccttgccca ccttggtgag gctcctgtgg cccctccctc cccctcctcc cctcttttac    7320
tctagacgac gaataaagcc ctgttgcttg agtgtacgta ccgc                     7364
```

<210> SEQ ID NO 6
<211> LENGTH: 2339
<212> TYPE: PRT
<213> ORGANISM: Homo Sapiens

<400> SEQUENCE: 6

```
Met Val Arg Phe Gly Asp Glu Leu Gly Gly Arg Tyr Gly Gly Pro Gly
 1               5                   10                  15

Gly Gly Glu Arg Ala Arg Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
```

```
                      50                  55                  60
Lys Gln Asn Cys Phe Thr Val Asn Arg Ser Leu Phe Val Phe Ser Glu
 65                  70                  75                  80

Asp Asn Val Val Arg Lys Tyr Ala Lys Arg Ile Thr Glu Trp Pro Pro
                     85                  90                  95

Phe Glu Tyr Met Ile Leu Ala Thr Ile Ile Ala Asn Cys Ile Val Leu
                100                 105                 110

Ala Leu Glu Gln His Leu Pro Asp Gly Asp Lys Thr Pro Met Ser Glu
                115                 120                 125

Arg Leu Asp Asp Thr Glu Pro Tyr Phe Ile Gly Ile Phe Cys Phe Glu
130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Val Leu Thr
                165                 170                 175

Gly Ile Leu Ala Thr Ala Gly Thr Asp Phe Asp Leu Arg Thr Leu Arg
                180                 185                 190

Ala Val Arg Val Leu Arg Pro Leu Lys Leu Val Ser Gly Ile Pro Ser
                195                 200                 205

Leu Gln Val Val Leu Lys Ser Ile Met Lys Ala Met Val Pro Leu Leu
210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
                260                 265                 270

Pro Ala Arg Leu Cys Glu Gly Asp Thr Glu Cys Arg Glu Tyr Trp Pro
                275                 280                 285

Gly Pro Asn Phe Gly Ile Thr Asn Phe Asp Asn Ile Leu Phe Ala Ile
                290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
                340                 345                 350

Gly Val Leu Ser Gly Glu Phe Ala Lys Glu Arg Glu Arg Val Glu Asn
                355                 360                 365

Arg Arg Ala Phe Leu Lys Leu Arg Arg Gln Gln Gln Ile Glu Arg Glu
370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
                420                 425                 430

Glu Gly Glu Asp Arg Phe Ala Asp Leu Cys Ala Val Gly Ser Pro Phe
                435                 440                 445

Ala Arg Ala Ser Leu Lys Ser Gly Lys Thr Glu Ser Ser Ser Tyr Phe
                450                 455                 460

Arg Arg Lys Glu Lys Met Phe Arg Phe Phe Ile Arg Arg Met Val Lys
465                 470                 475                 480
```

-continued

```
Ala Gln Ser Phe Tyr Trp Val Val Leu Cys Val Val Ala Leu Asn Thr
                485                 490                 495
Leu Cys Val Ala Met Val His Tyr Asn Gln Pro Arg Arg Leu Thr Thr
            500                 505                 510
Thr Leu Tyr Phe Ala Glu Phe Val Phe Leu Gly Leu Phe Leu Thr Glu
        515                 520                 525
Met Ser Leu Lys Met Tyr Gly Leu Gly Pro Arg Ser Tyr Phe Arg Ser
    530                 535                 540
Ser Phe Asn Cys Phe Asp Phe Gly Val Ile Val Gly Ser Val Phe Glu
545                 550                 555                 560
Val Val Trp Ala Ala Ile Lys Pro Gly Ser Ser Phe Gly Ile Ser Val
                565                 570                 575
Leu Arg Ala Leu Arg Leu Leu Arg Ile Phe Lys Val Thr Lys Tyr Trp
            580                 585                 590
Ser Ser Leu Arg Asn Leu Val Val Ser Leu Leu Asn Ser Met Lys Ser
        595                 600                 605
Ile Ile Ser Leu Leu Phe Leu Leu Phe Leu Phe Ile Val Val Phe Ala
    610                 615                 620
Leu Leu Gly Met Gln Leu Phe Gly Gly Gln Phe Asn Phe Gln Asp Glu
625                 630                 635                 640
Thr Pro Thr Thr Asn Phe Asp Thr Phe Pro Ala Ala Ile Leu Thr Val
                645                 650                 655
Phe Gln Ile Leu Thr Gly Glu Asp Trp Asn Ala Val Met Tyr His Gly
            660                 665                 670
Ile Glu Ser Gln Gly Gly Val Ser Lys Gly Met Phe Ser Ser Phe Tyr
        675                 680                 685
Phe Ile Val Leu Thr Leu Phe Gly Asn Tyr Thr Leu Leu Asn Val Phe
    690                 695                 700
Leu Ala Ile Ala Val Asp Asn Leu Ala Asn Ala Gln Glu Leu Thr Lys
705                 710                 715                 720
Asp Glu Glu Glu Met Glu Glu Ala Ala Asn Gln Lys Leu Ala Leu Gln
                725                 730                 735
Lys Ala Lys Glu Val Ala Glu Val Ser Pro Met Ser Ala Ala Asn Ile
            740                 745                 750
Ser Ile Ala Ala Arg Gln Gln Asn Ser Ala Lys Ala Arg Ser Val Trp
        755                 760                 765
Glu Gln Arg Ala Ser Gln Leu Arg Leu Gln Asn Leu Arg Ala Ser Cys
    770                 775                 780
Glu Ala Leu Tyr Ser Glu Met Asp Pro Glu Glu Arg Leu Arg Phe Ala
785                 790                 795                 800
Thr Thr Arg His Leu Arg Pro Asp Met Lys Thr His Leu Asp Arg Pro
                805                 810                 815
Leu Val Val Glu Leu Gly Arg Asp Gly Ala Arg Gly Pro Val Gly Gly
            820                 825                 830
Lys Ala Arg Pro Glu Ala Ala Glu Ala Pro Glu Gly Val Asp Pro Pro
        835                 840                 845
Arg Arg His His Arg His Arg Asp Lys Asp Lys Thr Pro Ala Ala Gly
    850                 855                 860
Asp Gln Asp Arg Ala Glu Ala Pro Lys Ala Glu Ser Gly Glu Pro Gly
865                 870                 875                 880
Ala Arg Glu Glu Arg Pro Arg Pro His Arg Ser His Ser Lys Glu Ala
                885                 890                 895
```

```
Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Ala Ala
        915                 920                 925

Glu Arg Glu Pro Arg Arg His Arg Ala His Arg His Gln Asp Pro Ser
    930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
            980                 985                 990

Glu Lys Glu Thr Thr Glu Lys Glu Ala Thr Glu Lys Glu Ala Glu Ile
        995                 1000                1005

Val Glu Ala Asp Lys Glu Lys Glu Leu Arg Asn His Gln Pro Arg Glu
    1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Gln Pro Glu
                1045                1050                1055

Asp Ala Asp Asn Gln Arg Asn Val Thr Arg Met Gly Ser Gln Pro Pro
            1060                1065                1070

Asp Pro Asn Thr Ile Val His Ile Pro Val Met Leu Thr Gly Pro Leu
        1075                1080                1085

Gly Glu Ala Thr Val Val Pro Ser Gly Asn Val Asp Leu Glu Ser Gln
    1090                1095                1100

Ala Glu Gly Lys Lys Glu Val Glu Ala Asp Val Met Arg Ser Gly
1105                1110                1115                1120

Pro Arg Pro Ile Val Pro Tyr Ser Ser Met Phe Cys Leu Ser Pro Thr
                1125                1130                1135

Asn Leu Leu Arg Arg Phe Cys His Tyr Ile Val Thr Met Arg Tyr Phe
            1140                1145                1150

Glu Val Val Ile Leu Val Val Ile Ala Leu Ser Ser Ile Ala Leu Ala
        1155                1160                1165

Ala Glu Asp Pro Val Arg Thr Asp Ser Pro Arg Asn Asn Ala Leu Lys
    1170                1175                1180

Tyr Leu Asp Tyr Ile Phe Thr Gly Val Phe Thr Phe Glu Met Val Ile
1185                1190                1195                1200

Lys Met Ile Asp Leu Gly Leu Leu His Pro Gly Ala Tyr Phe Arg
                1205                1210                1215

Asp Leu Trp Asn Ile Leu Asp Phe Ile Val Val Ser Gly Ala Leu Val
            1220                1225                1230

Ala Phe Ala Phe Ser Gly Ser Lys Gly Lys Asp Ile Asn Thr Ile Lys
        1235                1240                1245

Ser Leu Arg Val Leu Arg Val Leu Arg Pro Leu Lys Thr Ile Lys Arg
    1250                1255                1260

Leu Pro Lys Leu Lys Ala Val Phe Asp Cys Val Val Asn Ser Leu Lys
1265                1270                1275                1280

Asn Val Leu Asn Ile Leu Ile Val Tyr Met Leu Phe Met Phe Ile Phe
                1285                1290                1295

Ala Val Ile Ala Val Gln Leu Phe Lys Gly Lys Phe Phe Tyr Cys Thr
            1300                1305                1310

Asp Glu Ser Lys Glu Leu Glu Arg Asp Cys Arg Gly Gln Tyr Leu Asp
```

```
                  1315                1320                1325
Tyr Glu Lys Glu Glu Val Glu Ala Gln Pro Arg Gln Trp Lys Lys Tyr
            1330                1335                1340
Asp Phe His Tyr Asp Asn Val Leu Trp Ala Leu Leu Thr Leu Phe Thr
1345                1350                1355                1360
Val Ser Thr Gly Glu Gly Trp Pro Met Val Leu Lys His Ser Val Asp
                1365                1370                1375
Ala Thr Tyr Glu Glu Gln Gly Pro Ser Pro Gly Tyr Arg Met Glu Leu
            1380                1385                1390
Ser Ile Phe Tyr Val Val Tyr Phe Val Val Phe Pro Phe Phe Phe Val
            1395                1400                1405
Asn Ile Phe Val Ala Leu Ile Ile Ile Thr Phe Gln Glu Gln Gly Asp
            1410                1415                1420
Lys Val Met Ser Glu Cys Ser Leu Glu Lys Asn Glu Arg Ala Cys Ile
1425                1430                1435                1440
Asp Phe Ala Ile Ser Ala Lys Pro Leu Thr Arg Tyr Met Pro Gln Asn
                1445                1450                1455
Arg Gln Ser Phe Gln Tyr Lys Thr Trp Thr Phe Val Val Ser Pro Pro
            1460                1465                1470
Phe Glu Tyr Phe Ile Met Ala Met Ile Ala Leu Asn Thr Val Val Leu
            1475                1480                1485
Met Met Lys Phe Tyr Asp Ala Pro Tyr Glu Tyr Glu Leu Met Leu Lys
            1490                1495                1500
Cys Leu Asn Ile Val Phe Thr Ser Met Phe Ser Met Glu Cys Val Leu
1505                1510                1515                1520
Lys Ile Ile Ala Phe Gly Val Leu Asn Tyr Phe Arg Asp Ala Trp Asn
                1525                1530                1535
Val Phe Asp Phe Val Thr Val Leu Gly Ser Ile Thr Asp Ile Leu Val
            1540                1545                1550
Thr Glu Ile Ala Glu Thr Asn Asn Phe Ile Asn Leu Ser Phe Leu Arg
            1555                1560                1565
Leu Phe Arg Ala Ala Arg Leu Ile Lys Leu Leu Arg Gln Gly Tyr Thr
            1570                1575                1580
Ile Arg Ile Leu Leu Trp Thr Phe Val Gln Ser Phe Lys Ala Leu Pro
1585                1590                1595                1600
Tyr Val Cys Leu Leu Ile Ala Met Leu Phe Phe Ile Tyr Ala Ile Ile
                1605                1610                1615
Gly Met Gln Val Phe Gly Asn Ile Ala Leu Asp Asp Thr Ser Ile
            1620                1625                1630
Asn Arg His Asn Asn Phe Arg Thr Phe Leu Gln Ala Leu Met Leu Leu
            1635                1640                1645
Phe Arg Ser Ala Thr Gly Glu Ala Trp His Glu Ile Met Leu Ser Cys
            1650                1655                1660
Leu Ser Asn Gln Ala Cys Asp Glu Gln Ala Asn Ala Thr Glu Cys Gly
1665                1670                1675                1680
Ser Asp Phe Ala Tyr Phe Tyr Phe Val Ser Phe Ile Phe Leu Cys Ser
                1685                1690                1695
Phe Leu Met Leu Asn Leu Phe Val Ala Val Ile Met Asp Asn Phe Glu
            1700                1705                1710
Tyr Leu Thr Arg Asp Ser Ser Ile Leu Gly Pro His His Leu Asp Glu
            1715                1720                1725
Phe Ile Arg Val Trp Ala Glu Tyr Asp Pro Ala Ala Cys Gly Arg Ile
            1730                1735                1740
```

-continued

```
Ser Tyr Asn Asp Met Phe Glu Met Leu Lys His Met Ser Pro Pro Leu
1745                1750                1755                1760

Gly Leu Gly Lys Lys Cys Pro Ala Arg Val Ala Tyr Lys Arg Leu Val
                1765                1770                1775

Arg Met Asn Met Pro Ile Ser Asn Glu Asp Met Thr Val His Phe Thr
                1780                1785                1790

Ser Thr Leu Met Ala Leu Ile Arg Thr Ala Leu Glu Ile Lys Leu Ala
            1795                1800                1805

Pro Ala Gly Thr Lys Gln His Gln Cys Asp Ala Glu Leu Arg Lys Glu
            1810                1815                1820

Ile Ser Val Val Trp Ala Asn Leu Pro Gln Lys Thr Leu Asp Leu Leu
1825                1830                1835                1840

Val Pro Pro His Lys Pro Asp Glu Met Thr Val Gly Lys Val Tyr Ala
                1845                1850                1855

Ala Leu Met Ile Phe Asp Phe Tyr Lys Gln Asn Lys Thr Thr Arg Asp
                1860                1865                1870

Gln Met Gln Gln Ala Pro Gly Gly Leu Ser Gln Met Gly Pro Val Ser
            1875                1880                1885

Leu Phe His Pro Leu Lys Ala Thr Leu Glu Gln Thr Gln Pro Ala Val
            1890                1895                1900

Leu Arg Gly Ala Arg Val Phe Leu Arg Gln Lys Ser Ser Thr Ser Leu
1905                1910                1915                1920

Ser Asn Gly Gly Ala Ile Gln Asn Gln Glu Ser Gly Ile Lys Glu Ser
                1925                1930                1935

Val Ser Trp Gly Thr Gln Arg Thr Gln Asp Ala Pro His Glu Ala Arg
                1940                1945                1950

Pro Pro Leu Glu Arg Gly His Ser Thr Glu Ile Pro Val Gly Arg Ser
            1955                1960                1965

Gly Ala Leu Ala Val Asp Val Gln Met Gln Ser Ile Thr Arg Arg Gly
            1970                1975                1980

Pro Asp Gly Glu Pro Gln Pro Gly Leu Glu Ser Gln Gly Arg Ala Ala
1985                1990                1995                2000

Ser Met Pro Arg Leu Ala Ala Glu Thr Gln Pro Val Thr Asp Ala Ser
                2005                2010                2015

Pro Met Lys Arg Ser Ile Ser Thr Leu Ala Gln Arg Pro Arg Gly Thr
            2020                2025                2030

His Leu Cys Ser Thr Thr Pro Asp Arg Pro Pro Ser Gln Ala Ser
            2035                2040                2045

Ser His His His His Arg Cys His Arg Arg Asp Arg Lys Gln
2050                2055                2060

Arg Ser Leu Glu Lys Gly Pro Ser Leu Ser Ala Asp Met Asp Gly Ala
2065                2070                2075                2080

Pro Ser Ser Ala Val Gly Pro Gly Leu Pro Pro Gly Glu Gly Pro Thr
                2085                2090                2095

Gly Cys Arg Arg Glu Arg Glu Arg Arg Gln Glu Arg Gly Arg Ser Gln
            2100                2105                2110

Glu Arg Arg Gln Pro Ser Ser Ser Ser Glu Lys Gln Arg Phe Tyr
            2115                2120                2125

Ser Cys Asp Arg Phe Gly Gly Arg Glu Pro Pro Lys Pro Lys Pro Ser
            2130                2135                2140

Leu Ser Ser His Pro Thr Ser Pro Thr Ala Gly Gln Glu Pro Gly Pro
2145                2150                2155                2160
```

```
His Pro Gln Gly Ser Gly Ser Val Asn Gly Ser Pro Leu Leu Ser Thr
                2165                2170                2175
Ser Gly Ala Ser Thr Pro Gly Arg Gly Gly Arg Gln Leu Pro Gln
            2180                2185                2190
Thr Pro Leu Thr Pro Arg Pro Ser Ile Thr Tyr Lys Thr Ala Asn Ser
            2195                2200                2205
Ser Pro Ile His Phe Ala Gly Ala Gln Thr Ser Leu Pro Ala Phe Ser
            2210                2215                2220
Pro Gly Arg Leu Ser Arg Gly Leu Ser Glu His Asn Ala Leu Leu Gln
2225                2230                2235                2240
Arg Asp Pro Leu Ser Gln Pro Leu Ala Pro Gly Ser Arg Ile Gly Ser
                2245                2250                2255
Asp Pro Tyr Leu Gly Gln Arg Leu Asp Ser Glu Ala Ser Val His Ala
            2260                2265                2270
Leu Pro Glu Asp Thr Leu Thr Phe Glu Glu Ala Val Ala Thr Asn Ser
            2275                2280                2285
Gly Arg Ser Ser Arg Thr Ser Tyr Val Ser Ser Leu Thr Ser Gln Ser
            2290                2295                2300
His Pro Leu Arg Arg Val Pro Asn Gly Tyr His Cys Thr Leu Gly Leu
2305                2310                2315                2320
Ser Ser Gly Gly Arg Ala Arg His Ser Tyr His His Pro Asp Gln Asp
                2325                2330                2335
His Trp Cys

<210> SEQ ID NO 7
<211> LENGTH: 7177
<212> TYPE: DNA
<213> ORGANISM: Homo Sapiens

<400> SEQUENCE: 7
gcggcggcgg ctgcggcggt ggggccgggc gaggtccgct gcggtcccgg cggctccgtg      60
gctgctccgc tctgagcgcc tggcgcgccc cgcgccctcc ctgccggggc cgctgggccg     120
gggatgcacg cggggcccgg gagccatggt ccgcttcggg gacagctgg gcggccgcta     180
tggaggcccc ggcggcggag agcgggcccg gggcggcggg gccggcgggg cggggggccc     240
gggtcccggg gggctgcagc ccggccagcg ggtcctctac aagcaatcga tcgcgcagcg     300
cgcgcggacc atggcgctgt acaaccccat cccggtcaag cagaactgct tcaccgtcaa     360
ccgctcgctc ttcgtcttca gcgaggacaa cgtcgtccgc aaatacgcga agcgcatcac     420
cgagtggcct ccattcgagt atatgatcct ggccaccatc atcgccaact gcatcgtgct     480
ggccctggag cagcacctcc ctgatgggga caaaacgccc atgtccgagc ggctggacga     540
cacggagccc tatttcatcg ggatcttttg cttcgaggca gggatcaaaa tcatcgctct     600
gggctttgtc ttccacaagg gctcttacct gcggaacggc tggaacgtca tggacttcgt     660
ggtcgtcctc acagggatcc ttgccacggc tggaactgac ttcgacctgc gaacactgag     720
ggctgtgcgt gtgctgaggc ccctgaagct ggtgtctggg attccaagtt tgcaggtggt     780
gctcaagtcc atcatgaagg ccatggttcc actcctgcag attgggctgc ttctcttctt     840
tgccatcctc atgtttgcca tcattggcct ggagttctac atgggcaagt cccacaaggc     900
ctgtttcccc aacagcacag atgcggagcc cgtgggtgac ttcccctgtg caaggaggc     960
cccagcccgg ctgtgcgagg cgacactga gtgccgggag tactggcag gacccaactt    1020
tggcatcacc aactttgaca atatcctgtt tgccatcttg acggtgttcc agtgcatcac    1080
```

```
catggagggc tggactgaca tcctctataa tacaaacgat gcggccggca acacctggaa    1140
ctggctctac ttcatccctc tcatcatcat cggctccttc ttcatgctca acctggtgct    1200
gggcgtgctc tcgggggagt ttgccaagga gcgagagagg gtggagaacc gccgcgcctt    1260
cctgaagctg cgccggcagc agcagatcga gcgagagctc aacgggtacc tggagtggat    1320
cttcaaggcg gaggaagtca tgctggccga ggaggacagg aatgcagagg agaagtcccc    1380
tttggacgtg ctgaagagag cggccaccaa gaagagcaga aatgacctga tccacgcaga    1440
ggagggagag gaccggtttg cagatctctg tgctgttgga tcccccttcg cccgcgccag    1500
cctcaagagc gggaagacag agagctcgtc atacttccgg aggaaggaga gatgttccg    1560 gttttttatc cggcgcatgg tgaaggctca gagcttctac tgggtggtgc tgtgcgtggt    1620
ggccctgaac acactgtgtg tggccatggt gcattacaac cagccgcggc ggcttaccac    1680
gaccctgtat tttgcagagt ttgttttcct gggtctcttc ctcacagaga tgtccctgaa    1740
gatgtatggc ctggggccca gaagctactt ccggtcctcc ttcaactgct cgactttgg    1800 ggtcatcgtg gggagcgtct ttgaagtggt ctgggcggcc atcaagccgg gaagctcctt    1860
tgggatcagt gtgctgcggg ccctccgcct gctgaggatc ttcaaagtca cgaagtactg    1920
gagctccctg cggaacctgg tggtgtccct gctgaactcc atgaagtcca tcatcagcct    1980
gctcttcttg ctcttcctgt tcattgtggt cttcgccctg ctggggatgc agctgtttgg    2040
gggacagttc aacttccagg atgagactcc cacaaccaac ttcgacacct ccctgccgc    2100 catcctcact gtcttccaga tcctgacggg agaggactgg aatgcagtga tgtatcacgg    2160
gatcgaatcg caaggcggcg tcagcaaagg catgttctcg tccttttact tcattgtcct    2220
gacactgttc ggaaactaca ctctgctgaa tgtctttctg gccatcgctg tggacaacct    2280
ggccaacgcc caagagctga ccaaggatga agaggagatg gaagaagcag ccaatcagaa    2340
gcttgctctg caaaaggcca agaagtggc tgaagtcagc cccatgtctg ccgcgaacat    2400
ctccatcgcc gccaggcagc agaactcggc caaggcgcgc tcggtgtggg agcagcgggc    2460
cagccagcta cggctgcaga acctgcgggc cagctgcgag gcgctgtaca gcagatgga    2520 ccccgaggag cggctgcgct cgccactac gcgccacctg cggcccgaca tgaagacgca    2580
cctggaccgg ccgctggtgg tggagctggg ccgcgacggc gcgcggggc cgtgggagg    2640 caaagcccga cctgaggctg cggaggcccc cgagggcgtc gaccctccgc gcaggcacca    2700
ccggcaccgc gacaaggaca agaccccgc ggcgggggac caggaccgag cagaggcccc    2760
gaaggcggag agcggggagc ccggtgcccg ggaggagcgg ccgcggccgc accgcagcca    2820
cagcaaggag gccgcggggc ccccggaggc gcggagcgag cgcggccgag gcccaggccc    2880
cgagggcggc cggcggcacc accggcgcgg ctccccggag gaggcggccg agcgggagcc    2940
ccgacgccac cgcgcgcacc ggcaccagga tccgagcaag gagtgcgccg gcgccaaggg    3000
cgagcggcgc gcgcggcacc gcggcggccc cgagcggggg cccgggagg cggagagcgg    3060 ggaggagccg gcgcggcggc accgggcccg gcacaaggcg cagcctgctc acgaggctgt    3120
ggagaaggag accacggaga aggaggccac ggagaaggag gctgagatag tggaagccga    3180
caaggaaaag gagctccgga accaccagcc ccgggagcca cactgtgacc tggagaccag    3240
tgggactgtg actgtgggtc ccatgcacac actgcccagc acctgtctcc agaaggtgga    3300
ggaacagcca gaggatgcag acaatcagcg gaacgtcact cgcatgggca gtcagccccc    3360
agacccgaac actattgtac atatcccagt gatgctgacg ggcccctctg gggaagccac    3420
ggtcgttccc agtggtaacg tggacctgga aagccaagca gaggggaaga aggaggtgga    3480
```

-continued

```
agcggatgac gtgatgagga gcggccccccg gcctatcgtc ccatacagct ccatgttctg    3540
tttaagcccc accaacctgc tccgccgctt ctgccactac atcgtgacca tgaggtactt    3600
cgaggtggtc attctcgtgg tcatcgcctt gagcagcatc gccctggctg ctgaggaccc    3660
agtgcgcaca gactcgccca ggaacaacgc tctgaaatac ctggattaca ttttcactgg    3720
tgtctttacc tttgagatgg tgataaagat gatcgacttg ggactgctgc ttcaccctgg    3780
agcctatttc cgggacttgt ggaacattct ggacttcatt gtggtcagtg gcgccctggt    3840
ggcgtttgct ttctcaggat ccaaagggaa agacatcaat accatcaagt ctctgagagt    3900
ccttcgtgtc ctgcggcccc tcaagaccat caaacggctg cccaagctca aggctgtgtt    3960
tgactgtgtg gtgaactccc tgaagaatgt cctcaacatc ttgattgtct acatgctctt    4020
catgttcata tttgccgtca ttgcggtgca gctcttcaaa gggaagtttt tctactgcac    4080
agatgaatcc aaggagctgg agagggactg caggggtcag tatttggatt atgagaagga    4140
ggaagtggaa gctcagccca ggcagtggaa gaaatacgac tttcactacg acaatgtgct    4200
ctgggctctg ctgacgctgt tcacagtgtc cacgggagaa ggctggccca tggtgctgaa    4260
acactccgtg gatgccacct atgaggagca gggtccaagc cctgggtacc gcatggagct    4320
gtccatcttc tacgtggtct actttgtggt ctttcccttc ttcttcgtca acatctttgt    4380
ggctttgatc atcatcacct ccaggagca ggggacaag gtgatgtctg aatgcagcct    4440
ggagaagaac gagagggctt gcattgactt cgccatcagc gccaaacccc tgacacggta    4500 catgcccccaa aaccggcagt cgttccagta taagacgtgg acatttgtgg tctcccccgcc    4560 ctttgaatac ttcatcatgg ccatgatagc cctcaacact gtggtgctga tgatgaagtt    4620
ctatgatgca ccctatgagt acgagctgat gctgaaatgc ctgaacatcg tgttcacatc    4680
catgttctcc atggaatgcg tgctgaagat catcgccttt gggggtgctga actatttcag    4740 agatgcctgg aatgtctttg actttgtcac tgtgttggga agtattactg atattttagt    4800
aacagagatt gcggaaacga acaatttcat caacctcagc ttcctccgcc tctttcgagc    4860
tgcgcggctg atcaagctgc tccgccaggg ctacaccatc cgcatcctgc tgtggacctt    4920
tgtccagtcc ttcaaggccc tgcctacgt gtgtctgctc attgccatgc tgttcttcat    4980
ctacgccatc atcggcatgc aggtgtttgg aatattgcc ctggatgatg acaccagcat    5040
caaccgccac aacaacttcc ggacgtttt gcaagccctg atgctgctgt tcaggagcgc    5100
cacgggggag gcctggcacg agatcatgct gtcctgcctg agcaaccagg cctgtgatga    5160
gcaggccaat gccaccgagt gtggaagtga ctttgcctac ttctacttcg tctccttcat    5220
cttcctgtgc tcctttctga tgttgaacct ctttgtggct gtgatcatgg acaatttga    5280 gtacctcacg cgggactctt ccatcctagg tcctcaccac ttggatgagt tcatccgggt    5340
ctgggctgaa tacgacccgg ctgcgtgtgg gcgcatcagt acaatgaca tgtttgagat    5400 gctgaaacac atgtccccgc ctctggggct ggggaagaaa tgccctgctc gagttgctta    5460
caagcgcctg gttcgcatga acatgcccat tccaacgag acatgactg ttcacttcac    5520 gtccacgctg atggccctca tccggacggc actggagatc aagctggccc cagctgggac    5580
aaagcagcat cagtgtgacg cggagttgag gaaggagatt tccgttgtgt gggccaatct    5640
gccccagaag actttggact tgctggtacc accccataag cctgatgaga tgacagtggg    5700
gaaggtttat gcagctctga tgatatttga cttctacaag cagaacaaaa ccaccagaga    5760
ccagatgcag caggctcctg gaggcctctc ccagatgggt cctgtgtccc tgttccaccc    5820
```

-continued

```
tctgaaggcc accctggagc agacacagcc ggctgtgctc cgaggagccc gggttttcct    5880
tcgacagaag agttccacct ccctcagcaa tggcggggcc atacaaaacc aagagagtgg    5940
catcaaagag tctgtctcct ggggcactca aggacccag gatgcacccc atgaggccag     6000 gccaccctg gagcgtggcc actccacaga gatccctgtg gggcggtcag gagcactggc     6060
tgtggacgtt cagatgcaga gcataacccg gaggggccct gatggggagc cccagcctgg    6120
gctggagagc cagggtcgag cggcctccat gccccgcctt gcggccgaga ctcagcccgt    6180
cacagatgcc agcccatga agcgctccat ctccacgctg gcccagcggc cccgtgggac     6240
tcatctttgc agcaccaccc cggaccgcca accccctagc caggcgtcgt cgcaccacca    6300
ccaccaccgc tgccaccgcc gcagggacag gaagcagagg tccctggaga aggggcccag    6360
cctgtctgcc gatatggatg cgcaccaag cagtgctgtg gggccggggc tgcccccggg     6420 agagggcct acaggctgcc ggcgggaacg agagcgccgg caggagcggg gccggtccca    6480
ggagcggagg cagccctcat cctcctcctc ggagaagcag cgcttctact cctgcgaccg    6540 ctttggggc cgtgagcccc cgaagcccaa gccctccctc agcagccacc caacgtcgcc     6600
aacagctggc caggagccgg accccaccc acaggccggc tcagccgtgg gctttccgaa     6660
cacaacgccc tgctgcagag agacccctc agccagcccc tggcccctgg ctctcgaatt     6720
ggctctgacc cttacctggg gcagcgtctg gacagtgagg cctctgtcca cgccctgcct    6780
gaggacacgc tcactttcga ggaggctgtg gccaccaact cgggccgctc ctccaggact    6840
tcctacgtgt cctccctgac ctcccagtct caccctctcc gccgcgtgcc caacggttac    6900
cactgcaccc tgggactcag ctcgggtggc cgagcacggc acagctacca ccaccctgac    6960
caagaccact ggtgctagct gcaccgtgac cgctcagacg cctgcatgca gcaggcgtgt    7020
gttccagtgg atgagtttta tcatccacac ggggcagtcg gccctcgggg gaggccttgc    7080 ccacttggt gaggctcctg tggccccctcc ctccccctcc tcccctcttt tactctagac    7140
gacgaataaa gccctgttgc ttgagtgtac gtaccgc                              7177
```

<210> SEQ ID NO 8
<211> LENGTH: 2237
<212> TYPE: PRT
<213> ORGANISM: Homo Sapiens

<400> SEQUENCE: 8

```
Met Val Arg Phe Gly Asp Glu Leu Gly Gly Arg Tyr Gly Gly Pro Gly
 1               5                  10                  15

Gly Gly Glu Arg Ala Arg Gly Gly Ala Gly Gly Ala Gly Gly Pro
             20                  25                  30

Gly Pro Gly Gly Leu Gln Pro Gly Gln Arg Val Leu Tyr Lys Gln Ser
         35                  40                  45

Ile Ala Gln Arg Ala Arg Thr Met Ala Leu Tyr Asn Pro Ile Pro Val
     50                  55                  60

Lys Gln Asn Cys Phe Thr Val Asn Arg Ser Leu Phe Val Phe Ser Glu
 65                  70                  75                  80

Asp Asn Val Val Arg Lys Tyr Ala Lys Arg Ile Thr Glu Trp Pro Pro
                 85                  90                  95

Phe Glu Tyr Met Ile Leu Ala Thr Ile Ile Ala Asn Cys Ile Val Leu
                100                 105                 110

Ala Leu Glu Gln His Leu Pro Asp Gly Asp Lys Thr Pro Met Ser Glu
            115                 120                 125

Arg Leu Asp Asp Thr Glu Pro Tyr Phe Ile Gly Ile Phe Cys Phe Glu
```

```
              130                 135                 140
Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Leu Thr
                165                 170                 175

Gly Ile Leu Ala Thr Ala Gly Thr Asp Phe Asp Leu Arg Thr Leu Arg
                180                 185                 190

Ala Val Arg Val Leu Arg Pro Leu Lys Leu Val Ser Gly Ile Pro Ser
                195                 200                 205

Leu Gln Val Val Leu Lys Ser Ile Met Lys Ala Met Val Pro Leu Leu
210                 215                 220

Gln Ile Gly Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
                260                 265                 270

Pro Ala Arg Leu Cys Glu Gly Asp Thr Glu Cys Arg Glu Tyr Trp Pro
                275                 280                 285

Gly Pro Asn Phe Gly Ile Thr Asn Phe Asp Asn Ile Leu Phe Ala Ile
                290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
                340                 345                 350

Gly Val Leu Ser Gly Glu Phe Ala Lys Glu Arg Glu Arg Val Glu Asn
                355                 360                 365

Arg Arg Ala Phe Leu Lys Leu Arg Arg Gln Gln Ile Glu Arg Glu
370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
                420                 425                 430

Glu Gly Glu Asp Arg Phe Ala Asp Leu Cys Ala Val Gly Ser Pro Phe
                435                 440                 445

Ala Arg Ala Ser Leu Lys Ser Gly Lys Thr Glu Ser Ser Ser Tyr Phe
450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
                500                 505                 510

Thr Leu Tyr Phe Ala Glu Phe Val Phe Leu Gly Leu Phe Leu Thr Glu
                515                 520                 525

Met Ser Leu Lys Met Tyr Gly Leu Gly Pro Arg Ser Tyr Phe Arg Ser
530                 535                 540

Ser Phe Asn Cys Phe Asp Phe Gly Val Ile Val Gly Ser Val Phe Glu
545                 550                 555                 560
```

```
Val Val Trp Ala Ala Ile Lys Pro Gly Ser Ser Phe Gly Ile Ser Val
            565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
            595                 600                 605

Ile Ile Ser Leu Leu Phe Leu Leu Phe Leu Phe Ile Val Val Phe Ala
        610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
            645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
            675                 680                 685

Phe Ile Val Leu Thr Leu Phe Gly Asn Tyr Thr Leu Leu Asn Val Phe
        690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
            725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
            770                 775                 780

Glu Ala Leu Tyr Ser Glu Met Asp Pro Glu Glu Arg Leu Arg Phe Ala
785                 790                 795                 800

Thr Thr Arg His Leu Arg Pro Asp Met Lys Thr His Leu Asp Arg Pro
            805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
            835                 840                 845

Arg Arg His His Arg His Arg Asp Lys Asp Lys Thr Pro Ala Ala Gly
850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
            885                 890                 895

Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Glu Ala Ala
            915                 920                 925

Glu Arg Glu Pro Arg Arg His Arg Ala His Arg His Gln Asp Pro Ser
            930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
            965                 970                 975
```

-continued

```
Arg Arg His Arg Ala Arg His Lys Ala Gln Pro Ala His Glu Ala Val
            980                 985                 990

Glu Lys Glu Thr Thr Glu Lys Glu Ala Thr Glu Lys Glu Ala Glu Ile
            995                1000                1005

Val Glu Ala Asp Lys Glu Lys Glu Leu Arg Asn His Gln Pro Arg Glu
           1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Gln Pro Glu
           1045                1050                1055

Asp Ala Asp Asn Gln Arg Asn Val Thr Arg Met Gly Ser Gln Pro Pro
           1060                1065                1070

Asp Pro Asn Thr Ile Val His Ile Pro Val Met Leu Thr Gly Pro Leu
           1075                1080                1085

Gly Glu Ala Thr Val Val Pro Ser Gly Asn Val Asp Leu Glu Ser Gln
1090                1095                1100

Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
           1125                1130                1135

Asn Leu Leu Arg Arg Phe Cys His Tyr Ile Val Thr Met Arg Tyr Phe
           1140                1145                1150

Glu Val Val Ile Leu Val Val Ile Ala Leu Ser Ser Ile Ala Leu Ala
           1155                1160                1165

Ala Glu Asp Pro Val Arg Thr Asp Ser Pro Arg Asn Asn Ala Leu Lys
           1170                1175                1180

Tyr Leu Asp Tyr Ile Phe Thr Gly Val Phe Thr Phe Glu Met Val Ile
1185                1190                1195                1200

Lys Met Ile Asp Leu Gly Leu Leu His Pro Gly Ala Tyr Phe Arg
           1205                1210                1215

Asp Leu Trp Asn Ile Leu Asp Phe Ile Val Val Ser Gly Ala Leu Val
           1220                1225                1230

Ala Phe Ala Phe Ser Gly Ser Lys Gly Lys Asp Ile Asn Thr Ile Lys
           1235                1240                1245

Ser Leu Arg Val Leu Arg Val Leu Arg Pro Leu Lys Thr Ile Lys Arg
           1250                1255                1260

Leu Pro Lys Leu Lys Ala Val Phe Asp Cys Val Val Asn Ser Leu Lys
1265                1270                1275                1280

Asn Val Leu Asn Ile Leu Ile Val Tyr Met Leu Phe Met Phe Ile Phe
           1285                1290                1295

Ala Val Ile Ala Val Gln Leu Phe Lys Gly Lys Phe Phe Tyr Cys Thr
           1300                1305                1310

Asp Glu Ser Lys Glu Leu Glu Arg Asp Cys Arg Gly Gln Tyr Leu Asp
           1315                1320                1325

Tyr Glu Lys Glu Glu Val Glu Ala Gln Pro Arg Gln Trp Lys Lys Tyr
           1330                1335                1340

Asp Phe His Tyr Asp Asn Val Leu Trp Ala Leu Leu Thr Leu Phe Thr
1345                1350                1355                1360

Val Ser Thr Gly Glu Gly Trp Pro Met Val Leu Lys His Ser Val Asp
           1365                1370                1375

Ala Thr Tyr Glu Glu Gln Gly Pro Ser Pro Gly Tyr Arg Met Glu Leu
           1380                1385                1390

Ser Ile Phe Tyr Val Val Tyr Phe Val Val Phe Pro Phe Phe Phe Val
```

-continued

```
                1395                1400                1405
Asn Ile Phe Val Ala Leu Ile Ile Thr Phe Gln Glu Gln Gly Asp
            1410                1415                1420
Lys Val Met Ser Glu Cys Ser Leu Glu Lys Asn Glu Arg Ala Cys Ile
1425                1430                1435                1440
Asp Phe Ala Ile Ser Ala Lys Pro Leu Thr Arg Tyr Met Pro Gln Asn
            1445                1450                1455
Arg Gln Ser Phe Gln Tyr Lys Thr Trp Thr Phe Val Val Ser Pro Pro
            1460                1465                1470
Phe Glu Tyr Phe Ile Met Ala Met Ile Ala Leu Asn Thr Val Val Leu
            1475                1480                1485
Met Met Lys Phe Tyr Asp Ala Pro Tyr Glu Tyr Glu Leu Met Leu Lys
            1490                1495                1500
Cys Leu Asn Ile Val Phe Thr Ser Met Phe Ser Met Glu Cys Val Leu
1505                1510                1515                1520
Lys Ile Ile Ala Phe Gly Val Leu Asn Tyr Phe Arg Asp Ala Trp Asn
            1525                1530                1535
Val Phe Asp Phe Val Thr Val Leu Gly Ser Ile Thr Asp Ile Leu Val
            1540                1545                1550
Thr Glu Ile Ala Glu Thr Asn Asn Phe Ile Asn Leu Ser Phe Leu Arg
            1555                1560                1565
Leu Phe Arg Ala Ala Arg Leu Ile Lys Leu Leu Arg Gln Gly Tyr Thr
            1570                1575                1580
Ile Arg Ile Leu Leu Trp Thr Phe Val Gln Ser Phe Lys Ala Leu Pro
1585                1590                1595                1600
Tyr Val Cys Leu Leu Ile Ala Met Leu Phe Phe Ile Tyr Ala Ile Ile
            1605                1610                1615
Gly Met Gln Val Phe Gly Asn Ile Ala Leu Asp Asp Asp Thr Ser Ile
            1620                1625                1630
Asn Arg His Asn Asn Phe Arg Thr Phe Leu Gln Ala Leu Met Leu Leu
            1635                1640                1645
Phe Arg Ser Ala Thr Gly Glu Ala Trp His Glu Ile Met Leu Ser Cys
            1650                1655                1660
Leu Ser Asn Gln Ala Cys Asp Glu Gln Ala Asn Ala Thr Glu Cys Gly
1665                1670                1675                1680
Ser Asp Phe Ala Tyr Phe Tyr Phe Val Ser Phe Ile Phe Leu Cys Ser
            1685                1690                1695
Phe Leu Met Leu Asn Leu Phe Val Ala Val Ile Met Asp Asn Phe Glu
            1700                1705                1710
Tyr Leu Thr Arg Asp Ser Ser Ile Leu Gly Pro His His Leu Asp Glu
            1715                1720                1725
Phe Ile Arg Val Trp Ala Glu Tyr Asp Pro Ala Ala Cys Gly Arg Ile
            1730                1735                1740
Ser Tyr Asn Asp Met Phe Glu Met Leu Lys His Met Ser Pro Pro Leu
1745                1750                1755                1760
Gly Leu Gly Lys Lys Cys Pro Ala Arg Val Ala Tyr Lys Arg Leu Val
            1765                1770                1775
Arg Met Asn Met Pro Ile Ser Asn Glu Asp Met Thr Val His Phe Thr
            1780                1785                1790
Ser Thr Leu Met Ala Leu Ile Arg Thr Ala Leu Glu Ile Lys Leu Ala
            1795                1800                1805
Pro Ala Gly Thr Lys Gln His Gln Cys Asp Ala Glu Leu Arg Lys Glu
            1810                1815                1820
```

```
Ile Ser Val Val Trp Ala Asn Leu Pro Gln Lys Thr Leu Asp Leu Leu
1825                1830                1835                1840

Val Pro Pro His Lys Pro Asp Glu Met Thr Val Gly Lys Val Tyr Ala
                1845                1850                1855

Ala Leu Met Ile Phe Asp Phe Tyr Lys Gln Asn Lys Thr Thr Arg Asp
                1860                1865                1870

Gln Met Gln Gln Ala Pro Gly Gly Leu Ser Gln Met Gly Pro Val Ser
            1875                1880                1885

Leu Phe His Pro Leu Lys Ala Thr Leu Glu Gln Thr Gln Pro Ala Val
            1890                1895                1900

Leu Arg Gly Ala Arg Val Phe Leu Arg Gln Lys Ser Ser Thr Ser Leu
1905                1910                1915                1920

Ser Asn Gly Gly Ala Ile Gln Asn Gln Glu Ser Gly Ile Lys Glu Ser
                1925                1930                1935

Val Ser Trp Gly Thr Gln Arg Thr Gln Asp Ala Pro His Glu Ala Arg
                1940                1945                1950

Pro Pro Leu Glu Arg Gly His Ser Thr Glu Ile Pro Val Gly Arg Ser
            1955                1960                1965

Gly Ala Leu Ala Val Asp Val Gln Met Gln Ser Ile Thr Arg Arg Gly
    1970                1975                1980

Pro Asp Gly Glu Pro Gln Pro Gly Leu Glu Ser Gln Gly Arg Ala Ala
1985                1990                1995                2000

Ser Met Pro Arg Leu Ala Ala Glu Thr Gln Pro Val Thr Asp Ala Ser
                2005                2010                2015

Pro Met Lys Arg Ser Ile Ser Thr Leu Ala Gln Arg Pro Arg Gly Thr
            2020                2025                2030

His Leu Cys Ser Thr Thr Pro Asp Arg Pro Pro Ser Gln Ala Ser
            2035                2040                2045

Ser His His His His Arg Cys His Arg Arg Asp Arg Lys Gln
    2050                2055                2060

Arg Ser Leu Glu Lys Gly Pro Ser Leu Ser Ala Asp Met Asp Gly Ala
2065                2070                2075                2080

Pro Ser Ser Ala Val Gly Pro Gly Leu Pro Pro Gly Glu Gly Pro Thr
                2085                2090                2095

Gly Cys Arg Arg Glu Arg Glu Arg Arg Gln Glu Arg Gly Arg Ser Gln
            2100                2105                2110

Glu Arg Arg Gln Pro Ser Ser Ser Ser Glu Lys Gln Arg Phe Tyr
            2115                2120                2125

Ser Cys Asp Arg Phe Gly Gly Arg Glu Pro Pro Lys Pro Lys Pro Ser
2130                2135                2140

Leu Ser Ser His Pro Thr Ser Pro Thr Ala Gly Gln Glu Pro Gly Pro
2145                2150                2155                2160

His Pro Gln Ala Gly Ser Ala Val Gly Phe Pro Asn Thr Thr Pro Cys
            2165                2170                2175

Cys Arg Glu Thr Pro Ser Ala Ser Pro Trp Pro Leu Ala Leu Glu Leu
            2180                2185                2190

Ala Leu Thr Leu Thr Trp Gly Ser Val Trp Thr Val Arg Pro Leu Ser
            2195                2200                2205

Thr Pro Cys Leu Arg Thr Arg Ser Leu Ser Arg Arg Leu Trp Pro Pro
            2210                2215                2220

Thr Arg Ala Ala Pro Pro Gly Leu Pro Thr Cys Pro Pro
2225                2230                2235
```

-continued

<210> SEQ ID NO 9
<211> LENGTH: 7808
<212> TYPE: DNA
<213> ORGANISM: Homo Sapiens

<400> SEQUENCE: 9

| gatgtcccga | gctgctatcc | ccggctcggc | ccgggcagcc | gccttctgag | cccccgaccc | 60 |
| gaggcgccga | gccgccgccg | cccgatgggc | tgggccgtgg | agcgtctccg | cagtcgtagc | 120 |
| tccagccgcc | gcgctcccag | ccccggcagc | ctcagcatca | gcggcggcgg | cggcggcggc | 180 |
| ggcgtcttcc | gcatcgttcg | ccgcagcgta | acccggagcc | ctttgctctt | tgcagaatgg | 240 |
| cccgcttcgg | agacgagatg | ccggcccgct | acggggagg | aggctccggg | gcagccgccg | 300 |
| gggtggtcgt | gggcagcgga | ggcgggcgag | gagccggggg | cagccggcag | ggcgggcagc | 360 |
| ccggggcgca | aaggatgtac | aagcagtcaa | tggcgcagag | agcgcggacc | atggcactct | 420 |
| acaaccccat | ccccgtccga | cagaactgcc | tcacggttaa | ccgtctctc | ttcctcttca | 480 |
| gcgaagacaa | cgtggtgaga | aaatacgcca | aaaagatcac | cgaatggcct | cccctttgaat | 540 |
| atatgatttt | agccaccatc | atagcgaatt | gcatcgtcct | cgcactggag | cagcatctgc | 600 |
| ctgatgatga | caagaccccg | atgtctgaac | ggctggatga | cacagaacca | tacttcattg | 660 |
| gaattttttg | tttcgaggct | ggaattaaaa | tcattgccct | tgggtttgcc | ttccacaaag | 720 |
| gctcctactt | gaggaatggc | tggaatgtca | tggactttgt | ggtggtgcta | acggcatct | 780 |
| tggcgacagt | tgggacggag | tttgacctac | ggacgctgag | ggcagttcga | gtgctgcggc | 840 |
| cgctcaagct | ggtgtctgga | atcccaagtt | tacaagtcgt | cctgaagtcg | atcatgaagg | 900 |
| cgatgatccc | tttgctgcag | atcggcctcc | tcctattttt | tgcaatcctt | attttttgcaa | 960 |
| tcatagggtt | agaattttat | atgggaaaat | ttcataccac | ctgcttgaa | gaggggacag | 1020 |
| atgacattca | gggtgagtct | ccggctccat | gtgggacaga | agagcccgcc | cgcacctgcc | 1080 |
| ccaatgggac | caaatgtcag | ccctactggg | aagggcccaa | caacgggatc | actcagttcg | 1140 |
| acaacatcct | gtttgcagtg | ctgactgttt | tccagtgcat | aaccatgaa | gggtggactg | 1200 |
| atctcctcta | caatagcaac | gatgcctcag | ggaacacttg | gaactggttg | tacttcatcc | 1260 |
| ccctcatcat | catcggctcc | ttttttatgc | tgaaccttgt | gctgggtgtg | ctgtcagggg | 1320 |
| agtttgccaa | agaaagggaa | cgggtggaga | accggcgggc | tttctgaag | ctgaggcggc | 1380 |
| aacaacagat | tgaacgtgag | ctcaatgggt | acatggaatg | gatctcaaaa | gcagaagagg | 1440 |
| tgatcctcgc | cgaggatgaa | actgacgggg | agcagaggca | tccctttgat | ggagctctgc | 1500 |
| ggagaaccac | cataaagaaa | agcaagacag | atttgctcaa | ccccgaagag | gctgaggatc | 1560 |
| agctggctga | tatagcctct | gtgggttctc | ccttcgcccg | agccagcatt | aaaagtgcca | 1620 |
| agctggagaa | ctcgaccttt | tttcacaaaa | aggagaggag | gatgcgtttc | tacatccgcc | 1680 |
| gcatggtcaa | aactcaggcc | ttctactgga | ctgtactcag | tttggtagct | ctcaacacgc | 1740 |
| tgtgtgttgc | tattgttcac | tacaaccagc | ccgagtggct | ctccgacttc | ctttactatg | 1800 |
| cagaattcat | tttcttagga | ctctttatgt | ccgaaatgtt | tataaaatg | tacgggcttg | 1860 |
| ggacgcggcc | ttacttccac | tcttccttca | actgctttga | ctgtgggtt | atcattggga | 1920 |
| gcatcttcga | ggtcatctgg | gctgtcataa | acctggcac | atccttgga | atcagcgtgt | 1980 |
| tacgagccct | caggttattg | cgtatttca | aagtcacaaa | gtactgggca | tctctcagaa | 2040 |
| acctggtcgt | ctctctcctc | aactccatga | agtccatcat | cagcctgttg | tttctcctt | 2100 |
| tcctgttcat | tgtcgtcttc | gcccttttgg | gaatgcaact | cttcggcggc | cagtttaatt | 2160 |

-continued

```
tcgatgaagg gactcctccc accaacttcg atacttttcc agcagcaata atgacggtgt   2220
ttcagatcct gacgggcgaa gactggaacg aggtcatgta cgacgggatc aagtctcagg   2280
ggggcgtgca gggcggcatg gtgttctcca tctatttcat tgtactgacg ctctttggga   2340
actacaccct cctgaatgtg ttcttggcca tcgctgtgga caatctggcc aacgcccagg   2400
agctcaccaa ggtggaggcg gacgagcaag aggaagaaga agcagcgaac cagaaacttg   2460
ccctacagaa agccaaggag gtggcagaag tgagtcctct gtccgcggcc aacatgtcta   2520
tagctgtgaa agagcaacag aagaatcaaa agccagccaa gtccgtgtgg gagcagcgga   2580
ccagtgagat gcgaaagcag aacttgctgg ccagccggga ggccctgtat aacgaaatgg   2640
acccggacga gcgctggaag gctgcctaca cgcggcacct gcggccagac atgaagacgc   2700
acttggaccg gccgctggtg gtggacccgc aggagaaccg caacaacaac accaacaaga   2760
gccgggcggc cgagcccacc gtggaccagc gcctcggcca gcagcgcgcc gaggacttcc   2820
tcaggaaaca ggcccgctac cacgatcggg cccgggaccc cagcggctcg gcgggcctgg   2880
acgcacggag gccctgggcg ggaagccagg aggccgagct gagccgggag ggaccctacg   2940
gccgcgagtc ggaccaccac gcccggggag gcagcctgga gcaacccggg ttctgggagg   3000
gcgaggccga gcgaggcaag gccgggggacc cccaccggag gcacgtgcac cggcaggggg   3060
gcagcaggga gagccgcagc gggtccccgc gcacgggcgc ggacgggggag catcgacgtc   3120
atcgcgcgca ccgcaggccc ggggaggagg gtccggagga caaggcggag cggagggcgc   3180
ggcaccgcga gggcagccgg ccggcccggg gcggcgaggg cgaggcgag ggccccgacg   3240
ggggcgagcg caggagaagg caccggcatg gcgctccagc cacgtacgag ggggacgcgc   3300
ggagggagga caaggagcgg aggcatcgga ggaggaaaga gaaccagggc tccggggtcc   3360
ctgtgtcggg ccccaacctg tcaaccaccc ggccaatcca gcaggacctg gccgccaag   3420
acccaccccct ggcagaggat attgacaaca tgaagaacaa caagctggcc accgcggagt   3480
cggccgctcc ccacggcagc cttggccacg ccggcctgcc ccagagccca gccaagatgg   3540
gaaacagcac cgaccccggc cccatgctgg ccatccctgc catggccacc aaccccaga   3600
acgccgccag ccgccggacg cccaacaacc cggggaaccc atccaatccc ggccccccca   3660
agaccccga gaatagcctt atcgtcacca accccagcgg cacccagacc aattcagcta   3720
agactgccag gaaacccgac cacaccacag tggacatccc ccagcctgc ccacccccc   3780
tcaaccacac cgtcgtacaa gtgaacaaaa acgccaaccc agacccactg ccaaaaaag   3840
aggaagagaa gaaggaggag gaggaagacg accgtgggga agacggccct aagccaatgc   3900
ctccctatag ctccatgttc atcctgtcca cgaccaaccc ccttcgccgc ctgtgccatt   3960
acatcctgaa cctgcgctac tttgagatgt gcatcctcat ggtcattgcc atgagcagca   4020
tcgccctggc cgccgaggac cctgtgcagc ccaacgcacc tcggaacaac gtgctgcgat   4080
actttgacta cgttttttaca ggcgtcttca cctttgagat ggtgatcaag atgattgacc   4140
tggggctcgt cctgcatcag ggtgcctact tccgtgacct ctggaatatt ctcgacttca   4200
tagtggtcag tgggggccctg gtagcctttg ccttcactgg caatagcaaa ggaaaagaca   4260
tcaacacgat taaatccctc cgagtcctcc gggtgctacg acctcttaaa accatcaagc   4320
ggctgccaaa gctcaaggct gtgtttgact gtgtggtgaa ctcacttaaa aacgtcttca   4380
acatcctcat cgtctacatg ctattcatgt tcatcttcgc cgtggtggct gtgcagctct   4440
tcaaggggaa attcttccac tgcactgacg agtccaaaga gtttgagaaa gattgtcgag   4500
```

```
gcaaatacct cctctacgag aagaatgagg tgaaggcgcg agaccgggag tggaagaagt   4560
atgaattcca ttacgacaat gtgctgtggg ctctgctgac cctcttcacc gtgtccacgg   4620
gagaaggctg gccacaggtc ctcaagcatt cggtggacgc cacctttgag aaccagggcc   4680
ccagccccgg gtaccgcatg gagatgtcca ttttctacgt cgtctacttt gtggtgttcc   4740
ccttcttctt tgtcaatatc tttgtggcct tgatcatcat caccttccag gagcaagggg   4800
acaagatgat ggaggaatac agcctggaga aaaatgagag ggcctgcatt gatttcgcca   4860
tcagcgccaa gccgctgacc cgacacatgc cgcagaacaa gcagagcttc cagtaccgca   4920
tgtggcagtt cgtggtgtct ccgcctttcg agtacacgat catggccatg atcgccctca   4980
acaccatcgt gcttatgatg aagttctatg ggcttctgt tgcttatgaa aatgccctgc   5040
gggtgttcaa catcgtcttc acctccctct tctctctgga atgtgtgctg aaagtcatgg   5100
cttttgggat tctgaattat ttccgcgatg cctggaacat cttcgacttt gtgactgttc   5160
tgggcagcat caccgatatc ctcgtgactg agtttgggaa tccgaataac ttcatcaacc   5220
tgagctttct ccgcctcttc cgagctgccc ggctcatcaa acttctccgt cagggttaca   5280
ccatccgcat tcttctctgg accttttgtgc agtccttcaa ggccctgcct tatgtctgtc   5340
tgctgatcgc catgctcttc ttcatctatg ccatcattgg gatgcaggtg tttggtaaca   5400
ttggcatcga cgtggaggac gaggacagtg atgaagatga gttccaaatc actgagcaca   5460
ataacttccg gaccttcttc caggccctca tgcttctctt ccggagtgcc accggggaag   5520
cttggcacaa catcatgctt tcctgcctca gcgggaaacc gtgtgataag aactctggca   5580
tcctgactcg agagtgtggc aatgaatttg cttattttta ctttgtttcc ttcatcttcc   5640
tctgctcgtt tctgatgctg aatctctttg tcgccgtcat catggacaac tttgagtacc   5700
tcacccgaga ctcctccatc ctgggccccc accacctgga tgagtacgtg cgtgtctggg   5760
ccgagtatga ccccgcagct tgggggccgca tgccttacct ggacatgtat cagatgctga   5820
gacacatgtc tccgccctg ggtctgggga agaagtgtcc ggccagagtg gcttacaagc   5880
ggcttctgcg gatggacctg cccgtcgcag atgacaacac cgtccacttc aattccaccc   5940
tcatggctct gatccgcaca gccctggaca tcaagattgc caagggagga gccgacaaac   6000
agcagatgga cgctgagctg cggaaggaga tgatggcgat ttggcccaat ctgtcccaga   6060
agacgctaga cctgctggtc acacctcaca gtccacgga cctcaccgtg gggaagatct   6120
acgcagccat gatgatcatg gagtactacc ggcagagcaa ggccaagaag ctgcaggcca   6180
tgcgcgagga gcaggaccgg acacccctca tgttccagcg catggagccc ccgtccccaa   6240
cgcaggaagg gggacctggc cagaacgccc tcccctccac ccagctggac ccaggaggag   6300
ccctgatggc tcacgaaagc ggcctcaagg agagcccgtc ctgggtgacc cagcgtgccc   6360
aggagatgtt ccagaagacg ggcacatgga gtccggaaca aggcccccct accgacatgc   6420
ccaacagcca gcctaactct cagtccgtgg agatgcgaga gatgggcaga gatggctact   6480
ccgacagcga gcactacctc cccatggaag gccaggccg ggctgcctcc atgccccgcc   6540
tccctgcaga gaaccagagg agaagggggcc ggccacgtgg gaataacctc agtaccatct   6600
cagacaccag ccccatgaag cgttcagcct ccgtgctggg ccccaaggcc cgacgcctgg   6660
acgattactc gctggagcgg gtcccgcccg aggagaacca gcggcaccac cagcggcgcc   6720
gcgaccgcag ccaccgcgcc tctgagcgct ccctgggccg ctacaccgat gtggacacag   6780
gcttggggac agacctgagc atgaccaccc aatccgggga cctgccgtcg aaggagcggg   6840
accaggagcg gggccggccc aaggatcgga agcatcgaca gcaccaccac caccaccacc   6900
```

-continued

```
accaccacca tcccccgccc ccgacaagg accgctatgc caggaacgg ccggaccacg    6960 gccgggcacg ggctcgggac cagcgctggt cccgctcgcc cagcgagggc cgagagcaca    7020
tggcgcaccg gcagggcagt agttccgtaa gtggaagccc agccccctca acatctggta    7080
ccagcactcc gcggcggggc cgccgccagc tcccccagac ccctccacc cccggccac     7140 acgtgtccta ttccctgtg atccgtaagg ccggcggctc ggggcccccg cagcagcagc    7200
agcagcagca gcagcagcag caggcggtgg ccaggccggg ccggcggcc accagcggcc    7260 ctcggaggta cccaggcccc acggccgagc tctggccgg agatcggccg cccacggggg    7320
gccacagcag cggccgctcg cccaggatgg agaggcgggt cccaggcccg gcccggagcg    7380
agtcccccag ggcctgtcga cacggcgggg cccggtggcc ggcatctggc ccgcacgtgt    7440
ccgagggccc cccgggtccc cggcaccatg gctactaccg ggctccgac tacgacgagg     7500 ccgatggccc gggcagcggg ggcggcgagg aggccatggc cggggcctac gacgcgccac    7560 ccccgtacg acacgcgtcc tcgggcgcca ccgggcgctc gcccaggact ccccgggcct    7620
cgggcccggc ctgcgcctcg ccttctcggc acgccggcg actccccaac ggctactacc    7680
cggcgcacgg actggccagg ccccgcgggc cgggctccag gaagggcctg cacgaacccct  7740 acagcgagag tgacgatgat tggtgctaag cccgggcgag gtggcgcccg cccggccccc    7800
cacgcacc                                                              7808
```

<210> SEQ ID NO 10
<211> LENGTH: 2510
<212> TYPE: PRT
<213> ORGANISM: Homo Sapiens

<400> SEQUENCE: 10

```
Met Ala Arg Phe Gly Asp Glu Met Pro Ala Arg Tyr Gly Gly Gly Gly
  1               5                  10                  15

Ser Gly Ala Ala Ala Gly Val Val Gly Ser Gly Gly Gly Arg Gly
                 20                  25                  30

Ala Gly Gly Ser Arg Gln Gly Gly Gln Pro Gly Ala Gln Arg Met Tyr
             35                  40                  45

Lys Gln Ser Met Ala Gln Arg Ala Arg Thr Met Ala Leu Tyr Asn Pro
     50                  55                  60

Ile Pro Val Arg Gln Asn Cys Leu Thr Val Asn Arg Ser Leu Phe Leu
 65                  70                  75                  80

Phe Ser Glu Asp Asn Val Val Arg Lys Tyr Ala Lys Lys Ile Thr Glu
                 85                  90                  95

Trp Pro Pro Phe Glu Tyr Met Ile Leu Ala Thr Ile Ile Ala Asn Cys
            100                 105                 110

Ile Val Leu Ala Leu Glu Gln His Leu Pro Asp Asp Asp Lys Thr Pro
        115                 120                 125

Met Ser Glu Arg Leu Asp Asp Thr Glu Pro Tyr Phe Ile Gly Ile Phe
    130                 135                 140

Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
                165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
        195                 200                 205
```

```
Ile Pro Ser Leu Gln Val Val Leu Lys Ser Ile Met Lys Ala Met Ile
    210                 215                 220
Pro Leu Leu Gln Ile Gly Leu Leu Phe Phe Ala Ile Leu Ile Phe
225                 230                 235                 240
Ala Ile Ile Gly Leu Glu Phe Tyr Met Gly Lys Phe His Thr Thr Cys
                    245                 250                 255
Phe Glu Glu Gly Thr Asp Asp Ile Gln Gly Glu Ser Pro Ala Pro Cys
                260                 265                 270
Gly Thr Glu Glu Pro Ala Arg Thr Cys Pro Asn Gly Thr Lys Cys Gln
            275                 280                 285
Pro Tyr Trp Glu Gly Pro Asn Asn Gly Ile Thr Gln Phe Asp Asn Ile
    290                 295                 300
Leu Phe Ala Val Leu Thr Val Phe Gln Cys Ile Thr Met Glu Gly Trp
305                 310                 315                 320
Thr Asp Leu Leu Tyr Asn Ser Asn Asp Ala Ser Gly Asn Thr Trp Asn
                    325                 330                 335
Trp Leu Tyr Phe Ile Pro Leu Ile Ile Ile Gly Ser Phe Phe Met Leu
                340                 345                 350
Asn Leu Val Leu Gly Val Leu Ser Gly Glu Phe Ala Lys Glu Arg Glu
            355                 360                 365
Arg Val Glu Asn Arg Arg Ala Phe Leu Lys Leu Arg Arg Gln Gln Gln
    370                 375                 380
Ile Glu Arg Glu Leu Asn Gly Tyr Met Glu Trp Ile Ser Lys Ala Glu
385                 390                 395                 400
Glu Val Ile Leu Ala Glu Asp Glu Thr Asp Gly Glu Gln Arg His Pro
                405                 410                 415
Phe Asp Gly Ala Leu Arg Arg Thr Thr Ile Lys Lys Ser Lys Thr Asp
                420                 425                 430
Leu Leu Asn Pro Glu Glu Ala Glu Asp Gln Leu Ala Asp Ile Ala Ser
            435                 440                 445
Val Gly Ser Pro Phe Ala Arg Ala Ser Ile Lys Ser Ala Lys Leu Glu
    450                 455                 460
Asn Ser Thr Phe Phe His Lys Lys Glu Arg Arg Met Arg Phe Tyr Ile
465                 470                 475                 480
Arg Arg Met Val Lys Thr Gln Ala Phe Tyr Trp Thr Val Leu Ser Leu
                485                 490                 495
Val Ala Leu Asn Thr Leu Cys Val Ala Ile Val His Tyr Asn Gln Pro
                500                 505                 510
Glu Trp Leu Ser Asp Phe Leu Tyr Tyr Ala Glu Phe Ile Phe Leu Gly
            515                 520                 525
Leu Phe Met Ser Glu Met Phe Ile Lys Met Tyr Gly Leu Gly Thr Arg
    530                 535                 540
Pro Tyr Phe His Ser Ser Phe Asn Cys Phe Asp Cys Gly Val Ile Ile
545                 550                 555                 560
Gly Ser Ile Phe Glu Val Ile Trp Ala Val Ile Lys Pro Gly Thr Ser
                565                 570                 575
Phe Gly Ile Ser Val Leu Arg Ala Leu Arg Leu Leu Arg Ile Phe Lys
                580                 585                 590
Val Thr Lys Tyr Trp Ala Ser Leu Arg Asn Leu Val Val Ser Leu Leu
            595                 600                 605
Asn Ser Met Lys Ser Ile Ile Ser Leu Leu Phe Leu Leu Phe Leu Phe
610                 615                 620
```

```
Ile Val Val Phe Ala Leu Leu Gly Met Gln Leu Phe Gly Gly Gln Phe
625                 630                 635                 640

Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
            660                 665                 670

Val Met Tyr Asp Gly Ile Lys Ser Gln Gly Val Gln Gly Gly Met
        675                 680                 685

Val Phe Ser Ile Tyr Phe Ile Val Leu Thr Leu Phe Gly Asn Tyr Thr
690                 695                 700

Leu Leu Asn Val Phe Leu Ala Ile Ala Val Asp Asn Leu Ala Asn Ala
705                 710                 715                 720

Gln Glu Leu Thr Lys Val Glu Ala Asp Glu Gln Glu Glu Glu Glu Ala
                725                 730                 735

Ala Asn Gln Lys Leu Ala Leu Gln Lys Ala Lys Glu Val Ala Glu Val
            740                 745                 750

Ser Pro Leu Ser Ala Ala Asn Met Ser Ile Ala Val Lys Glu Gln Gln
        755                 760                 765

Lys Asn Gln Lys Pro Ala Lys Ser Val Trp Glu Gln Arg Thr Ser Glu
770                 775                 780

Met Arg Lys Gln Asn Leu Leu Ala Ser Arg Glu Ala Leu Tyr Asn Glu
785                 790                 795                 800

Met Asp Pro Asp Glu Arg Trp Lys Ala Ala Tyr Thr Arg His Leu Arg
                805                 810                 815

Pro Asp Met Lys Thr His Leu Asp Arg Pro Leu Val Val Asp Pro Gln
            820                 825                 830

Glu Asn Arg Asn Asn Asn Thr Asn Lys Ser Arg Ala Ala Glu Pro Thr
        835                 840                 845

Val Asp Gln Arg Leu Gly Gln Gln Arg Ala Glu Asp Phe Leu Arg Lys
850                 855                 860

Gln Ala Arg Tyr His Asp Arg Ala Arg Asp Pro Ser Gly Ser Ala Gly
865                 870                 875                 880

Leu Asp Ala Arg Arg Pro Trp Ala Gly Ser Gln Glu Ala Glu Leu Ser
                885                 890                 895

Arg Glu Gly Pro Tyr Gly Arg Glu Ser Asp His His Ala Arg Glu Gly
            900                 905                 910

Ser Leu Glu Gln Pro Gly Phe Trp Glu Gly Glu Ala Glu Arg Gly Lys
        915                 920                 925

Ala Gly Asp Pro His Arg Arg His Val His Arg Gln Gly Gly Ser Arg
930                 935                 940

Glu Ser Arg Ser Gly Ser Pro Arg Thr Gly Ala Asp Gly Glu His Arg
945                 950                 955                 960

Arg His Arg Ala His Arg Arg Pro Gly Glu Glu Gly Pro Glu Asp Lys
                965                 970                 975

Ala Glu Arg Arg Ala Arg His Arg Glu Gly Ser Arg Pro Ala Arg Gly
            980                 985                 990

Gly Glu Gly Glu Gly Glu Gly Pro Asp Gly Gly Glu Arg Arg Arg Arg
        995                 1000                1005

His Arg His Gly Ala Pro Ala Thr Tyr Glu Gly Asp Ala Arg Arg Glu
    1010                1015                1020

Asp Lys Glu Arg Arg His Arg Arg Arg Lys Glu Asn Gln Gly Ser Gly
1025                1030                1035                1040

Val Pro Val Ser Gly Pro Asn Leu Ser Thr Thr Arg Pro Ile Gln Gln
```

-continued

```
                1045                1050                1055
Asp Leu Gly Arg Gln Asp Pro Pro Leu Ala Glu Asp Ile Asp Asn Met
                1060                1065                1070
Lys Asn Asn Lys Leu Ala Thr Ala Glu Ser Ala Ala Pro His Gly Ser
                1075                1080                1085
Leu Gly His Ala Gly Leu Pro Gln Ser Pro Ala Lys Met Gly Asn Ser
                1090                1095                1100
Thr Asp Pro Gly Pro Met Leu Ala Ile Pro Ala Met Ala Thr Asn Pro
1105                1110                1115                1120
Gln Asn Ala Ala Ser Arg Arg Thr Pro Asn Asn Pro Gly Asn Pro Ser
                1125                1130                1135
Asn Pro Gly Pro Pro Lys Thr Pro Glu Asn Ser Leu Ile Val Thr Asn
                1140                1145                1150
Pro Ser Gly Thr Gln Thr Asn Ser Ala Lys Thr Ala Arg Lys Pro Asp
                1155                1160                1165
His Thr Thr Val Asp Ile Pro Pro Ala Cys Pro Pro Leu Asn His
                1170                1175                1180
Thr Val Val Gln Val Asn Lys Asn Ala Asn Pro Asp Pro Leu Pro Lys
1185                1190                1195                1200
Lys Glu Glu Glu Lys Lys Glu Glu Glu Asp Asp Arg Gly Glu Asp
                1205                1210                1215
Gly Pro Lys Pro Met Pro Pro Tyr Ser Ser Met Phe Ile Leu Ser Thr
                1220                1225                1230
Thr Asn Pro Leu Arg Arg Leu Cys His Tyr Ile Leu Asn Leu Arg Tyr
                1235                1240                1245
Phe Glu Met Cys Ile Leu Met Val Ile Ala Met Ser Ser Ile Ala Leu
                1250                1255                1260
Ala Ala Glu Asp Pro Val Gln Pro Asn Ala Pro Arg Asn Asn Val Leu
1265                1270                1275                1280
Arg Tyr Phe Asp Tyr Val Phe Thr Gly Val Phe Thr Phe Glu Met Val
                1285                1290                1295
Ile Lys Met Ile Asp Leu Gly Leu Val Leu His Gln Gly Ala Tyr Phe
                1300                1305                1310
Arg Asp Leu Trp Asn Ile Leu Asp Phe Ile Val Val Ser Gly Ala Leu
                1315                1320                1325
Val Ala Phe Ala Phe Thr Gly Asn Ser Lys Gly Lys Asp Ile Asn Thr
                1330                1335                1340
Ile Lys Ser Leu Arg Val Leu Arg Val Leu Arg Pro Leu Lys Thr Ile
1345                1350                1355                1360
Lys Arg Leu Pro Lys Leu Lys Ala Val Phe Asp Cys Val Val Asn Ser
                1365                1370                1375
Leu Lys Asn Val Phe Asn Ile Leu Ile Val Tyr Met Leu Phe Met Phe
                1380                1385                1390
Ile Phe Ala Val Val Ala Val Gln Leu Phe Lys Gly Lys Phe Phe His
                1395                1400                1405
Cys Thr Asp Glu Ser Lys Glu Phe Glu Lys Asp Cys Arg Gly Lys Tyr
                1410                1415                1420
Leu Leu Tyr Glu Lys Asn Glu Val Lys Ala Arg Asp Arg Glu Trp Lys
1425                1430                1435                1440
Lys Tyr Glu Phe His Tyr Asp Asn Val Leu Trp Ala Leu Leu Thr Leu
                1445                1450                1455
Phe Thr Val Ser Thr Gly Glu Gly Trp Pro Gln Val Leu Lys His Ser
                1460                1465                1470
```

```
Val Asp Ala Thr Phe Glu Asn Gln Gly Pro Ser Pro Gly Tyr Arg Met
        1475                1480                1485
Glu Met Ser Ile Phe Tyr Val Val Tyr Phe Val Val Phe Pro Phe Phe
        1490                1495                1500
Phe Val Asn Ile Phe Val Ala Leu Ile Ile Ile Thr Phe Gln Glu Gln
1505                1510                1515                1520
Gly Asp Lys Met Met Glu Glu Tyr Ser Leu Glu Lys Asn Glu Arg Ala
        1525                1530                1535
Cys Ile Asp Phe Ala Ile Ser Ala Lys Pro Leu Thr Arg His Met Pro
        1540                1545                1550
Gln Asn Lys Gln Ser Phe Gln Tyr Arg Met Trp Gln Phe Val Val Ser
        1555                1560                1565
Pro Pro Phe Glu Tyr Thr Ile Met Ala Met Ile Ala Leu Asn Thr Ile
        1570                1575                1580
Val Leu Met Met Lys Phe Tyr Gly Ala Ser Val Ala Tyr Glu Asn Ala
1585                1590                1595                1600
Leu Arg Val Phe Asn Ile Val Phe Thr Ser Leu Phe Ser Leu Glu Cys
        1605                1610                1615
Val Leu Lys Val Met Ala Phe Gly Ile Leu Asn Tyr Phe Arg Asp Ala
        1620                1625                1630
Trp Asn Ile Phe Asp Phe Val Thr Val Leu Gly Ser Ile Thr Asp Ile
        1635                1640                1645
Leu Val Thr Glu Phe Gly Asn Pro Asn Asn Phe Ile Asn Leu Ser Phe
        1650                1655                1660
Leu Arg Leu Phe Arg Ala Ala Arg Leu Ile Lys Leu Leu Arg Gln Gly
1665                1670                1675                1680
Tyr Thr Ile Arg Ile Leu Leu Trp Thr Phe Val Gln Ser Phe Lys Ala
        1685                1690                1695
Leu Pro Tyr Val Cys Leu Leu Ile Ala Met Leu Phe Phe Ile Tyr Ala
        1700                1705                1710
Ile Ile Gly Met Gln Val Phe Gly Asn Ile Gly Ile Asp Val Glu Asp
        1715                1720                1725
Glu Asp Ser Asp Glu Asp Glu Phe Gln Ile Thr Glu His Asn Asn Phe
        1730                1735                1740
Arg Thr Phe Phe Gln Ala Leu Met Leu Leu Phe Arg Ser Ala Thr Gly
1745                1750                1755                1760
Glu Ala Trp His Asn Ile Met Leu Ser Cys Leu Ser Gly Lys Pro Cys
        1765                1770                1775
Asp Lys Asn Ser Gly Ile Leu Thr Arg Glu Cys Gly Asn Glu Phe Ala
        1780                1785                1790
Tyr Phe Tyr Phe Val Ser Phe Ile Phe Leu Cys Ser Phe Leu Met Leu
        1795                1800                1805
Asn Leu Phe Val Ala Val Ile Met Asp Asn Phe Glu Tyr Leu Thr Arg
        1810                1815                1820
Asp Ser Ser Ile Leu Gly Pro His His Leu Asp Glu Tyr Val Arg Val
1825                1830                1835                1840
Trp Ala Glu Tyr Asp Pro Ala Ala Trp Gly Arg Met Pro Tyr Leu Asp
        1845                1850                1855
Met Tyr Gln Met Leu Arg His Met Ser Pro Pro Leu Gly Leu Gly Lys
        1860                1865                1870
Lys Cys Pro Ala Arg Val Ala Tyr Lys Arg Leu Leu Arg Met Asp Leu
        1875                1880                1885
```

-continued

```
Pro Val Ala Asp Asp Asn Thr Val His Phe Asn Ser Thr Leu Met Ala
    1890                1895                1900

Leu Ile Arg Thr Ala Leu Asp Ile Lys Ile Ala Lys Gly Gly Ala Asp
1905                1910                1915                1920

Lys Gln Gln Met Asp Ala Glu Leu Arg Lys Glu Met Met Ala Ile Trp
                1925                1930                1935

Pro Asn Leu Ser Gln Lys Thr Leu Asp Leu Leu Val Thr Pro His Lys
            1940                1945                1950

Ser Thr Asp Leu Thr Val Gly Lys Ile Tyr Ala Ala Met Met Ile Met
    1955                1960                1965

Glu Tyr Tyr Arg Gln Ser Lys Ala Lys Lys Leu Gln Ala Met Arg Glu
    1970                1975                1980

Glu Gln Asp Arg Thr Pro Leu Met Phe Gln Arg Met Glu Pro Pro Ser
1985                1990                1995                2000

Pro Thr Gln Glu Gly Gly Pro Gly Gln Asn Ala Leu Pro Ser Thr Gln
                2005                2010                2015

Leu Asp Pro Gly Gly Ala Leu Met Ala His Glu Ser Gly Leu Lys Glu
            2020                2025                2030

Ser Pro Ser Trp Val Thr Gln Arg Ala Gln Glu Met Phe Gln Lys Thr
            2035                2040                2045

Gly Thr Trp Ser Pro Glu Gln Gly Pro Pro Thr Asp Met Pro Asn Ser
    2050                2055                2060

Gln Pro Asn Ser Gln Ser Val Glu Met Arg Glu Met Gly Arg Asp Gly
2065                2070                2075                2080

Tyr Ser Asp Ser Glu His Tyr Leu Pro Met Glu Gly Gln Gly Arg Ala
                2085                2090                2095

Ala Ser Met Pro Arg Leu Pro Ala Glu Asn Gln Arg Arg Arg Gly Arg
            2100                2105                2110

Pro Arg Gly Asn Asn Leu Ser Thr Ile Ser Asp Thr Ser Pro Met Lys
            2115                2120                2125

Arg Ser Ala Ser Val Leu Gly Pro Lys Ala Arg Arg Leu Asp Asp Tyr
    2130                2135                2140

Ser Leu Glu Arg Val Pro Pro Glu Glu Asn Gln Arg His His Gln Arg
2145                2150                2155                2160

Arg Arg Asp Arg Ser His Arg Ala Ser Glu Arg Ser Leu Gly Arg Tyr
                2165                2170                2175

Thr Asp Val Asp Thr Gly Leu Gly Thr Asp Leu Ser Met Thr Thr Gln
            2180                2185                2190

Ser Gly Asp Leu Pro Ser Lys Glu Arg Asp Gln Glu Arg Gly Arg Pro
    2195                2200                2205

Lys Asp Arg Lys His Arg Gln His His His His His His His His His
    2210                2215                2220

His Pro Pro Pro Pro Asp Lys Asp Arg Tyr Ala Gln Glu Arg Pro Asp
2225                2230                2235                2240

His Gly Arg Ala Arg Ala Arg Asp Gln Arg Trp Ser Arg Ser Pro Ser
                2245                2250                2255

Glu Gly Arg Glu His Met Ala His Arg Gln Gly Ser Ser Ser Val Ser
            2260                2265                2270

Gly Ser Pro Ala Pro Ser Thr Ser Gly Thr Ser Thr Pro Arg Arg Gly
            2275                2280                2285

Arg Arg Gln Leu Pro Gln Thr Pro Ser Thr Pro Arg Pro His Val Ser
    2290                2295                2300

Tyr Ser Pro Val Ile Arg Lys Ala Gly Gly Ser Gly Pro Pro Gln Gln
```

```
                2305                2310                2315                2320
Gln Gln Gln Gln Gln Gln Gln Gln Ala Val Ala Arg Pro Gly Arg
                2325                2330                2335
Ala Ala Thr Ser Gly Pro Arg Arg Tyr Pro Gly Pro Thr Ala Glu Pro
            2340                2345                2350
Leu Ala Gly Asp Arg Pro Pro Thr Gly Gly His Ser Ser Gly Arg Ser
        2355                2360                2365
Pro Arg Met Glu Arg Arg Val Pro Gly Pro Ala Arg Ser Glu Ser Pro
    2370                2375                2380
Arg Ala Cys Arg His Gly Gly Ala Arg Trp Pro Ala Ser Gly Pro His
2385                2390                2395                2400
Val Ser Glu Gly Pro Pro Gly Pro Arg His His Gly Tyr Tyr Arg Gly
                2405                2410                2415
Ser Asp Tyr Asp Glu Ala Asp Gly Pro Gly Ser Gly Gly Gly Glu Glu
            2420                2425                2430
Ala Met Ala Gly Ala Tyr Asp Ala Pro Pro Val Arg His Ala Ser
        2435                2440                2445
Ser Gly Ala Thr Gly Arg Ser Pro Arg Thr Pro Arg Ala Ser Gly Pro
    2450                2455                2460
Ala Cys Ala Ser Pro Ser Arg His Gly Arg Arg Leu Pro Asn Gly Tyr
2465                2470                2475                2480
Tyr Pro Ala His Gly Leu Ala Arg Pro Arg Gly Pro Gly Ser Arg Lys
                2485                2490                2495
Gly Leu His Glu Pro Tyr Ser Glu Ser Asp Asp Asp Trp Cys
            2500                2505                2510

<210> SEQ ID NO 11
<211> LENGTH: 7791
<212> TYPE: DNA
<213> ORGANISM: Homo Sapiens

<400> SEQUENCE: 11
gatgtcccga gctgctatcc ccggctcggc ccgggcagcc gccttctgag ccccgaccc       60 gaggcgccga gccgccgccg cccgatgggc tgggccgtgg agcgtctccg cagtcgtagc     120
tccagccgcc gcgctcccag ccccggcagc ctcagcatca gcggcggcgg cggcggcggc     180
ggcgtcttcc gcatcgttcg ccgcagcgta acccggagcc ctttgctctt tgcagaatgg     240
cccgcttcgg agacgagatg ccggcccgct acggggagg aggctccggg gcagccgccg     300
gggtggtcgt gggcagcgga ggcgggcgag gagccggggg cagccggcag ggcgggcagc     360
ccggggcgca aggatgtac aagcagtcaa tggcgcagag agcgcggacc atggcactct     420
acaaccccat ccccgtccga cagaactgcc tcacggttaa ccgtctctc ttcctcttca     480 gcgaagacaa cgtggtgaga aaatacgcca aaagatcac cgaatggcct ccctttgaat     540
atatgatttt agccaccatc atagcgaatt gcatcgtcct cgcactggag cagcatctgc     600
ctgatgatga caagaccccg atgtctgaac ggctggatga cacagaacca tacttcattg     660
gaattttttg tttcgaggct ggaattaaaa tcattgccct tgggttgcc ttccacaaag     720 gctcctactt gaggaatggc tggaatgtca tggactttgt ggtggtgcta acgggcatct     780
tggcgacagt tgggacggag tttgacctac ggacgctgag ggcagttcga gtgctgcggc     840
cgctcaagct ggtgtctgga atcccaagtt tacaagtcgt cctgaagtcg atcatgaagg     900
cgatgatccc tttgctgcag atcggcctcc tcctattttt tgcaatcctt attttgcaa      960 tcatagggtt agaattttat atgggaaaat ttcataccac ctgctttgaa gagggacag   1020
```

-continued

```
atgacattca gggtgagtct ccggctccat gtgggacaga agagcccgcc cgcacctgcc    1080
ccaatgggac caaatgtcag ccctactggg aagggcccaa caacgggatc actcagttcg    1140
acaacatcct gtttgcagtg ctgactgttt tccagtgcat aaccatggaa gggtggactg    1200
atctcctcta caatagcaac gatgcctcag ggaacacttg gaactggttg tacttcatcc    1260
ccctcatcat catcggctcc tttttatgc tgaaccttgt gctgggtgtg ctgtcagggg     1320
agtttgccaa agaaagggaa cgggtggaga accggcgggc ttttctgaag ctgaggcggc    1380
aacaacagat tgaacgtgag ctcaatgggt acatggaatg gatctcaaaa gcagaagagg    1440
tgatcctcgc cgaggatgaa actgacgggg agcagaggca tcccttttgat ggagctctgc   1500
ggagaaccac cataaagaaa agcaagacag atttgctcaa ccccgaagag gctgaggatc    1560
agctggctga tatagcctct gtgggttctc ccttcgcccg agccagcatt aaaagtgcca    1620
agctggagaa ctcgaccttt tttcacaaaa aggagaggag gatgcgtttc tacatccgcc    1680
gcatggtcaa aactcaggcc ttctactgga ctgtactcag tttggtagct ctcaacacgc    1740
tgtgtgttgc tattgttcac tacaaccagc ccgagtggct ctccgacttc ctttactatg    1800
cagaattcat tttcttagga ctctttatgt ccgaaatgtt tataaaatg tacgggcttg     1860
ggacgcggcc ttacttccac tcttccttca actgctttga ctgtggggtt atcattggga    1920
gcatcttcga ggtcatctgg gctgtcataa aacctggcac atcctttgga atcagcgtgt    1980
tacgagccct caggttattg cgtattttca aagtcacaaa gtactgggca tctctcagaa    2040
acctggtcgt ctctctcctc aactccatga agtccatcat cagcctgttg tttctccttt    2100
tcctgttcat tgtcgtcttc gccctttgg gaatgcaact cttcggcggc cagtttaatt    2160
tcgatgaagg gactcctccc accaacttcg atacttttcc agcagcaata atgacggtgt    2220
ttcagatcct gacgggcgaa gactggaacg aggtcatgta cgacgggatc aagtctcagg    2280
ggggcgtgca gggcggcatg tgttctcca tctatttcat tgtactgacg ctctttggga    2340
actacaccct cctgaatgtg ttcttggcca tcgctgtgga caatctggcc aacgcccagg    2400
agctcaccaa ggtggaggcg gacgagcaag aggaagaaga agcagcgaac cagaaacttg    2460
ccctacagaa agccaaggag gtggcagaag tgagtcctct gtccgcggcc aacatgtcta    2520
tagctgtgaa agagcaacag aagaatcaaa agccagccaa gtccgtgtgg gagcagcgga    2580
ccagtgagat gcgaaagcag aacttgctgg ccagccggga ggccctgtat aacgaaatgg    2640
acccggacga gcgctggaag gctgcctaca cgcggcacct gcggccagac atgaagacgc    2700
acttggaccg gccgctggtg gtggacccgc aggagaaccg caacaacaac accaacaaga    2760
gccggggggc cgagcccacc gtggaccagc gcctcggcca gcagcgcgcc gaggacttcc    2820
tcaggaaaca ggcccgctac cacgatcggg cccgggaccc cagcggctcg gcgggcctgg    2880
acgcacggag gccctgggcg ggaagccagg aggccgagct gagccgggag ggaccctacg    2940
gccgcgagtc ggaccaccac gcccgggagg gcagcctgga gcaacccggg ttctgggagg    3000
gcgaggccga gcgaggcaag gccggggacc cccaccggag gcacgtgcac cggcagggg    3060
gcagcaggga gagccgcagc gggtccccgc gcacgggcgc ggacggggag catcgacgtc    3120
atcgcgcgca ccgcaggccc ggggaggagg gtcggaggga caaggcgag cggagggcgc     3180
ggcaccgcga gggcagccgg ccggcccggg gcggcgaggg cgagggcgag ggccccgacg    3240
ggggcgagcg caggagaagg caccggcatg gcgctccagc cacgtacgag ggggacgcgc    3300
ggagggagga caaggagcgg aggcatcgga ggaggaaaga gaaccagggc tccggggtcc    3360
```

-continued

```
ctgtgtcggg ccccaacctg tcaaccaccc ggccaatcca gcaggacctg ggccgccaag    3420
acccacccct ggcagaggat attgacaaca tgaagaacaa caagctggcc accgcggagt    3480
cggccgctcc ccacggcagc cttggccacg ccggcctgcc ccagagccca gccaagatgg    3540
gaaacagcac cgaccccggc cccatgctgg ccatccctgc catggccacc aaccccccaga   3600 acgccgccag ccgccggacg cccaacaacc cggggaaccc atccaatccc ggccccccca    3660
agacccccga gaatagcctt atcgtcacca acccacgcgg cacccagacc aattcagcta    3720
agactgccag gaaacccgac cacaccacag tggacatccc cccagcctgc ccaccccccc    3780
tcaaccacac cgtcgtacaa gtgaacaaaa acgccaaccc agacccactg ccaaaaaaag    3840
aggaagagaa gaaggaggag gaggaagacg accgtgggga agacggccct aagccaatgc    3900
ctccctatag ctccatgttc atcctgtcca cgaccaaccc ccttcgccgc ctgtgccatt    3960
acatcctgaa cctgcgctac tttgagatgt gcatcctcat ggtcattgcc atgagcagca    4020
tcgccctggc cgccgaggac cctgtgcagc ccaacgcacc tcggaacaac gtgctgcgat    4080
actttgacta cgttttttaca ggcgtcttca cctttgagat ggtgatcaag atgattgacc    4140
tggggctcgt cctgcatcag ggtgcctact tccgtgacct ctggaatatt ctcgacttca    4200
tagtggtcag tggggccctg gtagcctttg ccttcactgg caatagcaaa ggaaaagaca    4260
tcaacacgat taaatccctc cgagtcctcc gggtgctacg acctcttaaa accatcaagc    4320
ggctgccaaa gctcaaggct gtgtttgact gtgtggtgaa ctcacttaaa aacgtcttca    4380
acatcctcat cgtctacatg ctattcatgt tcatcttcgc cgtggtggct gtgcagctct    4440
tcaaggggaa attcttccac tgcactgacg agtccaaaga gtttgagaaa gattgtcgag    4500
gcaaataccr cctctacgag aagaatgagg tgaaggcgcg agaccgggag tggaagaagt    4560
atgaattcca ttacgacaat gtgctgtggg ctctgctgac cctcttcacc gtgtccacgg    4620
gagaaggctg gccacaggtc ctcaagcatt cggtggacgc cacctttgag aaccagggcc    4680
ccagccccgg gtaccgcatg gagatgtcca ttttctacgt cgtctacttt gtggtgttcc    4740
ccttcttctt tgtcaatatc tttgtggcct tgatcatcat caccttccag gagcaagggg    4800
acaagatgat ggaggaatac agcctggaga aaaatgagag ggcctgcatt gatttcgcca    4860
tcagcgccaa gccgctgacc cgacacatgc cgcagaacaa gcagagcttc cagtaccgca    4920
tgtggcagtt cgtggtgtct ccgccttccg agtacacgat catggccatg atcgccctca    4980
acaccatcgt gcttatgatg aagttctatg gggcttctgt tgcttatgaa aatgccctgc    5040
gggtgttcaa catcgtcttc acctcccctct tctctctgga atgtgtgctg aaagtcatgg    5100
cttttgggat tctgaattat ttccgcgatg cctggaacat cttcgacttt gtgactgttc    5160
tgggcagcat caccgatatc ctcgtgactg agtttgggaa tccgaataac ttcatcaacc    5220
tgagctttct ccgcctcttc cgagctgccc ggctcatcaa acttctccgt cagggttaca    5280
ccatccgcat tcttctctgg acctttgtgc agtccttcaa ggcctgcct tatgtctgtc    5340 tgctgatcgc catgctcttc ttcatctatg ccatcattgg gatgcaggtg tttggtaaca    5400
ttggcatcga cgtggaggac gaggacagtg atgaagatga gttccaaatc actgagcaca    5460
ataacttccg gaccttcttc caggcccctca tgcttctctt ccggagtgcc accggggaag    5520
cttggcacaa catcatgctt tcctgcctca gcgggaaacc gtgtgataag aactctggca    5580
tcctgactcg agagtgtggc aatgaatttg cttatttta ctttgtttcc ttcatcttcc    5640
tctgctcgtt tctgatgctg aatctctttg tcgccgtcat catggacaac tttgagtacc    5700
tcacccgaga ctcctccatc ctgggccccc accacctgga tgagtacgtg cgtgtctggg    5760
```

-continued

```
ccgagtatga ccccgcagct tggggccgca tgccttacct ggacatgtat cagatgctga      5820
gacacatgtc tccgcccctg ggtctgggga agaagtgtcc ggccagagtg gcttacaagc      5880
ggcttctgcg gatggacctg cccgtcgcag atgacaacac cgtccacttc aattccaccc      5940
tcatggctct gatccgcaca gccctggaca tcaagattgc aagggagga gccgacaaac       6000 agcagatgga cgctgagctg cggaaggaga tgatggcgat ttggcccaat ctgtcccaga      6060
agacgctaga cctgctggtc acacctcaca gtccacgga cctcaccgtg gggaagatct       6120
acgcagccat gatgatcatg gagtactacc ggcagagcaa ggccaagaag ctgcaggcca      6180
tgcgcgagga gcaggaccgg acacccctca tgttccagcg catggagccc ccgtccccaa      6240
cgcaggaagg gggacctggc cagaacgccc tcccctccac ccagctggac ccaggaggag      6300
ccctgatggc tcacgaaagc ggcctcaagg agagcccgtc ctgggtgacc cagcgtgccc      6360
aggagatgtt ccagaagacg ggcacatgga gtccggaaca aggccccccct accgacatgc     6420 ccaacagcca gcctaactct cagtccgtgg agatgcgaga gatggcagaa gatggctact      6480
ccgacacgcg gcactacctc cccatggaag gccaggccgg ggctgcctcc atgccccgcc      6540
tccctgcaga gaaccagagg agaaggggcc ggccacgtgg gaataacctc agtaccatct      6600
cagacaccag ccccatgaag cgttcagcct ccgtgctggg ccccaaggcc cgacgcctgg      6660
acgattactc gctggagcgg gtcccgcccg aggagaacca gcggcaccac cagcggcgcc      6720
gcgaccgcag ccaccgcgcc tctgagcgct ccctgggccg ctacaccgat gtggacacag      6780
gcttggggac agacctgagc atgaccaccc aatccgggga cctgccgtcg aaggagcggg      6840
accaggagcg gggccggccc aaggatcgga agcatcgaca gcaccaccac caccaccacc      6900
accaccacca tccccgccc cccgacaagg accgctatgc ccaggaacgg ccggaccacg        6960
gccgggcacg ggctcgggac cagcgctggt cccgctcgcc cagcgagggc cgagagcaca      7020
tggcgcaccg gcagtagttc cgtaagtgga agcccagccc cctcaacatc tggtaccagc      7080
actccgcggc ggggccgccg ccagctcccc cagacccct ccaccccccg gccacacgtg       7140
tcctattccc ctgtgatccg taaggccggc ggctcggggc cccgcagca gcagcagcag       7200 cagcaggcgg tggccaggcc gggccgggcg gccaccagcg gccctcggag gtacccaggc      7260
cccacggccc agcctctggc cggagatcgg ccgcccacgg ggggcacag cagcggccgc        7320 tcgcccagga tggagaggcg ggtcccaggc ccggcccgga gcgagtcccc cagggcctgt      7380
cgacacggcg gggcccggtg gccggcatct ggcccgcacg tgtccgaggg gccccggggt      7440
ccccggcacc atggctacta ccggggctcc gactacgacg aggccgatgg cccgggcagc      7500 ggggcggcg aggaggccat ggccgggcc tacgacgcgc caccccccgt acgacacgcg         7560
tcctcgggcg ccaccgggcg ctcgcccagg actccccggg cctcgggccc ggcctgcgcc      7620
tcgccttctc ggcacggccg gcgactcccc aacggctact acccggcgca cggactggcc      7680
aggccccgcg ggccgggctc caggaagggc ctgcacgaac cctacagcga gagtgacgat      7740
gattggtgct aagcccgggc gaggtggcgc ccgcccggcc ccccacgcac c               7791
```

<210> SEQ ID NO 12
<211> LENGTH: 2266
<212> TYPE: PRT
<213> ORGANISM: Homo Sapiens

<400> SEQUENCE: 12

```
Met Ala Arg Phe Gly Asp Glu Met Pro Ala Arg Tyr Gly Gly Gly Gly
1               5                   10                  15
```

```
Ser Gly Ala Ala Ala Gly Val Val Gly Ser Gly Gly Arg Gly
             20                  25              30

Ala Gly Gly Ser Arg Gln Gly Gly Gln Pro Gly Ala Gln Arg Met Tyr
         35                  40                  45

Lys Gln Ser Met Ala Gln Arg Ala Arg Thr Met Ala Leu Tyr Asn Pro
         50                  55                  60

Ile Pro Val Arg Gln Asn Cys Leu Thr Val Asn Arg Ser Leu Phe Leu
 65                  70                  75                  80

Phe Ser Glu Asp Asn Val Val Arg Lys Tyr Ala Lys Lys Ile Thr Glu
                 85                  90                  95

Trp Pro Pro Phe Glu Tyr Met Ile Leu Ala Thr Ile Ile Ala Asn Cys
             100                 105                 110

Ile Val Leu Ala Leu Glu Gln His Leu Pro Asp Asp Lys Thr Pro
             115                 120                 125

Met Ser Glu Arg Leu Asp Asp Thr Glu Pro Tyr Phe Ile Gly Ile Phe
         130                 135                 140

Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
                 165                 170                 175

Val Leu Thr Gly Ile Leu Ala Thr Val Gly Thr Glu Phe Asp Leu Arg
             180                 185                 190

Thr Leu Arg Ala Val Arg Val Leu Arg Pro Leu Lys Leu Val Ser Gly
         195                 200                 205

Ile Pro Ser Leu Gln Val Val Leu Lys Ser Ile Met Lys Ala Met Ile
         210                 215                 220

Pro Leu Leu Gln Ile Gly Leu Leu Leu Phe Phe Ala Ile Leu Ile Phe
225                 230                 235                 240

Ala Ile Ile Gly Leu Glu Phe Tyr Met Gly Lys Phe His Thr Thr Cys
                 245                 250                 255

Phe Glu Glu Gly Thr Asp Asp Ile Gln Gly Glu Ser Pro Ala Pro Cys
             260                 265                 270

Gly Thr Glu Glu Pro Ala Arg Thr Cys Pro Asn Gly Thr Lys Cys Gln
         275                 280                 285

Pro Tyr Trp Glu Gly Pro Asn Asn Gly Ile Thr Gln Phe Asp Asn Ile
         290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
                 325                 330                 335

Trp Leu Tyr Phe Ile Pro Leu Ile Ile Ile Gly Ser Phe Phe Met Leu
             340                 345                 350

Asn Leu Val Leu Gly Val Leu Ser Gly Glu Phe Ala Lys Glu Arg Glu
         355                 360                 365

Arg Val Glu Asn Arg Arg Ala Phe Leu Lys Leu Arg Arg Gln Gln Gln
         370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
                 405                 410                 415

Phe Asp Gly Ala Leu Arg Arg Thr Thr Ile Lys Lys Ser Lys Thr Asp
             420                 425                 430
```

-continued

```
Leu Leu Asn Pro Glu Glu Ala Glu Asp Gln Leu Ala Asp Ile Ala Ser
        435                 440                 445

Val Gly Ser Pro Phe Ala Arg Ala Ser Ile Lys Ser Ala Lys Leu Glu
    450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
                485                 490                 495

Val Ala Leu Asn Thr Leu Cys Val Ala Ile Val His Tyr Asn Gln Pro
            500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
    530                 535                 540

Pro Tyr Phe His Ser Ser Phe Asn Cys Phe Asp Cys Gly Val Ile Ile
545                 550                 555                 560

Gly Ser Ile Phe Glu Val Ile Trp Ala Val Ile Lys Pro Gly Thr Ser
                565                 570                 575

Phe Gly Ile Ser Val Leu Arg Ala Leu Arg Leu Leu Arg Ile Phe Lys
            580                 585                 590

Val Thr Lys Tyr Trp Ala Ser Leu Arg Asn Leu Val Val Ser Leu Leu
        595                 600                 605

Asn Ser Met Lys Ser Ile Ile Ser Leu Leu Phe Leu Leu Phe Leu Phe
    610                 615                 620

Ile Val Val Phe Ala Leu Leu Gly Met Gln Leu Phe Gly Gly Gln Phe
625                 630                 635                 640

Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
            660                 665                 670

Val Met Tyr Asp Gly Ile Lys Ser Gln Gly Gly Val Gln Gly Gly Met
        675                 680                 685

Val Phe Ser Ile Tyr Phe Ile Val Leu Thr Leu Phe Gly Asn Tyr Thr
    690                 695                 700

Leu Leu Asn Val Phe Leu Ala Ile Ala Val Asp Asn Leu Ala Asn Ala
705                 710                 715                 720

Gln Glu Leu Thr Lys Val Glu Ala Asp Glu Gln Glu Glu Glu Glu Ala
                725                 730                 735

Ala Asn Gln Lys Leu Ala Leu Gln Lys Ala Lys Glu Val Ala Glu Val
            740                 745                 750

Ser Pro Leu Ser Ala Ala Asn Met Ser Ile Ala Val Lys Glu Gln Gln
        755                 760                 765

Lys Asn Gln Lys Pro Ala Lys Ser Val Trp Glu Gln Arg Thr Ser Glu
    770                 775                 780

Met Arg Lys Gln Asn Leu Leu Ala Ser Arg Glu Ala Leu Tyr Asn Glu
785                 790                 795                 800

Met Asp Pro Asp Glu Arg Trp Lys Ala Ala Tyr Thr Arg His Leu Arg
                805                 810                 815

Pro Asp Met Lys Thr His Leu Asp Arg Pro Leu Val Val Asp Pro Gln
            820                 825                 830

Glu Asn Arg Asn Asn Asn Thr Asn Lys Ser Arg Ala Ala Glu Pro Thr
        835                 840                 845

Val Asp Gln Arg Leu Gly Gln Gln Arg Ala Glu Asp Phe Leu Arg Lys
```

-continued

```
                850                 855                 860
Gln Ala Arg Tyr His Asp Arg Ala Arg Asp Pro Ser Gly Ser Ala Gly
865                 870                 875                 880

Leu Asp Ala Arg Arg Pro Trp Ala Gly Ser Gln Glu Ala Glu Leu Ser
                885                 890                 895

Arg Glu Gly Pro Tyr Gly Arg Glu Ser Asp His His Ala Arg Glu Gly
                900                 905                 910

Ser Leu Glu Gln Pro Gly Phe Trp Glu Gly Glu Ala Glu Arg Gly Lys
                915                 920                 925

Ala Gly Asp Pro His Arg Arg His Val His Arg Gln Gly Gly Ser Arg
930                 935                 940

Glu Ser Arg Ser Gly Ser Pro Arg Thr Gly Ala Asp Gly Glu His Arg
945                 950                 955                 960

Arg His Arg Ala His Arg Pro Gly Glu Glu Gly Pro Glu Asp Lys
                965                 970                 975

Ala Glu Arg Arg Ala Arg His Arg Glu Gly Ser Arg Pro Ala Arg Gly
                980                 985                 990

Gly Glu Gly Glu Gly Glu Gly Pro Asp Gly Gly Glu Arg Arg Arg Arg
                995                 1000                1005

His Arg His Gly Ala Pro Ala Thr Tyr Glu Gly Asp Ala Arg Arg Glu
                1010                1015                1020

Asp Lys Glu Arg Arg His Arg Arg Lys Glu Asn Gln Gly Ser Gly
1025                1030                1035                1040

Val Pro Val Ser Gly Pro Asn Leu Ser Thr Thr Arg Pro Ile Gln Gln
                1045                1050                1055

Asp Leu Gly Arg Gln Asp Pro Pro Leu Ala Glu Asp Ile Asp Asn Met
                1060                1065                1070

Lys Asn Asn Lys Leu Ala Thr Ala Glu Ser Ala Ala Pro His Gly Ser
                1075                1080                1085

Leu Gly His Ala Gly Leu Pro Gln Ser Pro Ala Lys Met Gly Asn Ser
                1090                1095                1100

Thr Asp Pro Gly Pro Met Leu Ala Ile Pro Ala Met Ala Thr Asn Pro
1105                1110                1115                1120

Gln Asn Ala Ala Ser Arg Arg Thr Pro Asn Asn Pro Gly Asn Pro Ser
                1125                1130                1135

Asn Pro Gly Pro Pro Lys Thr Pro Glu Asn Ser Leu Ile Val Thr Asn
                1140                1145                1150

Pro Ser Gly Thr Gln Thr Asn Ser Ala Lys Thr Ala Arg Lys Pro Asp
                1155                1160                1165

His Thr Thr Val Asp Ile Pro Pro Ala Cys Pro Pro Leu Asn His
                1170                1175                1180

Thr Val Val Gln Val Asn Lys Asn Ala Asn Pro Asp Pro Leu Pro Lys
1185                1190                1195                1200

Lys Glu Glu Glu Lys Glu Glu Glu Asp Asp Arg Gly Glu Asp
                1205                1210                1215

Gly Pro Lys Pro Met Pro Pro Tyr Ser Ser Met Phe Ile Leu Ser Thr
                1220                1225                1230

Thr Asn Pro Leu Arg Arg Leu Cys His Tyr Ile Leu Asn Leu Arg Tyr
                1235                1240                1245

Phe Glu Met Cys Ile Leu Met Val Ile Ala Met Ser Ser Ile Ala Leu
                1250                1255                1260

Ala Ala Glu Asp Pro Val Gln Pro Asn Ala Pro Arg Asn Asn Val Leu
1265                1270                1275                1280
```

```
Arg Tyr Phe Asp Tyr Val Phe Thr Gly Val Phe Thr Phe Glu Met Val
            1285                1290                1295
Ile Lys Met Ile Asp Leu Gly Leu Val Leu His Gln Gly Ala Tyr Phe
        1300                1305                1310
Arg Asp Leu Trp Asn Ile Leu Asp Phe Ile Val Val Ser Gly Ala Leu
    1315                1320                1325
Val Ala Phe Ala Phe Thr Gly Asn Ser Lys Gly Lys Asp Ile Asn Thr
1330                1335                1340
Ile Lys Ser Leu Arg Val Leu Arg Val Leu Arg Pro Leu Lys Thr Ile
1345                1350                1355                1360
Lys Arg Leu Pro Lys Leu Lys Ala Val Phe Asp Cys Val Val Asn Ser
            1365                1370                1375
Leu Lys Asn Val Phe Asn Ile Leu Ile Val Tyr Met Leu Phe Met Phe
        1380                1385                1390
Ile Phe Ala Val Ala Val Gln Leu Phe Lys Gly Lys Phe Phe His
    1395                1400                1405
Cys Thr Asp Glu Ser Lys Glu Phe Glu Lys Asp Cys Arg Gly Lys Tyr
    1410                1415                1420
Leu Leu Tyr Glu Lys Asn Glu Val Lys Ala Arg Asp Arg Glu Trp Lys
1425                1430                1435                1440
Lys Tyr Glu Phe His Tyr Asp Asn Val Leu Trp Ala Leu Leu Thr Leu
            1445                1450                1455
Phe Thr Val Ser Thr Gly Glu Gly Trp Pro Gln Val Leu Lys His Ser
        1460                1465                1470
Val Asp Ala Thr Phe Glu Asn Gln Gly Pro Ser Pro Gly Tyr Arg Met
    1475                1480                1485
Glu Met Ser Ile Phe Tyr Val Val Tyr Phe Val Val Phe Pro Phe Phe
    1490                1495                1500
Phe Val Asn Ile Phe Val Ala Leu Ile Ile Ile Thr Phe Gln Glu Gln
1505                1510                1515                1520
Gly Asp Lys Met Met Glu Glu Tyr Ser Leu Glu Lys Asn Glu Arg Ala
            1525                1530                1535
Cys Ile Asp Phe Ala Ile Ser Ala Lys Pro Leu Thr Arg His Met Pro
        1540                1545                1550
Gln Asn Lys Gln Ser Phe Gln Tyr Arg Met Trp Gln Phe Val Val Ser
    1555                1560                1565
Pro Pro Phe Glu Tyr Thr Ile Met Ala Met Ile Ala Leu Asn Thr Ile
    1570                1575                1580
Val Leu Met Met Lys Phe Tyr Gly Ala Ser Val Ala Tyr Glu Asn Ala
1585                1590                1595                1600
Leu Arg Val Phe Asn Ile Val Phe Thr Ser Leu Phe Ser Leu Glu Cys
            1605                1610                1615
Val Leu Lys Val Met Ala Phe Gly Ile Leu Asn Tyr Phe Arg Asp Ala
        1620                1625                1630
Trp Asn Ile Phe Asp Phe Val Thr Val Leu Gly Ser Ile Thr Asp Ile
    1635                1640                1645
Leu Val Thr Glu Phe Gly Asn Pro Asn Asn Phe Ile Asn Leu Ser Phe
    1650                1655                1660
Leu Arg Leu Phe Arg Ala Ala Arg Leu Ile Lys Leu Leu Arg Gln Gly
1665                1670                1675                1680
Tyr Thr Ile Arg Ile Leu Leu Trp Thr Phe Val Gln Ser Phe Lys Ala
            1685                1690                1695
```

```
Leu Pro Tyr Val Cys Leu Leu Ile Ala Met Leu Phe Phe Ile Tyr Ala
        1700                1705                1710

Ile Ile Gly Met Gln Val Phe Gly Asn Ile Gly Ile Asp Val Glu Asp
        1715                1720                1725

Glu Asp Ser Asp Glu Asp Phe Gln Ile Thr Glu His Asn Asn Phe
        1730                1735            1740

Arg Thr Phe Phe Gln Ala Leu Met Leu Leu Phe Arg Ser Ala Thr Gly
1745                1750                1755                1760

Glu Ala Trp His Asn Ile Met Leu Ser Cys Leu Ser Gly Lys Pro Cys
            1765                1770                1775

Asp Lys Asn Ser Gly Ile Leu Thr Arg Glu Cys Gly Asn Glu Phe Ala
        1780                1785                1790

Tyr Phe Tyr Phe Val Ser Phe Ile Phe Leu Cys Ser Phe Leu Met Leu
        1795                1800                1805

Asn Leu Phe Val Ala Val Ile Met Asp Asn Phe Glu Tyr Leu Thr Arg
    1810                1815                1820

Asp Ser Ser Ile Leu Gly Pro His His Leu Asp Glu Tyr Val Arg Val
1825                1830                1835                1840

Trp Ala Glu Tyr Asp Pro Ala Ala Trp Gly Arg Met Pro Tyr Leu Asp
            1845                1850                1855

Met Tyr Gln Met Leu Arg His Met Ser Pro Pro Leu Gly Leu Gly Lys
        1860                1865                1870

Lys Cys Pro Ala Arg Val Ala Tyr Lys Arg Leu Leu Arg Met Asp Leu
        1875                1880                1885

Pro Val Ala Asp Asp Asn Thr Val His Phe Asn Ser Thr Leu Met Ala
        1890                1895                1900

Leu Ile Arg Thr Ala Leu Asp Ile Lys Ile Ala Lys Gly Gly Ala Asp
1905                1910                1915                1920

Lys Gln Gln Met Asp Ala Glu Leu Arg Lys Glu Met Met Ala Ile Trp
        1925                1930                1935

Pro Asn Leu Ser Gln Lys Thr Leu Asp Leu Leu Val Thr Pro His Lys
        1940                1945                1950

Ser Thr Asp Leu Thr Val Gly Lys Ile Tyr Ala Ala Met Met Ile Met
        1955                1960                1965

Glu Tyr Tyr Arg Gln Ser Lys Ala Lys Lys Leu Gln Ala Met Arg Glu
    1970                1975                1980

Glu Gln Asp Arg Thr Pro Leu Met Phe Gln Arg Met Glu Pro Pro Ser
1985                1990                1995                2000

Pro Thr Gln Glu Gly Gly Pro Gly Gln Asn Ala Leu Pro Ser Thr Gln
            2005                2010                2015

Leu Asp Pro Gly Gly Ala Leu Met Ala His Glu Ser Gly Leu Lys Glu
        2020                2025                2030

Ser Pro Ser Trp Val Thr Gln Arg Ala Gln Glu Met Phe Gln Lys Thr
        2035                2040                2045

Gly Thr Trp Ser Pro Glu Gln Gly Pro Pro Thr Asp Met Pro Asn Ser
    2050                2055                2060

Gln Pro Asn Ser Gln Ser Val Glu Met Arg Glu Met Gly Arg Asp Gly
2065                2070                2075                2080

Tyr Ser Asp Ser Glu His Tyr Leu Pro Met Glu Gly Gln Gly Arg Ala
            2085                2090                2095

Ala Ser Met Pro Arg Leu Pro Ala Glu Asn Gln Arg Arg Gly Arg
        2100                2105                2110

Pro Arg Gly Asn Asn Leu Ser Thr Ile Ser Asp Thr Ser Pro Met Lys
```

-continued

```
                2115                2120                  2125
Arg Ser Ala Ser Val Leu Gly Pro Lys Ala Arg Arg Leu Asp Asp Tyr
        2130                2135            2140

Ser Leu Glu Arg Val Pro Pro Glu Glu Asn Gln Arg His His Gln Arg
2145                2150                2155                2160

Arg Arg Asp Arg Ser His Arg Ala Ser Glu Arg Ser Leu Gly Arg Tyr
                2165            2170                2175

Thr Asp Val Asp Thr Gly Leu Gly Thr Asp Leu Ser Met Thr Thr Gln
            2180            2185            2190

Ser Gly Asp Leu Pro Ser Lys Glu Arg Asp Gln Glu Arg Gly Arg Pro
        2195            2200                2205

Lys Asp Arg Lys His Arg Gln His His His His His His His His His
    2210            2215            2220

His Pro Pro Pro Pro Asp Lys Asp Arg Tyr Ala Gln Glu Arg Pro Asp
2225            2230            2235            2240

His Gly Arg Ala Arg Ala Arg Asp Gln Arg Trp Ser Arg Ser Pro Ser
            2245            2250            2255

Glu Gly Arg Glu His Met Ala His Arg Gln
            2260            2265
```